US010495654B2

(12) United States Patent
Keller et al.

(10) Patent No.: US 10,495,654 B2
(45) Date of Patent: Dec. 3, 2019

(54) THERMAL MANAGEMENT IN THE CONTEXT OF AUTOMATED HISTOLOGICAL PROCESSING OF BIOLOGICAL SPECIMENS AND ASSOCIATED TECHNOLOGY

(71) Applicant: Ventana Medical Systems, Inc., Tucson, AZ (US)

(72) Inventors: Tim Keller, Oro Valley, AZ (US); Matthew Mette, Marana, AZ (US); Christine Tse, San Diego, CA (US); Glen Ward, Tucson, AZ (US); Chad Wilkinson, Alameda, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 491 days.

(21) Appl. No.: 15/179,862

(22) Filed: Jun. 10, 2016

(65) Prior Publication Data
US 2016/0282376 A1   Sep. 29, 2016

Related U.S. Application Data

(63) Continuation of application No. PCT/EP2014/076814, filed on Dec. 8, 2014.
(Continued)

(51) Int. Cl.
*G01N 1/00* (2006.01)
*G01N 35/00* (2006.01)
(Continued)

(52) U.S. Cl.
CPC .......... *G01N 35/00029* (2013.01); *B01L 7/52* (2013.01); *G01N 1/30* (2013.01);
(Continued)

(58) Field of Classification Search
CPC ...................................................... G01N 1/00
See application file for complete search history.

(56) References Cited

U.S. PATENT DOCUMENTS

| 3,431,886 A | 3/1969 | McCormick et al. |
| 4,043,292 A | 8/1977 | Rogers et al. |

(Continued)

FOREIGN PATENT DOCUMENTS

| CN | 86207758 | 9/1987 |
| CN | 2586964 | 11/2003 |

(Continued)

OTHER PUBLICATIONS

International Search Report dated Feb. 11, 2015 for PCT/EP2014/076894 filed Dec. 8, 2014.
(Continued)

*Primary Examiner* — Jyoti Nagpaul
(74) *Attorney, Agent, or Firm* — Ventana Medical Systems, Inc.

(57) ABSTRACT

Methods and system capable of processing specimens carried by slides within an automated histological staining system. A slide carrier is moved toward and into a temperature-controlled internal environment of a stainer within the system. The slide carrier carries a first slide and a second slide, and the first and second slides can carry a first specimen and a second specimen, respectively. The first and second specimens are stained with at least one of a staining reagent and a counterstaining reagent while the first and second slides are within the internal environment and while an average temperature of the internal environment is greater than ambient temperature. The slide carrier can be moved out of the internal environment after staining one or both specimens.

41 Claims, 60 Drawing Sheets

Related U.S. Application Data

(60) Provisional application No. 61/916,126, filed on Dec. 13, 2013.

(51) Int. Cl.
  _G01N 1/31_ (2006.01)
  _B01L 7/00_ (2006.01)
  _G01N 1/30_ (2006.01)
  _G01N 1/28_ (2006.01)
  _G01N 35/10_ (2006.01)

(52) U.S. Cl.
  CPC ......... _G01N 1/312_ (2013.01); _G01N 35/0099_ (2013.01); _G01N 35/00722_ (2013.01); _B01L 2300/0822_ (2013.01); _B01L 2300/1844_ (2013.01); _G01N 1/2813_ (2013.01); _G01N 35/1002_ (2013.01); _G01N 2001/302_ (2013.01); _G01N 2035/00039_ (2013.01); _G01N 2035/0091_ (2013.01); _G01N 2035/00138_ (2013.01); _G01N 2035/00306_ (2013.01); _G01N 2035/00356_ (2013.01); _G01N 2035/00376_ (2013.01)

(56) References Cited

U.S. PATENT DOCUMENTS

| | | | |
|---|---|---|---|
| 4,413,584 A | 11/1983 | DiMaggio, Jr. et al. | |
| 4,477,287 A | 10/1984 | Kush et al. | |
| 5,766,549 A | 6/1998 | Gao et al. | |
| 6,387,326 B1 | 5/2002 | Edwards et al. | |
| 7,303,725 B2 | 12/2007 | Reinhardt et al. | |
| 7,468,161 B2 | 12/2008 | Reinhardt et al. | |
| 7,875,242 B2 * | 1/2011 | Shah | G01N 1/312 422/536 |
| 2003/0175852 A1 | 9/2003 | Kalra et al. | |
| 2004/0092024 A1 | 5/2004 | Reinhardt et al. | |
| 2004/0253661 A1 | 12/2004 | Goldrick et al. | |
| 2005/0186114 A1 | 8/2005 | Reinhardt et al. | |
| 2006/0014806 A1 | 1/2006 | Zambach et al. | |
| 2006/0148063 A1 | 7/2006 | Fauzzi et al. | |
| 2006/0252025 A1 | 11/2006 | Nitta et al. | |
| 2007/0172911 A1 | 7/2007 | Farrell et al. | |
| 2010/0028978 A1 | 2/2010 | Angros | |
| 2012/0276584 A1 | 11/2012 | Kosmeder et al. | |
| 2013/0203100 A1 | 8/2013 | Otter et al. | |
| 2013/0244252 A1 | 9/2013 | Weidner et al. | |
| 2013/0302818 A1 | 11/2013 | Angros | |

FOREIGN PATENT DOCUMENTS

| | | |
|---|---|---|
| CN | 201149563 | 11/2008 |
| CN | 102589948 A | 7/2012 |
| CN | 102967499 | 3/2013 |
| JP | 2002-257821 | 9/2001 |
| WO | 9510035 A2 | 4/1995 |
| WO | 9943434 A1 | 9/1999 |
| WO | 1999044030 A1 | 9/1999 |
| WO | 00/14507 A1 | 3/2000 |
| WO | 01/22086 A1 | 3/2001 |
| WO | 03/091710 A1 | 11/2003 |
| WO | 2004/057307 A1 | 7/2004 |
| WO | 2005/066327 A1 | 7/2005 |
| WO | 2007084429 A2 | 7/2007 |
| WO | 2011/069507 A1 | 6/2011 |
| WO | 2011139978 A1 | 11/2011 |
| WO | 2012064873 A1 | 5/2012 |
| WO | 2013112891 A1 | 8/2013 |
| WO | 2013127990 A1 | 9/2013 |
| WO | 2015/086484 A1 | 6/2015 |
| WO | 2015/086531 A1 | 6/2015 |
| WO | 2015/086534 A1 | 6/2015 |

OTHER PUBLICATIONS

International Search Report dated Feb. 12, 2015 for PCT/EP2014/076898 filed Dec. 8, 2014.
International Search Report dated Feb. 16, 2015 for PCT/EP2014/076813 filed Dec. 8, 2014.
International Search Report dated Feb. 16, 2015 for PCT/EP2014/076814 filed Dec. 8, 2014.

* cited by examiner

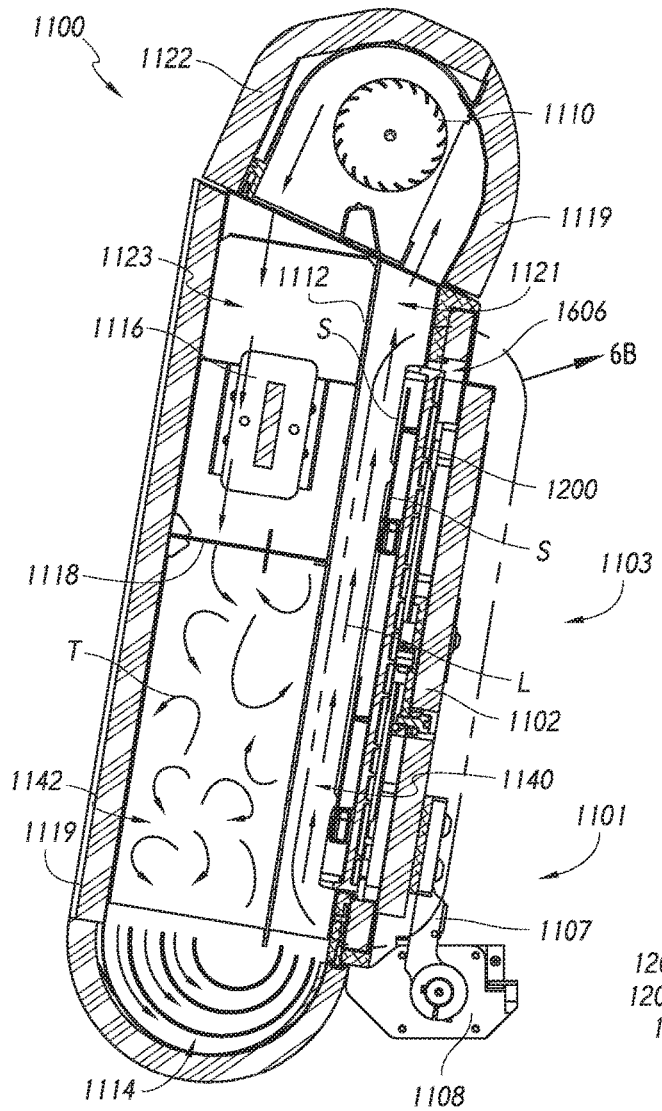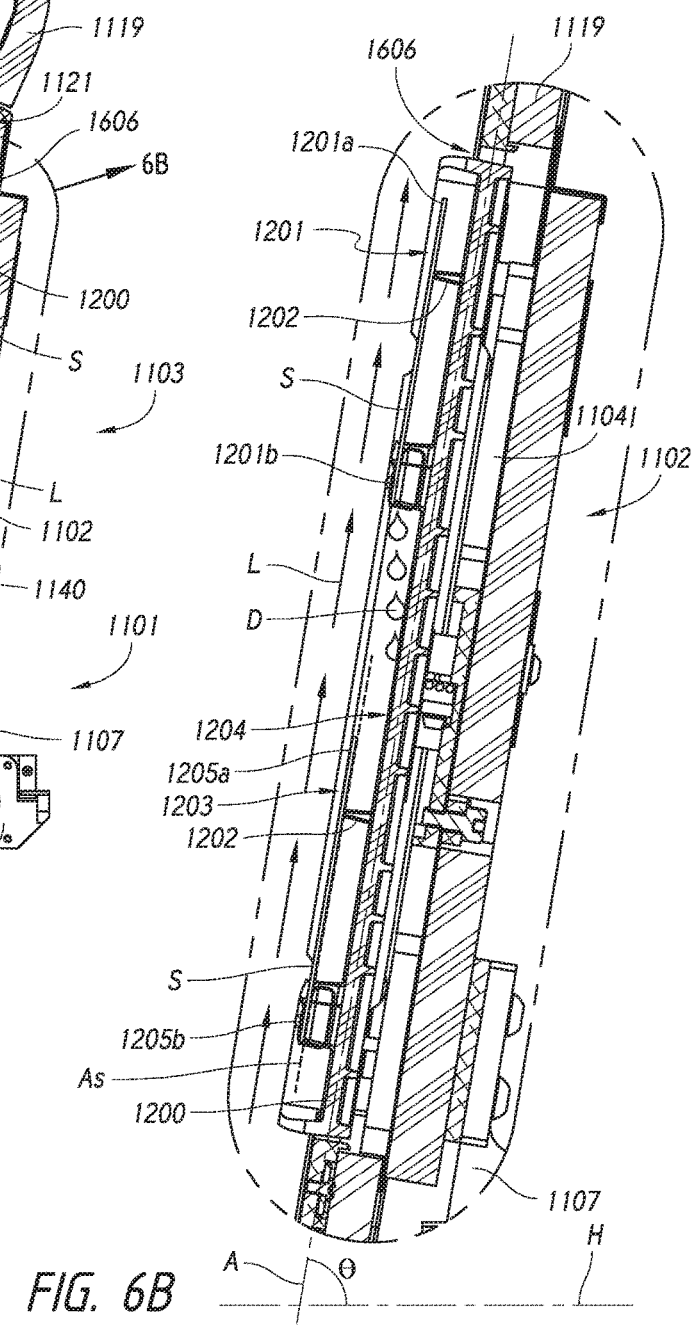
FIG. 6A
FIG. 6B

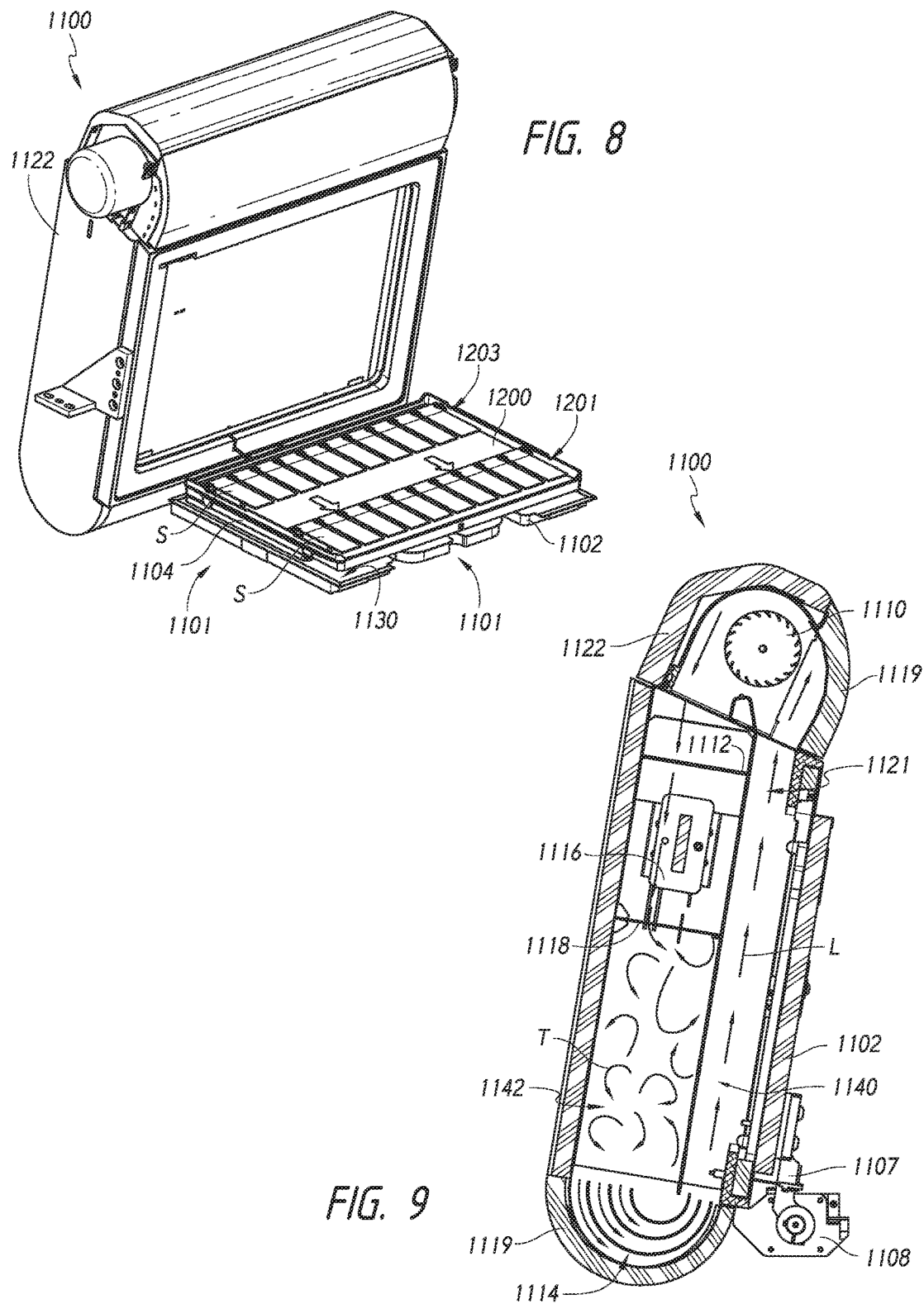

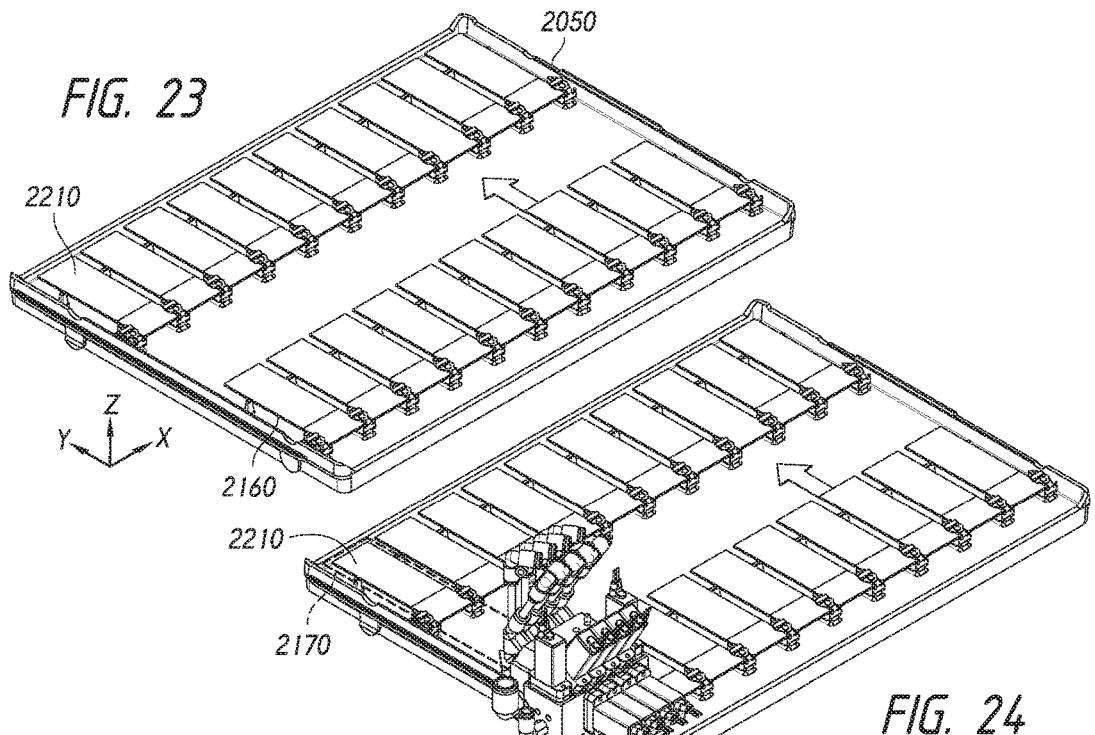
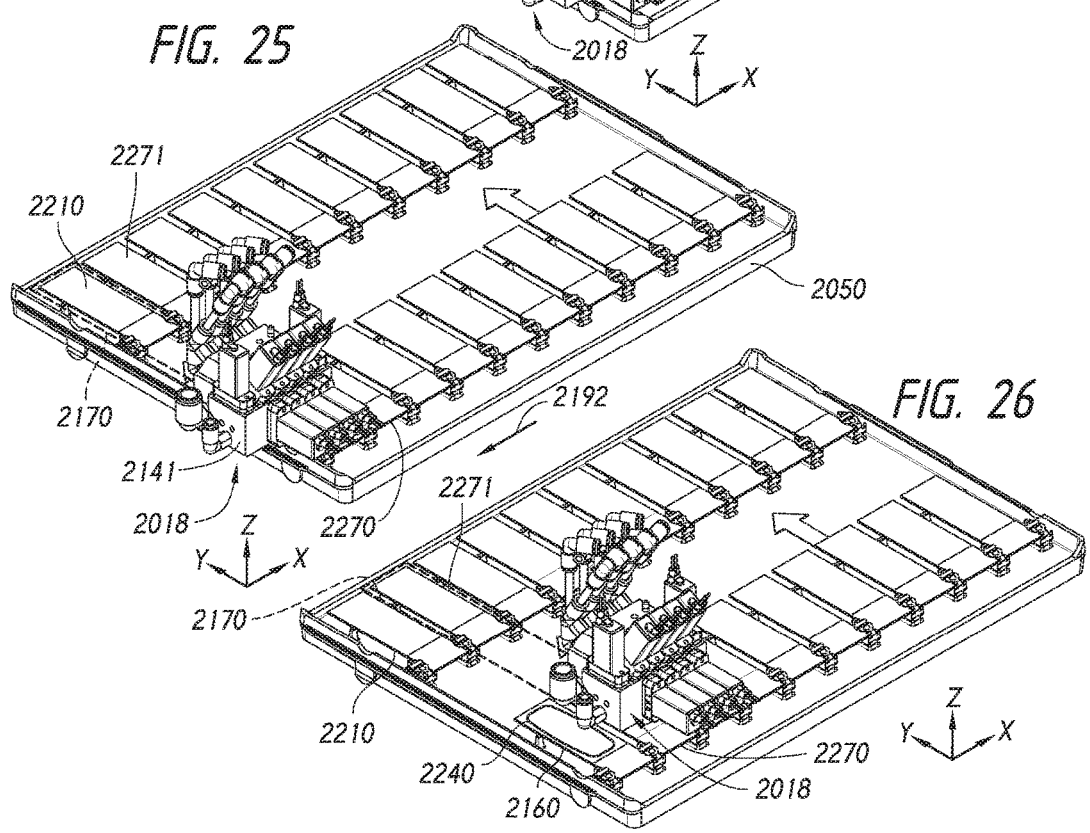

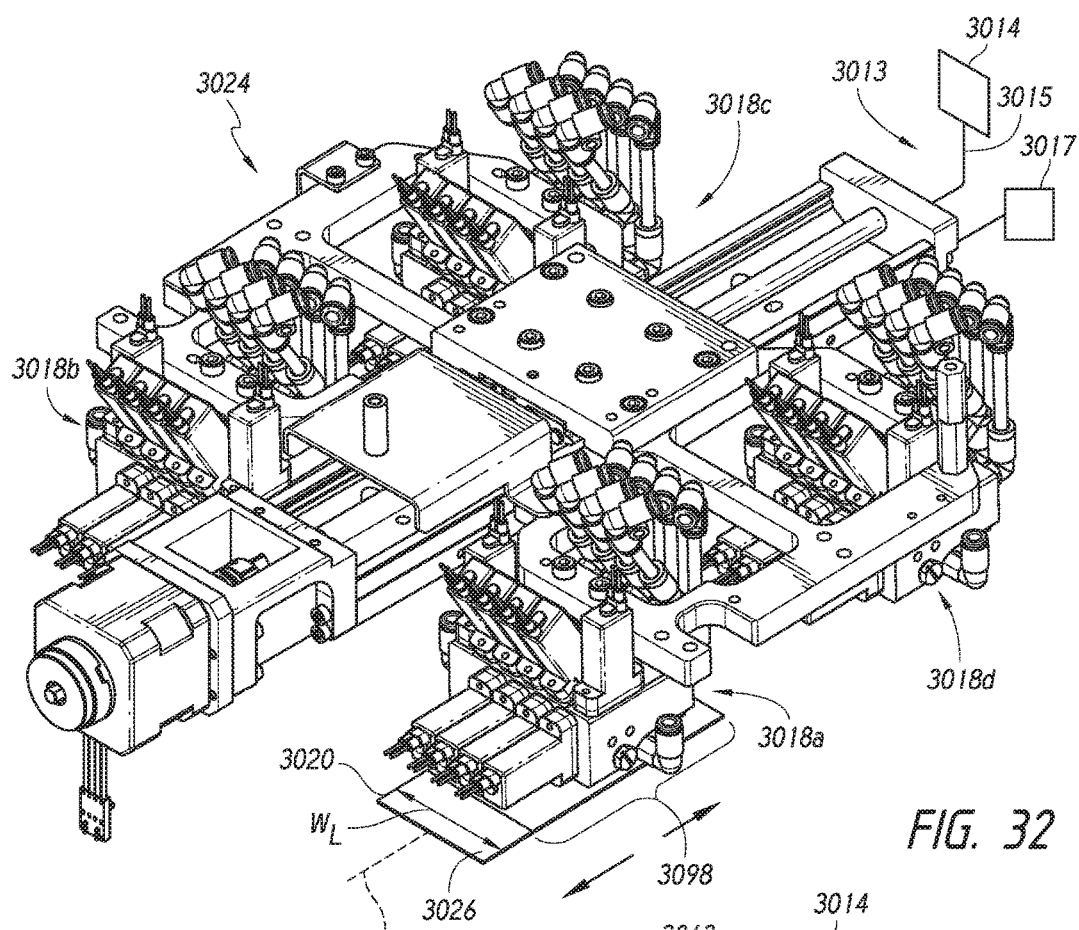
FIG. 32
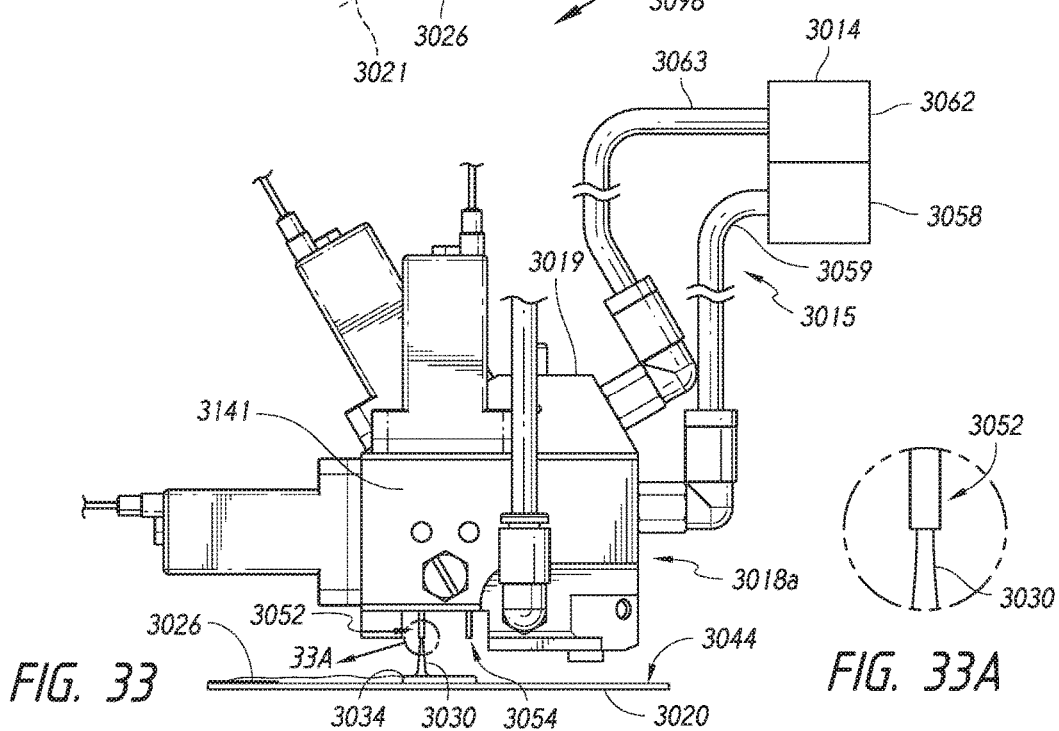
FIG. 33
FIG. 33A

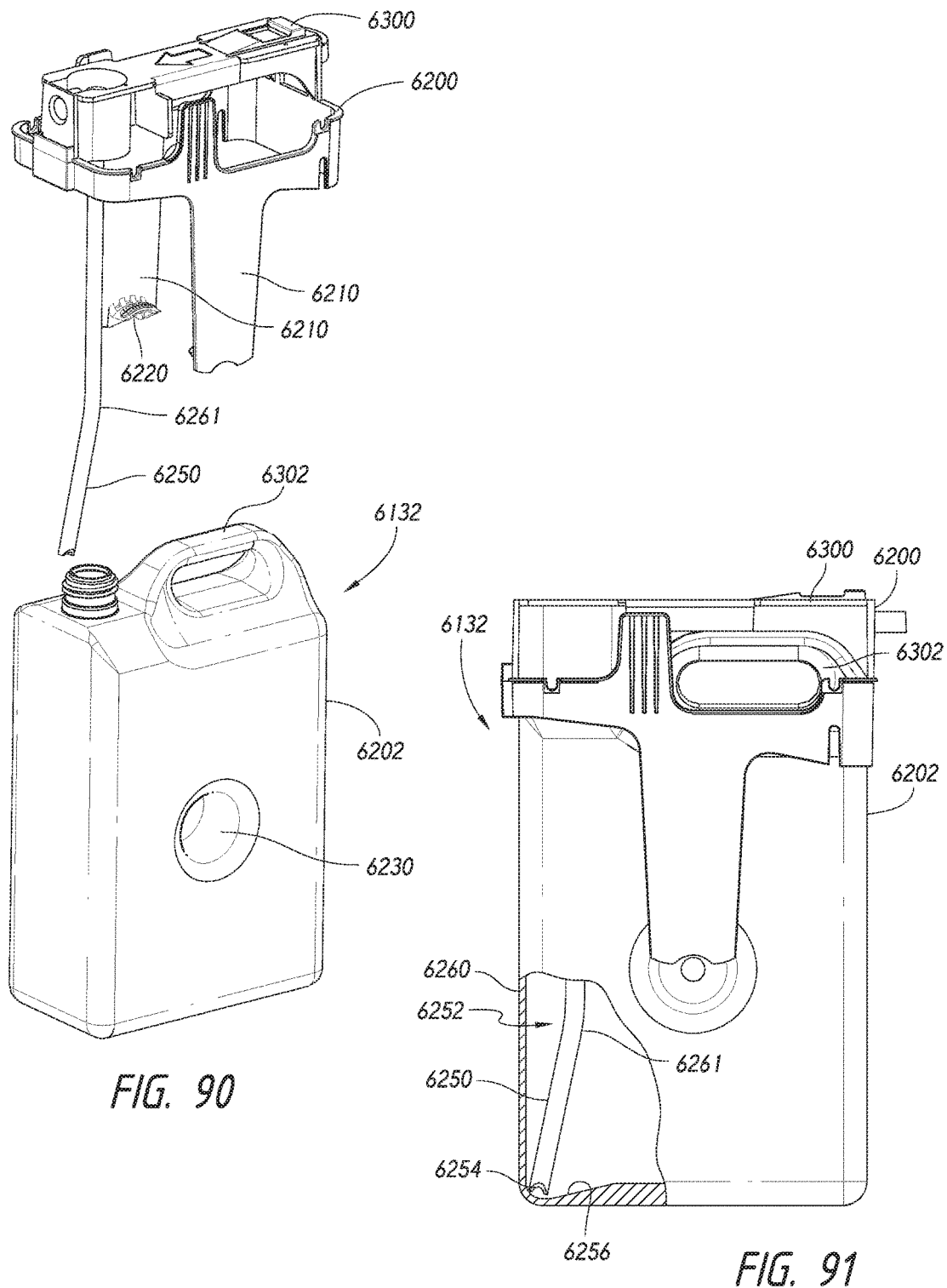

THERMAL MANAGEMENT IN THE CONTEXT OF AUTOMATED HISTOLOGICAL PROCESSING OF BIOLOGICAL SPECIMENS AND ASSOCIATED TECHNOLOGY

CROSS-REFERENCE TO RELATED APPLICATIONS

This patent application is a continuation of International Patent Application No. PCT/EP2014/076814 filed Dec. 8, 2014, which claims priority to and the benefit of U.S. Provisional Patent Application No. 61/916,126 filed Dec. 13, 2013. Each patent application is incorporated herein by reference as if set forth in its entirety.

TECHNICAL FIELD

The present technology is generally related to automated histological processing of biological specimens (e.g., tissue samples), such as systems, devices, methods, and compositions that enhance the quality, precision, efficiency and/or other aspects of this processing.

BACKGROUND

A wide variety of techniques may be used to analyze biological specimens. Examples of analysis techniques useful in this context include microscopy, microarray analysis (e.g., protein and nucleic acid microarray analysis), and mass spectrometry. Preparing specimens for these and other types of analysis typically includes contacting the specimens with a series of processing liquids. Some of these processing liquids (e.g., staining reagents and counterstaining reagents) may add color and contrast or otherwise change the visual characteristics of invisible or poorly visible specimen components (e.g., at least some types of cells and intracellular structures). Other processing liquids (e.g., deparaffinizing liquids) may be used to achieve other processing objectives. If a specimen is treated with multiple processing liquids, both the application and the subsequent removal of each processing liquid can be important for producing specimens suitable for analysis. In some cases, treating specimens with multiple processing liquids includes manually applying the processing liquids to microscope slides respectively carrying the specimens. This approach to processing specimens tends to be relatively labor intensive and imprecise.

"Dip and dunk" automated machines can be used as an alternative to manual specimen processing. These machines automatically process specimens by submerging racks of specimen-bearing slides in open baths of processing liquids. Unfortunately, operation of dip and dunk machines inevitably causes carryover of processing liquids from one bath to another. Over time, this carryover leads to the degradation of the processing liquids. Furthermore, when specimens are immersed in a shared bath, there is a potential for cross-contamination. For example, cells may slough off a specimen on one slide and be transported within a shared bath onto another slide, even on a slide processed much later (e.g., if the cells remain suspended in the bath). This form of contamination can adversely affect the accuracy of certain types of specimen analysis. To mitigate this issue and to address degradation of processing liquids due to carryover, baths of processing liquids in dip and dunk machines typically need to be replaced frequently. Accordingly, these machines tend to consume relatively large volumes of processing liquids, which increases the economic and environmental costs associated with operating these machines. Open baths of processing liquids are also prone to evaporative losses and oxidative degradation of some processing-liquid components. Oxidation of certain components of staining reagents, for example, can alter the staining performance of these components and thereby adversely affect the precision of staining operations.

Some example of conventional histological processing machines that avoid certain disadvantages of dip and dunk machines are known. For example, U.S. Pat. No. 6,387,326 (the '326 patent) to Edwards et al. describes an apparatus for delivering fresh processing liquids directly onto individual slides. The slides are expelled one at a time from a slide storage device onto a conveyor belt. Specimens carried by the slides are individually treated at various stations as the slides move along the conveyor belt. Among other drawbacks, the apparatus described in the '326 patent and similar machines tend to have throughput limitations that make them unsuitable for primary staining applications, such as hematoxylin and eosin (H&E) staining applications. A typical laboratory that performs primary staining, for example, may process hundreds or even thousands of specimens per day. Using the apparatus described in the '326 patent and similar machines for this processing would be unacceptably slow. Furthermore, these machines do not allow for control over staining characteristics. Such control can be important in primary staining applications.

OVERVIEW OF TECHNOLOGY

At least some embodiments are an automated system configured to perform one or more slide processing operations on slides bearing biological samples. The system can provide high sample throughput while also minimizing or limiting the potential for cross-contamination of slides. The automated systems can include features that facilitate consistency, controllability of processing time, and/or processing temperature.

At least some embodiments are a method for drying a plurality of specimens carried by a plurality of microscope slides. The method includes positioning a slide carrier at a first position while the slide carrier holds the microscope slides. Each of the specimens can be carried by one of the microscope slides. The slide carrier can be robotically moved to move the slide carrier into a circulation loop defined by a heater apparatus. The specimens and/or microscope slides can be heated while the slide carrier is located in the circulation loop. In certain embodiments, the specimens and/or microscope slides can be convectively, conductively, and/or radiantly heated.

In some embodiments, a heater apparatus for heating a plurality of specimens carried by a plurality of microscope slides includes a housing, a blower, and a door assembly. The housing can at least partially define a circulation loop. The blower can be positioned to produce a fluid flow along the circulation loop. The door assembly is moveable between a first position and a second position. In some embodiments, the apparatus includes a heat source configured to heat the fluid flow such that the specimens are convectively heated by the fluid flow when the door assembly holds a slide carrier along the circulation loop.

The apparatus, in some embodiments, can be configured to provide conductive and/or radiant heating. Conductive heating can be provided via a plate with a resistive heater. One or more lamps can provide radiant heating. The apparatus can controllably increase or decrease the temperature of the specimens. In some embodiments, when in the first position, the door assembly can be configured to receive the slide carrier that carries the microscope slides. When in the second position, the door assembly can be configured to hold the slide carrier at a vertically-oriented position along the circulation loop. The door assembly can also be moved to other positions.

In some embodiments, a method for thermally processing coverslips is provided. One or more specimens can be covered by a coverslip and carried by one of a plurality of microscope slides. The method includes positioning a slide carrier at a first position while the slide carrier holds the microscope slides. The slide carrier can be robotically positioned at a second position within a circulation loop defined by a heater apparatus. In some embodiments, convective heating is used to heat the coverslips and/or microscope slides positioned within the circulation loop. Conductive and/or radiant heating can also be used. For example, convective heating/cooling can be used for one or more periods of time and radiant heating can be used for one or more periods of time.

At least some embodiments can be a method for processing a specimen carried by a slide within an automated histological system. The method includes automatically dispensing a first liquid so as to form a first puddle on the slide. The first puddle has a shape maintained at least partially by surface tension and can be one of a staining reagent and a counterstaining reagent. The specimen is stained with the first liquid while the specimen is in contact with the first puddle. At least a portion of the first puddle is removed from the specimen so as to at least partially uncover the specimen a first time. The specimen is contacted with an intermediate fluid after at least partially uncovering the specimen the first time. The specimen is at least partially uncovered a second time after contacting the intermediate fluid and the specimen. A second liquid is automatically dispensed so as to form a second puddle on the slide. The second puddle has a shape maintained at least partially by surface tension, and the second liquid can be the other of the staining reagent and the counterstaining reagent. The specimen can be stained by the second liquid while the specimen is in contact with the second puddle, for example, after at least partially uncovering the specimen the second time.

In some embodiments, a method for processing specimens carried by slides within an automated histological system includes dispensing a liquid so as to form a first puddle on a first slide. The liquid can be one of a staining reagent and a counterstaining reagent. Liquid can be dispensed so as to form a second puddle on a second slide. The first and second specimens can be stained (e.g., non-immunohistochemically stained) while the first and second specimens are in contact with the first and second puddles, respectively. At least a portion of the first puddle is removed from the first specimen so as to at least partially uncover the first specimen without contacting the first puddle with a solid structure and/or displacing the first puddle with a liquid. At least a portion of the second puddle can be removed from the second specimen so as to at least partially uncover the second specimen without contacting the second puddle with a solid structure or displacing the second puddle with a liquid. In some embodiments, the first and second puddles are freestanding puddles.

At least some embodiments are a method that includes delivering a liquid from a fluid dispense mechanism at an anti-splatter fluid exit speed. The liquid flows at the anti-splatter fluid exit speed and is directed toward a microscope slide (e.g., an upper surface of the slide) such that the microscope slide carries a collected volume of the liquid. The liquid can be at least partially supported on the slide by, for example, surface tension. In some embodiments, the anti-splatter fluid exit speed is less than a splattering fluid exit speed at which the directed liquid would tend to cause at least a portion of the collected volume to splatter from the upper surface. In some embodiments, the anti-splatter fluid exit speed is greater than a trampoline fluid exit speed at which at least a portion of the directed liquid would tend to bounce off a surface of the collected volume of liquid.

In some embodiments, a method for processing one or more microscope slides includes delivering a liquid at an anti-splatter fluid flow rate that is less than a splattering fluid flow rate at which the directed liquid would tend to cause at least a portion of the collected volume to not stay on the slide. For example, the anti-splatter fluid flow rate can be sufficiently low to prevent appreciable splattering of the collected liquid. In some embodiments, the anti-splatter flow rate is greater than a trampoline flow rate at which at least a portion of the directed liquid would tend to bounce off a surface of the collected volume of liquid. The anti-splatter flow rate can be selected based on characteristics of the liquid.

In yet other embodiments, a method for processing a specimen on an upper surface of a microscope slide includes moving the microscope slide to a processing position. A liquid barrier material can be dispensed onto the microscope slide at the processing position to form a barrier comprised of the barrier material along at least a portion of a label of the microscope slide. A liquid (e.g., reagent) can be delivered onto the microscope slide such that the liquid contacts the specimen while the barrier covers at least the portion of the label. In some embodiments, the microscope slide can be robotically moved to the processing position using a an automated mechanism, such as a transport mechanism.

In yet further embodiments, a method for processing a specimen on a microscope slide includes dispensing reagent from outlets of a fluid dispense mechanism aligned with a width of an upper surface of the microscope slide. The width of the upper surface can be substantially perpendicular to a longitudinal axis of the microscope slide. The outlets can be moved in a direction substantially parallel to the longitudinal axis of the slide to distribute the reagent within a mounting area of the upper surface so as to form a layer of the reagent that contacts a specimen located at the mounting area.

At least some embodiments are a system for processing a specimen on a microscope slide includes a transporter device, an automated slide processing module, and a dispenser assembly. The automated slide processing module can be positioned to receive a slide carrier from the transporter device and can include a dispenser assembly movable along a microscope slide held by the slide carrier when the slide carrier is located within a holding chamber. The dispenser assembly includes a plurality of outlets configured to be aligned with a width of an upper surface of the microscope slide such that the outlets apply a reagent across most or all of the width of the upper surface.

In some embodiments, a system comprises a transporter device and a stainer module configured to receive a slide carrier from the transporter device. In certain embodiments, the stainer module includes one or more fluid lines and a head assembly movable to dispense reagent along a slide carried by the slide carrier. The head assembly can be coupled to the fluid lines and can be configured to dispense reagent from one or all of the fluid lines. In one embodiment, a manifold of the head assembly includes a distribution chamber, a plurality of inlets opening into the distribution chamber, and a plurality of outlets from the distribution chamber. The fluid can be delivered through the manifold and dispensed from the head assembly.

In yet further embodiments, a microscope slide processing system comprises a transporter device and a stainer module configured to receive a slide carrier from the transporter device. The stainer module can include a plurality of manifolds and a plurality of nozzles in fluid communication with the manifolds. In some embodiments, the stainer module includes a plurality of first fluid lines, a plurality of second fluid lines, and a dispenser head movable relative the slide carrier, if any, positioned in the stainer module. The dispenser head can comprise a plurality of first nozzles, a first manifold configured to distribute fluid from each of the first fluid lines to the first nozzles, a plurality of second nozzles, and a second manifold configured to distribute fluid from each of the second fluid lines to the second nozzles. The dispenser head can include additional manifolds and/or nozzles to distribute liquid from any number of fluid lines.

At least some embodiments are an automated slide processing apparatus for staining a specimen on a microscope slide located within the slide processing apparatus. The slide processing apparatus includes a liquid removal device, a gas knife, and a suction element. The liquid removal device is movable relative to the slide. In some embodiments, the gas knife generates a gas curtain and a low pressure region to facilitate liquid removal. In some embodiments, the gas knife is configured to generate a gas curtain that tends to collect liquid on an upper surface of the slide at a collection zone at least partially defined by the gas curtain as the liquid removal device moves relative to the slide. A suction element is positioned to remove liquid collected at the collection zone from the upper surface as the liquid removal device moves relative to the slide.

In some embodiments, a slide processing apparatus for staining a specimen on a microscope slide located within the slide processing apparatus comprises a fluid removal device movable relative to the slide. The fluid removal device includes a fluid knife configured to output one or more gas flows to urge a volume of liquid on an upper surface of the slide toward a collection zone on the upper surface. The collection zone can be at least partially defined by the one or more gas flows. In certain embodiments, the collection zone is a central collection zone. In other embodiments, the collection zone is at other locations along the slide.

In another embodiment, a slide processing apparatus comprises a suction element and a fluid knife movable relative to a microscope slide to captivate at least a portion of a volume of liquid on the slide. The suction element and the gas knife are configured to cooperate to draw most or all of the volume of liquid into the suction element. In some embodiments, the slide processing apparatus includes a plurality of suction elements to draw in liquid at different locations.

In yet another embodiment, a method for processing a specimen on a microscope slide includes applying a liquid onto the slide to cover the specimen with the liquid. A stream of fluid is delivered toward an upper surface of the slide to move the applied liquid along the upper surface while confining the applied liquid such that the confined liquid is increasingly spaced apart from longitudinal edges of the slide. The confined liquid is removed from the upper surface of the slide.

In some embodiments, a method for processing a specimen on a microscope slide includes applying a liquid onto the slide and directing a non-planar or multiplanar gas curtain toward an upper surface of the slide. A vertex section of the gas curtain can be moved along a central region of the upper surface and toward an end of the slide so as to urge the applied liquid toward the central region of the slide. In other embodiments, the vertex section of the gas curtain can be moved along other regions of the upper surface.

In particular embodiments, a method for processing a specimen on a microscope slide includes delivering the slide into a stainer module. Liquid is applied onto the slide to contact the specimen with the liquid. The liquid is blown along and removed from an upper surface of the slide. The slide can then be removed from the stainer module. In some embodiments, the slides are robotically delivered into and/or removed from the stainer module.

At least some embodiments are a method that includes moving a head assembly of a stainer module relative to a first microscope slide positioned at a processing zone within the stainer module so as to apply one or more reagents onto the first microscope slide. After applying the one or more reagents onto the first microscope slide, the first microscope slide is moved away from the processing zone and a second microscope slide is moved to the processing zone. The head assembly is moved relative to the second microscope slide while the second microscope slide is positioned at the processing zone so as to apply one or more reagents onto the second microscope slide.

In some embodiments, a method for processing a plurality of microscope slides carrying specimens using a stainer module includes delivering a slide carrier tray carrying the microscope slides into the stainer module. The stainer module includes a movable dispenser apparatus having head assemblies. At least one of the microscope slides is processed by delivering one or more liquids from the dispenser assembly while the slide carrier tray obstructs a first set of vertical delivery paths from a first set of the head assemblies and obstructs a second set of vertical delivery paths from a second set of the head assemblies. The slide carrier tray can be moved to a purge position to unobstruct the first set of vertical delivery paths such that the collection pan collects liquid outputted by the first set of the head assemblies. The slide carrier tray can be moved to a second position to unobstruct the second set of vertical delivery paths such that the collection pan collects liquid outputted by the second set of the head assemblies. The first set can be different from the second set.

In additional embodiments, an apparatus for processing a plurality of microscope slides includes at least one stainer module. The stainer module can include a tray holder and a head assembly. The tray holder can be configured to receive and hold a tray carrying a first microscope slide and a second microscope slide in a chamber of the stainer module.

The head assembly is movable relative to a processing zone in the stainer module so as to deliver one or more liquids outputted from the head assembly along the first microscope slide positioned at the processing zone. In some embodiments, the tray holder is movable to transport the first microscope slide away from the processing zone and to transport the second microscope slide to the processing zone after delivering the one or more liquids onto the first microscope slide.

In yet additional embodiments, an apparatus for processing a plurality of microscope slides comprises a stainer module including fluid lines, a tray holder, and a head assembly. The tray holder is configured to receive and hold a tray carrying a first microscope slide and a second microscope slide in the stainer module. The head assembly includes a dispenser head and one or more valves mounted on the dispenser head. The valves can control which fluid from the plurality of fluid lines flows through and out of the head. The dispenser head can carry the valves and is movable relative to tray holder so as to deliver one or more fluids outputted from the dispenser head along the microscope slides.

At least some embodiments are directed to a method for processing specimens carried by slides within an automated histological staining system. The method includes moving a slide carrier toward and into a temperature-controlled internal environment of a stainer within the system. The slide carrier carries a first slide and a second slide, and the first and second slides can carry a first specimen and a second specimen, respectively. The first and second specimens are stained with at least one of a staining reagent and a counterstaining reagent while the first and second slides are within the internal environment and while an average temperature of the internal environment is greater than ambient temperature. The slide carrier can be moved out of the internal environment after staining one or both specimens.

In some embodiments, an automated histological staining system comprises a main housing and a stainer. The stainer includes a stainer housing defining an internal environment of the stainer, one or more heaters configured to internally heat the stainer, and a transporter. The transporter can be configured to move a slide carrier robotically within the main housing toward the stainer. In one embodiment, the transporter moves the slide carrier between multiple modules in the main housing.

At least some embodiments are directed to a method for processing specimens in an automated histological staining system. The method comprises robotically moving a slide carrier into a stainer of the system. The slide carrier carries slides which respectively carry the specimens, and the specimens are at least partially embedded in paraffin. Liquids are automatically dispensed onto the slides according to a predetermined recipe for at least deparaffinizing, staining, and counterstaining the specimens. The slide carrier can be robotically moved out of the stainer after automatically dispensing the liquids. In some embodiments, a total of all liquid dispensed onto the slides after moving the slide carrier into the stainer and before moving the slide carrier out of the stainer has a greater volumetric concentration of polyol than of monohydric alcohol.

In one embodiment, a method for processing specimens within an automated histological staining system comprises contacting the specimens with a staining reagent. The specimens can be contacted by a washing liquid to at least partially remove the staining reagent from the specimens. The specimens can be contacted with a counterstaining reagent after contacting the specimens and the washing liquid. The specimens can be contacted with the washing liquid to differentiate counterstaining of the specimens after contacting the specimens and the counterstaining reagent. In some embodiments, one or more of the staining reagent, washing liquid, and/or counterstaining reagent has a greater volumetric concentrations of polyol than of monohydric alcohol. In one embodiment, the staining reagent, the washing liquid, and the counterstaining reagent each have greater volumetric concentrations of polyol than of monohydric alcohol.

BRIEF DESCRIPTION OF THE DRAWINGS

Many aspects of the present disclosure can be better understood with reference to the following drawings. The relative dimensions in the drawings may be to scale with respect to some embodiments. With respect to other embodiments, the drawings may not be to scale. For ease of reference, throughout this disclosure identical reference numbers may be used to identify identical or at least generally similar or analogous components or features.

FIG. 6A is an enlarged cross-sectional side elevation view of the dryer apparatus of FIG. 4A in a closed configuration supporting the slide carrier of FIG. 5 in accordance with an embodiment of the present technology.

FIG. 6B is an enlarged cross-sectional side elevation view of a portion of FIG. 6B.

FIG. 8 is a perspective view of the dryer apparatus of FIG. 4A in an open configuration holding a slide carrier in accordance with an embodiment of the present technology.

FIG. 9 is a cross-sectional side elevation view of the dryer apparatus of FIG. 4A in a closed configuration without a slide carrier in accordance with an embodiment of the present technology.

FIG. 23 is an isometric view of a tray holding microscope slides in accordance with an embodiment of the present technology.

FIGS. 24-26 are perspective views of stages of applying substances to microscope slides.

FIG. 32 is an isometric view of a dispenser apparatus in accordance with an embodiment of the present technology.

FIG. 33 is a side elevation view of a head assembly dispensing liquid onto a microscope slide in accordance with an embodiment of the present technology.

FIG. 33A is a detailed view of a nozzle of the head assembly of FIG. 33.

FIG. 90 is an isometric exploded view of a container in accordance with one embodiment of the present technology.

FIG. 91 is a partial cross-sectional side elevation view of the container of FIG. 90.

DETAILED DESCRIPTION

Figure 1:
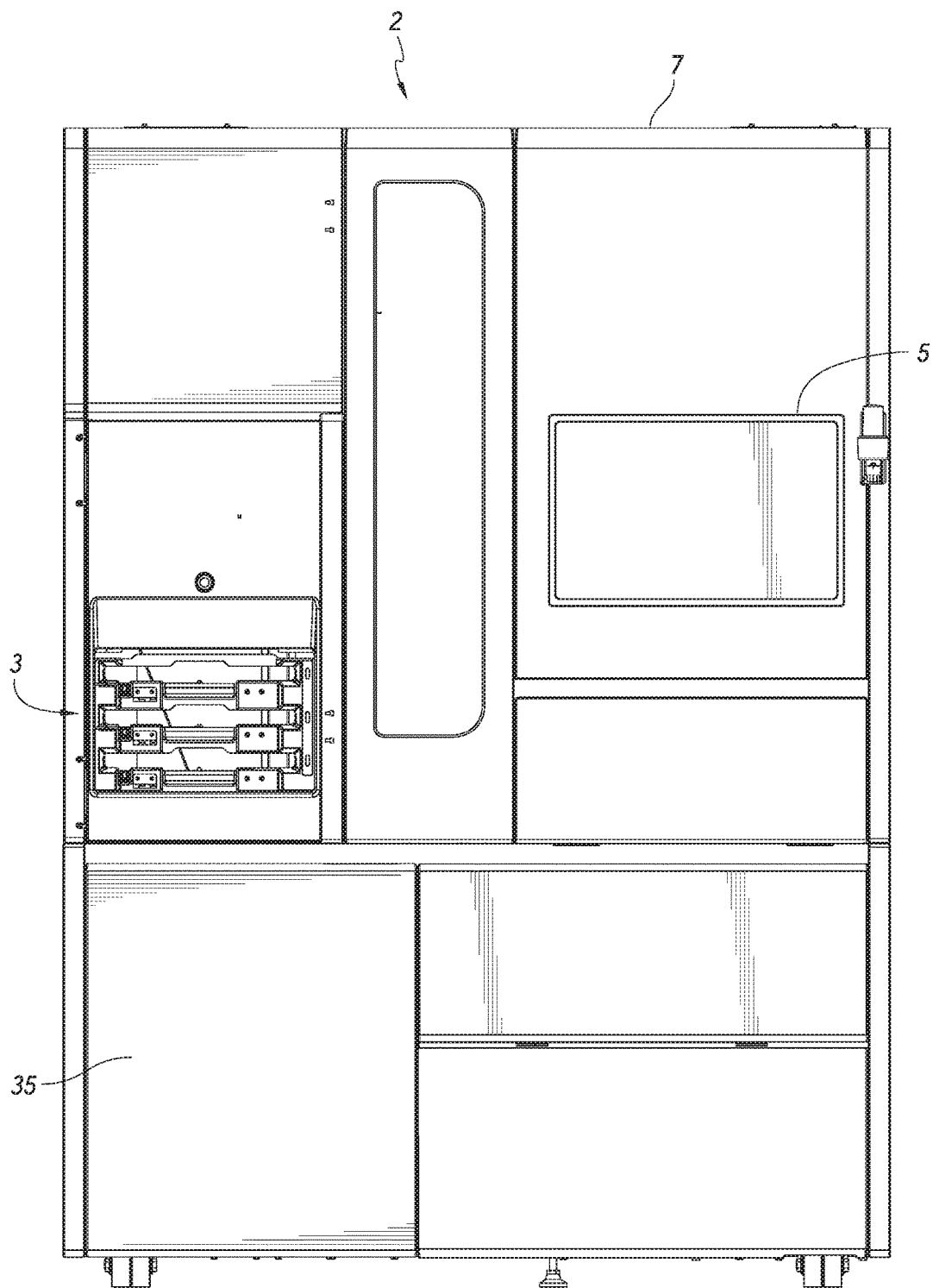
FIG. 1 is a front elevation view of an automated slide processing system in accordance with an embodiment of the present technology.

Increasing the consistency and controllability of certain attributes (e.g., stain intensity) of histologically processed specimens is often desirable. Processing time (i.e., the duration of a given histological process) and processing temperature (i.e., the temperature at which a given histological process is carried out) are two variables that affect most, if not all, of these attributes. Automated histological systems configured in accordance with at least some embodiments of the present technology include features that facilitate consistency and/or controllability of processing time and/or processing temperature. For example, at least some of these systems include stainers having processing heads capable of executing precisely controlled liquid dispensing and removing operations. These stainers can also have internal environments that can be maintained at elevated baseline temperatures. The performance (e.g., with respect to quality and/or versatility) of these and other systems configured in accordance with embodiments of the present technology is expected to far exceed that of conventional counterparts. Furthermore, systems configured in accordance with at least some embodiments of the present technology can include features that provide other desirable enhancements, such as reduced processing costs, reduced waste generation, and increased throughput.

Processing liquids selected or formulated in accordance with at least some embodiments of the present technology can differ from corresponding conventional processing liquids. For example, processing liquids selected or formulated in accordance certain embodiments of the present technology are less volatile than corresponding conventional liquids. For this reason and/or other reasons, these liquids may be well suited for use in stainers maintained at elevated baseline temperatures. In contrast, corresponding conventional liquids may tend to evaporate at unacceptably high rates when used in these stainers. Evaporation of processing liquids in automated histological systems is generally undesirable. Furthermore, processing liquids selected or formulated in accordance with embodiments of the present technology can be less toxic than corresponding conventional processing liquids. This can facilitate disposal of the processing liquids and/or reduce or eliminate the release of noxious fumes from systems in which the processing liquids are used. In at least some cases, some or all processing liquids used with an automated histological system configured in accordance with an embodiment of the present technology have relatively low concentrations of monohydric alcohol (e.g., ethanol). For example, these processing liquids can include greater volumetric concentrations of polyol (e.g., propylene glycol) than of monohydric alcohol. This can reduce evaporation, enhance certain aspects of specimen processing, and decrease process complexity, among other advantages. Furthermore, processing liquids selected or formulated in accordance with embodiments of the present technology can include other features that provide these and/or other desirable enhancements.

Figure 93:
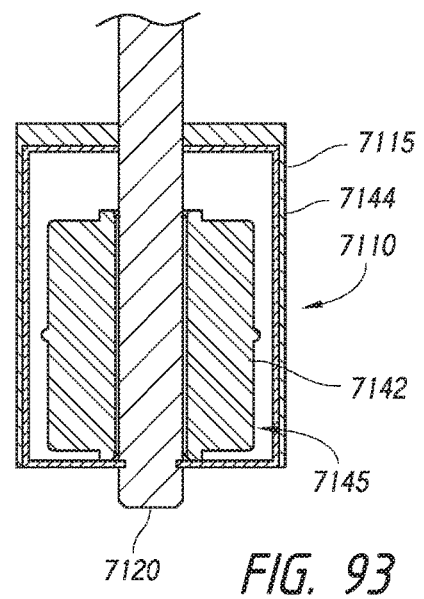
FIG. 93 is a cross-sectional side elevation view of a sensor of the waste container of FIG. 92.

Specific details of several embodiments of the present technology are disclosed herein with reference to FIGS. 1-93. It should be noted that other embodiments in addition to those disclosed herein are within the scope of the present technology. For example, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

Selected Examples of System Architecture

FIG. 1 is an elevation view an automated slide processing system 2 ("system 2") in accordance with an embodiment of the present technology. The system 2 can include an access port 3 and an input device in the form of a touch screen 5. A user can load the system with slide-carrying trays ("slide trays"), such as by placing the slide trays into the access port 3. A given slide tray can carry slides respectively carrying specimens to be processed. Before, during, or after loading the system, the user use the touch screen 5 to select processes (e.g., protocols, recipes, etc.) to be performed on the specimens. The system 2 can then automatically process the specimens, apply coverslips to the slides, and return the slide tray to the access port 3. Thereafter, the coverslipped slides (e.g., slides carrying coverslips permanently coupled to the slides) can be retrieved from the access port 3 for subsequent analysis, pathologist interpretation, and/or archiving.

Figure 2:
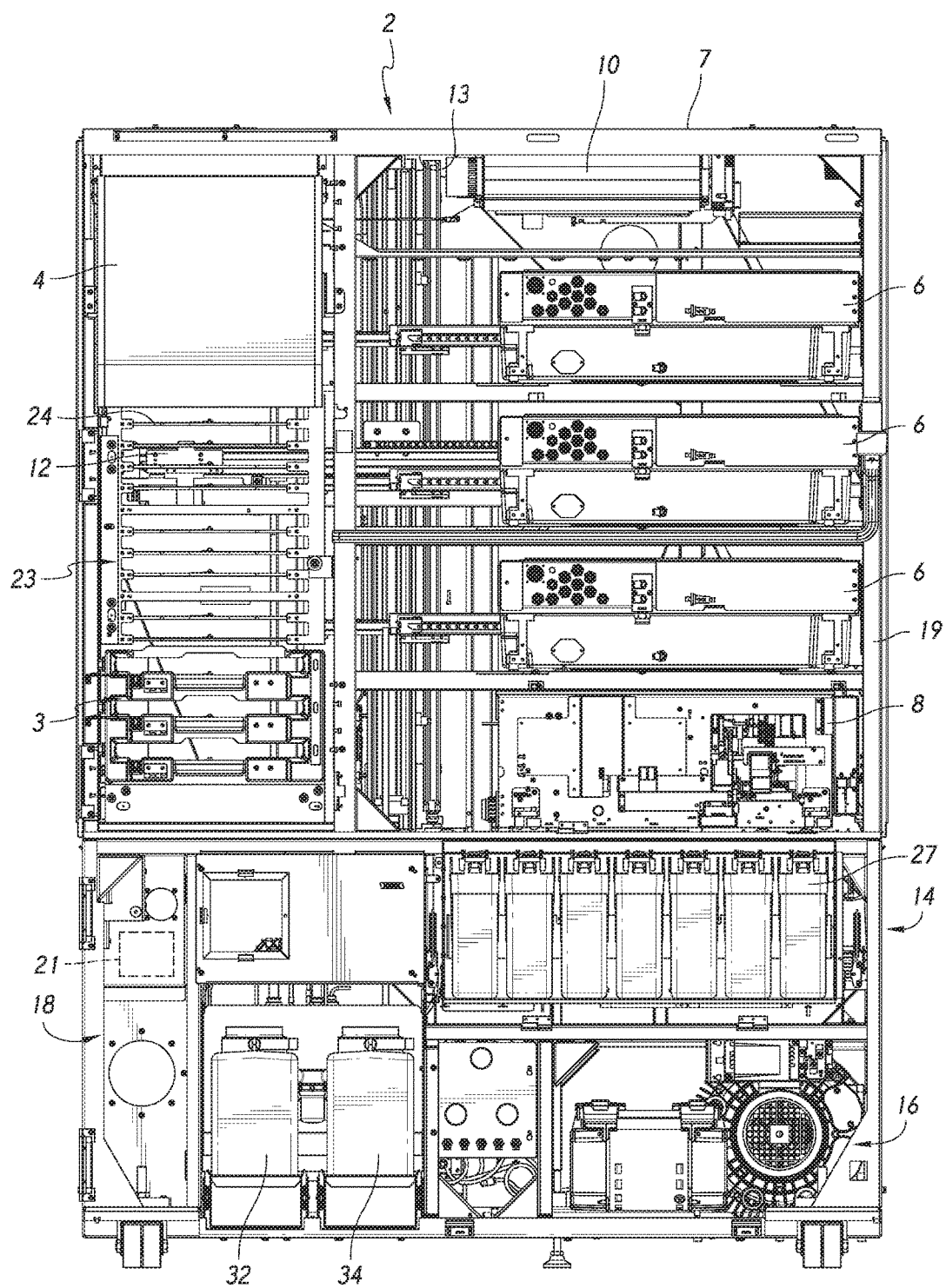
FIG. 2 is a front elevation view of the automated slide processing system of FIG. 1 showing internal components of the system.

FIG. 2 is a side elevation view of system 2 showing some of its internal components. The system 2 can include a housing 7 and modules (e.g., workstations) 4, 6, 8 and 10 disposed within the housing 7. Also within the housing 7, the system 2 can include a transporter 12, a liquid supply 14, a pressurization apparatus 16, and a controller 18. The housing 7 can maintain a generally contaminate-free internal environment and/or help maintain a desired internal temperature suitable for operating one or more of the modules 4, 6, 8, 10. A slide tray holding specimen-bearing slides can be carried by the transporter 12 between the modules 4, 6, 8, 10 to dry the specimens, stain the specimens, and apply coverslips to the slides. The specimens can be individually processed on slide without the use of shared baths of processing liquids. In this way, cross-contamination, carry-over of processing liquids, excessive waste (e.g., liquid waste), inconsistent processing liquid performance and other disadvantages of dip and dunk machines can be reduced or avoided. Furthermore, stain intensity and/or other post-processing attributes of the specimens can be highly controllable and precisely executable. The transporter 12 and modules 4, 6, 8 and 10 can be under the control of the controller 18, which can be controlled by a user using the touch screen 5 (FIG. 1).

The module 4 can be a heater apparatus in the form of a dryer ("dryer 4"), modules 6 can be stainers ("stainers 6"), module 8 can be a coverslipper ("coverslipper 8"), and module 10 can be a heater apparatus in the form of a curing unit ("curing unit 10"). The modules can be arranged in a vertical stack with the dryer 4 and curing unit 10 positioned higher than the stainers 6. This can be useful, for example, because the dryer 4 and the curing unit 10 can generate heat, which can be released through the top of the housing 7. The stainers 6 can be connected to a fluidics manifold 19 that supplies liquids, such as staining reagent (e.g., hematoxylin reagent) and counterstaining reagent (e.g., eosin reagent) from the liquid supply 14. The fluidics manifold 19 can include, without limitation, one or more lines, valves, orifices, sensors, pumps, filters, and/or other components capable of controllably delivering liquid. An electronics manifold (not shown) can communicatively couple the modules to the controller 18 to provide power to and control over components of the modules and components thereof. In one embodiment, individual modules are connected to the fluidics manifold 19 and the electrical manifold through common interfaces and plugs, respectively. The interchangeability afforded by using common interfaces and plugs may make it possible to add and remove modules quickly and easily, thereby facilitating system reconfiguration, maintenance, and/or repair.

The transporter 12 can robotically move slide trays from module to module in an efficient manner so to enhance system throughput. The transporter 12 can comprise, without limitation, one or more elevators (e.g., rail and carriage assemblies), robotic arms, motors (e.g., stepper motors, drive motors, etc.), tray interfaces or holders (e.g., forks, clamps, etc.), and/or sensors, as well as other components for providing motion. In at least some embodiments, the transporter 12 includes an elevator and an inserter (e.g., an X-Y shuttle table) to function as an X-Y-Z transport mechanism (e.g., X-left to right; Y-front to back; Z-up and down). Sensors (not shown) can be placed adjacent to the transporter 12 to detect the position of the transporter 12 and used to index the transporter 12 at sensing locations to provide precise slide-tray positioning.

Sensors can be located at various locations throughout the system 2, including on the transporter 12, within the modules, and on the slide trays. In some embodiments, sensors (including, without limitation, strain gauges, accelerometers, contact sensors, optical sensors, or other sensing devices capable of sensing certain events) can be used to detect collisions, impacts, or other events within the system 2. The sensors can output one or more signals that are received by the controller 18, which can determine whether a given event requires user notification or other action. For example, if an unexpected slide tray impact is detected, the controller 18 can alert a user to open the housing 7 to visually inspect the tray to determine whether slides are properly positioned on the tray. Sensors can be mounted to a ceiling 13 of the housing 7 to help prevent contact between the ceiling 13 and the slide trays and/or slides.

A holding station 23 with vertically spaced apart shelves 24 (one identified) can be positioned adjacent to and in front of the transporter 12. An uppermost shelf 24 can be positioned underneath the dryer 4 and a lowermost shelf can be positioned above the access port 3. The transporter 12 can robotically move slide trays from the shelves 24 to the dryer 4 to dry wet biological specimens, bake biological specimens onto slides, or otherwise thermally process specimen-bearing slides. In some embodiments, the dryer 4 convectively heats specimen-bearing slides while holding the slides at orientations that facilitate drying. High convective flow rates can be used to provide substantially uniform heating of the specimen-bearing slides to reduce (e.g., minimize) temperature differences across the specimens and/or slides due to, for example, the respective locations of the specimens and/or the slides in a slide tray.

The controller 18 can be part of a laboratory information management system that can be connected, for example, to additional automated staining systems. The controller 18 can include, without limitation, one or more printed circuit boards including any number of microprocessors that control, for example, the supply of processing liquids to the modules and module operation. Additionally or alternatively, printed circuit boards, microprocessors, power sources, memory, readers (e.g., label readers) and can be part of the individual modules and in communication with the controller 18 or another controller, such as a remote controller. The controller 18 can command system components and can generally include, without limitation, one or more central processing units, processing devices, microprocessors, digital signal processors (DSPs), application-specific integrated circuits (ASICs), readers, and the like. To store information, the controller 18 can include, without limitation, one or more storage elements 21 (illustrated in phantom), such as volatile memory, non-volatile memory, read-only memory (ROM), random access memory (RAM), or the like. The stored information can include heating programs, staining programs, curing programs, coverslipping programs, optimization programs, specimen-processing programs (e.g., arbitrary user-defined sets of operations and/or pre-defined sets of operations), calibration programs, indexing programs, purge/prime programs, or other suitable executable programs. Specimen-processing programs can include recipes or protocols that can be selected based on user preferences, such as pathologist preferences. Optimization programs can be executed to optimize performance (e.g., enhance heating, reduce excess processing-liquid consumption, increase productivity, enhance processing consistency, or the like). System processing may be optimized by determining, for example, an optimum schedule to (1) increase processing speeds, (2) reduce the time of heating cycles in the dryer 4 and/or in the curing unit 10, (3) increase throughput (e.g., increase the number of slides processed in a certain length of time), (4) improve stain consistency and/or quality, and/or (5) reduce liquid waste.

The liquid supply 14 can include slots for holding supply containers 27 (one identified) and can include container identifiers, such as identifiers with of RFID antennae that can read RFID tags associated with the supply containers 27. The supply containers 27 can include, without limitation, one or more human readable labels, machine readable labels (e.g., a barcode to be read by the system 2), or other types of labels. For example, the supply containers 27 can include RFID tags encoded with information (e.g., container contents information, manufacture dates, expiration dates, etc.) about a particular processing liquid. One example of a container is discussed in connection with FIGS. 90 and 91, and one example of a liquid supply is discussed in connection with FIG. 89. The liquid supply 14 can also include, without limitation, sensors (e.g., pressure sensors, temperature sensors, etc.), pumps (e.g., pneumatic pumps), valves, filters, lines, and/or other fluidic components that can cooperate to supply liquids to the stainers 6, for example.

The pressurization apparatus 16 can be located below the liquid supply 14 and can include a plurality of pumps, compressors, vacuum devices (e.g., a blower), and/or other devices capable of pressurizing fluids and/or providing a vacuum (including a partial vacuum). Pressurized air can be delivered to, for example, air knives of the stainers 6, and vacuum level pressures can be used by liquid removal devices of the stainers 6.

Liquid waste can be delivered through lines and into waste containers 32, 34. This waste can be generated within the system 2 from a variety of sources. For example, liquid waste collected in the slide trays can be removed and routed to the waste containers 32, 34. Periodically removing this liquid waste can be useful to keep the waste from spilling out of the slide trays during handling. In the dryer 4, the slide trays may collect mounting media (e.g., water), which can be sucked from the slide trays and pumped to one of the waste containers 32, 34. In the stainers 6, the slide trays can collect processing liquids that fall off the slides, as well as liquids that inadvertently drip from nozzles of dispenser apparatuses. In the coverslipper 8, the slide trays can collect coverslipping liquids used to apply coverslips to the slides. The mounting media, processing liquids, coverslipping liquids, and any other collected waste liquids can be pumped to the waste containers 32, 34. A door 35 (FIG. 1) of the housing 7 can be opened to access and empty the waste containers 32, 34.

In operation, the slide trays can be loaded into the system 2 via the access port 3. Referring now to FIG. 2, the transporter 12 can retrieve the slide trays from the access port 3 and transport the slide trays to desired locations. The system 2 can individually process a particular specimen-bearing slide and/or slide tray according to an arbitrary user-defined set of operations, a pre-defined set of operations, or other sets of operations. The slide trays can be transported to an interrogation station where the slides in the tray are analyzed by detectors (e.g., optical sensors, cameras, etc.). The slide tray may then then moved to the dryer 4 where specimens are dried and/or adhered to the slides. In some processes, the dryer 4 can help remove paraffin from paraffin-embedded specimens by melting and spreading the paraffin across the surfaces of the slides. The resulting thin layers of paraffin, having greater surface area once spread across the slides, may be more easily removed by deparaffinizing liquid applied to the slides within the stainers 6. Once the specimens and/or slides have been at least partially dried, the slide tray can be moved to one of the stainers 6 where the biological specimens are processed. The stainers 6 can perform deparaffinizing, staining, conditioning (e.g., solvent exchange), and other specimen processing operations by individually applying fresh liquids to the specimens.

This can facilitate control over the post-processing characteristics of the specimens. The stainers 6 can controllably dispense fresh processing liquids onto the slides without splattering onto adjacent slides and can controllably remove the processing liquids from the slides. The controlled dispensing/removal can be used to efficaciously process specimens while also reducing volumes of liquid waste by, for example, minimizing or otherwise limiting volumes of liquid waste collected by slide trays. The illustrated system 2 includes three stainers 6 that respectively provide parallel processing of three slide trays to increase system throughput, but a greater or lesser number of stainers can be used to prevent undue limiting of the throughput of the system based on operation of the stainers 6.

As used herein, the terms "reagent" and "processing liquid" refer to any liquid or liquid composition used in a specimen processing operation that involves adding liquid or liquid composition to a slide. Examples of reagents and processing liquids include solutions, emulsions, suspensions, and solvents (either pure or mixtures thereof). These and other examples can be aqueous or non-aqueous. Further examples include solutions or suspensions of antibodies, solutions or suspensions of nucleic acid probes, and solutions or suspensions of dye or stain molecules (e.g., H&E staining solutions, Pap staining solutions, etc.). Still further examples include solvents and/or solutions for deparaffinizing paraffin-embedded biological specimens, aqueous detergent solutions, and hydrocarbons (e.g., alkanes, isoalkanes and aromatic compounds such as xylene). Still further examples include solvents (and mixtures thereof) used to dehydrate or rehydrate biological specimens. The stainers 6 can receive a wide range of reagents and processing liquids from the containers 27.

The term "staining" is used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system 2 can be used to visualize an outline of a cell. Other staining performed by the system 2 may rely on certain cell components (such as molecules or structures) being stained without or with relatively little staining other cell components. Examples of types of staining methods performed by the system 2 include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

After processing the specimens, the transporter 12 can transport the slide trays from the stainer 6 to the coverslipper 8. The coverslipper 8 can apply solvent to the slides and can place coverslips with pre-applied adhesive onto the slides. In some embodiments, the slide tray holds a plurality of slides in, for example, a substantially horizontal position, and coverslips are individually added to the slides. In one embodiment, the coverslipper 8 is substantially as described in U.S. Patent Application Publication No. 2004/0092024A1 or U.S. Pat. No. 7,468,161, which are incorporated by reference herein in their entireties. The coverslippers described in U.S. Patent Application Publication No. 2004/0092024A1 or U.S. Pat. No. 7,468,161 and their operation can be implemented to enhance coverslip handling by, for example, detecting broken coverslips, facilitating single coverslip pickup, increasing coverslipper placement precision, and/or increasing system throughput.

Once coverslips are placed onto the slides, the transporter 12 can transport the slide tray from the coverslipper 8 to the curing unit 10 where coverslips are cured onto the slides (at least partially) and the tray itself is dried (at least partially) if the tray has collected liquid. During curing, the slides can be held in substantially horizontal positions to expose surface areas of the coverslips and slides to convective flows. This may facilitate quick and efficient curing of adhesive. Even if coverslipping solvent underneath a given coverslip is not completely removed, a skin of adhesive can form around the coverslip that holds the coverslip in place during subsequent handling by, for example, a health care professional, such as a pathologist. In other embodiments, the curing unit 10 can include one or more radiant heaters or conductive heaters, as well as combinations of convective heaters and radiant or conductive heaters. Once the slides are cover-slipped, the slide tray can be moved from the curing unit 10 back to the access port 3 for retrieval.

The system 2 can have any number of modules arranged in any suitable relationship relative to each other. In the illustrated embodiment, three stainers 6 and the curing unit 10 are positioned substantially directly above and below one another in a vertical stack. Additionally or alternatively, modules can be arranged side-by-side in a horizontal configuration (e.g., the dryer 4 positioned next to the curing unit 10). The modules can also be arranged in a sloped vertical stack with workstations arranged side-by-side at any intermediate level in the sloped stack. Examples of modules that can be included in the disclosed automated slide processing systems include, but are not limited to, a heater apparatuses (e.g., convection or radiant heaters), a reader (e.g., code reader), a stainer module, a coverslipper module, and a combination module, such as a combined dryer and deparaffinizer, a combined deparaffinizer/stainer, a combined deparaffinizer/stainer/solvent exchanger), and other types of workstations (including workstations disclosed in U.S. Pat. No. 7,468,161) that can perform one or more slide processing operations (such as two or more) in a single workstation. Example heater apparatus are discussed in connection with FIGS. 3-14 and example stainers are discussed in connection with FIGS. 15-88. Additional modules can be added to the automated slide processing system 2 to provide any number of functionalities for automated processing of specimens with minimal or no human intervention during normal operation.

The slide trays may have any suitable shape, and the slides held in a given slide tray can be arranged in any suitable manner to hold any suitable number of slides, for example, 5 or more slides, 10 or more slides, 20 or more slides, or 30 or more slides. Several examples of slide trays of different shapes and holding capacities are disclosed in U.S. Pat. No. 7,468,161, which is incorporated by reference in its entirety. In some embodiments, the slide trays are generally rectangular trays configured to hold two rows of slides that are held side-by-side on both sides of the central long axis of the slide tray so that the long dimensions of the slides are disposed outward from the long central axis of the tray. The rectangular trays can have a bottom and sidewalls that define a reservoir for liquid collection. In other embodiments, the slide tray is a circular slide tray configured to hold slides in radial positions in which the long dimensions (or longitudinal axes) of the slides are disposed inward from the outer edge of the tray toward the center of the tray. In yet other embodiments, the tray can be a generally square tray configured to hold slides in two or three rows. The configuration of the slide tray can be selected based on the dimensions of the slides, dimensions of the modules, and/or the configuration of the transporter 12.

The slide trays can hold specimen slides in a spaced apart arrangement and in substantially horizontal positions. Holding all the slides in separation and in essentially the same plane (e.g., a horizontal plane during staining) can limit or prevent cross-contamination of slides during, for example, drying, deparaffinizing, staining, washing and solvent exchanging, and other acts that involve dispensing liquids onto slide surfaces. Although the terms "slide tray" or "tray" are used herein for ease of reference to items that carry slides, unless the context clearly indicates otherwise, other slide carriers capable of holding an array of slides can be utilized. The system 2 can be used with a variety of slide carriers that have, without limitation, slide retainers (e.g., clamps, suction cups, etc.), slide standoffs, suction devices (e.g., tubes, nozzles, etc.) used to remove liquids from the trays, or other features for holding, manipulating, or otherwise processing slides.

The term "slide" refers to any substrate (e.g., substrates made, in whole or in part, glass, quartz, plastic, silicon, etc.) of any suitable dimensions on which a biological specimen is placed for analysis, and more particularly to a "microscope slide" such as a standard 3 inch by 1 inch microscope slide or a standard 75 mm by 25 mm microscope slide. Examples of biological specimens that can be placed on a slide include, without limitation, a cytological smear, a thin tissue section (such as from a biopsy), and an array of biological specimens, for example a tissue array, a DNA array, an RNA array, a protein array, or any combination thereof. Thus, in one embodiment, tissue sections, DNA samples, RNA samples, and/or proteins are placed on a slide at particular locations.

The term "biological specimen" refers to any specimen (e.g., sample) including biomolecules (e.g., proteins, peptides, nucleic acids, lipids, carbohydrates, and combinations thereof) that is obtained from (or includes) any organism, including viruses. Biological specimens can include tissue samples (e.g., tissue sections), cell samples (e.g., cytological smears such as Pap or blood smears or samples of cells obtained by microdissection), samples of whole organisms (e.g., samples of yeast, bacteria, etc.), or cell fractions, fragments or organelles, such as those obtained by lysing cells and separating their components by centrifugation or otherwise. Other examples of biological specimens include, without limitation, blood, serum, urine, semen, fecal matter, cerebrospinal fluid, interstitial fluid, mucous, tears, sweat, pus, biopsied tissue (e.g., obtained by a surgical biopsy or a needle biopsy), nipple aspirates, milk, vaginal fluid, saliva, swabs (e.g., buccal swabs), or any material containing biomolecules derived therefrom.

Selected Examples of Drying and Curing Ovens and Associated Methods

Figure 3:
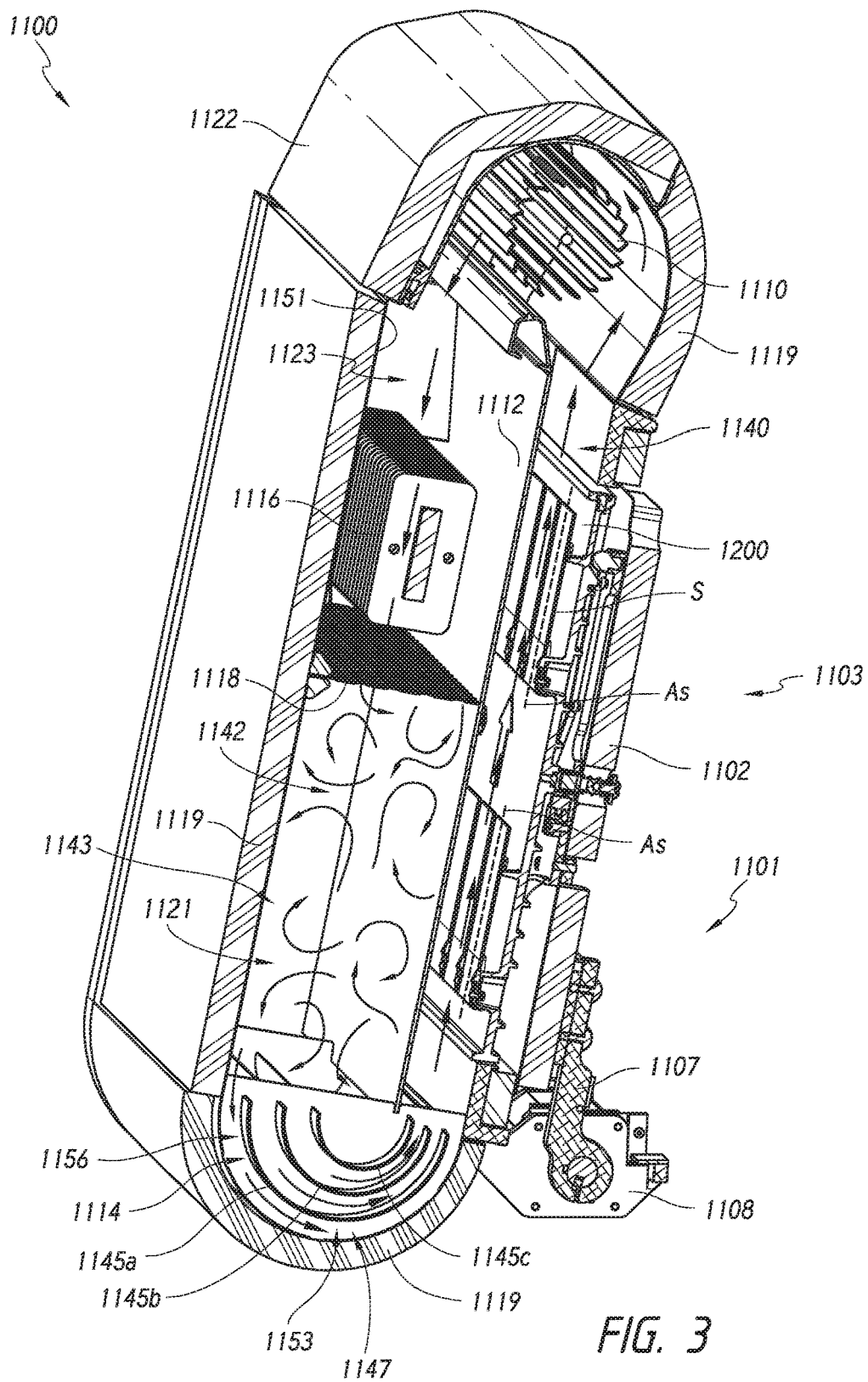
FIG. 3 is a cross-sectional perspective view of a dryer apparatus heating specimen-bearing microscope slides in accordance with an embodiment of the present technology.

FIG. 3 is a cross-sectional perspective view of a heater apparatus in the form of a dryer apparatus 1100 ("apparatus 1100") in a closed configuration holding a slide carrier 1200 configured in accordance with an embodiment of the present technology. Generally, the apparatus 1100 can heat a flow of gas that becomes a heated turbulent gas flow for promoting a generally uniform heat distribution across the flow. The turbulent gas flow can be converted to a laminar gas flow that flows across and heats specimen-bearing slides S (one identified) carried by the slide carrier 1200. The specimen-bearing slides S can be vertically-oriented to promote draining of liquid, such as residual mounting media (e.g., water), from the slides S. The upwardly directed laminar gas flow can flow across the specimens to inhibit, limit, or substantially prevent downward movement of the specimens relative to the slides S due to, for example, gravity while the specimens dry.

The apparatus 1100 can include a housing 1122, a blower 1110, and a heater 1116. The housing 1122 can have one or more walls 1119 and a door assembly 1101 that define an interior space 1123. The interior space 1123 can be a chamber divided by a septum 1112 into a back chamber 1142 and a carrier-receiving or front chamber 1140 ("front chamber 1140") that are fluidly connected to form a circulation loop 1121 within the housing 1122. The cross-sectional area (i.e., the area generally perpendicular to the direction of the gas flow) of the front chamber 1140 can be less than the cross-sectional area of the back chamber 1142 such that a relatively high speed flow travels over the slides S while a relatively low speed flows travels along the back chamber 1142. The door assembly 1101 can move the slide carrier 1200 into a vertically-oriented position within the front chamber 1140 to convectively heat the specimen-bearing slides S. The blower 1110 can include, without limitation, one or more fans, pumps, or other pressurization devices suitable for forced flow convection. In some embodiments, the blower 1110 is positioned along the circulation loop 1121 and is configured to direct the gas flow towards the heater 1116.

The heater 1116 can be configured to raise an average temperature of the gas flowing along the circulation loop 1121. As the gas flows along the heater 1116, the heater 1116 can transfer thermal energy to the gas flow and can be positioned within the back chamber 1142 opposite from an upper row of slides (separated by the septum 1112) to improve heating of an upper row of slides S. Such positioning of the heater 1116 can offset the potential reduction in the temperature of the gas passing over the upper row of slides caused by evaporation of liquid on a lower row of slides. In some embodiments, the heater 1116 can include, without limitation, one or more resistive heater elements and one or more heat transfer elements (e.g., fins, tubes, etc.). In other embodiments, the heater 1116 can include both a resistive heater and a non-resistive heaters, such as Peltier devices.

The apparatus 1100 can include flow modifiers configured to alter the characteristics of the gas flow along various portions of the circulation loop 1121. For example, as shown in FIG. 3, the apparatus 1100 can include a flow modifier in the form of a turbulence promoter 1118 positioned downstream of the heater 1116. The turbulence promoter 1118 can include one or more baffles, perforated plates, ribs, bumps, grooves and/or any structure configured to create eddies, swirling, or other generally turbulent or chaotic states of gas motion. As used herein, "turbulent" refers to a gas flow having a Reynolds number greater than 4,000. By way of example, the majority of the gas flow in a turbulent flow portion 1143 along a substantial majority (e.g., at least 90%, 95%, or 98%) of the cross-sectional area perpendicular to the direction of flow can have a Reynolds number greater than 4,000. In some embodiments, the turbulence promoter 1118 extends between the septum 1112 and the back wall 1119 and across the back chamber 1142. In other embodiments, the turbulence promoter 1118 can be positioned along an interior surface 1151 of the housing 1122 and/or a surface of the septum 1112 and extend into, but not necessarily across, the circulation loop 1121. The turbulent gas flow created by the turbulence promoter 1118 can induce mixing of gas along the turbulent flow portion 1143 of the back chamber 1142, thereby improving heat transfer efficiency by, for example, doubling or tripling the heat transfer efficiency within the circulation loop 1121. In some embodiments, the turbulence promoter 1118 is configured to produce sufficient turbulence that the gas flow exiting the turbulent flow portion 1143 has a substantially uniform temperature across the flow (i.e., a substantially uniform temperature in a direction perpendicular to the direction of flow). In other embodiments, the flow modifier can have other configurations to promote, for example, mixing of the gas flow.

Additionally, the apparatus 1100 can include a flow modifier in the form of a laminar flow promoter 1114 positioned downstream of the turbulent flow portion 1143. The laminar flow promoter 1114 can include one or more guide vanes, tapered channels, arcuate surfaces, and/or any structure configured to create a substantially laminar gas flow. As used herein, "laminar flow" or "substantially laminar flow" refers to a gas flow having a Reynolds number less than 2,100. The circulation loop 1121 can have one or more laminar flow portions 1156. In some embodiments, the majority of the gas flow along a majority (e.g., at least 60%) of the cross-sectional area perpendicular to the direction of flow has a Reynolds number less than 2,100. For example, the portion of the circulation loop 1121 containing the laminar flow promoter 1114 (e.g., between the turbulent flow portion 1143 and the front chamber 1140) can be a laminar flow portion. Also, at least a portion of the front chamber 1140 (e.g., between the specimen-bearing faces of the slides S and the septum 1112) can be a laminar flow portion. In some embodiments, the apparatus 1100 can have a transitional gas flow (e.g., a gas flow having a Reynolds number between 2,100 and 4,000) in at least a portion of the turbulent and/or laminar flow portions.

As shown in FIG. 3, the laminar flow promoter 1114 can be positioned at a bend 1153 in the circulation loop 1121 to guide the heated gas from the turbulent flow portion 1143 to the front chamber 1140. In some embodiments, the laminar flow promoter 1114 can be a plurality of spaced apart, arcuate members 1145a, 1145b, 1145c that can reduce the head loss around the bend 1153. Once downstream of the arcuate members 1145a-1145c, the gas can flow upwardly along the lengths of the slides S (e.g., substantially parallel to longitudinal axes $A_S$ of the slides S (one identified)) to, for example, evaporate liquid on the slides S, thermally process the specimens (e.g., melt wax in the specimen), and/or dry the specimens (as discussed in greater detail below with reference to FIGS. 6A-7). In other embodiments, the laminar flow promoter 1114 can be positioned anywhere along the circulation loop 1121, such as along a relatively straight section of the circulation loop 1121.

In some embodiments, the laminar flow promoter 1114 can also accelerate the gas flow to produce a relatively high speed laminar flow and increase the rate of convective heating and/or evaporation rate. For example, in particular embodiments, the arcuate members 1145a-1145c can define channels 1147 (one identified) that narrow in the downstream direction. As the gas flows through the channels 1147, the flow can be accelerated to produce a high speed flow. In some embodiments, a ratio of the flow speed in the front chamber 1140 to the flow speed in the back chamber 1142 is equal to or greater than 2, 3, 4, 5, or 6. The ratio can be selected based on the desired specimen heating rates, evaporation rates, or the like.

One exemplary drying process is discussed below with reference to FIGS. 4A-9. Generally, the slide carrier 1200 can be moved to a loading position while the slide carrier 1200 holds the slides S. The slide carrier 1200 is robotically moved from the loading position to a processing position to move the slide carrier 1200 into the circulation loop 1121. The processing position can be angled relative to the loading position to facilitate drying of the specimens. The specimen-bearing microscope slides S are heated while the slide carrier 1200 is held at the processing position. Details of the drying process are discussed below.

Figure 4A:
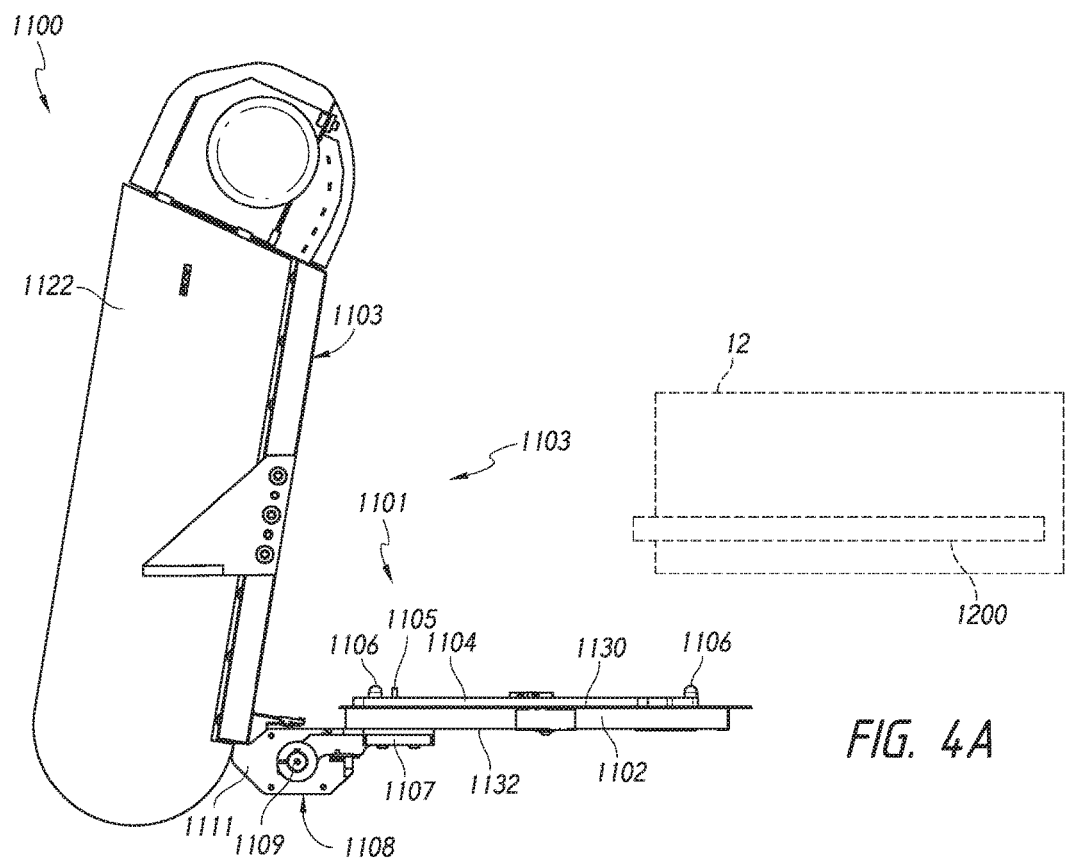
FIG. 4A is a side elevation view of a dryer apparatus having a door in an open configuration in accordance with an embodiment of the present technology.
Figure 4B:
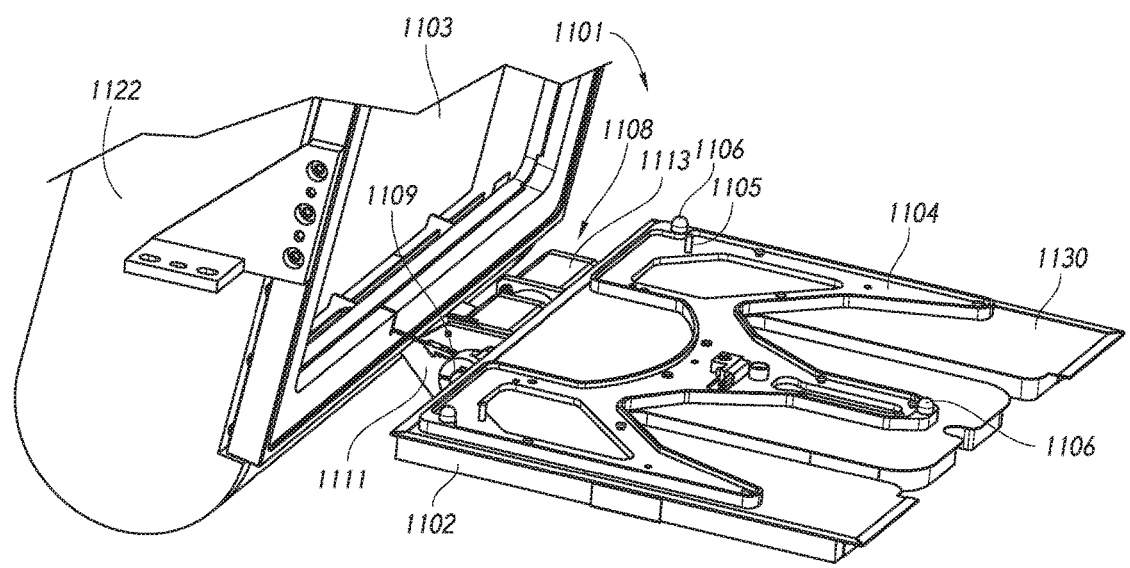
FIG. 4B is an enlarged perspective view of a door assembly of the dryer apparatus of FIG. 4A.

FIG. 4A is a side view of the apparatus 1100 in an open configuration before a slide carrier 1200 (shown schematically) has been placed on the door assembly 1101 by the transporter 12 (shown schematically), and FIG. 4B is an enlarged top perspective view of the door assembly 1101. Referring to FIGS. 3-4B together, the door assembly 1101 can be disposed at a front portion 1103 (FIGS. 4A and 4B) of the apparatus 1100 and can include a door 1102, an actuation device 1108, and a kinematic mount 1104. The door 1102 is moveable between a closed configuration (e.g., FIG. 3) and an open configuration (e.g., FIGS. 4A-4B). The door 1102 can have an interior surface 1130 that faces an interior portion of the housing 1122 (within the circulation loop 1121) when the door 1102 is in the closed configuration and an exterior surface 1132 (FIG. 4A) that faces outwardly when the door 1102 is in the closed configuration. The door 1102 can be automatically moved between the closed and open configurations via the actuation device 1108. If the apparatus 1100 shuts down (e.g., during a power outage), a user can manually open the door 1102 to retrieve any slide carrier in the apparatus 1100.

The actuation device 1108 can pivotally couple the door 1102 to the housing 1122. In some embodiments, the actuation device 1108 includes a mount 1111, a drive device 1113 (FIG. 4B), and a rotatable arm 1107 (FIG. 4A). The mount 1111 is connected to the housing 1122 such that drive device 1113 is capable of rotating the arm 1107 (FIG. 4A) about a pin 1109 of the mount 1111. The drive device 1113 can include, for example, one or more drive motors, stepper motors, or other devices capable of rotating the arm 1107. The configuration of the actuation device 1108 can be selected based on the desired motion of the door 1102.

The kinematic mount 1104 can be coupled to the door 1102 and can include supports 1106 (one identified) configured to hold and stabilize the slide carrier 1200 at a wide range of positions, including a horizontal position and a vertically-oriented position (for example, as shown in FIG. 3). The kinematic mount 1104 can also include one or more kinematic mount sensors 1105 configured to detect the presence and/or position of the slide carrier 1200. In some embodiments, the sensor(s) 1105 can detect the presence and/or position of the slide carrier 1200 and also help inhibit or limit movement of the slide carrier 1200. For example, the sensor(s) 1105 can be magnetic sensors that are capable of detecting the presence/position of the slide carrier 1200 via a magnetic force. The magnetic force can help prevent sliding of the slide carrier 1200 relative to the kinematic mount 1104. Other types of mounts can be used to hold the slide carrier 1200, if needed or desired.

Referring now to FIG. 4A, when the door 1102 is in the open configuration, the door 1120 can be substantially horizontal and configured to receive the slide carrier 1200 from the transporter 12. The term "substantially horizontal" with reference to the door assembly 1101 generally refers to an angle within about +/−2 degrees of horizontal, for example, within about +/−1 degree of horizontal such as within about +/−0.8 degrees of horizontal. When the door 1102 is substantially horizontal it can have an orientation such that the interior 1130 and exterior 1132 surfaces of the door 1102 are generally facing up and down, respectively.

Once the transporter 12 delivers the slide carrier 1200 to the apparatus 1100 vicinity, the transporter 12 can place the slide carrier 1200 onto the kinematic mount 1104. At this point, both the transporter 12 and the kinematic mount 1104 can be engaged with the slide carrier 1200. If needed, the transporter 12 can reposition the slide carrier 1200 relative to the door 1102 and/or kinematic mount 1104 based on signals received from the kinematic mount sensors 1105 and/or transporter sensors (not shown). Once a desired positioning is achieved, the transporter 12 relinquishes the slide carrier 1200 to the door assembly 1101, as shown in FIG. 5.

Figure 5:
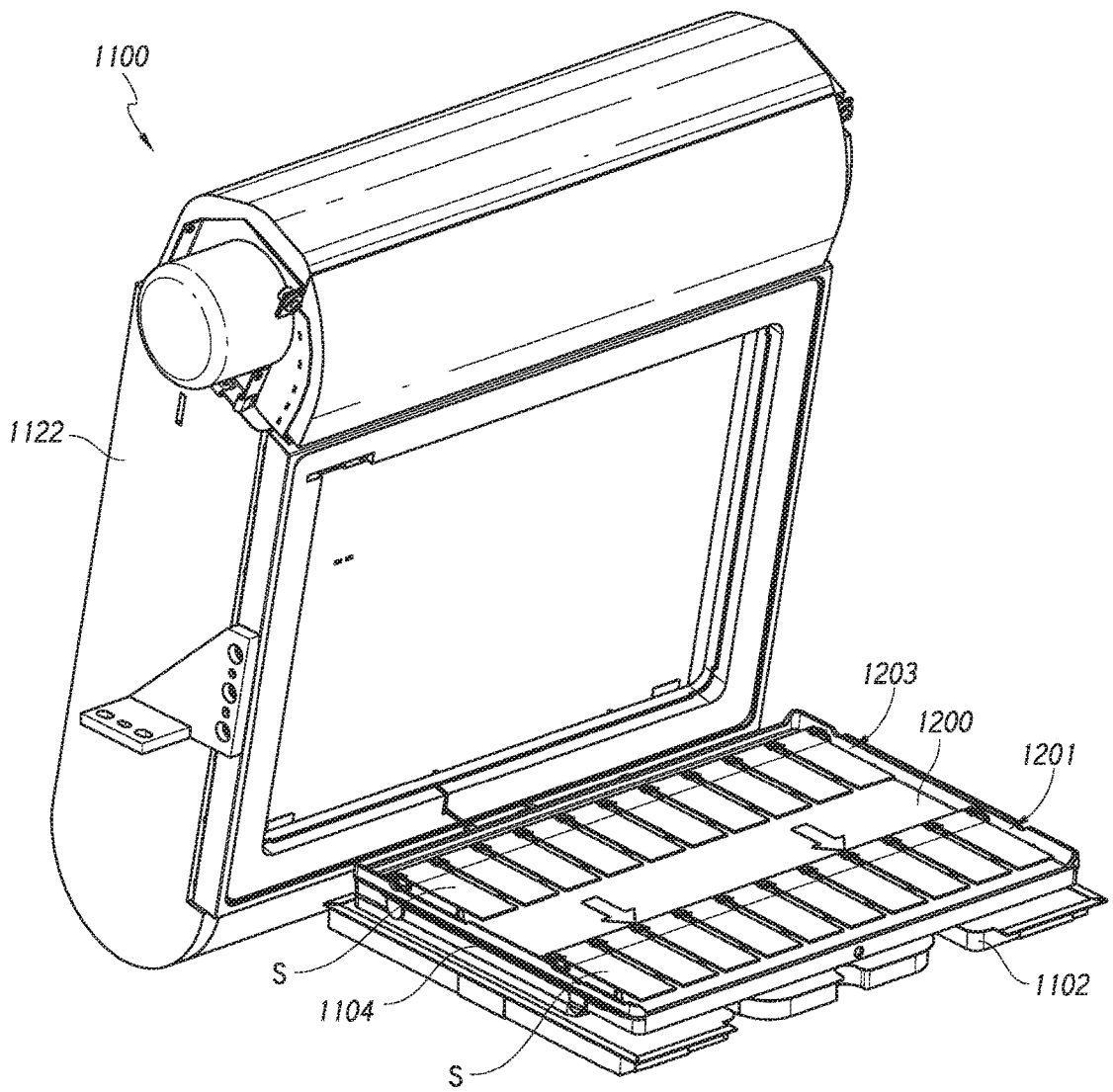
FIG. 5 is a perspective view of the dryer apparatus of FIG. 4A in an open configuration holding a slide carrier.

Referring now to FIG. 5, the door 1102 in the open configuration can support the slide carrier 1200 in a substantially horizontal position such that such that the largest surfaces of the slides (collectively referred to as "S") are generally facing up and down. In the illustrated embodiment, the slide carrier 1200 is shown including a first row 1201 of slides S (one identified) and a second row 1203 of slides S (one identified). In other embodiments, however, the slide carrier 1200 can contain more or less than two rows (e.g., a single row, three rows, etc.) and/or each row can include any number of slides (e.g., one, five, ten, twelve, etc.).

FIG. 6A is a cross-sectional side view of the apparatus 1100 after the door 1102 carrying the slide carrier 1200 has rotated upwardly to an vertically-oriented, closed configuration. FIG. 6B is an enlarged cross-sectional side view of a portion of the door assembly 1101 holding the slide carrier 1200. Referring to FIGS. 6A-6B together, the slide carrier 1200 is enclosed within the housing 1122 and holds the slides S within the front chamber 1140 of the circulation loop 1121. The blower 1110 pushes a gas (e.g., air or other suitable gas) over the heater 1116, through and/or over the turbulence promoter 1118, through and/or over the laminar flow promoter 1114, and upwardly along the specimen-carrying faces of the slides S to convectively heat extraneous liquid on the slides S and/or specimens carried by the slides S. Once the gas leaves the front chamber 1140, the gas can be re-circulated by the blower 1110. In the illustrated embodiment, the gas flow moves through the circulation loop 1121 in a generally counterclockwise direction. However, in other embodiments, the gas flow can be in a clockwise direction. The flow rate across the slides S can be generally uniform, and can be between 1.8 m/s and 2.9 m/s (e.g., 2.8 m/s). Because the laminar gas flow can travel across the specimens without pushing the specimens off the slides S, relatively high flow rates can be used. If the flow rate is too low, extraneous liquid can remain on the slides, thereby allowing specimen migration (e.g., migration of a distance equal to or greater than 2 mm) and possibly staining. If the flow rate is too high, the gas flow can cause specimen migration (e.g., the gas can push specimens up the slides a distance equal to or greater than 2 mm) or in some instances, damage the specimens. The blower 1110 can selectively increase or decrease the flow rate to achieve target processing (e.g., evaporation rates, draining rates, etc.) while limiting or preventing specimen migration and/or damage.

As discussed, drying of the specimens and/or slides is achieved by convective heating using the heater 1116 and the blower 1110. Generally, the temperature of the gas flow within the circulation loop 1121 can be maintained within a desired processing temperature range, such as a range of about 65° C. to about 80° C. (e.g., about 72-73° C.). As such, during the drying process the slides S and/or specimens are uniformly heated such that at any point during the drying process, the temperature of the individual slides S are within 5° C. of one another (including none, all or a subset of the slides being at substantially the same temperature). Achieving an appropriate temperature can be advantageous because, for example, if the temperature is not low enough, the slides and/or specimens may not be dried within the allotted time for the drying process. Moreover, delivering a heated gas flow having an average temperature greater than 65° C. allows liquid within and/or underneath any wax or other material associated with the specimen to evaporate.

Referring now to FIG. 6B, the slide carrier 1200 can be vertically-oriented such that an axis A of the slide carrier 1200 and/or longitudinal axes $A_S$ (one identified) of the respective slides S are oriented at angle θ with respect to a horizontal plane H. As used herein, "vertically-oriented" can refer to both an inclined/angled position and a substantially vertical position. As used herein, an "inclined" or "angled" position refers to an orientation of the slide carrier 1200 and/or slides S where the slide carrier 1200 and/or longitudinal axis $A_S$ (one identified) of the slides S are positioned at an angle θ that is between 70 degrees and 90 degrees (e.g., between 77 degree and 84 degrees, 80 degrees, 90 degrees, etc.). As used herein, the term "substantially vertical" refers to an orientation of the slide carrier 1200 and/or slides S where the slide carrier 1200 and/or longitudinal axes $A_S$ of the slides S are positioned at an angle θ that is within about +/−2 degrees of 90 degrees (including 90 degrees), for example, within about +/−1 degree of 90 degrees such as within about +/−0.8 degrees of 90 degrees. In either position, the first row 1201 of slides is positioned vertically above the second row 1203 of slides such that a first end (1201a, 1205a) of each slide S is vertically above a second end (1201b, 1205b) of the same slide S. The vertically-oriented slide carrier 1200 and/or slides S leverage the effect of gravity to pull extraneous liquid off the slides S, thereby expediting the drying time. Accordingly, the methods of the present technology are faster and more effective than conventional horizontal slide drying methods. For example, the drying time (i.e., the time between when the door 1102 receives a slide carrier 1200 to when the transporter 12 removes the slide carrier 1200) can be between 2 minutes and 8 minutes (e.g., 3 minutes, 4 minutes, 4.5 minutes, 5 minutes, etc.). For example, in one embodiment the drying time can be 4 minutes and 52 seconds.

Figure 7:
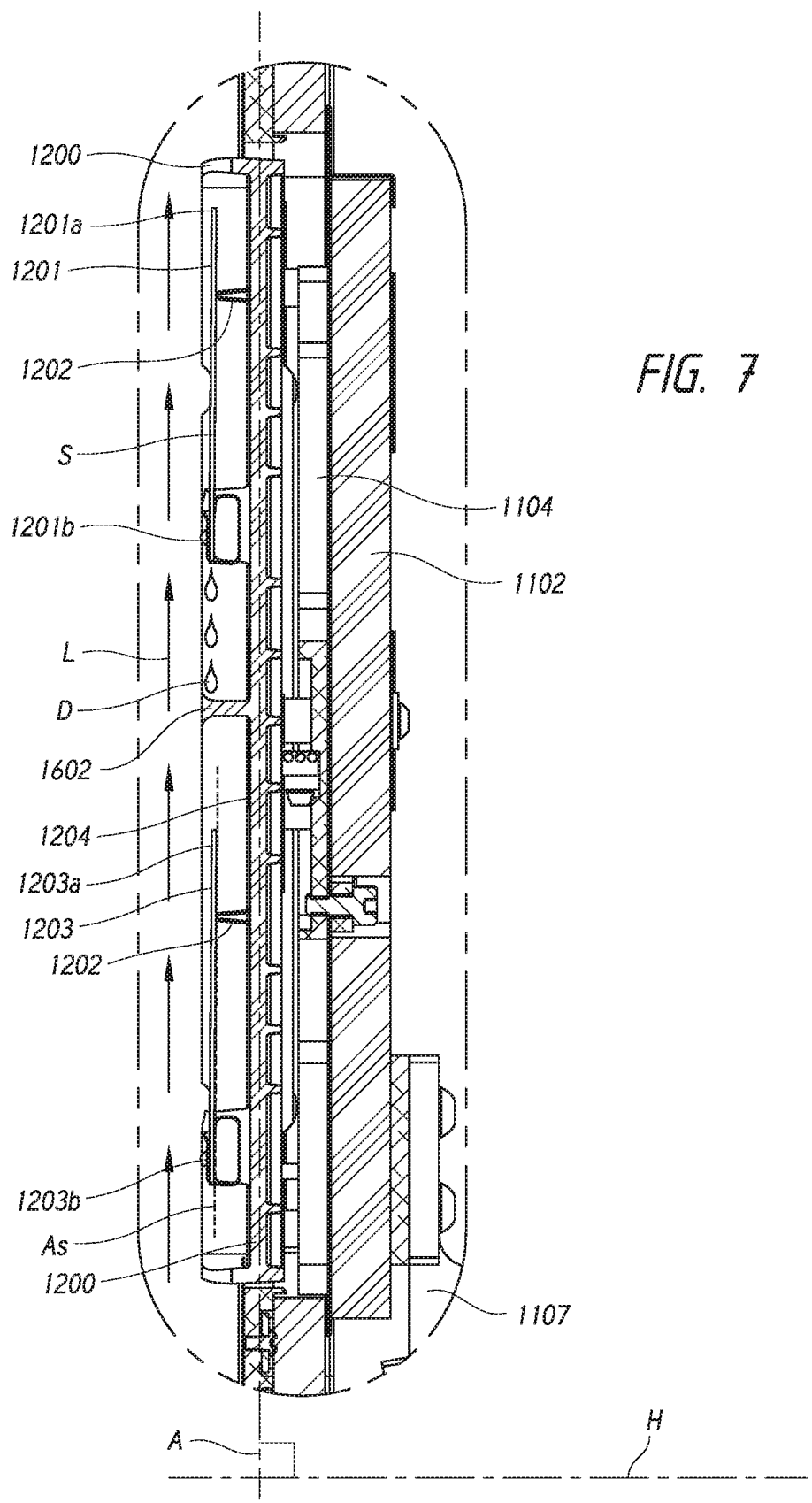
FIG. 7 is an enlarged cross-sectional side elevation view of a portion of a dryer apparatus door assembly and a slide carrier in a substantially vertical position in accordance with another embodiment of the present technology.

As discussed above, placing the slide carrier 1200 and/or slides S at a vertically-oriented position during drying utilizes gravity to effectively drain freestanding liquid on the mounting surfaces of the slides S. However, such a position also raises the possibility of a portion of a specimen in the first or upper row 1201 falling and contaminating a slide S in the second or lower row 1203. Such cross-contamination can impair subsequent analysis of the specimens. Accordingly, the position and the configuration of the slide carrier 1200 can be adjusted to increase drying efficiency while avoiding or limiting cross-contamination of the slides S. For example, FIG. 6B shows the slide carrier 1200 and slides S in an inclined position. The labeled ends of the slides S can be lower than their non-labeled ends such that labels (e.g., adhesive bar code labels) can inhibit or limit migration of the specimens, if the specimens slide along the mounting surfaces of the slides. Thus, the labels can serve as physical barriers to keep the specimens on the slides. In the illustrated embodiment, the slide carrier 1200 includes one or more standoffs 1202 that separate the slides S from a surface 1204 of the slide carrier 1200 and the upper and lower slides S are horizontally spaced apart from one another. As such, liquid and/or specimens dripping from the upper row 1201 (depicted schematically as "D") can fall directly downward onto the inclined surface 1204 of the slide carrier 1200, thereby avoiding cross-contamination of the lower slide S. In comparison, FIG. 7 shows the slide carrier 1200 and slides S in a substantially vertical position. Here, the slide carrier 1200 includes one or more barriers 1602 between adjacent rows of slides S. As gravity pulls liquid off of the specimens and/or slides S, the liquid D can be caught by the barrier(s) 1602, thereby preventing cross-contamination of the lower slides S. The apparatus 1100 of FIGS. 3-6 can be modified to hold the slide carrier 1200 in such vertical orientation shown in FIG. 7.

Referring again to FIGS. 6A and 6B, ambient air can enter the circulation loop 1121 via an opening 1606 to compensate for increased humidity within the housing 1122 due to evaporation of liquid of the wet specimen-bearing slides S. The ambient air can have a relatively low humidity to help limit the humidity levels within the housing 1122 and thereby limit the humidity of the gas flow along the circulation loop 1121. In some embodiments, the housing 1122 and/or sidewalls 1119 can be substantially sealed to retain heat, although during the opening and closing of the door 1102, gas and thermal energy is necessarily exchanged with the external environment. This exchange allows the relative humidity within the interior space 1123 (FIG. 6A) and/or circulation loop 1121 to equilibrate to an appropriate level and prevents moisture build-up as wet specimens are introduced.

Once the drying cycle is complete, the slide carrier 1200 is rotated downwardly to a substantially horizontal position, as shown in FIG. 8. The transporter 12 can position itself adjacent to the door 1102 and subsequently removes the slide carrier 1200 from the door assembly 1101. In some embodiments, the transporter 12 can have one or more extensions that project into the space between the slide carrier 1200 and the interior surface 1130 of the door 1102 and engage a downward-facing surface of the slide carrier 1200. At this stage, both the transporter 12 and the kinematic mount 1104 can confirm engagement with the slide carrier 1200. The transporter 12 can then automatically remove the slide carrier 1200 from the kinematic mount 1104 and remove the slide carrier 1200 from the immediate vicinity of the apparatus 1100. Feedback from the kinematic mount sensors 1105 and/or transporter sensors (not shown) can help guide the slide carrier removal process.

FIG. 9 is a cross-sectional side view of the apparatus 1100 in the closed configuration, either after the slide carrier 1200 has been removed and the door 1102 has closed, or before the door 1102 opens to receive a slide carrier 1200 from the transporter 12. Regardless, when the apparatus 1100 is in the closed configuration and the slide carrier 1200 is not present, the heater 1116 can continuously or periodically generate heat to maintain a desired standby temperature. Accordingly, when a subsequent slide carrier is introduced, there is less lag time for the apparatus 1100 to recover to a desired operating temperature.

In some embodiments, the apparatus 1100 can include additional features. For example, in some embodiments, the apparatus 1100 can include heater safety features. For example, the apparatus 1100 can include a heat sensor (not shown) on the heater 1116 that monitors a temperature of the heater 1116 and cuts power to the heater 1116 if the heater 1116 goes above a specified temperature. Additionally, the heater 1116 itself can include a switch (e.g., a mechanical switch, electromechanical switch, etc.) that breaks the power circuit path if the heater 1116 goes above a specified temperature. If the heater temperature returns to an appropriate level (e.g., below the specified temperature), the switch can close the circuit, thereby enabling power delivery to the heater 1116. The apparatus 1100 can include additional features to ensure robust drying. For example, the apparatus 1100 can include one or more layers of insulation that surround the housing 1122 and/or walls 1119 to retain heat and maintain proper heat distribution. Additionally, the apparatus 1100 can include one or more dehumidifying elements that limit the humidity in the housing 1122 to enhance drying.

Figure 10:
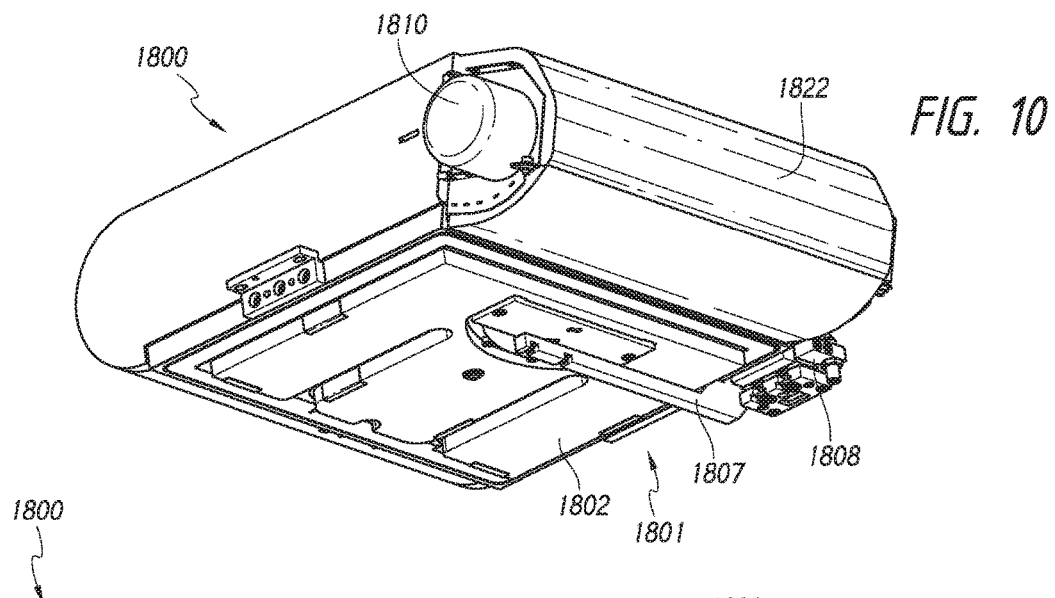
FIG. 10 is a perspective view of a curing oven in a closed configuration in accordance with an embodiment of the present technology.

FIG. 10 is a perspective view of another embodiment of a heater apparatus in the form of curing oven 1800 ("oven 1800"), in a closed configuration in accordance with an embodiment of the present technology. The oven 1800 is generally identical to the apparatus 1100 discussed in connection with FIGS. 3-9, except as detailed below. The oven 1800 is configured to thermally process slides carrying coverslips to cure the coverslips onto the slides in order to protect the specimens. The oven 1800 can also alleviate any "carrier messiness" (i.e., free-standing extraneous liquid on the slides and/or slide carrier) by heating the slides and/or slide carrier and evaporating superfluous liquids (if present). Moreover, a substantially horizontal position can be advantageous to help maintain the positioning or placement of the coverslip on the slide (and likewise avoid coverslip migration). The oven 1800 can include a housing 1822 having one or more walls 1819 (FIG. 13) and a door assembly 1801. The door assembly 1801 can hold a slide carrier to keep the coverslipped slides in substantially horizontally orientations or other suitable orientations. An actuation device 1808 of the door assembly 1801 can include one or more rails, carriages, drive mechanisms, or other components suitable for vertically moving a door 1802 between a closed configuration (e.g., FIG. 10) and an open configuration (e.g., FIG. 11).

One exemplary curing process is discussed below with reference to FIGS. 11-14. Generally, a slide carrier 1200 is moved to the door assembly 1801 while the slide carrier 1200 holds the coverslipped slides CS. The slide carrier 1200 is moved robotically by the door assembly 1801 from a first position (e.g., a horizontal lowered position) to a second position (e.g., a horizontal raised position) to move the slide carrier 1200 into a circulation loop. The coverslipped slides CS are heated while the slide carrier 1200 into a circulation loop. Details of the oven 1800 and the curing process are discussed below.

Figure 11:
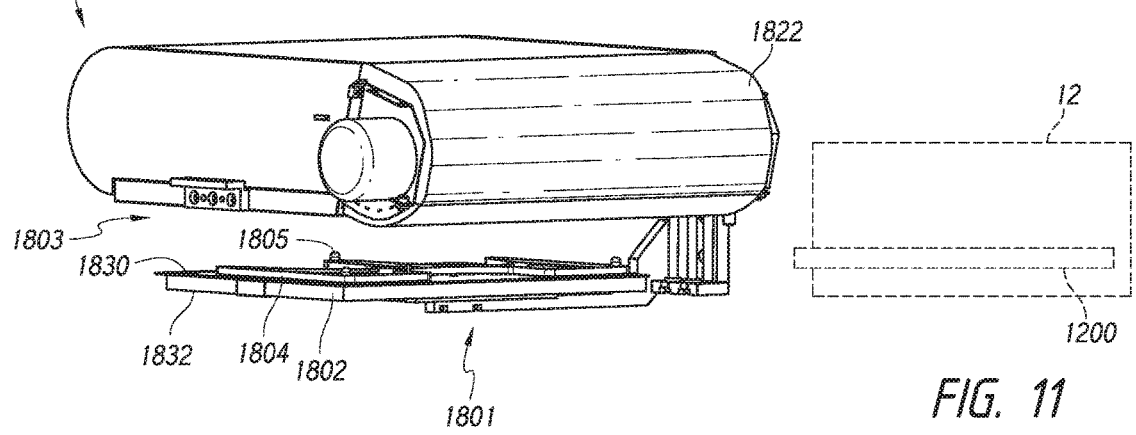
FIG. 11 is a perspective view of the curing oven of FIG. 10 in an open configuration in accordance with an embodiment of the present technology.

FIG. 11 is a perspective view of the curing oven 1800 in an open configuration before a slide carrier 1200 (shown schematically) has been placed on the door assembly 1801 by the transporter 12 (shown schematically). As shown in FIG. 11, the door assembly 1801 can be disposed at a bottom portion 1803 of the oven 1800 and can include the door 1802 and the actuation device 1808. The door 1802 can have an interior surface 1830 that faces an interior portion of the housing 1822 and an exterior surface 1832 that faces outwardly. In some embodiments, including the illustrated embodiment, a kinematic mount 1804 is carried by door 1802 and can include vertically oriented supports 1805 (one identified) configured to hold and stabilize a slide carrier 1200.

Figure 12:
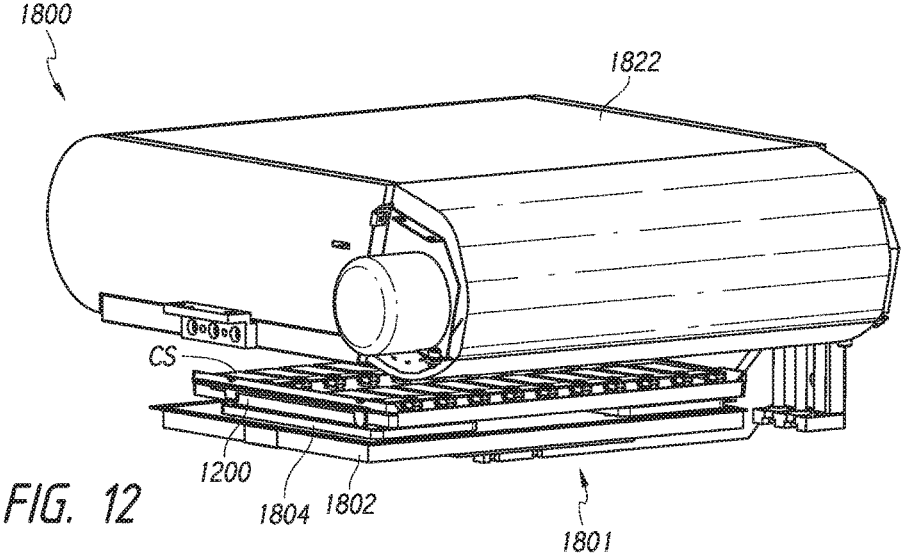
FIG. 12 is a perspective view of the curing oven with a door assembly supporting a slide carrier holding microscope slides with coverslips in accordance with an embodiment of the present technology.

When the door 1802 is in the open configuration, the door 1802 can be substantially horizontal and configured to receive the slide carrier 1200 from the transporter 12. Once the transporter 12 delivers the slide carrier 1200 to the curing oven 1800 vicinity, the transporter 12 places the slide carrier 1200 on the kinematic mount 1804. At this point, both the transporter 12 and the kinematic mount 1804 can be engaged with the slide carrier 1200. Once a desired positioning is achieved, the transporter 12 relinquishes the slide carrier 1200 to the door 1802, as shown in FIG. 12.

Figure 13:
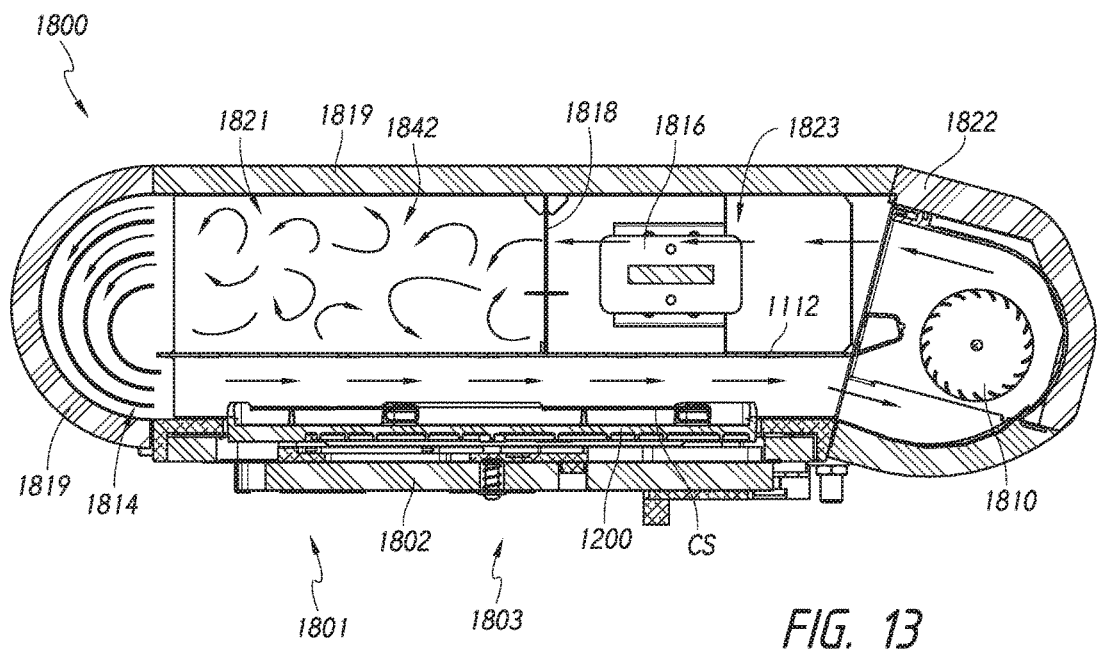
FIG. 13 is a cross-sectional side elevation view of a curing oven in a closed configuration in accordance with an embodiment of the present technology.

FIG. 13 is a cross-sectional side view of the curing oven 1800 after the door 1802 carrying the slide carrier 1200 has moved to the closed configuration. The slide carrier 1200 is enclosed within the housing 1822 such that the coverslips and slides (together referred to as "coverslipped slides CS") are exposed to laminar flow in the circulation loop 1821. In operation, the blower 1810 pushes a gas over the heater 1816, through and/or over the vertically oriented turbulence promoter 1818, through and/or over the laminar flow promoter 1814, and along the specimen-carrying face of the coverslipped slides CS to convectively heat and/or cure the coverslipped slides CS. The flow rate across the coverslipped slides CS can be generally uniform, and on average can be between 5 m/s and 7 m/s (e.g., 6 m/s). If the flow rate is too low, the flow rate may not efficiently cure the coverslips (i.e., cure the adhesive/glue carried by the coverslips) in the allotted processing time and/or extraneous liquid may be left on the slide carrier 1200 and/or coverslipped slides CS. Insufficient curing and/or drying can affect archiveability (i.e., specimens can be stored upright in common slide drawers without being stuck together, the stain can be retained and the coverslip adhered to the specimen for at least 10 years). If the flow rate is too high, the flow rate can cause specimen or coverslip migration or in some instances, damage the specimens. Accordingly, the flow rate can be selected based on the desired curing time while limiting or preventing migration of the specimens and/or coverslips.

Achieving an appropriate curing temperature can be advantageous because, for example, if the temperature rises above a specified threshold, the temperature can affect the material properties of the coverslip material. For example, without being bound by theory, it is believed that going above certain temperatures can cause the coverslip to embed deeply into the specimen, causing the coverslip to remain in the specimen during de-stain and therefore negatively impact re-stains. Additionally, the higher the temperature in the oven 1800, the higher the temperature of the slide carrier 1200, possibly requiring a "cool down" period (or a longer cool down period) due to the fact that the slide carrier 1200 must be at an acceptable handling temperature when exiting the oven 1800. A long cool down time can impact throughput. Also, maintaining an average curing temperature of less than 100° C. can be advantageous to avoid burning or permanently damaging the specimens and/or slides. If the temperature is not low enough, the slides and/or specimens may not be dried within the allotted time for the curing process. During the curing process the slide carrier 1200 can be enclosed or positioned within the circulation loop 1821 such that the cover-slipped slides CS are convectively heated. Accordingly, the methods of the present technology may be faster and more effective than conventional horizontal drying methods. For example, the curing time (i.e., the time between when the door 1802 receives a slide carrier 1200 to when the transporter 12 removes the slide carrier 1200) can be between 2 minutes and 8 minutes (e.g., 3 minutes, 4 minutes, 4.5 minutes, 5 minutes, etc.). For example, in one embodiment the curing time can be 4 minutes and 52 seconds. Generally, the average temperature of the gas flow within the circulation loop 1821 can be between 90° C. and 110° C. However, other temperatures can be achieved to cure other types of adhesives used with coverslips.

Figure 14:
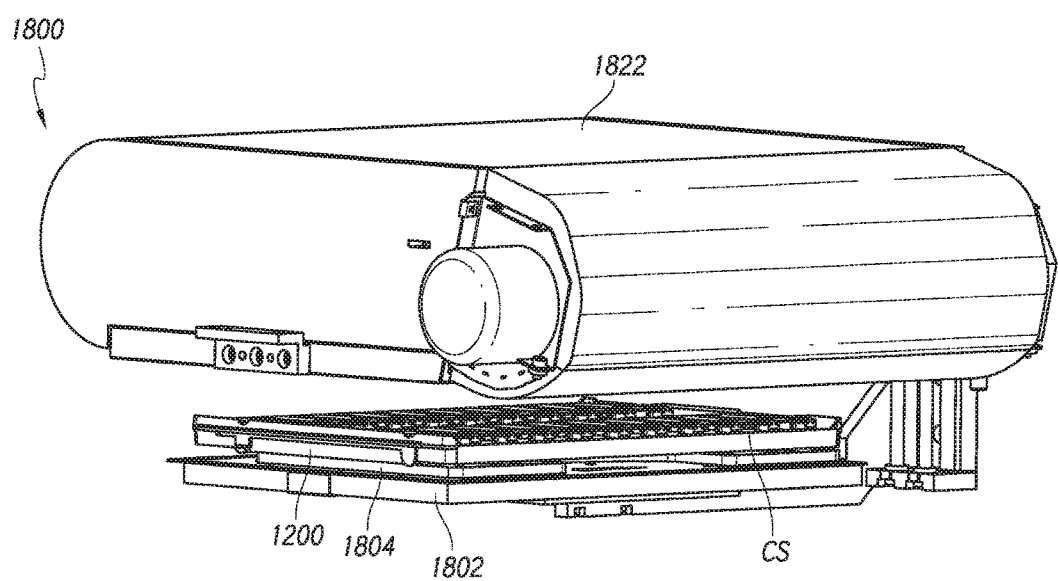
FIG. 14 is a perspective view of a curing oven in an open configuration holding a slide carrier with cured coverslipped slides in accordance with an embodiment of the present technology.

Once the curing cycle is complete, the slide carrier 1200 is lowered for removal by the transporter 12, as shown in FIG. 14. The transporter 12 positions itself adjacent to the door 1802 and subsequently removes the slide carrier 1200 from the door assembly 1801. In some embodiments, the transporter 12 can have one or more extensions that project into the space between the slide carrier 1200 and the interior surface 1830 of the door 1802 and engage a downward-facing surface of the slide carrier 1200. At this stage, both the transporter 12 and the kinematic mount 1804 can confirm engagement with the slide carrier 1200. The transporter 12 can then automatically remove the slide carrier 1200 from the door assembly 1801 and transport the slide carrier 1200 away from the immediate vicinity of the oven 1800. Feedback from the kinematic mount sensors and/or transporter sensors (not shown) can help guide the slide carrier removal process.

The curing oven 1800 can include additional features to ensure robust curing. For example, the oven 1800 can include a layer of insulation that surrounds the housing 1822 and/or sidewalls 1819 to retain heat and maintain proper heat distribution. The housing 1822 and/or sidewalls 1819 are substantially sealed to retain heat, although during the opening and closing of the door 1802, gas is necessarily exchanged with the external environment. This exchange allows the relative humidity within the interior space 1823 and/or circulation loop 1821 to equilibrate to an appropriate level and prevents moisture build-up as wet specimens are introduced.

Selected Examples of Tray and Slide Handling in Stainers

Figure 15:
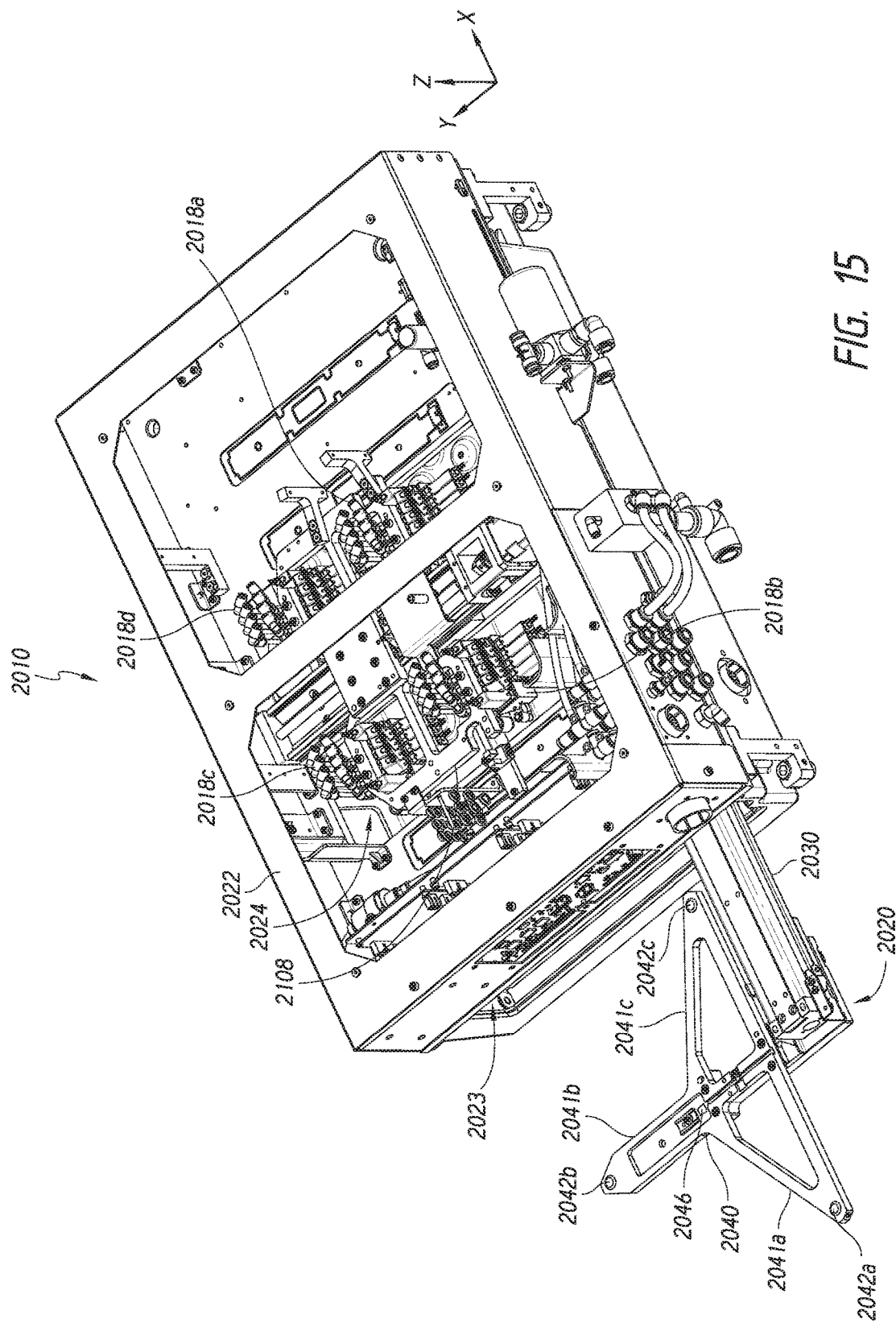
FIG. 15 is an isometric view of a stainer module in an open configuration in accordance with an embodiment of the present technology.

FIG. 15 is an isometric view of a stainer module 2010 in an open configuration in accordance with an embodiment of the present technology. The stainer module 2010 can include a tray handler 2020, a housing 2022, and a dispenser apparatus 2024. The tray handler 2020 can move a slide carrier in the form of a portable tray (not shown in FIG. 15) through an opening 2023 of the housing 2022 and can position the tray underneath the dispenser apparatus 2024. The dispenser apparatus 2024 can include four head or manifold assemblies 2018*a*, 2018*b*, 2018*c*, 2018*d* (collectively "head assemblies 2018") that provide valve-controlled, pressurized liquid delivery onto specimen-bearing microscope slides carried by the tray. To maintain a high processing throughput, the head assemblies 2018 can be purged/primed while the tray remains positioned in the stainer module 2010. In dispense processes, the head assemblies 2018 can individually dispense predetermined volumes of fresh liquid onto slides and can remove the liquid from the slides to perform multi-step staining protocols. After processing the slides, the tray handler 2020 can move the tray out of the housing 2022.

The tray handler 2020 can include a tray holder transport mechanism 2030 ("transport mechanism 2030") and a tray holder in the form of a kinematic mount 2040. The transport mechanism 2030 can include, without limitation, a home flag and a relative encoder used to accurately position the kinematic mount 2040. The kinematic mount 2040 can include arms 2041*a*, 2041*b*, 2041*c* (collectively "arms 2041"), supports 2042*a*, 2042*b*, 2042*c* (collectively "supports 2042"), and a sensor 2046. In some embodiments, the supports 2042 are mount balls connected to free ends of the arms 2041 to provide multi-dimensional constraints (e.g., three-dimensional constraints). When the supports 2042 interface with the tray, the sensor 2046 can detect the presence and/or position of the tray.

The transport mechanism 2030 and kinematic mount 2040 can minimize or limit unintended motion of the tray that affects spacing between upper surfaces of the slides and the head assemblies 2018. Increased spacing can lead to splattering of liquids, whereas decreased spacing may result in physical contact between the head assemblies 2018 and the specimen-bearing slides. Splattering can lead to increased overall processing-liquid waste and understaining of specimens. If the splattered liquid lands on adjacent slides, the specimens on the adjacent slides may be improperly stained. If the tray experiences significant pitch motion (e.g., pitch motion about the illustrated X-axis) and/or roll motion (e.g., roll motion about the illustrated Y-axis), the head assemblies 2018 may contact and break slides and/or may dislodge specimens. Unintended yaw motion (e.g., rotation about the illustrated Z-axis) of the tray can affect distances (e.g., X-axis distances and Y-axis distances) between the edges of slides and the head assemblies 2018, which can result in processing liquid being directly dispensed into the tray. Because the desired volume of processing liquid is not delivered onto the slides, the specimens could be understained. The transport mechanism 2030 and kinematic mount 2040 can cooperate to inhibit, limit, or substantially eliminate unintentional motion of the tray (e.g., pitch motion, roll motion, and/or yaw motion) to inhibit, limit, or prevent one or more of the following: splattering of liquids, physically contact between the head assemblies 2018 and the specimen-bearing slides, dislodging of specimens, and misaligning slides. By dispensing all (or substantially all) of the liquid directly onto the slides, the liquids can be efficiently used, and the trays can remain substantially free of liquid throughout processing. As such, volumes of processing liquid used by the stainer module 2010 can be significantly less than volumes of liquid used by conventional automated slide stainers.

Figure 16:
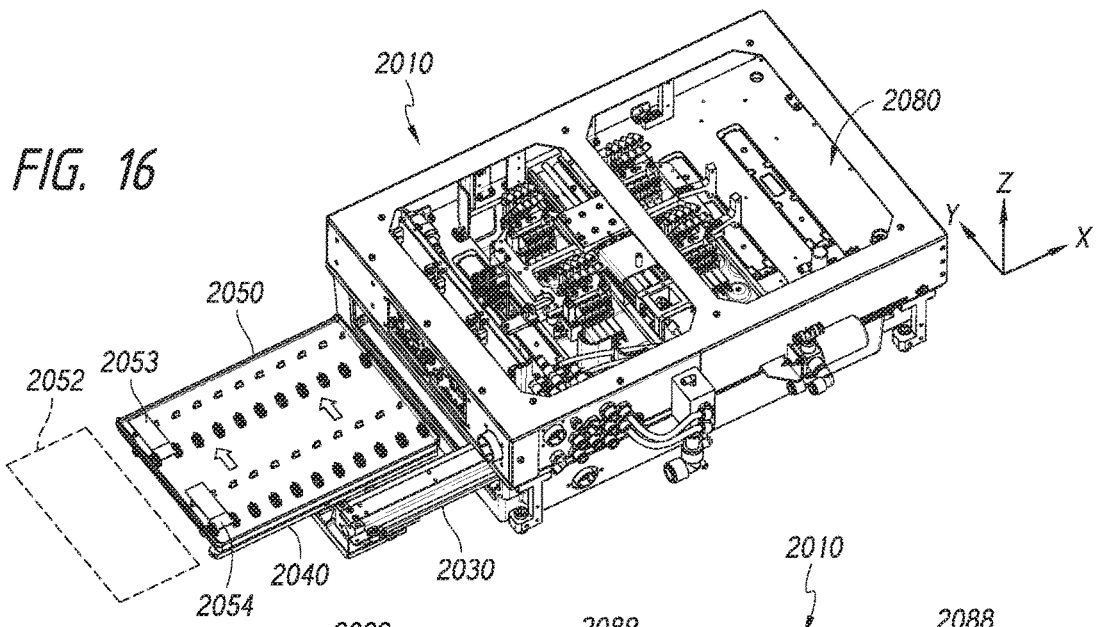
FIG. 16 is an isometric view of the stainer module holding a tray.

FIG. 16 is an isometric view of the stainer module 2010 after a tray transporter 2052 (shown schematically in phantom line) has placed a tray 2050 onto the kinematic mount 2040. The tray transporter 2052 can reposition the tray 2050 based on signals from the sensor 2046 (FIG. 15). The tray 2050 can hold slides in substantially horizontal orientations such that large surfaces of the slides are generally facing up and down. The term "substantially horizontal" generally refers to an angle within about +/−3 degrees of horizontal, for example, within about +/−1 degree of horizontal, such as within about +/−0.8 degrees of horizontal. Substantially horizontal also refers to ranges of small angles from horizontal, for example, angles between about 0.1 degrees and 1.8 degrees from horizontal, such as angles between about 0.2 degrees and about 1.2 degrees, for example angles between about 0.3 degrees and about 0.8 degrees. In particular embodiments, an angle with upper surfaces of substantially horizontal slides relative to an imaginary horizontal plane can be between about 0 degrees and about 3 degrees along its short axis, and an angle with respect to the imaginary horizontal plane of between about 0 degrees and 2 degrees along its long axis, again with the large surfaces of the slides generally facing up and down. The illustrated tray 2050 is capable of holding twenty slides, but it is shown holding only two slides 2053, 2054.

Figure 17:
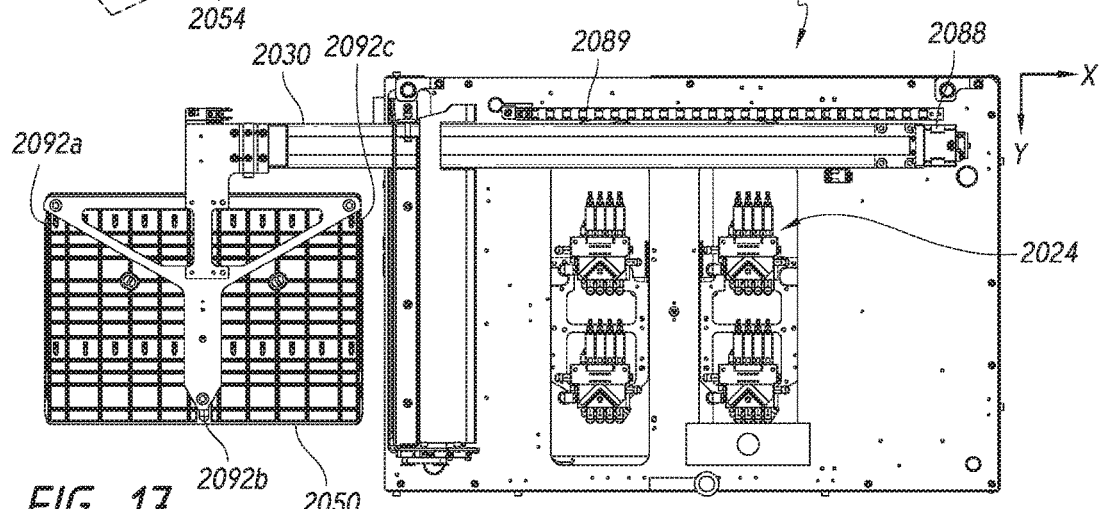
FIG. 17 is a bottom view of the stainer module holding the tray.

FIG. 17 is a bottom view of the stainer module 2010 holding the tray 2050. The tray 2050 can include receiving features 2092*a*, 2092*b*, 2092*c* (collectively "receiving features 2092") that interface with respective supports 2042*a*, 2042*b*, 2042*c* (FIG. 15). The receiving features 2092 can be curved features, recesses, elongate slots, or other features that engage the supports 2042. In one embodiment, the receiving features 2092 are partially spherical surfaces or arcuate grooves along which the supports 2042 can slide to provide self-leveling of the tray 2050, thereby keeping the tray 2050 substantially horizontal throughout process.

The transport mechanism 2030 can include, without limitation, one or more motors 2088 (e.g., drive motors, stepper motors, etc.) and a drive device 2089. The drive device 2089 can include, without limitation, rails, carriages, extendable arms, belts, chains, gear mechanisms, or combinations thereof to provide translation of the tray 2050 along a single axis or multiple axes. The transport mechanism 2030 can move the tray 2050 from a tray load/unload position (shown in FIGS. 16 and 17) to a processing position (shown in FIG. 18) with a chamber 2080 (FIG. 16) of the stainer module 2010. Due to small gaps between slide surfaces and the head assemblies 2018, interferences are possible if a slide is misaligned within the tray 2050 or if the tray 2050 is misaligned on the kinematic mount 2040, and such interferences may result in a shut-down event. In the event of shut down of the stainer module 2010, a user can manually manipulate the transport mechanism 2030 to position the tray 2050 at an accessible position suitable for manually retrieving and/or repositioning the tray 2050.

Figure 18:
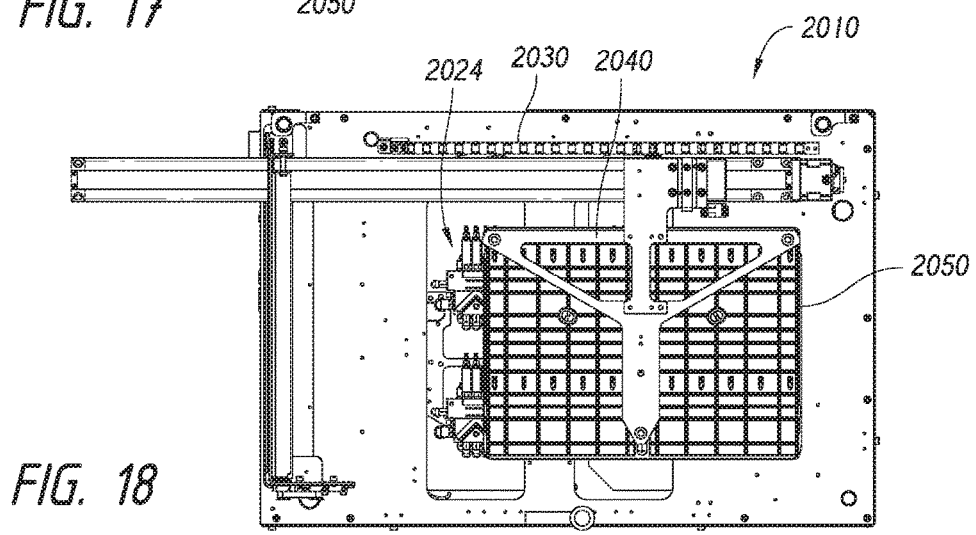
FIG. 18 is a bottom view of the stainer module in a closed configuration in accordance with an embodiment of the present technology.
Figure 19:
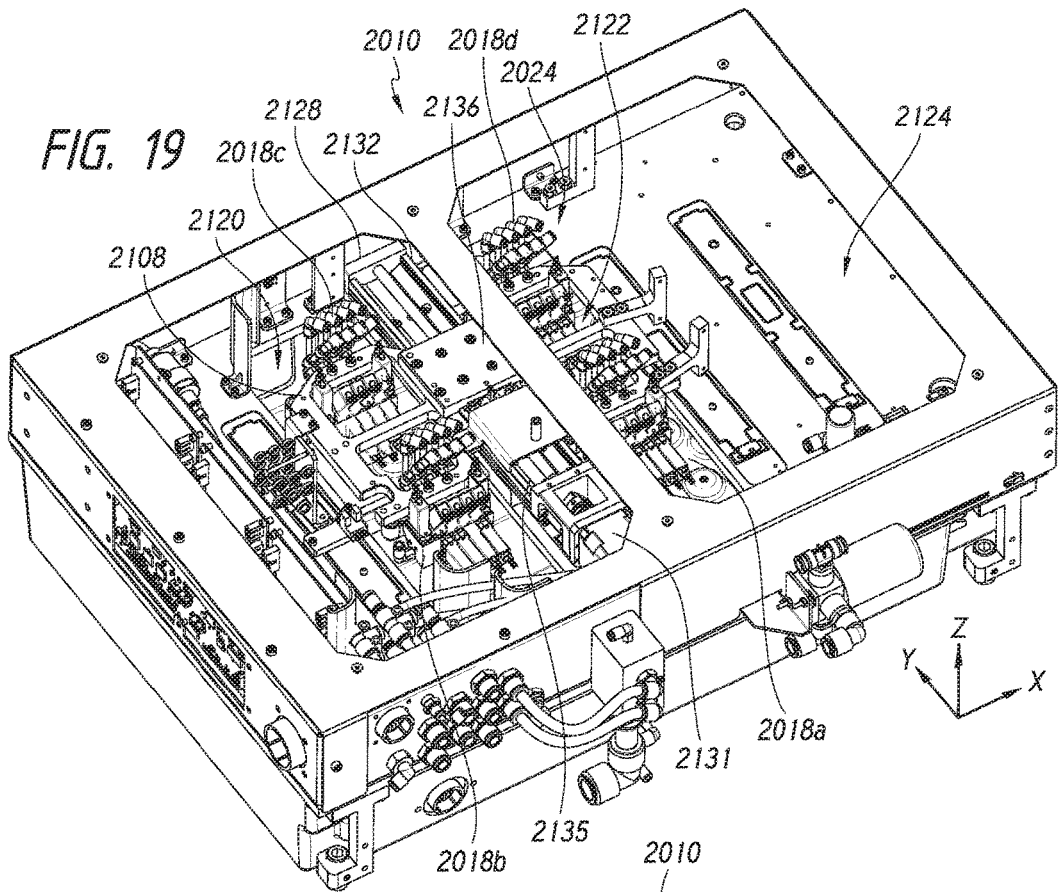
FIG. 19 is an isometric view of the stainer module of FIG. 15 ready to process specimen-bearing slides positioned underneath a dispenser apparatus.

FIG. 18 shows the stainer module 2010 after the transport mechanism 2030 has positioned the tray 2050 generally underneath the dispenser apparatus 2024. FIG. 19 is an isometric view of the dispenser apparatus 2024 ready to process slides. The dispenser apparatus 2024 and the tray 2050 can be moved in orthogonal directions to accurately position the slides relative to paths of travel of the head assemblies 2018. After processing the slides, the dispenser apparatus 2024 can be held stationary or moved while the tray 2050 is indexed relative to the head assemblies 2018. The next four slides can be processed. This process can be repeated until all the slides carried by the tray 2050 are processed.

Figure 20:
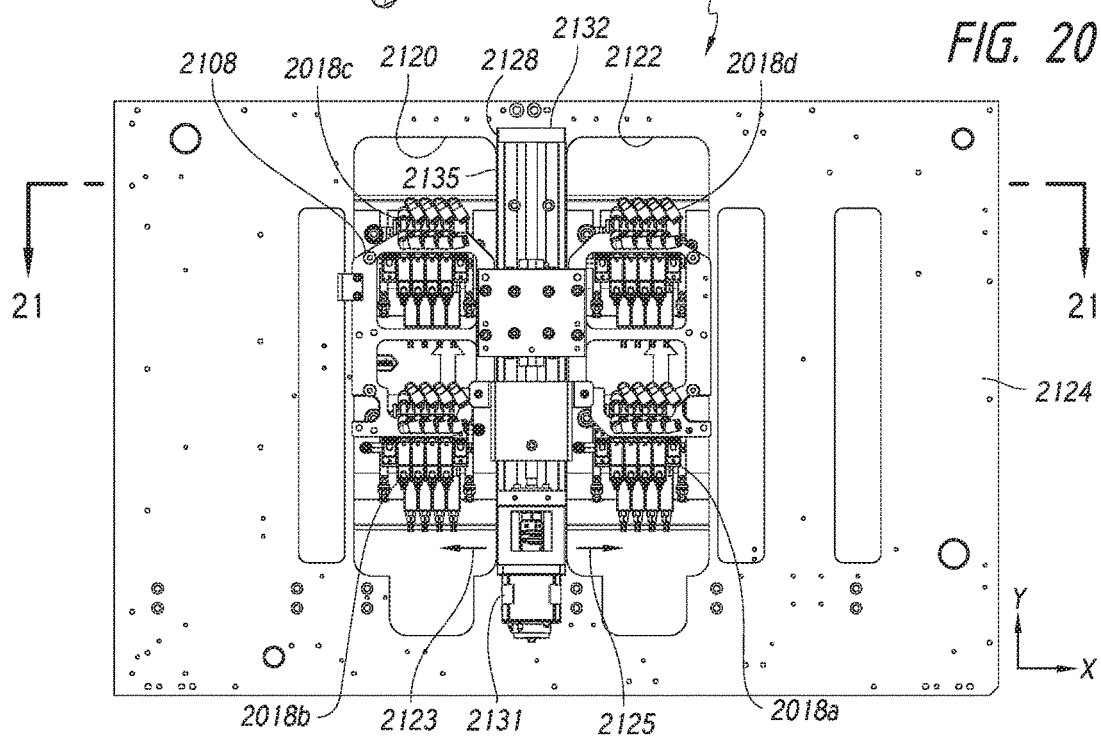
FIG. 20 is a top plan view of the stainer module of FIG. 15.

Referring to FIGS. 19 and 20, a dispenser drive mechanism 2128 ("drive mechanism 2128") can move the dispenser apparatus 2024 in the Y-axis direction (i.e., a direction parallel to the illustrated Y-axis). The paths of travel of the head assemblies 2018 can be aligned with the long axes of the slides extending in the Y-axis direction such that the head assemblies 2018 sweep along the lengths of the slides. In various embodiments, the drive mechanism 2128 can include, without limitation, one or more rails, carriages, extendable arms, gear mechanisms, or combinations thereof to provide translation along a single axis. In some embodiments, including the illustrated embodiment, the drive mechanism 2128 includes a motor 2131 and a translator device 2132. The translator device 2132 includes a rail 2135 and a carriage 2136 (FIG. 19) movable along the rail 2135. A frame 2108 of the dispenser apparatus 2024 can carry the head assemblies 2018 and is coupled to the carriage 2136.

Figure 21:
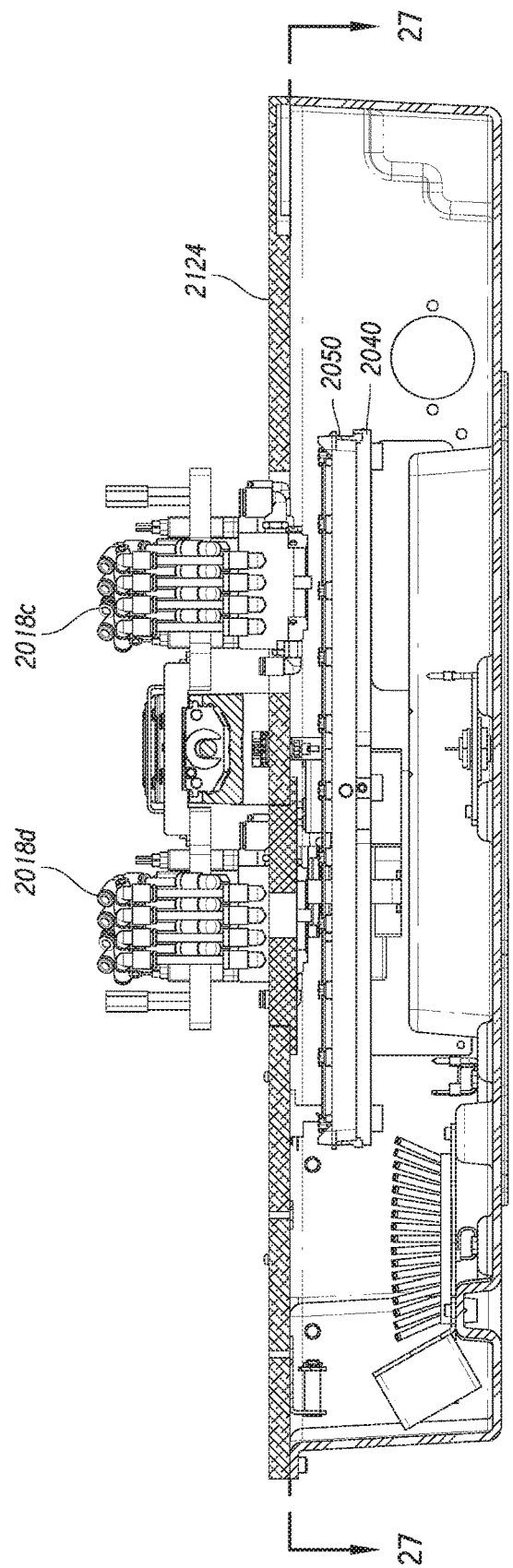
FIG. 21 is a cross-sectional side elevation view of the stainer module taken along line 21-21 of FIG. 20.
Figure 22A:
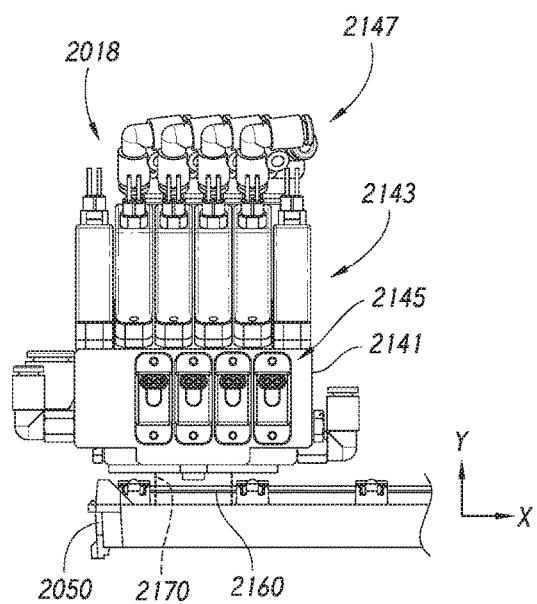
FIGS. 22A and 22B are detailed elevation views of head assemblies processing specimen-bearing microscope slides.
Figure 22B:
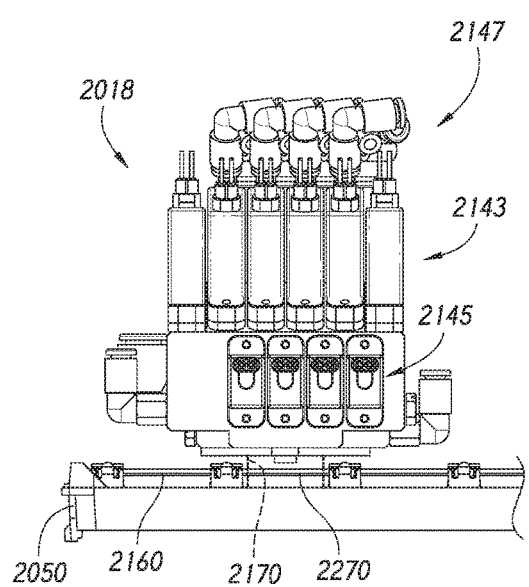

The head assemblies 2018b, 2018c can apply liquids to slides positioned under an opening 2120 in a plate 2124, and the head assemblies 2018d, 2018a can apply liquids to slides positioned under an opening 2122 (FIG. 20) in the plate 2124. The transport mechanism 2030 can move the tray 2050 in the X-axis direction (i.e., a direction parallel to the illustrated X-axis as indicated by arrows 2123, 2125 in FIG. 20) to sequentially position slides under the head assemblies 2018. Single-axis motion of the tray 2050 can facilitate lateral alignment of the slides with the head assemblies 2018. FIG. 21 shows the head assemblies 2018c, 2018d positioned above the tray 2050. FIG. 22A is a detailed view of the head assembly 2018 positioned above a slide 2160 at a processing zone 2170. (Hoses and other components of the stainer module are not shown to avoid obscuring features in the images.) The head assembly 2018 can include a dispenser head 2141, valves 2143, 2145, and lines 2147. FIG. 22B shows tray 2050 moved to position another slide at the processing zone 2170.

FIGS. 23-26 are views of stages of applying substances to microscope slides. Generally, slides can be sequentially positioned underneath and individually processed by the head assemblies 2018. Slide processing is discussed in connection with a single head assembly 2018. However, multiple head assemblies 2018 can simultaneously or sequentially process slides in a similar manner. FIG. 23 shows twenty slides spaced apart from one another in two rows. When the tray 2050 is in substantially horizontal orientation, the mounting areas of the slides can face upwardly. However, the slides can be held in other arrangements and at different orientations, if needed or desired.

Referring to FIGS. 22A and 24, the head assembly 2018 is ready to process slides at the processing zone 2170 (illustrated in phantom line). Each distributed dispense can form a relatively thick film (or puddle) over any specimens on the slide 2160 (FIG. 22A) to incubate in a desired mode, such as a quasi-static mode. Each dispense, for example, can form a puddle having a shape at least partially maintained by surface tension. In some embodiments, the head assembly 2018 can move lengthwise along the stationary slide 2160 at a speed in a range of about 1 inch/second to about 15 inches/second and can be accelerated up to 100 inch/second. Other speeds can be used to match liquid flow/valve times for dispensing or homing operations. For example, the head assembly 2018 can be moved relatively slowly (e.g., 1 inch/second to about 2 inches/second) during homing operations, such as movement of the head assembly 2018 to a home position. In other embodiments, the head assembly 2018 can move lengthwise along the slide 2160 while the slide 2160 moves in the X-direction, Y-direction, and/or Z-direction. For example, the slide 2160 can be moved in the X-direction to periodically or continuously laterally reposition the slide 2160 during the dispensing process.

FIG. 25 shows the head assembly 2018 after processing the slide 2160. The head assembly 2018 can then process a slide 2210 position at the processing zone 2170, and after processing the slide 2210, the tray 2050 can be moved in the X-direction (indicated by arrow 2192) to move the slides 2270, 2271 to the processing zone 2170. In some embodiments, tray movement can occur after the Y-axis motion of the head assembly 2018 has been initiated or completed to minimize the potential of interference impacts and/or to enhance system throughput. The head assembly 2018 can be moved to a "safe" position to provide interference points that are spaced apart from the path of the tray 2050, which can be moved at a speed selected to keep processing times as low as possible without compromising controlled liquid distribution. For example, the tray 2050 can move at a speed in a range of about 5 inches/second to about 6 inches/second. Other speeds can be used, if needed or desired. FIGS. 22B and 26 shows one of the head assemblies 2018 ready to process the slide 2270. A puddle 2240 is shown dispensed on a surface of the slide 2160. Each of the head assemblies 2018 can sequentially process the slides within a given quadrant. In some embodiments, the tray 2050 is moved during the dispense process. For example, the trays 2050 can be moved relative to the head assembly 2018 while the head assembly 2018 dispenses liquid to form, for example, zig-zag shaped puddles (as viewed from above), serpentine puddles, or other shaped puddles. The movement of the tray 2050 and head assembly 2018 can be coordinated to produce a wide range of different shaped puddles.

Figure 27:
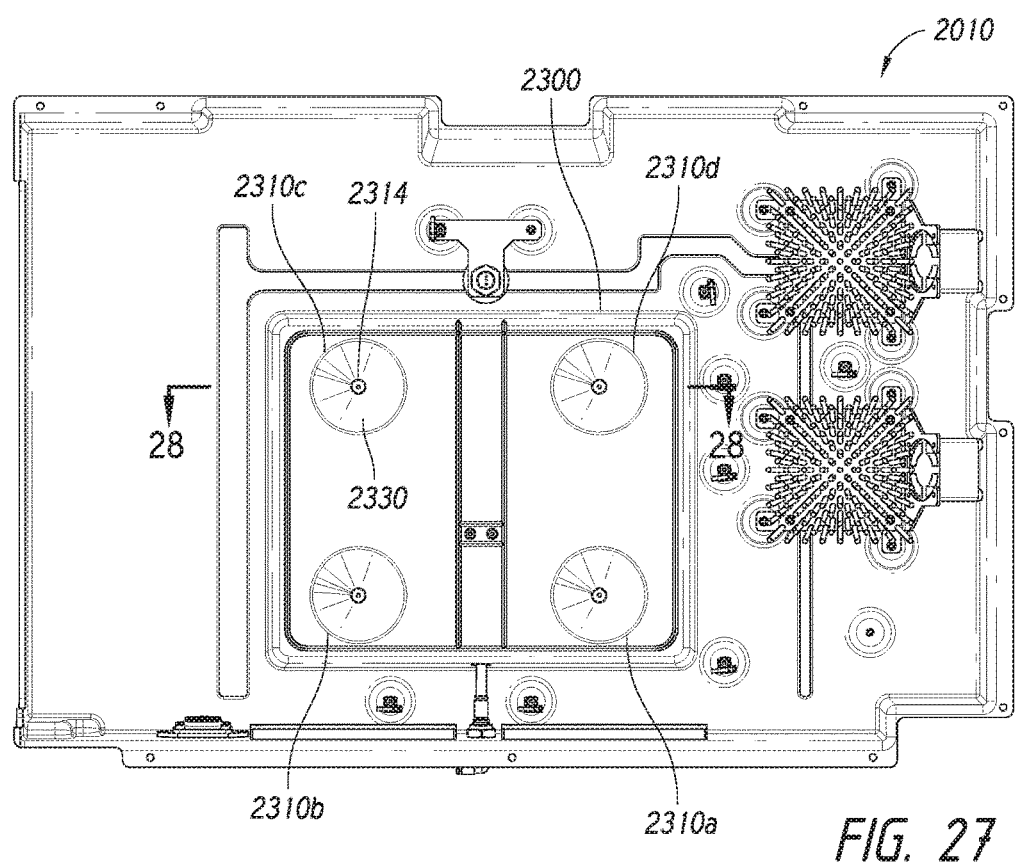
FIG. 27 is a top plan view of lower components of the stainer module along line 27-27 of FIG. 21.
Figure 28:
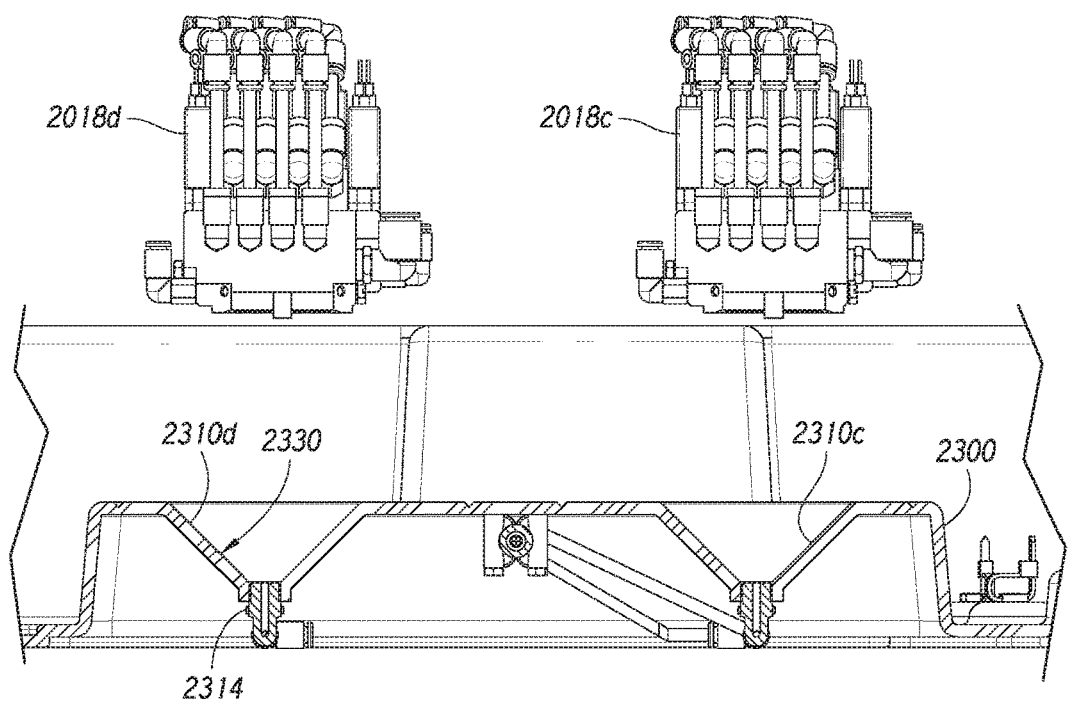
FIG. 28 is a cross-sectional side elevation view of a liquid collector taken along line 28-28 of FIG. 27.

FIG. 27 is a view of the stainer module 2010 taken along line 27-27 of FIG. 21 with tray not shown. FIG. 28 is a cross-sectional view of a liquid collector 2300 taken along line 28-28 of FIG. 27 and a front view of two head assemblies 2018d, 2018c. Referring now to FIG. 27, the liquid collector 2300 can be a tray or a pan with spaced apart reservoirs 2310a, 2310b, 2310c, 2310d (collectively "reservoirs 2310") positioned to collect liquid from the head assemblies 2018a, 2018b, 2018c, 2018d, respectively. The description of one reservoir 2310 applies equally to the other reservoirs 2310, unless indicated otherwise.

Referring now to FIG. 28, the reservoir 2310d can include a drain 2314 and a sloped surface 2330 for directing liquid to the drain 2314. The drain 2314 can be fluidically coupled to a waste module (or waste container) or other component by one or more lines. Liquid can be continuously or periodically drained from the reservoir 2310d. In some embodiments, the reservoir 2310d has a conical shape. In other embodiments, the reservoir 2310d has a frusto-conical shape, but the reservoir 2310d can have other configurations. The head assemblies 2018 can dispense liquid directly into the reservoirs 2310 to perform, for example, purge/prime cycles.

Figure 29A:
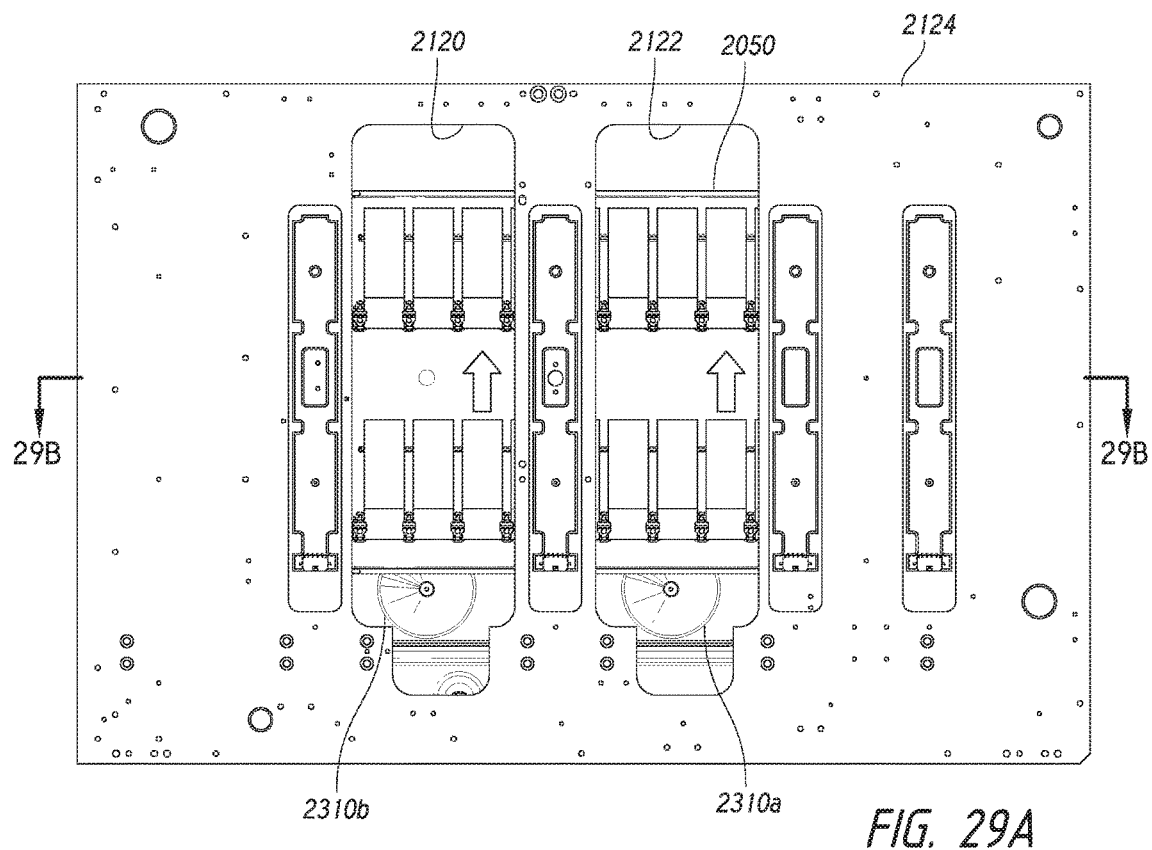
FIGS. 29A-31B are top plan and side elevation views show stages of a purge/prime process in accordance with an embodiment of the present technology.
Figure 29B:
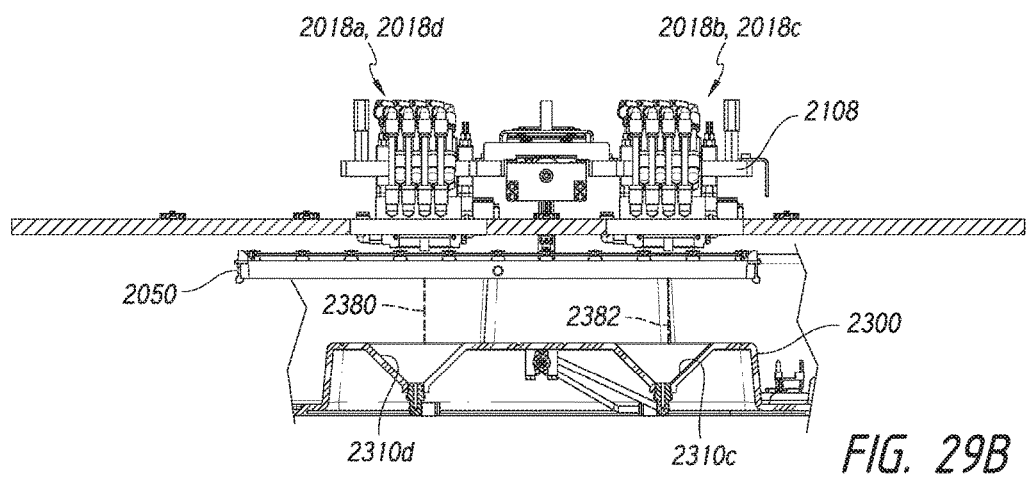

FIGS. 29A-29B show stages of a purge/prime cycle in accordance with an embodiment of the present technology. Generally, sets of head assemblies 2018 can sequentially dispense liquid directly into the reservoirs 2310. When the tray 2050 is positioned to expose about half of the reservoirs 2310, one pair of head assemblies 2018 can dispense liquid into exposed reservoirs 2310. The tray 2050 can be moved to expose the other half of the reservoirs 2310. Another pair of head assemblies 2018 can dispense liquid into those exposed reservoirs 2310. The head assemblies 2018 can sequentially dispense liquid while the tray 2050 is positioned within the stainer module 2010 to minimize, limit, or avoid off-line times, excessive handling, and/or tray hand-offs. As such, a high level of throughput can be maintained, even if a large number of purge/prime cycles are performed. Additionally, transport problems caused by repeatedly transporting trays into and out of the stainer module can be avoided. In a purging process, the reservoirs 2310 can collect streams of liquid from the head assemblies 2018 produced when liquid is pumped through the dispenser heads 2141 to clean any air bubbles from internal passages. In a priming process, the reservoirs 2310 can collect any excess liquid when overfilling the head assemblies 2018 with processing liquid to be dispensed. After performing the purge/prime process, the tray 2050 can be returned to the slide processing position to position slides underneath each of the head assemblies.

FIGS. 29A and 29B show the tray 2050 at a slide processing position. Referring to FIG. 29B, processing liquid can be delivered onto four slides while the tray 2050 obstructs a set of vertical delivery paths 2380 from the head assembly 2018d and obstructs a set of vertical delivery paths 2382 from the head assembly 2018c. Although the delivery paths 2380 are illustrated as a single dashed line, each delivery path 2380 can extend from one nozzle of the head assemblies 2018 to one of the reservoirs 2310. The tray 2050 can collect dispensed liquid that is not collected by the slides. For example, the tray 2050 can catch liquid that falls from the slides or drops that fall from the head assemblies 2018 (e.g., drops that fall while the tray 2050 is moved to index the slides).

Figure 30A:
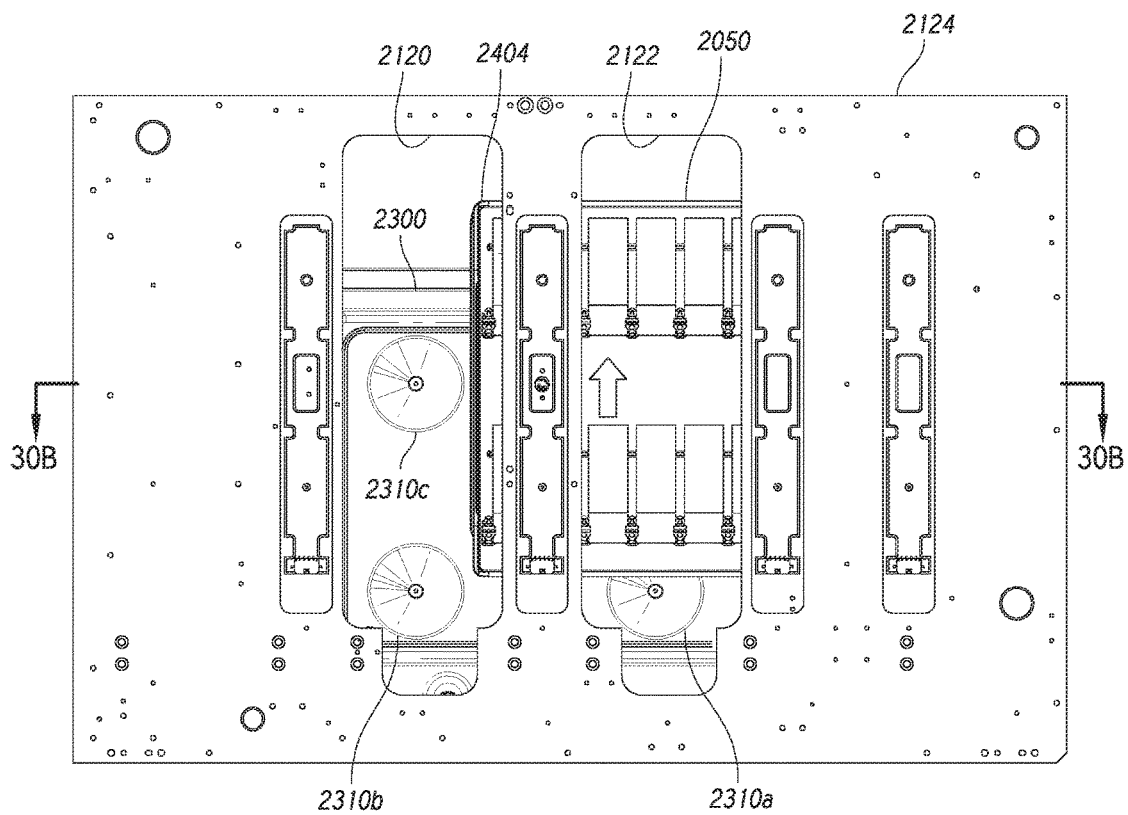
Figure 30B:
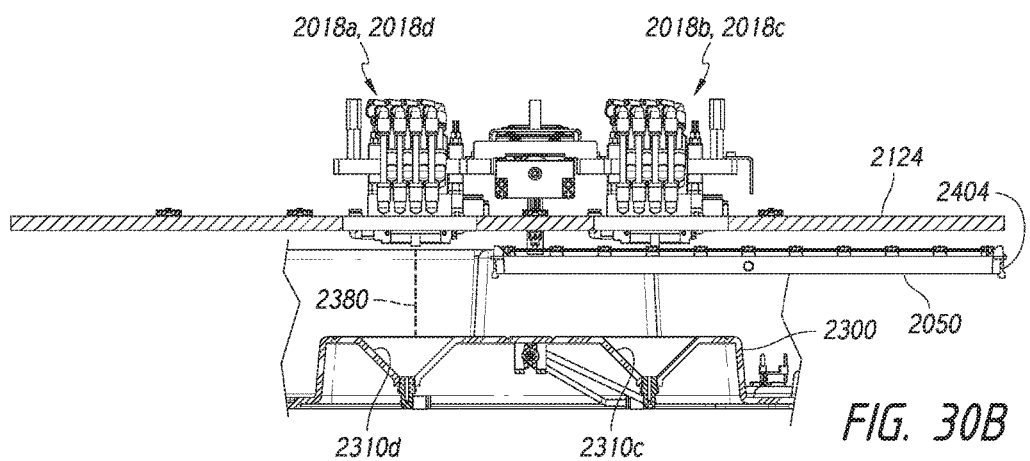
Figure 31A:
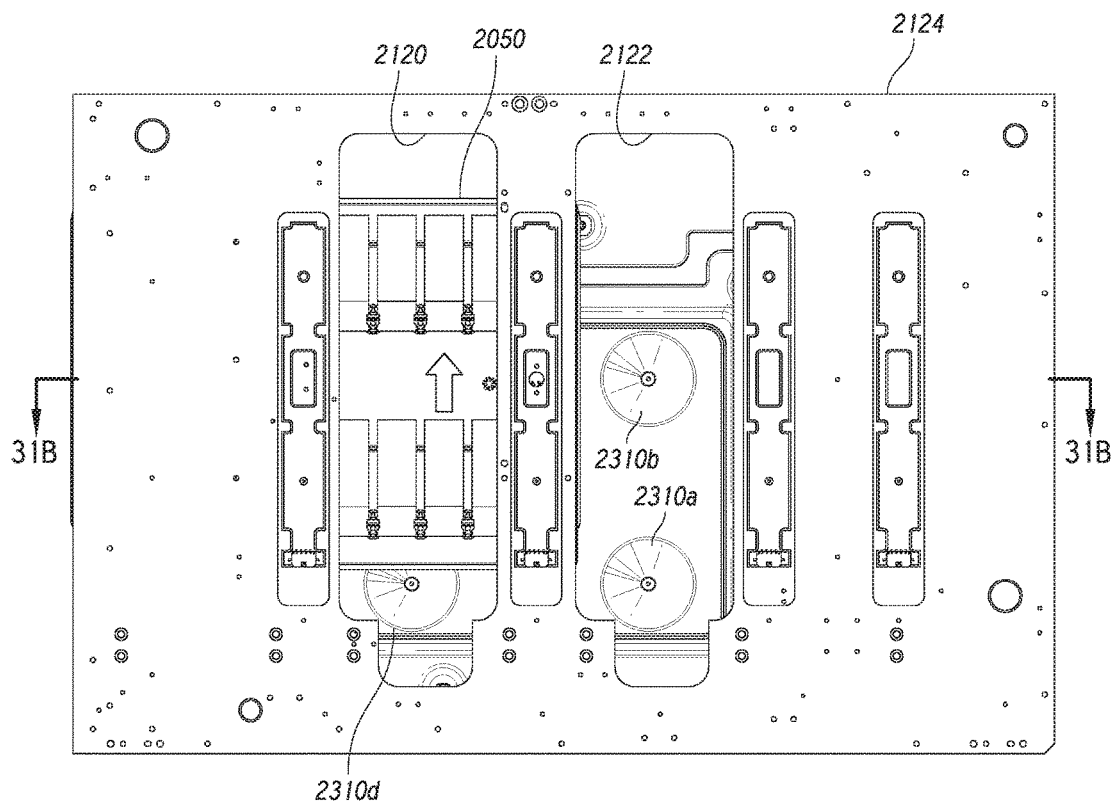
Figure 31B:
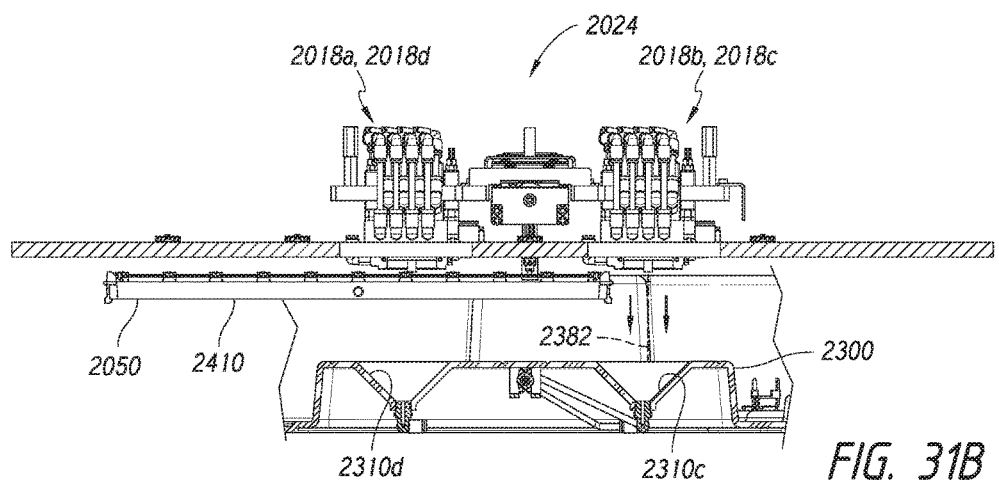

The tray 2050 can be moved from the slide processing position (FIGS. 29A and 29B) to a purge/prime position 2404 (FIGS. 30A and 30B) for unobstructing the delivery paths 2380. The head assemblies 2018d, 2018a (head assembly 2018a is behind the head assembly 2018d in FIG. 30B) can output liquid along the unobstructed delivery paths 2380. The reservoirs 2310a (FIG. 30A), 2310d can collect the liquid. The tray 2050 can be moved from the purge/prime position 2404 (FIGS. 30A and 30B) to another purge/prime position 2410 (FIGS. 31A and 31B) for unobstructing the set of vertical delivery paths 2382. A purge/prime cycle can be performed by the head assemblies 2018b, 2018c (head assemblies 2018b is behind head assembly 2018c in FIG. 31B). In some embodiments, streams of processing liquid are delivered along the vertical delivery paths 2382.

Selected Examples of Liquid Dispensing in Stainers

FIG. 32 is an isometric view of a dispenser apparatus 3024 in accordance with an embodiment of the present technology. The dispenser apparatus 3024 can provide valve-controlled, pressurized liquid delivery and controlled movements of head or manifold assemblies 3018a, 3018b, 3018c, 3018d (collectively "head assembles 3018"). A liquid handling system 3013 can deliver liquid to the dispenser apparatus 3024 and can include, without limitation, a liquid source 3014 and a liquid conveyance system 3015 including conduits or other suitable liquid conveyance elements. A controller 3017 can command the dispenser apparatus 3024 to dispense and distribute protocol-driven liquids over processing zones (i.e., specimen staining areas of a tray). Controlled liquid distribution can be achieved by, for example, wetting label areas of microscope slides with flowable hydrophobic substances (e.g., to create barriers on label areas of the slides), employing specific liquid exit velocities (e.g., non-dribbling liquid exit velocities), dispensing specific volumes of liquid (e.g., volumes of liquid less than an upper volume limit), moving a tray at target speeds and accelerations, dispensing at appropriate dispense locations along the slides, and/or dispensing from target dispense heights (e.g., heights suitable to minimize or limit splashing, splattering, bouncing of liquid, etc.).

The head assembly 3018a can move in a direction substantially parallel to a longitudinal axis 3021 of the slide 3020 held by a tray (not shown) while the head assembly 3018a dispenses liquid. FIG. 33 is a side view of the head assembly 3018a with a liquid dispense mechanism 3019 ("dispenser mechanism 3019") dispensing liquid 3030 to form an open-thick film that covers a specimen 3034 located on an upper surface 3044 of the slide 3020. The dispenser mechanism 3019 can include a dispenser head 3141, arrays of nozzles 3052, 3054, and shared manifolds within the dispenser head 3141. A line 3059 of the liquid conveyance system 3015 can deliver liquid from a liquid source 3058 (e.g., multiple containers respectively carrying processing liquids) to the dispenser mechanism 3019. The liquid flows through the dispenser head 3141 and exits via the nozzles 3052. FIG. 33A shows a flat or non-beveled end of the nozzle 3052 through which the stream of liquid flows. A line 3063 of FIG. 33 can deliver liquid from a liquid source 3062 to the dispenser mechanism 3019. The liquid flows through the dispenser head 3141 and exits via the nozzles 3054. In some embodiments, the dispenser head 3141 has an internal shared manifold comprised of two separate manifolds, each shared by multiple liquids to isolate incompatible liquids to prevent undesirable liquid interactions. In one embodiment, one manifold shares up to four compatible liquids that are sequentially dispensed via the nozzles 3052 and the other manifold shares up to four compatible liquids that are sequentially dispensed via the nozzles 3054.

Figure 34:
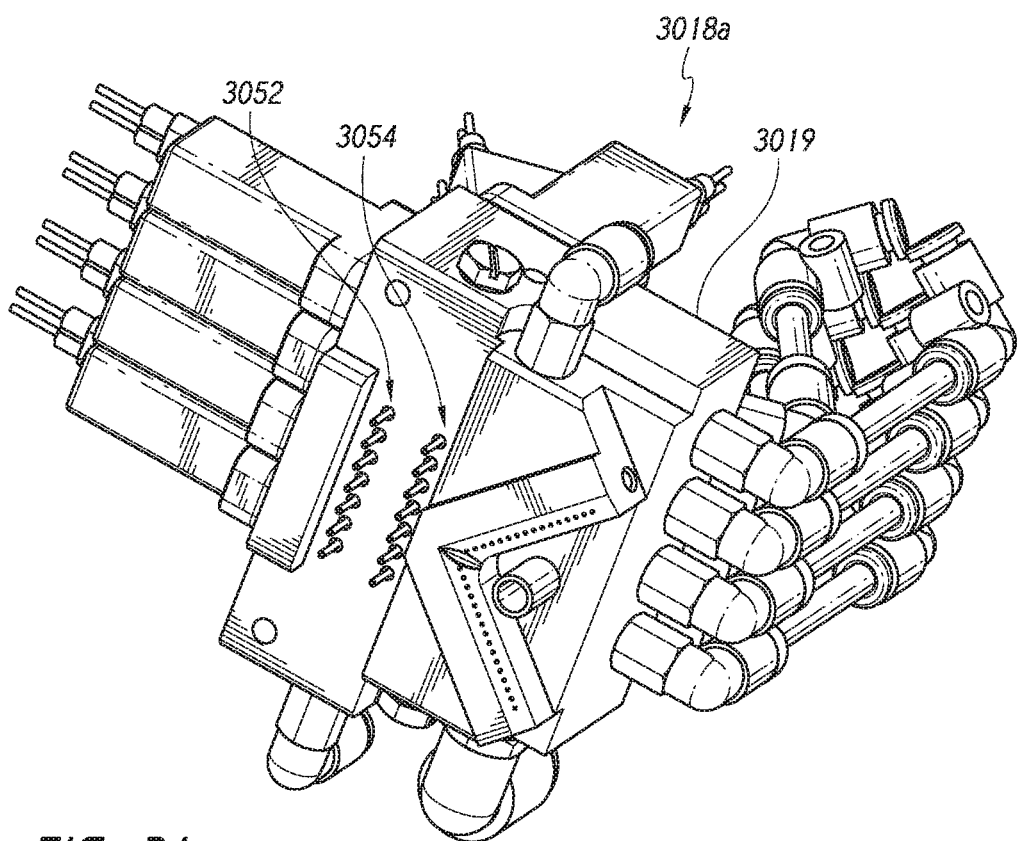
FIG. 34 is an isometric view of a head assembly in accordance with an embodiment of the present technology.
Figure 35:
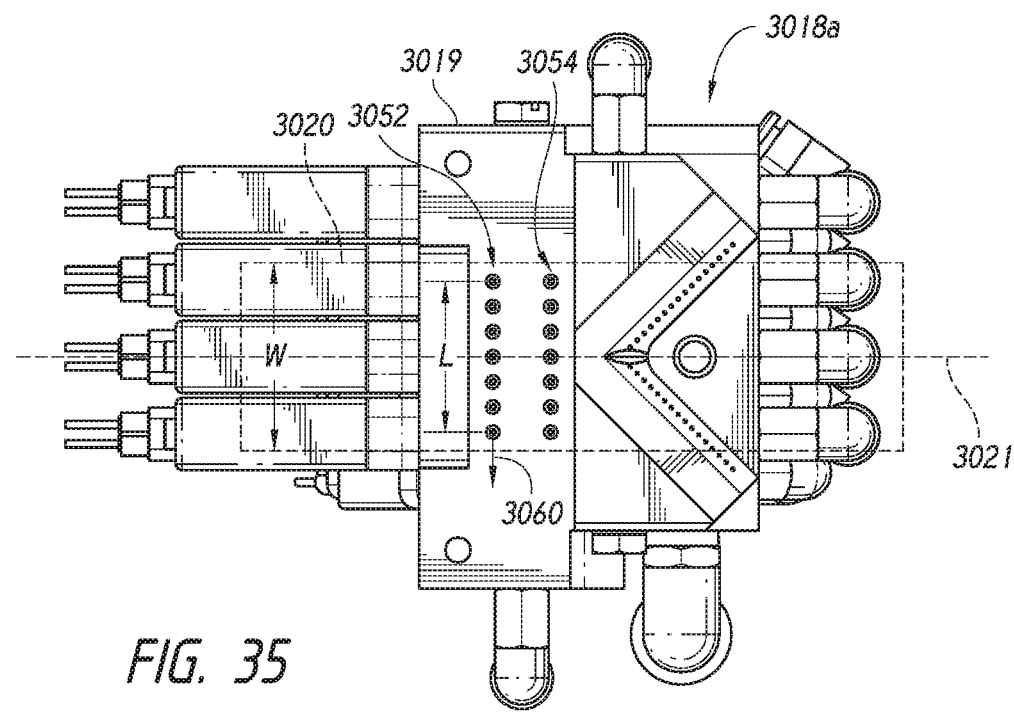
FIG. 35 is a bottom view of the head assembly of FIG. 34 and a microscope slide.

FIGS. 34 and 35 are isometric and bottom views, respectively, of the head assembly 3018a. The description of the array of nozzles 3052 applies equally to the array of nozzles 3054, except as indicated otherwise. Referring to FIG. 35, the array of nozzles 3052 can be a row that spans widthwise (slide edge to slide edge) relative to specimen locations along the slide 3020 (illustrated in phantom line) such that the array of nozzles 3052 is generally aligned with a width W of the microscope slide 3020. The nozzles 3052 can be evenly or unevenly spaced apart in a direction (indicated by arrow 3060) that is generally parallel to the slide width W.

An angle, if any, defined by the direction of spacing and the slide width W can be less than about 5 degrees, 3 degrees, or 2 degrees. A length L of the array of nozzles 3052 can be less than the slide width W such that all of the liquid streams are directed toward the upper surface 3044 of the slide 3020. In some embodiments, the array length L is about 70%, 80%, 90%, or 95% of the slide width W.

However, other array lengths can be used to direct streams of liquid toward an interior region of the slide 3020 to keep the liquid spaced apart from the edges of the slide 3020. If the dispensed liquid reaches a position near the edges of the slide 3020 (e.g., up to about 0.05 inches from the edge of the slide 3020), surface tension can help keep the liquid from falling off the slide 3020. The nozzles 3052 are spaced apart in a generally linear arrangement. In other embodiments, the nozzles 3052 are spaced apart in a U-shaped arrangement, V-shaped arrangement, saw-tooth arrangement (e.g., with different sized nozzles 3052), or other suitable arrangement with any desired number of nozzles 3052 and any desired nozzle geometries.

Figure 36:
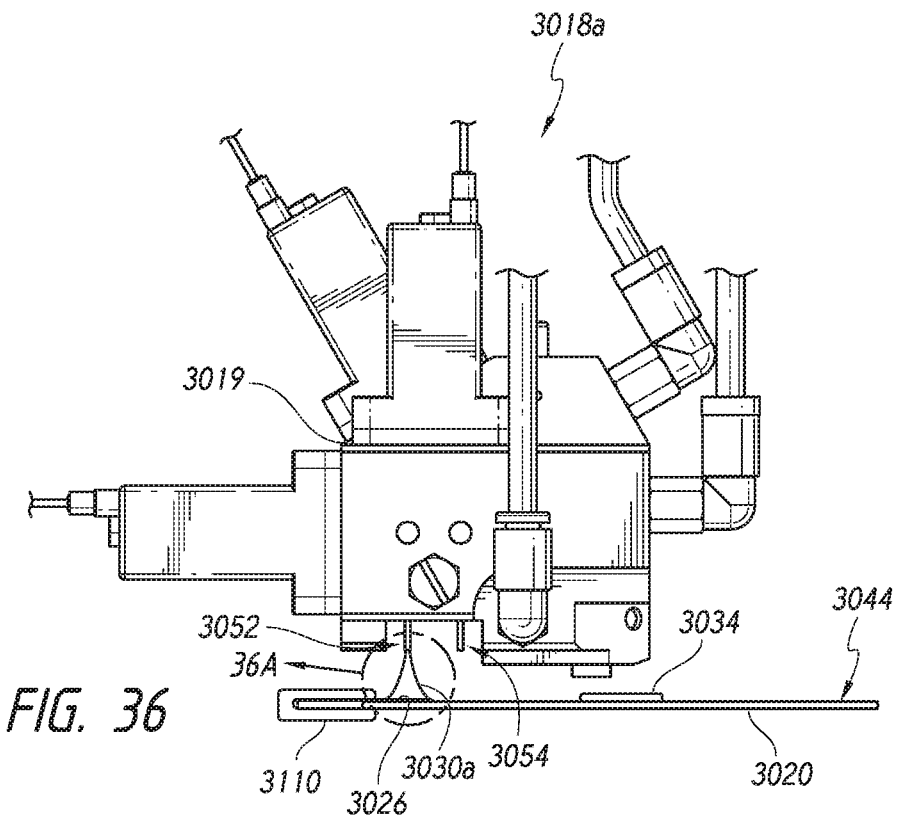
FIG. 36 is a side elevation view of the head assembly dispensing liquid onto a label of a microscope slide in accordance with an embodiment of the present technology.
Figure 37:
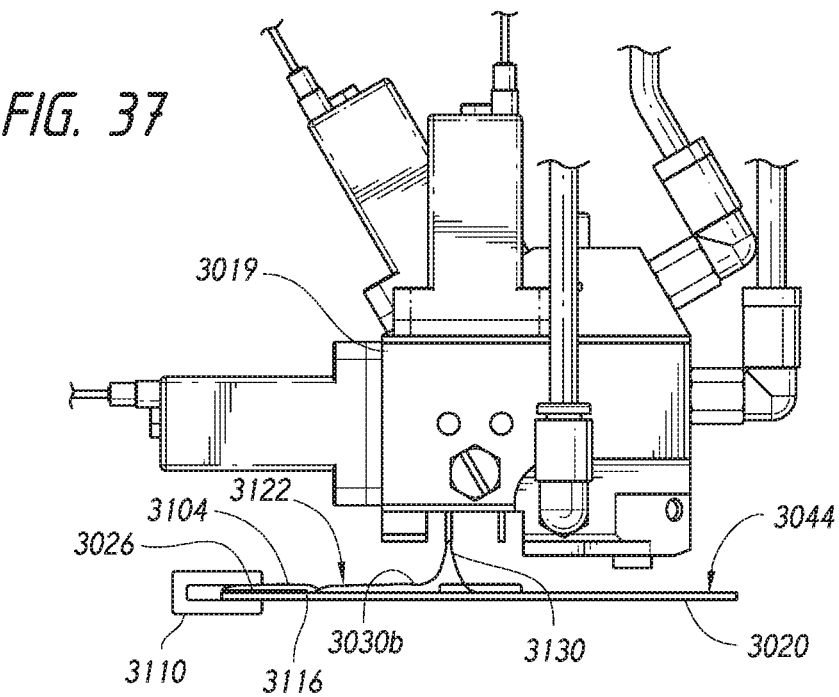
FIG. 37 is a side elevation view of the head assembly dispensing liquid onto a mounting area of the microscope slide.
Figure 38:
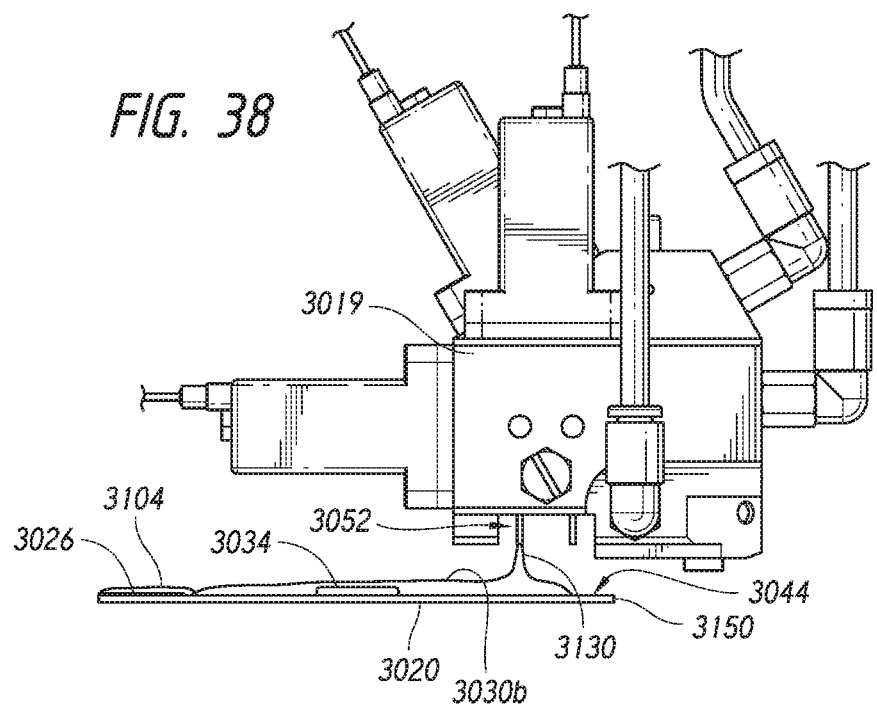
FIG. 38 is a side elevation view of the head assembly dispensing liquid onto an end of the microscope slide.

FIGS. 36-38 show stages of dispensing liquid in accordance with an embodiment of the present technology. Generally, the dispenser mechanism 3019 can deliver liquid at an anti-splatter liquid exit speed to minimize or limit splattering to avoid misprocessing nearby specimen-bearing microscope slides. In "painting" dispense processes, the dispenser mechanism 3019 can produce continuous, unbroken lines of liquid on the upper surface 3044. In "multi-step" dispense processes, liquid can be dispensed in short bursts at specific target locations along the slide 3020. The lines of liquid or discrete volumes can spread out along the upper surface 3044 to cover the specimen 3034 with liquid. In some embodiments, the dispensed liquid can form a matrix of liquid volumes or lanes of liquid volumes capable of dynamically transforming into a consolidated film (e.g., a thick film or a puddle). Because dispense positions relative to the length of the slide 3020 can vary between liquids, the lengthwise dispense positions can be selected based on individual liquid characteristics, as well as variability in slide dimensions and slide placement (e.g., placement of slides in the slide carrier/tray).

Figure 36A:
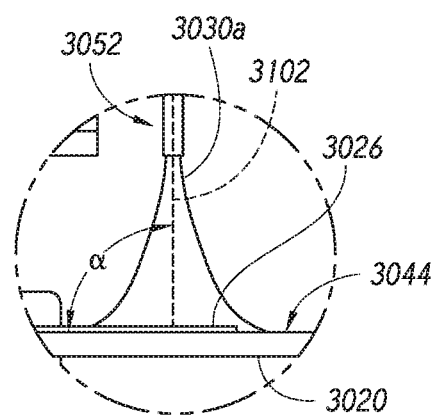
FIG. 36A is a detailed view of a nozzle directing a stream of liquid toward the label.

FIGS. 36 and 36A show the nozzles 3052 located above a label area of the slide 3020. Referring to FIG. 36A, the nozzles 3052 are oriented vertically to define a flow path 3102, which is substantially perpendicular to the upper surface 3044 of the slide 3020. The term "substantially perpendicular" generally refers to an angle within about +/−5 degrees of 90 degrees. For example, an angle $\alpha$ defined by the flow path 3102 and the upper surface 3044 can be within about +/−5 degrees of 90 degrees, such as within about +/−3 degrees of 90 degrees. If the slide 3020 is horizontal, the flow path 3102 can be in a substantially vertical orientation. The term "substantially vertical" generally refers to ranges of small angles from vertical, for example, angles between about 0 degrees and 3 degrees from vertical, such as angles less about 2 degrees from vertical, for example, angles less than 1 degree from vertical. The orientation of the nozzles 3052 can be selected based on the desired liquid interaction with the liquid on the slide 3020. By way of example, the nozzles 3052 can be at non-vertical orientations to, for example, produce streams of liquid that push liquid along the slide 3020. In some embodiments, the nozzles 3052 can be at substantially vertical orientations, and the nozzles 3054 can be at non-vertical orientations.

FIG. 36 shows a slide retainer 3110 ("retainer 3110") of a tray (not shown) holding the slide 3020. If liquid contacts the retainer 3110, the liquid may tend to wick along the retainer 3110. This wicking may reduce the liquid available for specimen processing and/or cause the formation of undesirable liquid residues. The reductions in liquid available for specimen processing due to wicking may be relatively imprecise and may adversely affect the precision of specimen processing. To avoid wicking, the dispenser mechanism 3019 can dispense liquid 3030a onto the label 3026 to form a barrier that keeps subsequently dispensed liquid from contacting the retainer 3110. The liquid 3030a can comprise, without limitation, hydrophobic substances, wax, deparaffinizing liquid, or other suitable substances. The liquid 3030a can be selected to hydrophobically repel later dispensed aqueous liquids. The barrier can be temporary, with the residue of the liquid 3030a eventually evaporating. Alternatively, the liquid 3030a can be selected to solidify to form a physical barrier after being dispensed.

FIG. 37 shows a barrier 3104 comprised of the liquid 3030a. The barrier 3104 covers an edge 3116 of the label 3026 and can extend along most of a width $W_L$ (FIG. 32) of the label 3026. In some embodiments, the barrier 3104 extends along a majority of the width $W_L$. For example, the barrier 3104 can extend along at least about 70%, 80%, 90%, or 95% of the width $W_L$. In one embodiment, the entire label 3026 can be covered by the barrier 3104. The label 3026 can include machine-readable code (such as a one- or multi-dimensional bar code or infoglyph, an RFID tag, a Bragg-diffraction grating, a magnetic stripe or a nanobarcode) with coded instructions that specify the type, sequence, and timing of the liquid(s) delivered for treatment of a particular specimen. In some embodiments, the label 3026 is a bar code label adhered to the upper surface 3044.

The dispenser mechanism 3019 can dispense liquid 3030b (e.g., staining reagent) at an exit speed (i.e., an anti-splatter exit speed) that is less than a splattering exit speed at which the liquid 3030b would tend to splatter a liquid film or puddle at least partially supported on the upper surface 3044 by surface tension. In some embodiments, the liquid 3030b is delivered at an anti-splatter exit speed greater than 50 cm/second, greater than 57 cm/second, within a range from 50 cm/second to 60 cm/second, within a range from 54 cm/second to 57 cm/second, above another suitable threshold or within another suitable range. The corresponding volumetric flow rate can be, for example, from 0.9 to 1.4 mL/second, such as from 1.1 to 1.2 mL/second. In one embodiment, 100 µL to 1500 µL of liquid 3030b can be applied to the upper surface 3044 in less than about 5 seconds without any splattering. In some embodiments, 100 µL of liquid 3030b can be delivered onto the upper surface 3044 in less than about 0.1 second, and 1500 µL of the liquid 3030b can be delivered onto the upper surface 3044 in less than about 1.5 seconds. By minimizing or limiting splattering, substantially all of the dispensed liquid 3030b is collected on the upper surface 3044. For example, at least about 90% (e.g., at least about 99%) by volume of the dispensed liquid 3030b can be collected on the upper surface 3044. Thus, less than about 10% (e.g., less than about 1%) by volume of the dispensed liquid 3030b falls into the tray or splatter onto adjacent slides. In a particular embodiment, from about 99% to about 99.9% or 100% by volume of the dispensed liquid 3030b is collected on the upper surface 3044.

Additionally or alternatively, the liquid 3030b can be delivered at a liquid exit speed greater than a trampoline liquid exit speed. The trampoline liquid exit speed is a flow rate at which at least a significant portion of the stream 3130 would tend to bounce off a surface 3122 of the film or puddle on the slide 3020. The exit speed of the stream 3130 can be sufficiently high to avoid trampoline effects but sufficiently low to avoid appreciable splattering. In some embodiments, the liquid 3030b can exit the nozzles 3052, with inner diameters of about 0.24 inch (0.6 mm), at a flow speed in a range about 55 cm/second to about 60 cm/second. In one embodiment, the liquid 3030b exits the nozzles 3052 at a flow speed equal to about 57 cm/second. The exit speed of the stream 3130 can be selected based on, for example, the number of nozzles, nozzle inner diameters, liquid pressures, orientation of the nozzles, height of the nozzles, characteristics of the liquid 3030b (e.g., viscosity, density, surface tension, etc.), surface characteristics of the slide 3020, and/or environmental characteristics (e.g., surrounding air flow, temperature, humidity, etc.). In some embodiments, at least one nozzle 3052 is spaced apart from the upper surface of the microscope slide by a distance in a range from about 5 mm to about 10 mm.

FIG. 38 shows the nozzles 3052 dispensing the liquid 3030b onto an end portion 3150 of the slide 3020 and a film of liquid 3030b covering most of a longitudinal length of a processing area 3098 (FIG. 32), such as a mounting region or a staining area. The speed of the dispenser mechanism 3019, path of the dispenser mechanism 3019, liquid volumetric flow rate, and/or dispense timing can be selected based on the desired liquid coverage. The dispenser mechanism 3019 can move back and forth along the slide 3020 while dispensing liquid continuously or periodically to maintain desired coverage. In such processes, the dispensed streams of liquid can combine with film or puddle upon contact.

The process of FIGS. 36-38 can be used to dispense a wide range of liquids. By intentionally over-wetting with deparaffinizing liquid (or other oily hydrophobic liquid), a sufficient volume of deparaffinizing liquid can be dispensed at the processing area 3098 (FIG. 32) to provide appropriate liquid spreading to, for example, create the barrier 3104 (FIGS. 37 and 38) in order to mitigate unintentional liquid wicking along the retainer 3110 (FIG. 36). Relatively large deparaffinizing liquid volumes (e.g., 0.92 mL (+11%/−11%)) can be dispensed for initial label and tissue area wetting, and the next largest deparaffinizing volume (e.g., 0.58 mL (+20%/−20%)) can be used for second dispenses (including key deparaffinization dispenses), and relatively small deparaffinizing volumes (e.g., 0.44 mL (+59%/−62%)) can be used for additional deparaffinizing dispenses. Other volumes of deparaffinizing liquids can be dispensed in other sequences. Conditioning liquid (e.g., transfer or bridging liquid) can be dispensed to maintain a minimum kinetic liquid thickness above the specimen 3034, but the volume of conditioning liquid can be sufficiently low to prevent spreading to the label area, which can affect the barrier 3104. In some embodiments, conditioning liquid comprising di(propylene glycol) propyl ether can be delivered with a liquid exit speed equal to about 54 cm/second in order to dispense a volume of about 0.4 mL (+50%/−50%). In some embodiments, washing liquid can be delivered with a liquid exit speed equal to about 57 cm/second to dispense a volume of about 1.0 mL (+10%/−10%), 0.9 mL (+22%/−22%), or 1.1 mL (+10%/−10%). The liquid exit speed of staining reagent (e.g., hematoxylin reagent) can be equal to about 57 cm/second to dispense a volume of about 1.05 mL (+14/−14%). The liquid exit speed of stain-setting reagent can be equal about 57 cm/second in order to dispense a volume of about 1.2 mL (+16/−16%). The liquid exit speed of counterstaining reagent (e.g., eosin reagent) can be equal to about 57 cm/second in order to dispense a volume of about 1.35 mL (+11/−11%). Other liquid exit speeds can be selected based on, for example, liquid characteristics, spacing between slides, target processing volumes, target dispense times, target processing times, and/or other processing parameters.

Dispense locations, both along the slide length and width, can be registered with respect to particular slide boundaries in order to achieve desired coverage (e.g., full and uniform liquid coverage of the processing area) while limiting or preventing unintentional liquid contact. The width of the head assembly 3018, number of nozzles (e.g., number of nozzles 3052, number of nozzles 3054, etc.), the spacing between nozzles (e.g., spacing between nozzles 3052, 3054), tray movements, and dispense volumes can be selected to accommodate the spreadability of the dispensed volume and positional tolerances impacted by tray handling. In general, both "painting" dispense routines or "multi-step" dispense routines can achieve liquid coverage of the entire processing area (or at least about 90%, 95%, or 100% of the area of the processing area 3098 of FIG. 32), but painting dispenses may have less splash potential than multi-step dispenses. This is because painting dispenses may have limited breaks in liquid flow between the nozzles and dispensed liquid. Painting dispenses can also reduce or limit processing times due to the coordinated relatively high speed movement of the head assemblies 3018. In contrast to painting dispenses which rely on liquid flow rates/valve timing matched to movement of the head assembly 3018, multi-step dispenses can depend on multiple dispenses with relatively short valve times and can be generally implemented independent of movement speed of the head assembly 3018. For hematoxylin and eosin staining, both painting and multi-step dispense routines can be used to promote uniform and consistent stain quality. Multi-step dispense and assisted liquid movement (e.g., airknife assisted liquid movement) can enhance rinsing (e.g., rinsing after applying hematoxylin). The total time to accomplish dispensing and liquid removal can impact the ability to achieve a desired overall processing time, as well as the ability to support short incubation times (e.g., 2 minutes, 1 minute, 30 seconds, 20 seconds, etc.). The dispense process discussed in connection with FIGS. 36-38 can be modified to reduce processing times. For example, specimen 3034 can be processed without utilizing the liquid 3030a discussed in connection with FIGS. 36 and 37. The dispenser mechanism 3019 can initially dispense liquid 3030b (FIG. 37) onto a region of the upper surface 3044 spaced apart from the label 3026 to prevent physical contact between the label 3026 (or retainer 3110) and the liquid 3030b.

Referring again to FIG. 32, the controller 3017 can contain instructions for commanding the four head assemblies 3018 to process up to four slides in parallel using, without limitation, label-to-end dispense routines (discussed with respect to FIG. 36), end-to-label dispense routines, end-to-label-to-middle dispense routines, or other dispense routines. In end-to-label dispense routines, liquid can be applied to the entire length of the slide 3020. In end-to-label-to-middle dispense routines, liquid can be delivered while moving the head assembly 3018 along the entire length of the slide 3020. After liquid is applied along the length of the slide 3020, the head assembly 3018 can be moved back to the middle of the slide while continuing to dispense liquid. The controller 3017 can adjust processing based on one or more signals from sensors that detect overflow from either a liquid collector (e.g., a purge tray or a purge pan) or slide tray, as well as sensors that can detect, without limitation, inadequate flow velocity (e.g., low flow velocity due to contamination), nozzle blockages, changes in valve timing (e.g., valve timing that may affect processing reliability), wicking along slide retainment features (e.g., retainer 3110, clips or posts of a tray, etc.), contamination (e.g., non-nominal slide surface contamination), and/or stainer module's inability to remove bubbles/air pockets along flow paths using, for example, dispense routines, such as purge cycles, prime cycles, combinations thereof (e.g., purge/prime cycles). In the event of stainer module 3010 shut down or the detection of liquid overflow, all liquid dispense valves of the head assemblies 3018 can be shut off.

The stainer module 3010 can process trays independent of the slide positional content within the trays. The controller 3017 can execute instructions to move the head assemblies 3018 independent of whether a slide is underneath the head assembly 3018. Movements and delays for dispensing and removing liquids can be performed for all slide positions for consistent processing between trays. However, the stainer module 3010 only dispenses liquid at slide positions at which a slide is positioned. Thus, processing times for filled trays (i.e., trays completely filled with microscope slides) can be the same as processing times for partially filled trays.

The dispenser apparatus 3024 can have head assemblies with different configurations. FIGS. 39-48C show one embodiment of the head assembly 3018 and its components and functionality. Valves and liquid components are generally discussed in connection with FIGS. 39-41. Manifolds and vacuum features are generally discussed in connection with FIGS. 42A-48C. FIGS. 49-53 show another head assembly and its components and functionality. A person skilled in the relevant art will understand that the stainer module 3010 may have other embodiments of head assemblies without several of the features described below with reference to FIGS. 39-53.

Figure 39:
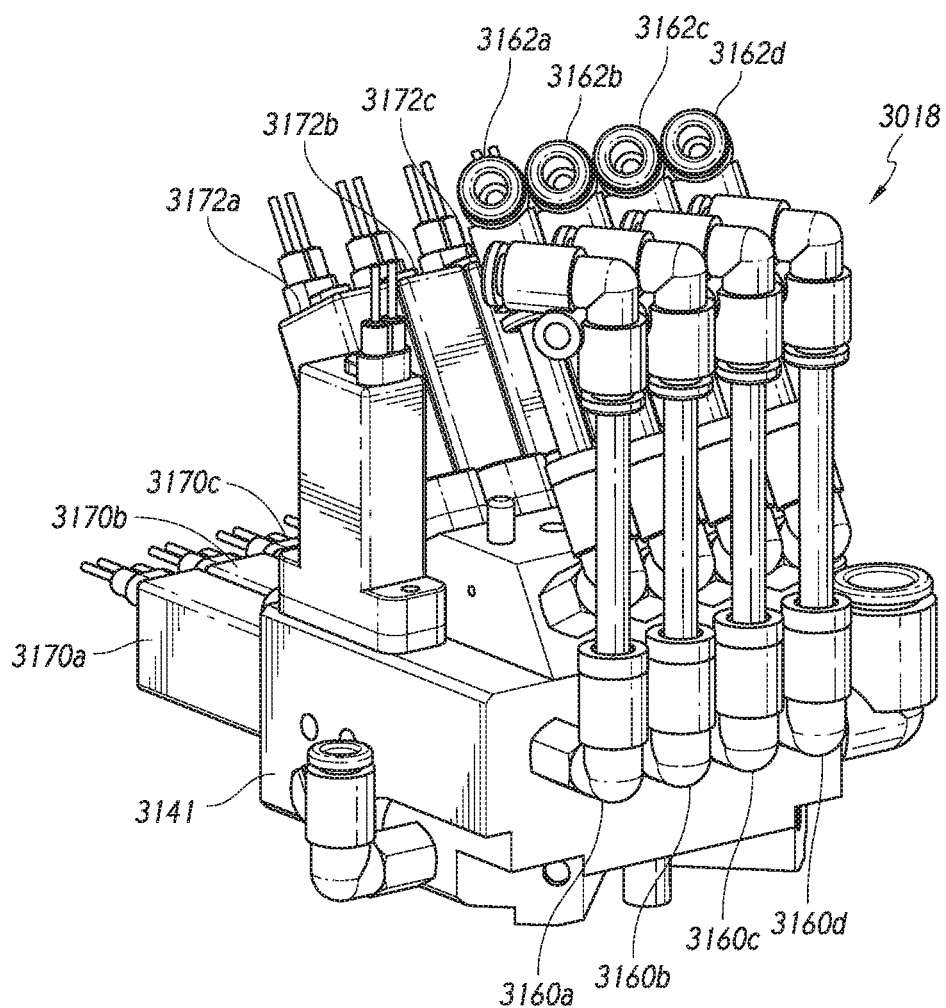
FIGS. 39, 40, and 41 are isometric, side, and front views, respectively, of the head assembly in accordance with an embodiment of the present technology.
Figure 40:
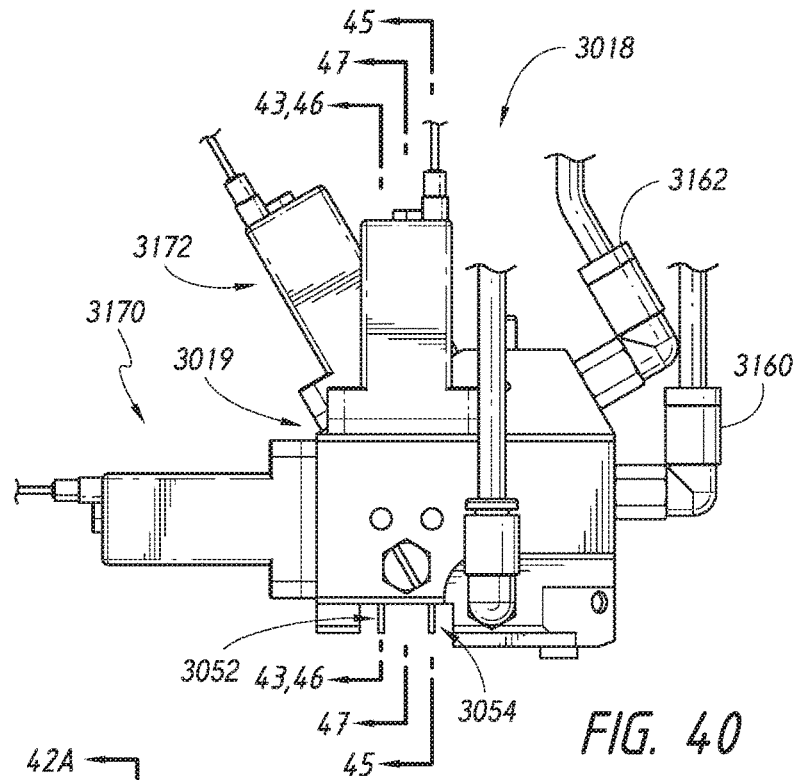
Figure 41:
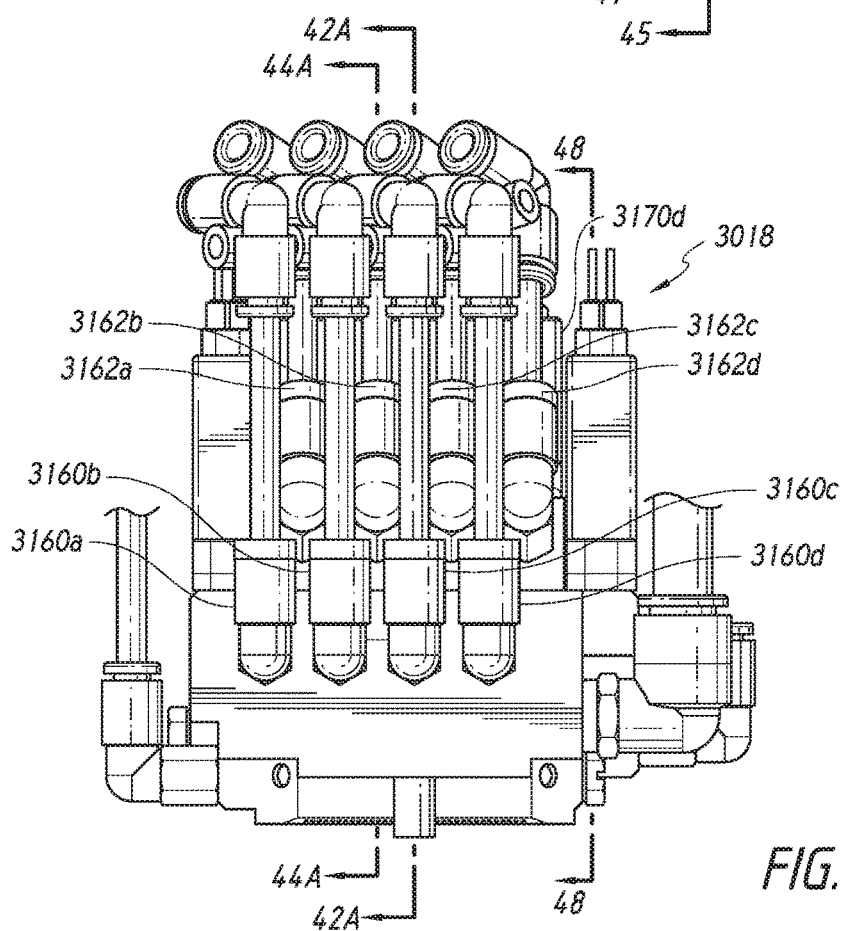

Referring now to FIGS. 39-41 together, the head assembly 3018 can include an array of lines 3160a, 3160b, 3160c, 3160d (collectively "lines 3160") and an array of lines 3162a, 3162b, 3162c, 3162d (collectively "lines 3162"). The lines 3160, 3162 can include one or more flow elements that facilitate controlled liquid dispensing. Such flow elements can be orifices configured to produce generally uniform liquid pressures within the dispenser head 3141. In some embodiments, the orifices can be configured to induce most of the pressure drop (e.g., at least about 80% of a total pressure drop) along the respective line at one location to minimize or limit pressure variation, if any, induced from other system geometry (e.g., tubing lengths, elevation, fittings, valves, etc.) resulting in controlled/low variation liquid dispensing. In one embodiment, the orifices include a jewel orifice and a housing holding the jewel orifice. The jewel orifice can be a ruby orifice having an opening with an inner diameter of about 0.18 inch (0.3046 mm) Other orifices with different configurations and diameters can also be used.

The head assembly 3018 can include valves 3170a, 3170b, 3170c, 3170d (collectively "valves 3170") and valves 3172a, 3172b, 3172c, 3172d (collectively "valves 3172") that are staggered to allow increased routing density in the dispenser head 3141, but other mounting arrangements can be used. The configurations of the valves 3170, 3172 can be selected based on, for example, material compatibility, operating pressures, target response times, etc. By mounting the valves 3170, 3172 directly to the dispenser head 3141, drops caused by "pumping" action from movement of the head assembly 3018 can be reduced or avoided. The valves 3170, 3172 can be operated to dispense liquid at appropriate exit velocities and to prime the nozzles 3052, 3054 prior to dispensing on-slide. Periodic purging/priming cycles can be performed to mitigate nozzle occlusion/plugging caused by, for example, hematoxylin precipitate or bluing stain salts. In a single liquid dispense state, the head assembly 3018 can dispense processing liquid from only one of the lines 3160, 3162. For example, the valve 3170a can be in an open state to dispense processing liquid from the line 3160a while the valves 3170b, 3170c, 3170d and valves 3172 are in closed states. After dispensing the processing liquid, the valve 3170a can be switched from the open state to a closed state, and one of the valves 3170b, 3170c, 3170d can be switched from the closed state to an open state to dispense another liquid. In a mixed liquid dispense state, two or more valves (e.g., two or more valves 3170 or two or more valves 3172) can be in open states to deliver multiple liquids into a single manifold in which the liquids mix. The mixture can flow out of the manifold and the head assembly 3018. In some stain routines, the head assembly 3018 can switch between single liquid dispense states and mixed liquid dispense states.

Figure 42A:
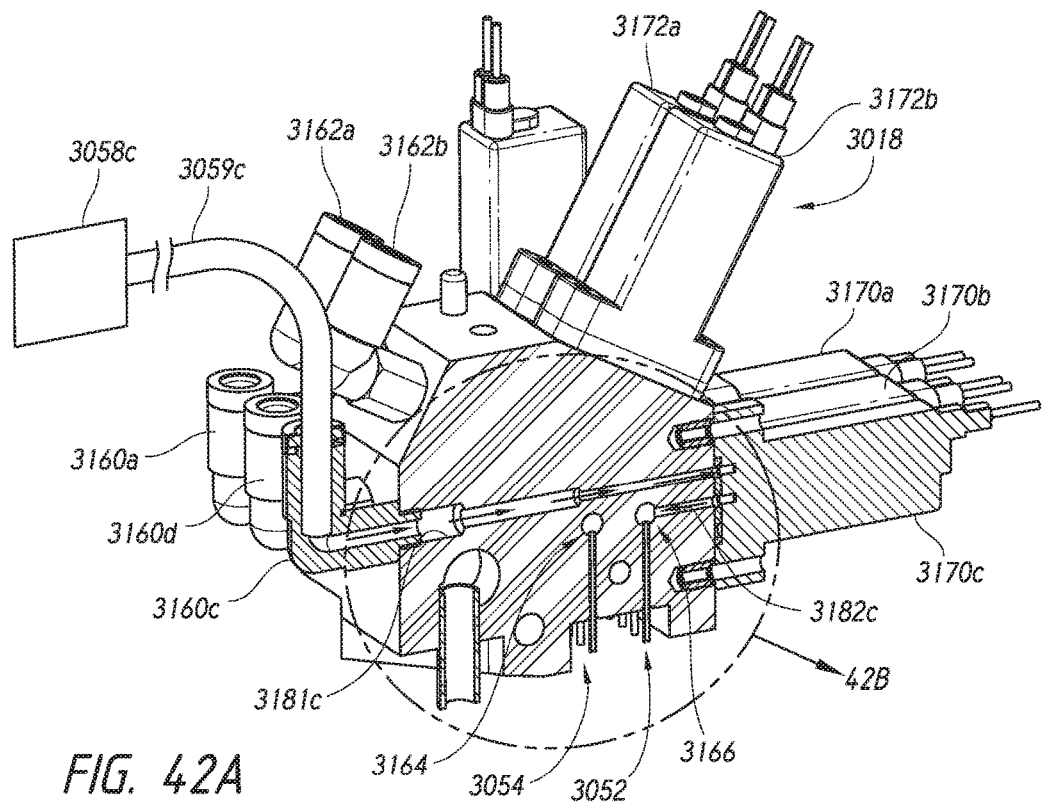
FIG. 42A is a cross-sectional perspective view of the head assembly taken along line 42A-42A of FIG. 41.

FIG. 42A is a cross-sectional view of the head assembly 3018 taken along line 42A-42A of FIG. 41. The head assembly 3018 includes a manifold 3166 for distributing liquid from the lines 3160 to the nozzles 3052 and a manifold 3164 for distributing liquid from the lines 3162 to the nozzles 3054. Liquids delivered through the lines 3160 may be incompatible with the liquids delivered through the lines 3162. The two manifolds 3164, 3166 can physically separate liquids that have high potential for undesirable interactions. If stain-setting reagent (e.g., bluing) and hematoxylin contact each other, hematoxylin, even at relatively low concentrations, can precipitate out and occlude or plug the nozzles. If stain-setting reagent contacts certain washing or conditioning liquids, there may be unintended stain artifacts. To avoid these problems, stain-setting reagent can flow through the manifold 3166 and hematoxylin reagent, washing liquid, and conditioning liquid can flow through the manifold 3164. The assignment of liquids (e.g., deparaffinizing liquid, conditioning liquid, washing liquid, and hematoxylin reagent sharing one manifold while eosin reagent, stain-setting reagent, and stain-differentiating reagent share another manifold) not only keeps appropriate liquids separated from each other but also may allow for efficient liquid exchange. Conditioning liquid, deparaffinizing liquid, washing liquid, and hematoxylin reagent can be delivered through the lines 3162a, 3162b, 3162c, 3162d, respectively. Stain-setting reagent, eosin reagent, washing liquid (e.g., washing liquid compatible with bluing), and stain-differentiating reagent (e.g., acid wash) can be delivered through the lines 3160a, 3160b, 3160c, 3160d, respectively. Other assignments of liquids to the lines 3160, 3162 can be selected based on the compatibility of the liquids in a given staining protocol.

Figure 42B:
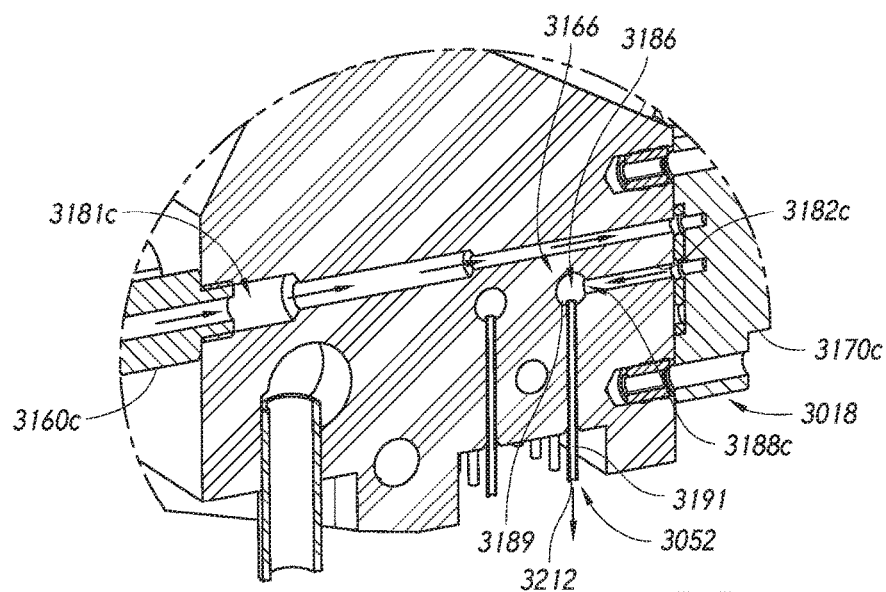
FIG. 42B is a detailed view of manifolds of the head assembly of FIG. 42A.
Figure 43:
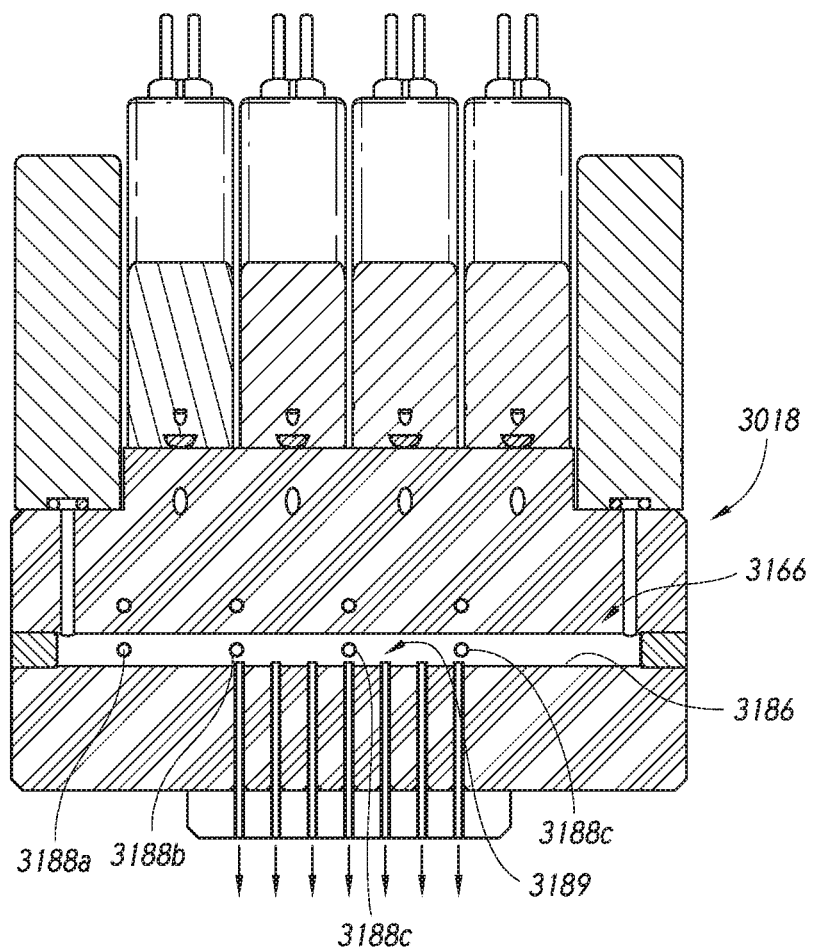
FIG. 43 is a cross-sectional elevation view of the head assembly taken along line 43-43 of FIG. 40.

FIG. 42B is a detailed view of the manifold 3166. FIG. 43 is a cross-sectional view of the head assembly 3018 taken along line 43-43 of FIG. 40. The manifold 3166 can include a distribution chamber 3186, inlets 3188a-d (collectively "inlets 3188"), and outlets 3189. Each valve 3170 can control liquid flow through a respective inlet 3188, which opens into the distribution chamber 3186. The size, shape, and configuration of the distribution chamber 3186 can be selected based on, for example, the desired liquid flow through the manifold 3166. Processing liquids can be individually delivered through respective inlets 3188 and into the distribution chamber 3186, which in turn distributes the processing liquid to the outlets 3189. The number of inlets, location of the inlets, and dimensions (e.g., diameters) of inlets can be selected based on the desired flow through the manifold 3166.

Referring now to FIGS. 42A and 42B, the line 3059c can deliver liquid (represented by arrows) from a liquid source 3058c to the line 3160c. The liquid flows through the line 3160c and proceeds along a valve feed passageway 3181c. The valve 3170c, in an open state, delivers the liquid into a valve outlet passageway 3182c. Referring now to FIG. 42B, the liquid flows along the valve outlet passageway 3182c, through the inlet 3188c, and into the distribution chamber 3186. The liquid flows through the distribution chamber 3186, outlets 3189, and channels 3191 and exits via the row of nozzle outlets 3212.

As shown in FIG. 42B, the nozzle 3052 can extend slightly into the distribution chamber 3186 to mitigate burrs or other features that may impede liquid flow and can be made, in whole or in part, of metal (e.g., stainless steel, aluminum, or the like), plastic, or other materials suitable for contacting the processing liquids and can have lengths in a range of about 5 mm to about 25 mm. For example, the nozzles 3052 can be hollow metal needles. Additionally, the nozzles 3052 can comprise one or more coatings to enhance performance Inner surfaces and/or outer surfaces of the nozzles 3052 can include a hydrophobic coating to avoid hanging drops. Non-stick coatings (e.g., polytetrafluoroethylene coatings), low-friction coatings, or other types of coatings can be used to reduce liquid carryover between dispense cycles. The inner diameters of the nozzles 3052, 3054 can be small enough and the liquid supply pressure high enough to achieve desired exit velocities/flow rates for each type of liquid. In some embodiments, for example, the inner diameters of the nozzles 3052, 3054 can be 0.24 inch (0.6 mm), but other inner diameters can be selected based on desired back pressures.

The nozzles 3052 may have some variation in tolerance due to manufacturing tolerances that affects where hanging drops tend to form. This is because hanging drops tend to form on the nozzle 3052 with the largest inner diameter. One of the nozzles 3052 (or a group of nozzles 3052) can have slightly larger inner diameters to promote hanging drops, if any, at that larger diameter nozzle 3052. In some embodiments, six nozzles 3052 can have inner diameters of 0.233 inch+/−0.005 inch (0.69 mm+/−0.13 mm) and the inner diameter of another nozzle 3052 can be 0.263 inch+/−0.005 inch (0.69 mm+/−0.13 mm) such that the 0.263 inch diameter nozzle 3052 will be the largest, even if all the other nozzles 3052 are at extreme ends of their tolerance ranges. The largest inner diameter nozzle 3052 will have the least resistance to liquid flow and droplets, if any, will preferentially form on the outlet of that nozzle 3052. In some embodiments, the largest inner diameter nozzle 3052 can be positioned and/or oriented to keep hanging drops from falling onto a slide. For example, the largest inner diameter nozzle 3052 can be angled such that its outlet 3212 is spaced away from the slide (e.g., to the side of the slide). During high flow periods (e.g., during dispensing), the liquid can impinge upon the upper surface of the slide, but during low flows periods, any drops at the outlet 3212 of the largest diameter nozzle 3052 will fall without contacting the slide, thus not interfering with the incubating liquid.

Figure 44A:
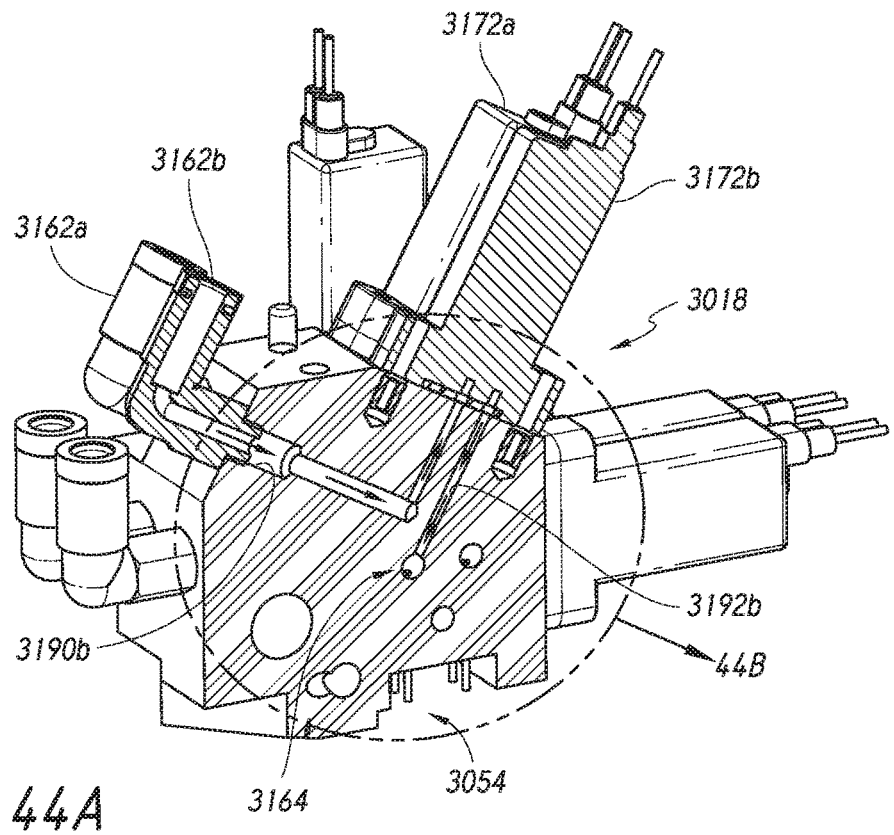
FIG. 44A is a cross-sectional perspective view of the head assembly taken along line 44A-44A of FIG. 41.
Figure 44B:
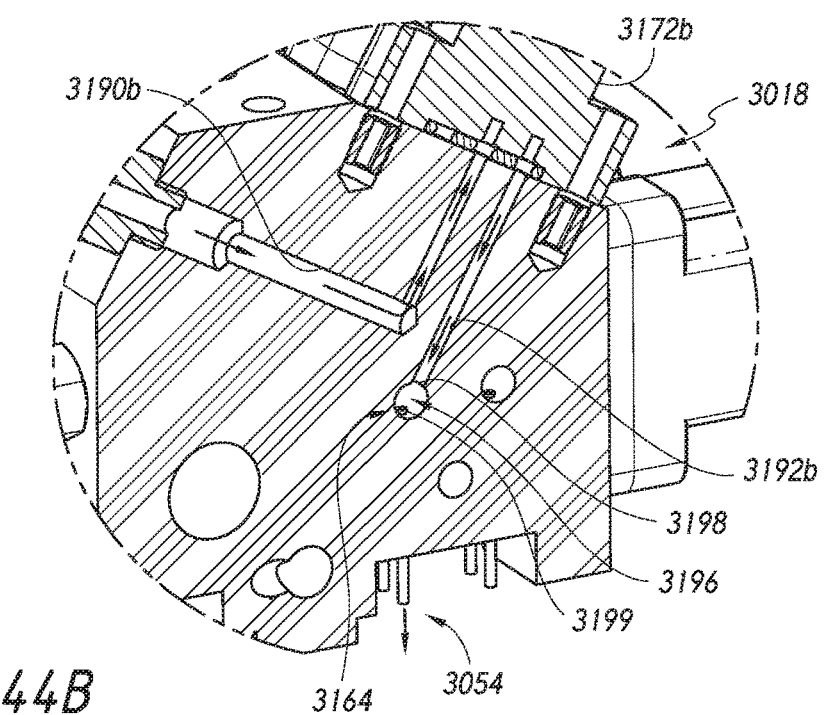
FIG. 44B is a detailed view of manifolds of the head assembly of FIG. 44A.
Figure 45:
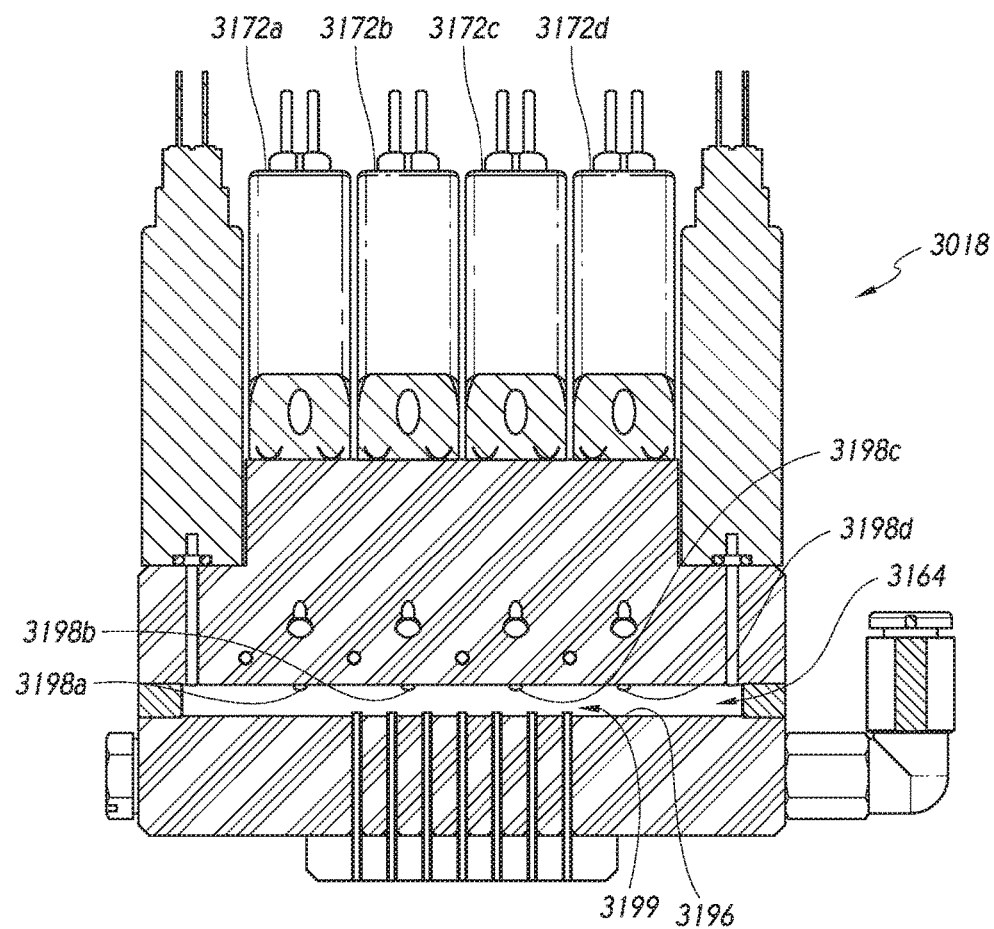
FIG. 45 is a cross-sectional elevation view of the head assembly taken along line 45-45 of FIG. 40.

FIG. 44A is a cross-sectional view of the head assembly 3018 taken along line 44A-44A of FIG. 41. FIG. 44B is a detailed view of the manifold 3164. FIG. 45 is a cross-sectional view of the head assembly 3018 taken along line 45-45 of FIG. 40. Referring to FIG. 44B, the manifold 3164 can include a distribution chamber 3196, inlets 3198a-d (collectively "inlets 3198"), and outlets 3199. Each valve 3172 can control liquid flow through a respective inlet 3198, which opens into the distribution chamber 3196. Referring now to FIGS. 44A and 44B, the line 3162b delivers liquid (represented by arrows) to a valve feed passageway 3190b. The liquid proceeds along the valve feed passageway 3190b to the valve 3172b, which in turn delivers the liquid into a valve outlet passageway 3192b. The liquid flows into the distribution chamber 3196 and exits via the nozzles 3054.

FIGS. 46A-46F show stages of operation of the head assembly 3018. Generally, when switching to a new liquid, vacuum valves 3200, 3202 are energized (i.e., opened) to remove liquid from the manifold 3166. A valve connected to one of the lines 3160 can be opened to displace the previous processing liquid and fill the manifold 3166 with new liquid. Dead legs can be minimized and a liquid exchange process can be performed to inhibit, limit, or substantially eliminate cross-contamination and/or carry-over. To reduce purge/prime volumes for liquid exchanges, the manifolds 3164, 3166 can be configured to provide uniform flow-through of liquids to limit or prevent pockets of low flow velocities. By dispensing lengthwise on slides and matching the manifold sizes to the width of the slide, manifold volumes can be further reduced. A single purge/prime cycle can generally include (1) a purge process involving drawing a vacuum and/or rinsing of a manifold with the next liquid to be dispensed and (2) a prime cycle involving dispensing of the next liquid through the manifold and the nozzles. Liquid exchanges can include multiple exchange steps. For example, an exchange from hematoxylin to washing liquid can include multiple exchanges (e.g., three-mini-cycle exchange processes) with wait times to more efficiently clean the manifold. Stages of sequentially dispensing two liquids are discussed in connection with FIGS. 46A-46F.

Figure 46A:
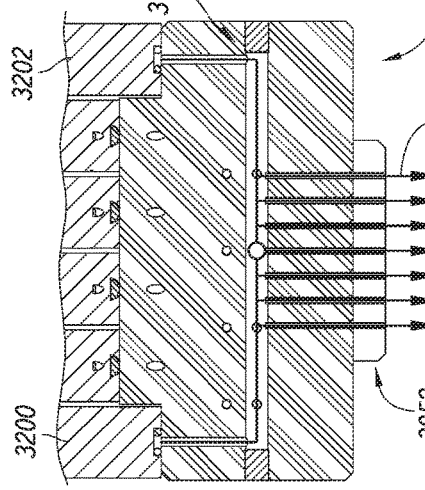
FIGS. 46A-46F are cross-sectional elevation views of the head assembly taken along line 46-46 of FIG. 40.
Figure 46D:
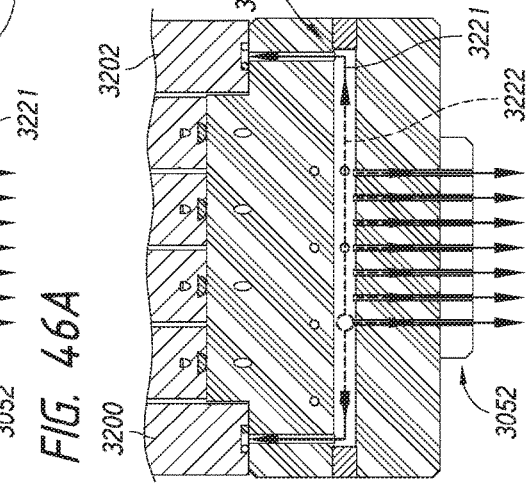
Figure 46B:
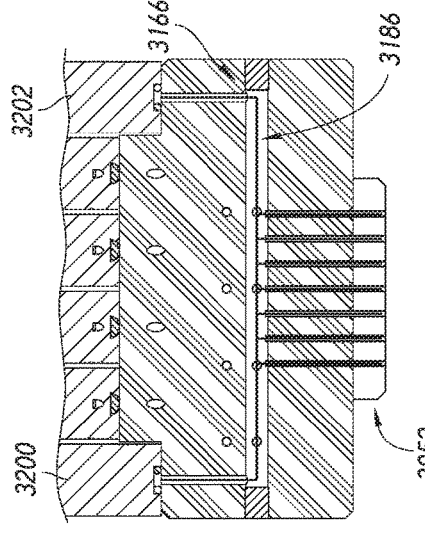
Figure 46E:
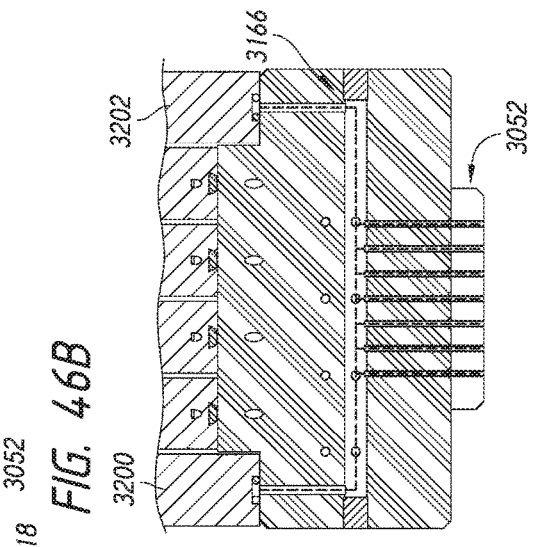
Figure 46C:
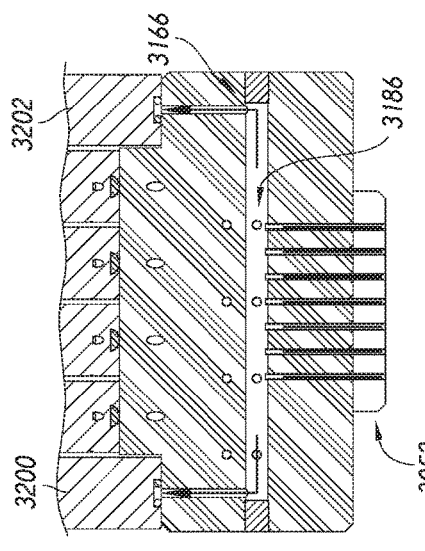
Figure 46F:
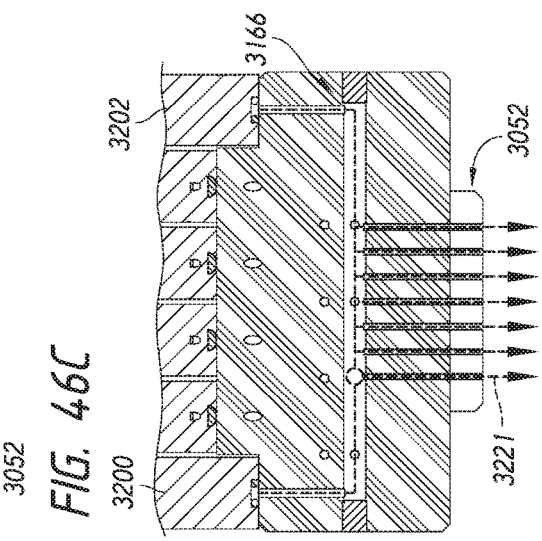

FIG. 46A is a cross-sectional view of the head assembly 3018 taken along line 46-46 of FIG. 40. Valve 3170c (FIG. 39) can be in an open state to dispense liquid (represented by arrows 3221) from the nozzles 3052. FIG. 46B shows the manifold 3166 filled with liquid and all of the valves 3170 in a closed state. FIG. 46C shows the liquid being evacuated from the distribution chamber 3186 by opening the valves 3200, 3202. After evacuating the distribution chamber 3186, the valve 3170b (FIG. 39) can be turned on to deliver another liquid into the distribution chamber 3196. FIG. 46D shows exchanging of liquid 3221 with another liquid represented by dashed line arrows 3222. The liquid 3222 flows toward the valves 3200, 3202 until the manifold 3166 is completely filled with the liquid 3222, which can also flow through the nozzles 3052. FIG. 46E shows the nozzles 3052 filled with the liquid 3222 and all of the valves 3170 closed. Once the nozzles 3052 are positioned above the slide to be processed, the valve 3170b can be opened to dispense the liquid 3221, as shown in FIG. 46F. The liquid exchange process described in connection with FIGS. 46A-46F can be performed to dispense liquid from any one of the lines 3160, 3162.

Figure 47:
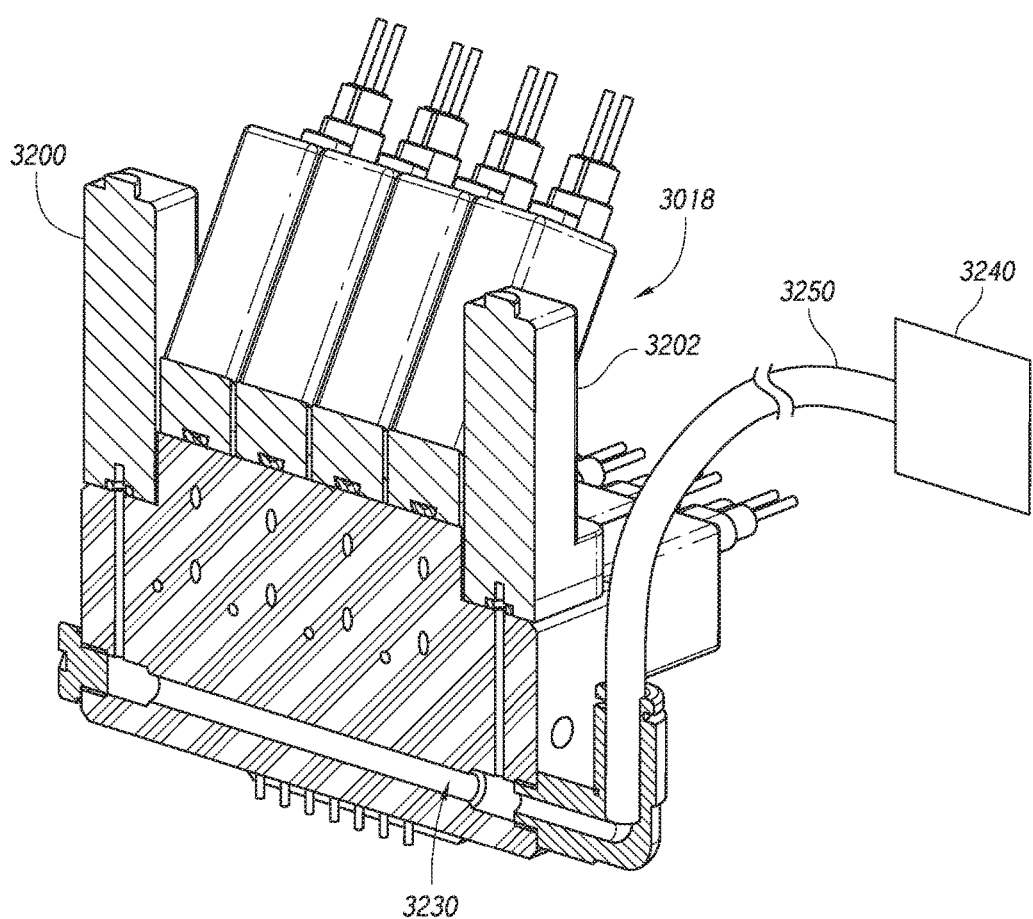
FIG. 47 is an isometric cross-sectional view of the head assembly taken along line 47-47 of FIG. 40.

FIG. 47 is a cross-sectional view of the head assembly 3018 taken along line 47-47 of FIG. 40. The head assembly 3018 can include a vacuum chamber 3230 in fluid communication with a vacuum source 3240. The vacuum source 3240 can draw a vacuum via a line 3250 to draw fluid out of the vacuum chamber 3230. In some embodiments, the vacuum source 3240 can include, without limitation, one or more pressurization devices, pumps, or other types of devices capable of drawing vacuum pressure greater than −0.3 psi with a 4 L/min flow rate, although other vacuum pressures and flow rates can be used. In some embodiments, a vacuum can draw liquid away from the outlets of the nozzles to mitigate hanging drops. Additionally or alternatively, vacuums can be used to remove liquid from the head assembly 3018 to, for example, perform a rinse/purge cycle, a calibration routine, etc. The line 3250 can include, without limitation, one or more valves (e.g., one-way valves, check valves, etc.), connectors, sensors, orifices, and/or other fluidic components.

Figure 48A:
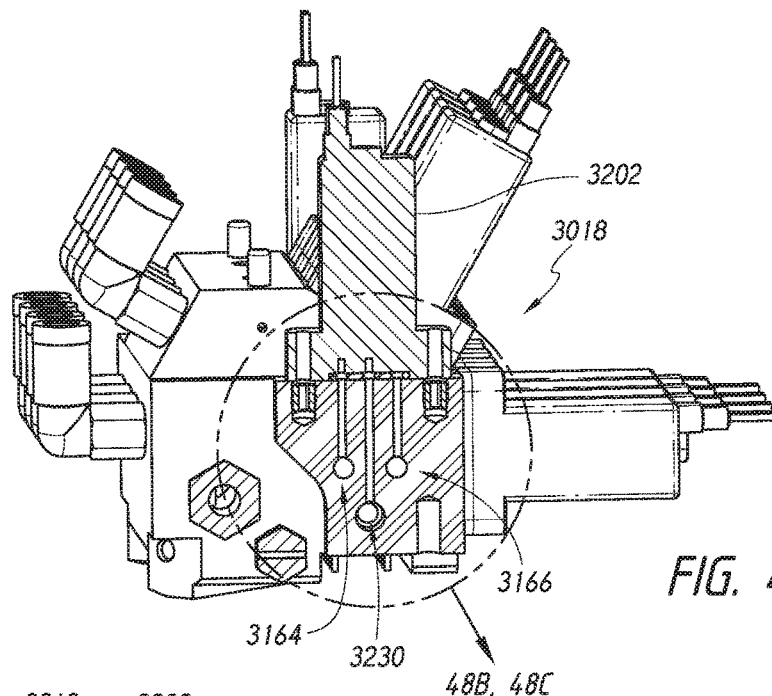
FIGS. 48A-C are cross-sectional views of the head assembly taken along line 48-48 of FIG. 41.
Figure 48B:
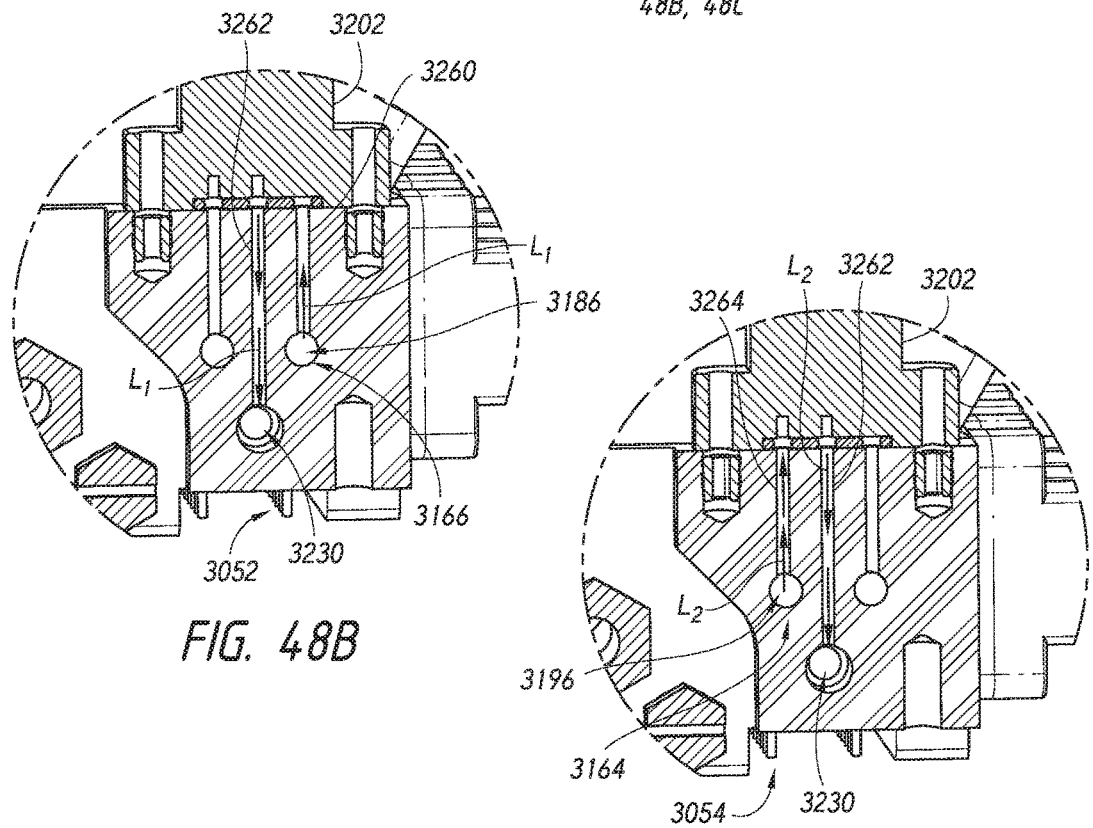
Figure 48C:
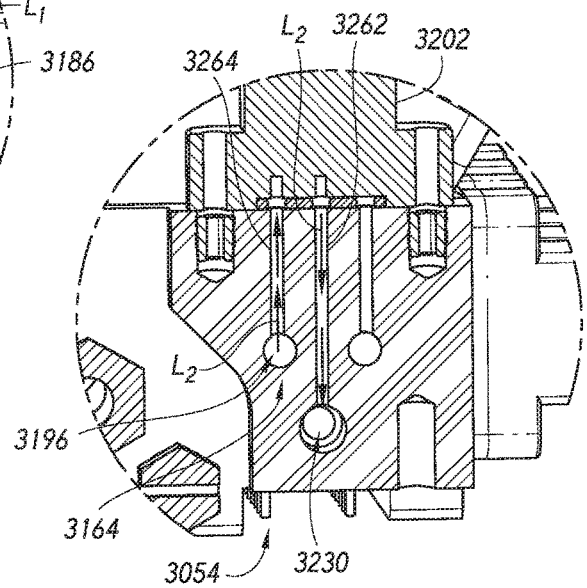

FIG. 48A is a cross-sectional view of the head assembly 3018 taken along line 48-48 of FIG. 41. FIGS. 48B and 48C are detailed views of portions of the head assembly 3018 in two different evacuation states. In the evacuation state shown in FIG. 48B, the valve 3202 and the valve 3200 (FIG. 47) allow liquid flow between the manifold 3166 and the vacuum chamber 3230. The liquid $L_1$ (represented by arrows) is drawn upwardly through the nozzles 3052 and into the distribution chamber 3186. $L_1$ flows through a passageway 3260 and into the valves 3200, 3202, which in turn delivers $L_1$ into a passageway 3262. $L_1$ flows through the passageway 3262, the vacuum chamber 3230, and the line 3250 (FIG. 47), thereby evacuating the manifold 3166. In the evacuation state shown in FIG. 48C, the valve 3202 has been opened to allow liquid flow between the manifold 3164 and the vacuum chamber 3230. Liquid $L_2$ is drawn upwardly through the nozzles 3054 and into the distribution chamber 3196. $L_2$ flows through a passageway 3264 and into the valve 3202, which in turn delivers the $L_2$ into the passageway 3262. $L_2$ flows through the passageway 3262, the vacuum chamber 3230, and the line 3250 (FIG. 47), thereby evacuating the manifold 3164. In some modes of operation, one of the manifolds 3164, 3166 can be empty and maintained under vacuum while the other manifold 3164, 3166 is filled with processing liquid. Thus, only one processing liquid will be ready to be dispensed at any given time. The vacuum can be used to avoid or limit hanging drops or other problems that may adversely affect staining.

The dual manifolds 3164, 3166 and vacuum chamber 3230 can help minimize the complexity and improve reliability of fluidic and wire routing management and also flow characteristic differences between slide tray quadrants and between stainer modules. The manifolds 3164, 3166, their associated valves (e.g., valves 3170, 3172), wires, lines (e.g., lines 3160, 3162), and fluidic connections can move along slides multiple times throughout a protocol to consistently distribute liquids along each slide, regardless of the slide location. An energy chain bend radius, flexible and material compatible tubing, and a fluidic design can be selected such that each individual dispense line has the bulk of the pressure drop as defined by a precision restrictor orifice, as discussed above, and that the shared delivery lines have as little pressure drop as possible.

Figure 49:
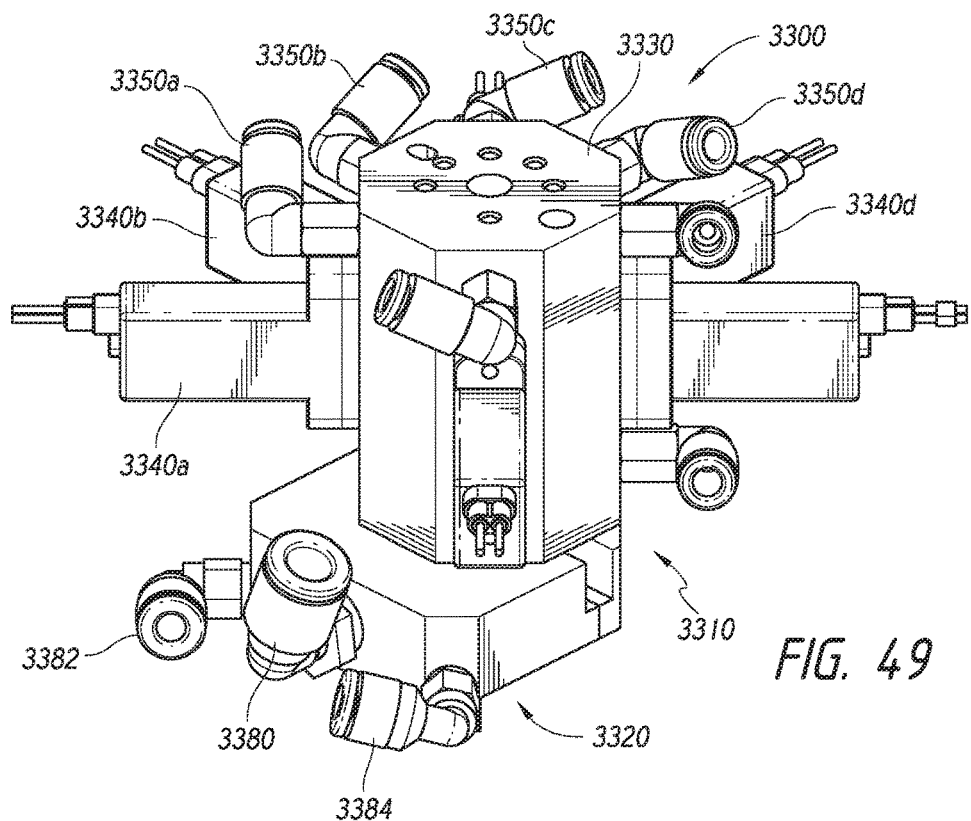
FIG. 49 is an isometric view of a head assembly in accordance with an embodiment of the present technology.
Figure 50:
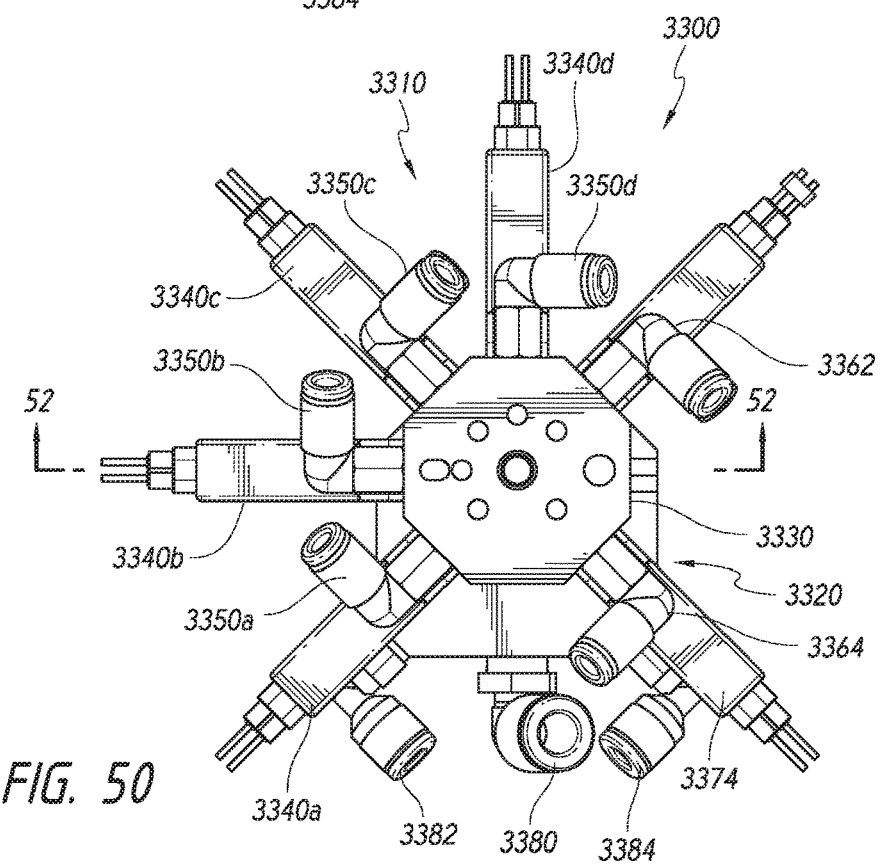
FIG. 50 is a top plan view of the head assembly of FIG. 49.
Figure 51:
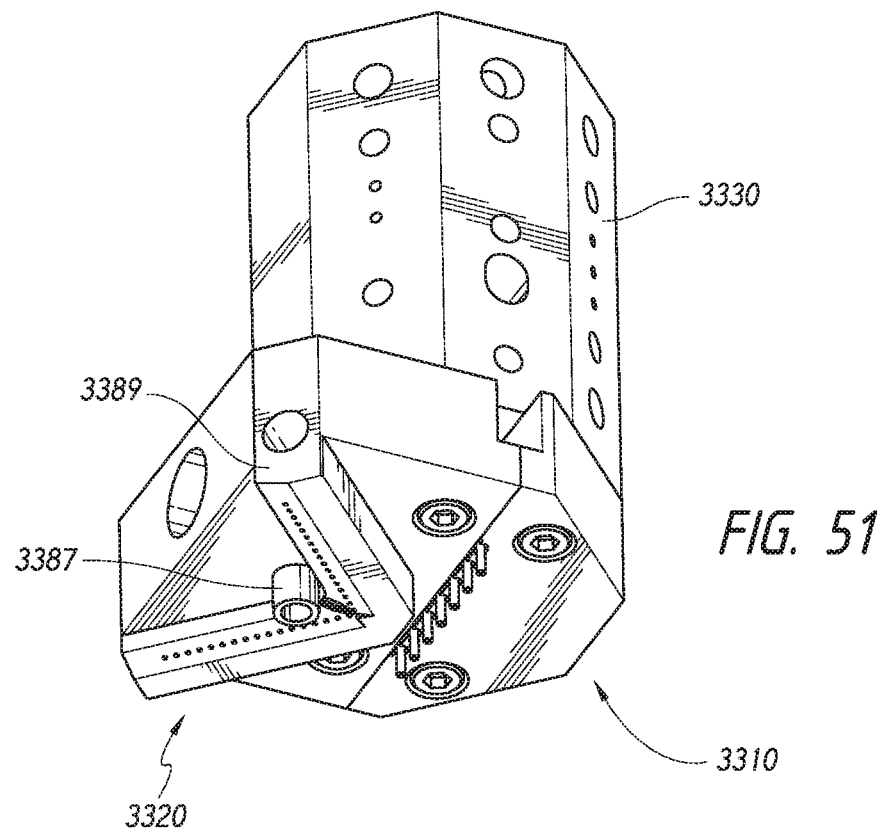
FIG. 51 is an isometric view of a dispenser head in accordance with an embodiment of the present technology.

FIG. 49 is an isometric view of a head assembly 3300 in accordance with an embodiment of the present technology. FIG. 50 is a top plan view of the head assembly 3300. Referring to FIGS. 49 and 50 together, the head assembly 3300 can include a dispenser mechanism 3310 and a liquid removal device 3320. The dispenser mechanism 3310 includes a dispenser head 3330 and valves 3340a, 3340b, 3340c, 3340d (collectively "valves 3340") positioned in a radial arrangement. The valves 3340 control liquid delivery from lines 3350a, 3350b, 3350c, 3350d (collectively "lines 3350"). A vacuum can be drawn via lines 3362, 3364 to evacuate liquid from the dispenser head 3330. Referring now to FIGS. 49 and 51, the liquid removal device 3320 has a line 3380 (FIG. 49) fluidically coupled to the nozzle 3387 (FIG. 51) and lines 3382, 3384 (FIG. 49) fluidically coupled to a V-shaped airknife 3389 (FIG. 51), respectively. Air delivered via the lines 3382, 3384 (FIG. 49) exits the airknife 3389 (FIG. 51).

Figure 52:
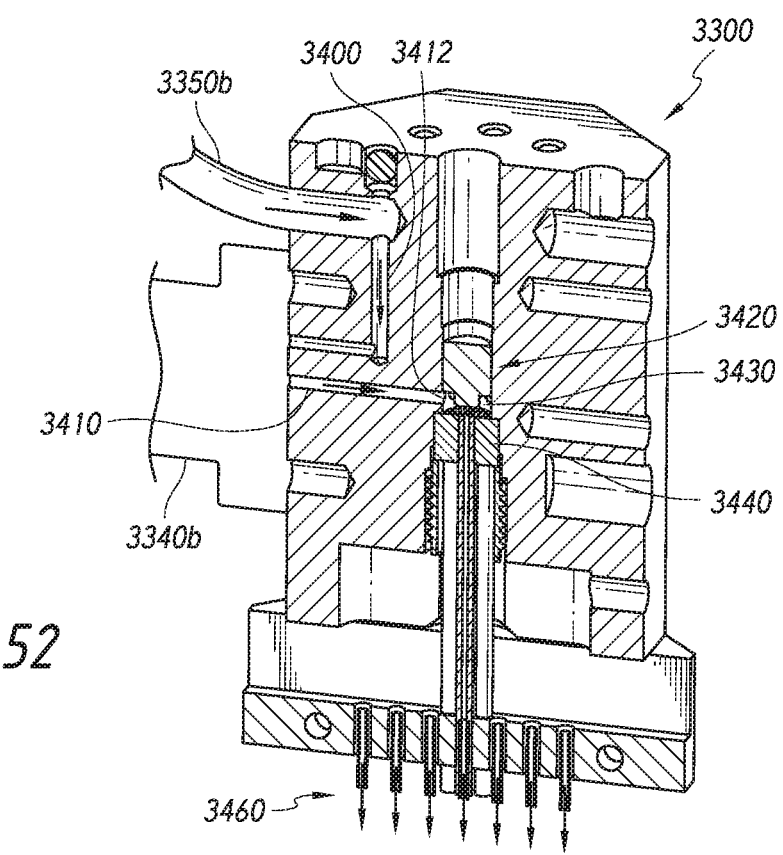
FIG. 52 is a cross-sectional perspective view of the dispenser head taken along line 52-52 of FIG. 50.

FIG. 52 is a cross-sectional view of the head assembly 3300 taken along line 52-52 of FIG. 50. A manifold 3420 includes an inlet 3412, distribution chamber 3430, and a liquid distributor device 3440. The distribution chamber 3430 can have a relatively small volume to minimize or limit the volume of liquid within the head assembly 3300. The inlets 3412 can be circumferentially positioned about the distribution chamber 3430 to help equalize the pressure within the distribution chamber 3430. When the valve 3340b is in an open state, liquid from the line 3350b flows through passageways 3400, 3410, and the inlet 3412. The liquid flows through the distribution chamber 3430 and the liquid distributor device 3440 exits via nozzles 3460.

Figure 53:
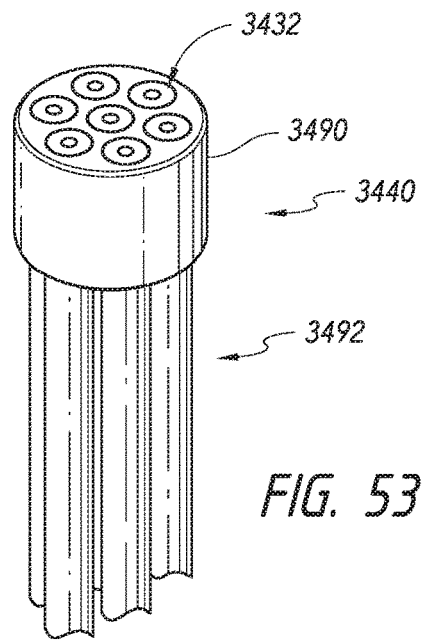
FIG. 53 is an isometric view of a liquid distributor device in accordance with an embodiment of the present technology.

FIG. 53 is an isometric view of the liquid distributor device 3440 in accordance with an embodiment of the present technology. The liquid distributor device 3440 can include a bundle of lines 3492 and a flow separator 3490. In some embodiments, each line 3492 fluidically couples one manifold outlet 3432 of the flow separator 3490 to one nozzle. The liquid distributor device 3440 can have other configurations to distribute liquid to other types of nozzles.

Figure 54:
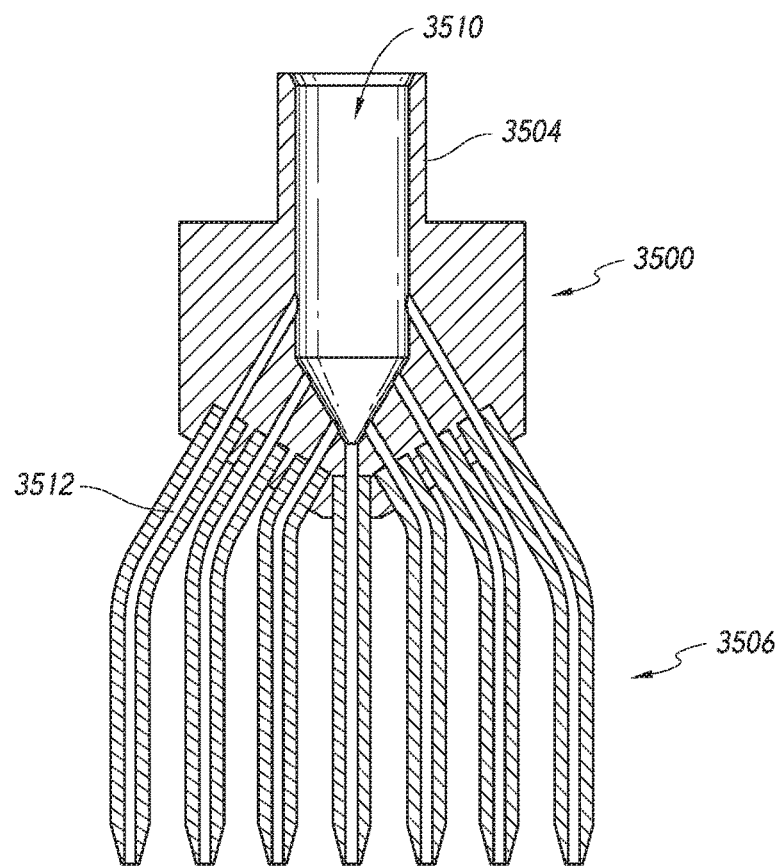
FIG. 54 is a cross-sectional elevation view of a nozzle apparatus in accordance with an embodiment of the present technology.

FIG. 54 is a cross-sectional view of a nozzle apparatus 3500 in accordance with an embodiment of the present technology. The nozzle apparatus 3500 can include a main body 3504 and nozzles 3506 coupled the main body 3504. The nozzle apparatus 3500 can be incorporated into the head assemblies disclosed herein to produce generally uniform flows. Liquid can flow through a main passageway 3510 and nozzle channels 3512 (one identified) of the nozzles 3506. In some embodiments, each line 3492 can be positioned in one of the channels 3512. However, other components and configurations can be used to dispense liquid.

Selected Examples of Liquid Removal in Stainers

Automated histological systems configured in accordance with at least some embodiments of the present technology include stainers having configured to remove dispensed liquid volumes at precisely controlled times without displacing the liquid volumes with other liquids. For example, a processing head configured in accordance with a particular embodiment of the present technology uses an air knife and an associated vacuum port to respectively gather and remove dispensed liquid volumes. This manner of dispensing and removing liquid volumes may facilitate washing and other specimen-processing operations using stationary puddles or thick films with shapes maintained at least partially by surface tension. At least partially uncovering a specimen by manipulating a previously dispensed processing liquid before contacting the specimen with another processing liquid is expected to enhance the consistency and controllability of processing times. By way of theory, and not to limit the scope of the present technology, this advantage may be associated with reducing timing imprecisions associated with imprecise dilution of processing liquids occurring during direct liquid-to-liquid exchanges. Alternatively or in addition, washing a specimen in a stationary pool of liquid may cause residue to be released from the specimen more evenly and precisely than would occur if the specimen were washed in a flowing stream of liquid. Other mechanisms are also possible. Furthermore, the liquid removal features can have different or additional advantages, such as reducing liquid waste.

Figure 55:
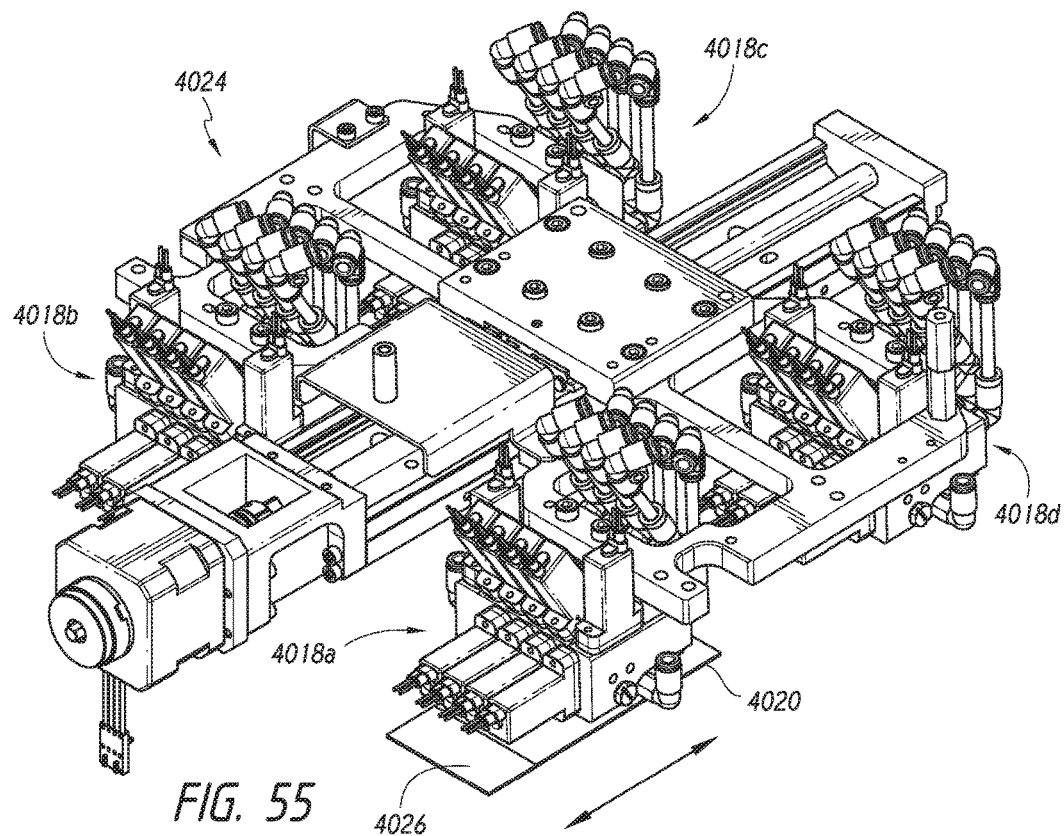
FIG. 55 is an isometric view of a dispenser apparatus in accordance with an embodiment of the present technology.

FIG. 55 is an isometric view of a dispenser apparatus 4024 that includes four head assemblies 4018a, 4018b, 4018c, 4018d (collectively "head assembles 4018"). FIGS.

56-58 illustrate stages of a liquid removal process performed by the head assembly 4018a. With reference to FIGS. 55-58 together, the head assembly 4018a can be positioned above a microscope slide 4020 ("slide 4020") to dispense liquid onto an upper surface of the slide 4020. After the liquid has contacted the specimen for a desired length of time, the head assembly 4018a can blow the liquid along the slide 4020 (e.g., lengthwise) and draw a partial vacuum to contactlessly remove collected liquid from the slide 4020. For example, the head assembly 4018a can move (as indicated by arrows) relative to the slide 4020 while blowing the liquid and simultaneously draw the partial vacuum. Thereafter, additional liquids can be sequentially applied to and removed from the slide 4020. In some cases, dispensing a subsequent liquid begins while a previously dispensed liquid is being removed, such as in the same pass of the head assembly 4018a over the length of the slide 4020. In other cases, removal of a previously dispensed liquid can be complete when dispensing a subsequent liquid begins.

Figure 56:
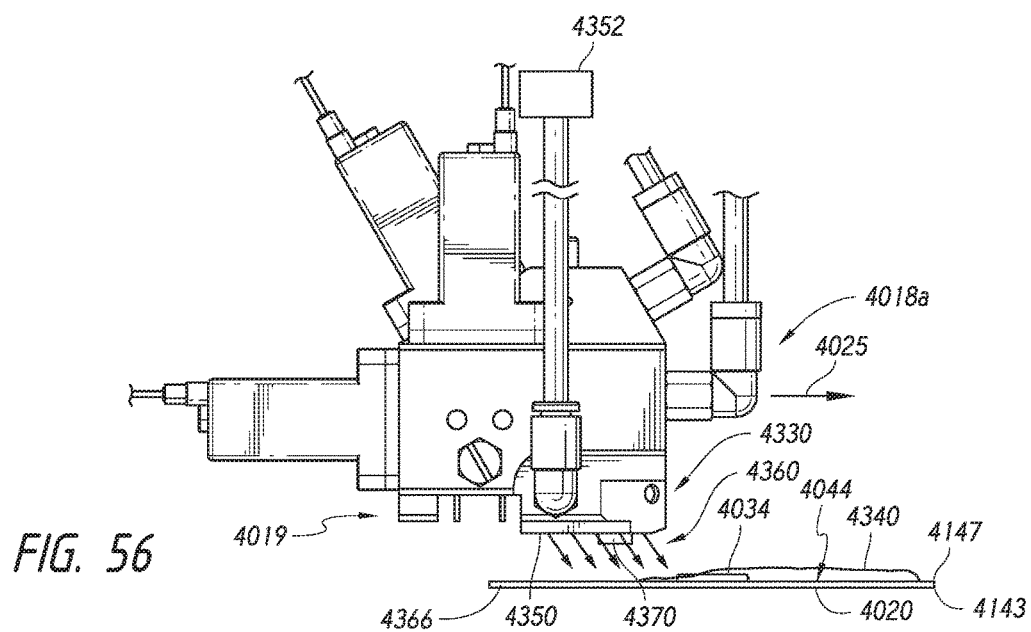
FIGS. 56-58 are side elevation views illustrating stages of a liquid removal process in accordance with an embodiment of the present technology.

Referring to FIG. 56, a sufficient volume of liquid 4340 can be located on the upper surface 4044 of the slide 4020 to maintain a desired liquid volume (e.g., a kinetic liquid volume) throughout most or all of a target time period (e.g., a target incubation time) for contact between the specimen and the liquid 4340. The volume of liquid 4340 can provide sufficient mass for wholly or incrementally processing the specimen 4034 in a desired manner during a predetermined specimen-processing protocol. A flow generator 4352 (e.g., a pump, an air compressor, a blower, a fan, etc.) can pressurize gas (e.g., air, nitrogen, or other gas) that is delivered to a liquid removal device 4330 of the head assembly 4018a. The liquid removal device 4330 receives the pressurized gas and produces a gas curtain 4360 (represented by arrows). As the head assembly 4018a moves (indicated by the arrow 4025) away from an initial position, the gas curtain 4360 pushes the volume of liquid 4340 (e.g., a puddle or a thick film of liquid 4340) toward the end 4143 of the stationary slide 4020 and can also urge the liquid 4340 toward a suction element 4370 of the liquid removal device 4330.

Figure 57:
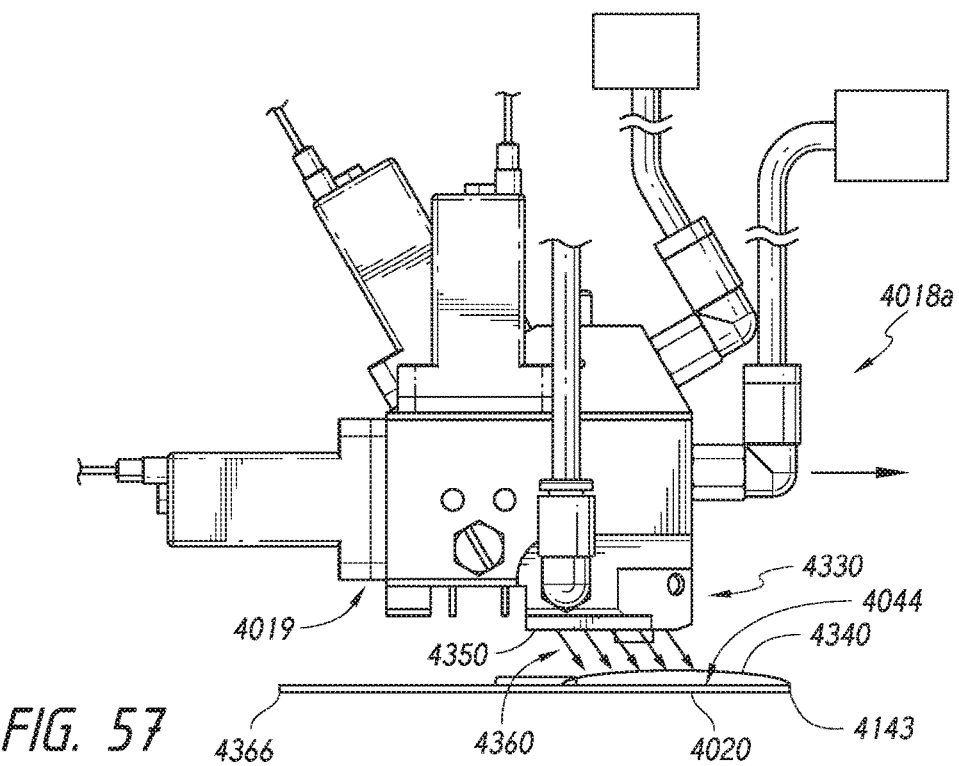

FIG. 57 shows the liquid removal device 4330 at an intermediate position generally midway between the slide ends 4143, 4366. The volume of liquid 4340 is contained on a section of the upper surface 4044 in front of the gas curtain 4360 and a section of the mounting area behind the gas curtain 4360 can be substantially free of the liquid 4340.

Figure 58:
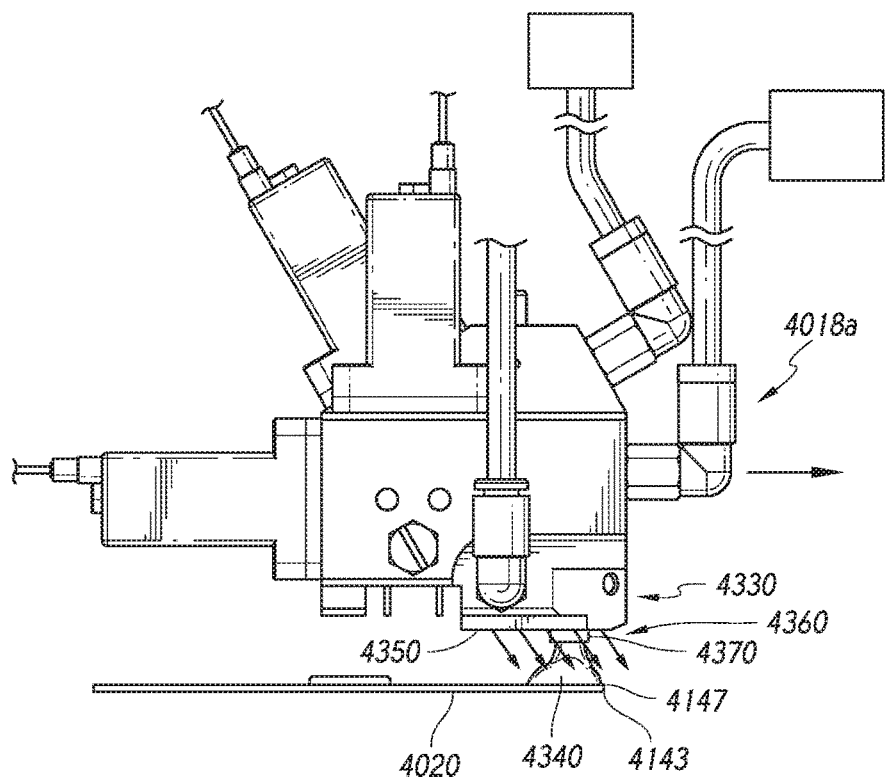

The suction element 4370 can draw a partial vacuum to suck the liquid 4340 from the slide 4020. The head assembly 4018a can continue to move toward the slide end 4143 as and/or until the volume of liquid 4340 is captivated at the slide end 4143. FIG. 58 shows the volume of liquid 4340 captivated by the gas curtain 4360 at an edge 4147 along the slide end 4143. The liquid 4340 can be sucked into the suction element 4370 to limit the volume of liquid 4340, if any, that falls from the slide 4020 into a tray (not shown) carrying the slide 4020. In some embodiments, substantially no liquid 4340 falls from the slide 4020 to keep substantially all processing liquids on-slide.

Figure 59:
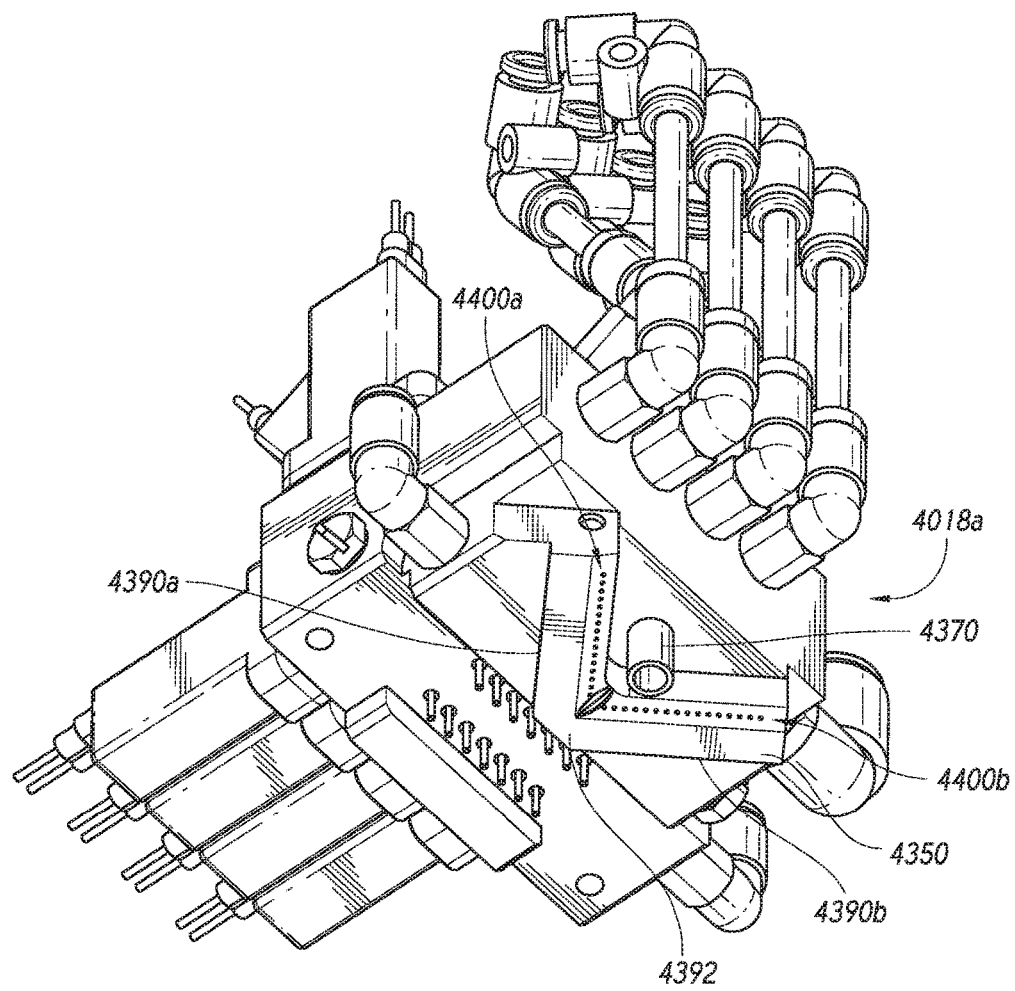
FIGS. 59-61 are isometric, front, and bottom views, respectively, of a head assembly in accordance with an embodiment of the present technology.
Figure 60:
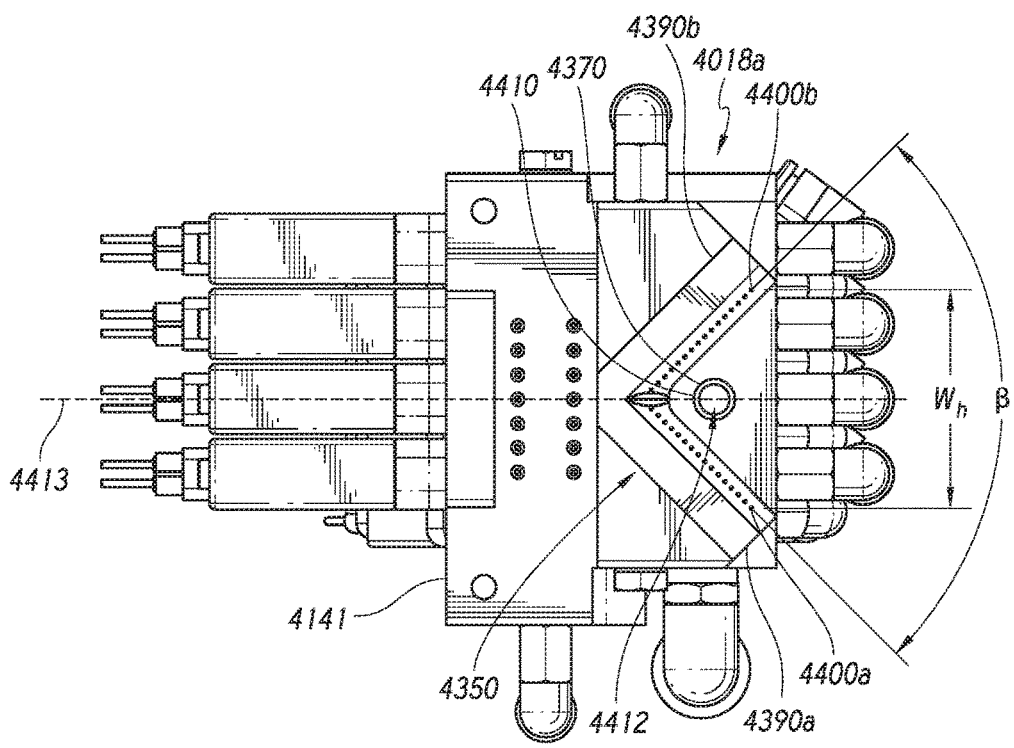
Figure 61:
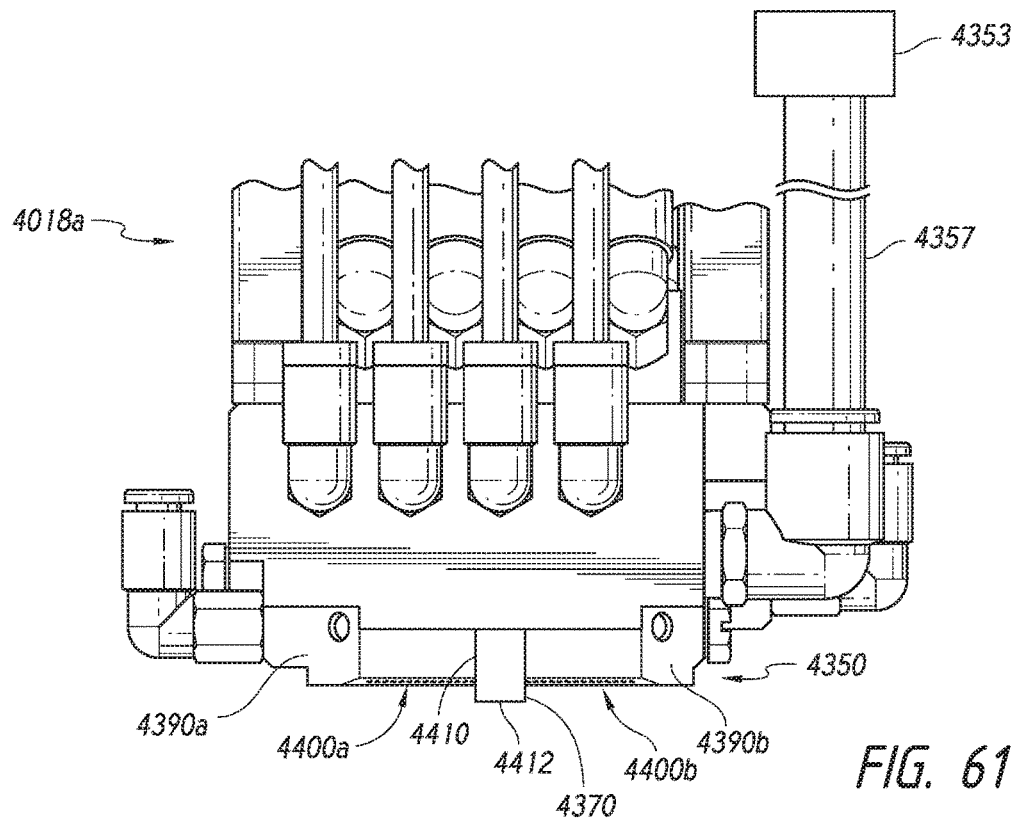

FIGS. 59, 60, and 61 are isometric, bottom, and front views of the head assembly 4018a in accordance with an embodiment of the present technology. A gas knife 4350 can be V-shaped to partially surround the suction element 4370. The gas knife 4350 can be used with a variety of suitable gases, such as air, nitrogen, air/nitrogen mixtures, or other gases compatible with processing liquids and tissue specimens. As such, although the term "airknife" may be used herein for ease of reference, unless the context clearly indicates otherwise, the term refers to gas knives capable of producing gas curtains comprised of any suitable gases. Thus, the gas knife 4350 can output streams of air (e.g., ambient air, filtered air, etc.) to produce an air curtain, streams of nitrogen to produce a nitrogen curtain, or streams of other gases to produce other types of gas curtains.

Referring now to FIG. 59, the gas knife 4350 can include a manifold with side portions 4390a, 4390b and a vertex portion 4392. The side portions 4390a, 4390b are generally similar to one another, and accordingly, the description of one side portion applies equally to the other side portion, unless indicated otherwise. The side portion 4390a can have a number of holes 4400a (one identified) selected based on, for example, the desired width of the gas curtain 4360. In some embodiments, the side portion 4390a has about 10 to about 20 holes. In one embodiment, including the illustrated embodiment, the side portion 4390a has sixteen linearly arranged holes 4400a. To produce a generally uniform substantially V-shaped gas curtain, the holes 4400a, 4400b (collectively "holes 4400") can have a generally uniform pitch (i.e., distances between the centers of adjacent holes 4400). To produce a non-uniform V-shaped gas curtain, the holes 4400 can be unevenly spaced apart. Other numbers, patterns, and spacings of the holes 4400 can be selected based on the desired configuration and shape of the gas curtain.

Referring now to FIG. 60, an angle β can be defined by the series of holes 4400a and the series of holes 4400b and can be selected based on geometric factors, such as the width of a corresponding slide surface and the geometric relationship between the holes 4400 and the suction element 4370. In addition or alternatively, the angle β can be selected based on the properties (e.g., viscosity, spreadability, etc.) of the liquid to be collected. In some embodiments, the angle β is in a range from about 80 degrees to about 100 degrees. In one embodiment, the angle β is about 90 degrees (i.e., 90 degrees+/−3 degrees). In other embodiments, the angle β is greater than 100 degrees to collect a relatively large volume of relatively low viscosity liquid. In yet other embodiments, the angle β is less than 80 degrees to collect a small volume of relatively high viscosity liquid.

A width $W_h$ of the set of holes 4400 is measured in a direction generally perpendicular to either the path of travel of the head assembly 4018a during use or the direction of the longitudinal axis of the slide. In some embodiments, the width $W_h$ is selected such that the gas curtain 4360 extends across the majority of width of the slide 4020. For example, the width $W_h$ can be equal to or greater than about 25 mm, 30 mm, 40 mm, 50 mm, for slides having widths of 25 mm, 30 mm, 40 mm, 50 mm, respectively.

The suction element 4370 can be positioned generally along a centerline 4413 of the dispenser head 4141 of the head assembly 4018a. However, the suction element 4370 can be located at other locations, if needed or desired. The suction element 4370 can include a tubular body 4410 and an inlet port 4412. The tubular body 4410 is spaced apart from the gas knife 4350 such that the inlet port 4412 is positioned directly between the two series of holes 4400a, 4400b. In some embodiments, the inlet 4112 can be positioned rearwardly of the distal or forward holes 4400a, 4400b (i.e., the two holes 4400a, 4400b identified in FIG. 60), which produce leading portions of the gas curtain. The inlet port 4412 can have a circular opening with a maximum width in a range of about 0.5 mm to about 2 mm, from about 0.5 mm to about 4 mm, from about 3.2 mm to about 4 mm, or within another suitable range. In other embodiments, the inlet port 4412 can have non-circular openings (e.g., elliptical openings, polygonal openings, etc.) to achieve a desired vacuum level. Furthermore, the opening of the inlet port 4412 can be flared or annular.

FIG. 61 shows the suction element 4370 extending downwardly past the holes 4400a, 4400b and bottom surface of the gas knife 4350. A line 4357 fluidically couples a vacuum source 4353 to the suction element 4370. The vacuum source 4353 can include one or more pumps or pressurization devices capable of drawing a partial vacuum such that the flow rate through the suction element 4370 is at or above a target flow rate (e.g., 30 liters/minute, 40 liters/minute, 50 liters/minute). In some embodiments, the vacuum source 4353 produces a vacuum pressure in a range of about −10 psi to about −0.5 psi (e.g., −2.2 psi+/−0.2 psi) for producing a flow rate through the suction element 4370 in a range of about 37 liters/minute to 50 liters/minute. Other arrangements (e.g., fluidic systems, vacuum sources, etc.) can be used to provide vacuum pressure to the head assembly 4018a.

Figure 62:
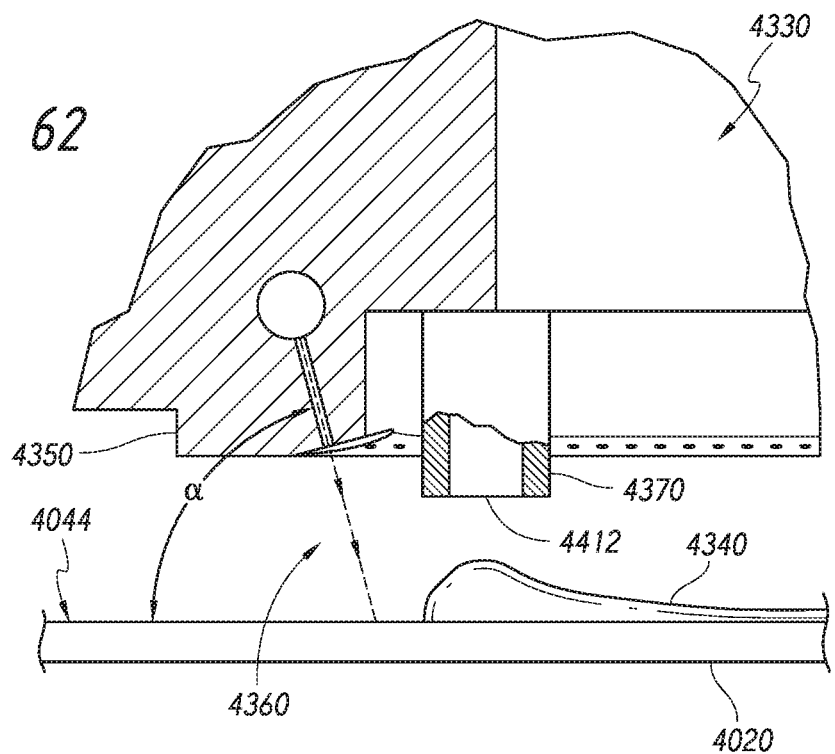
FIG. 62 is a partial cross-sectional side view of a liquid removal device positioned above a microscope slide.
Figure 63:
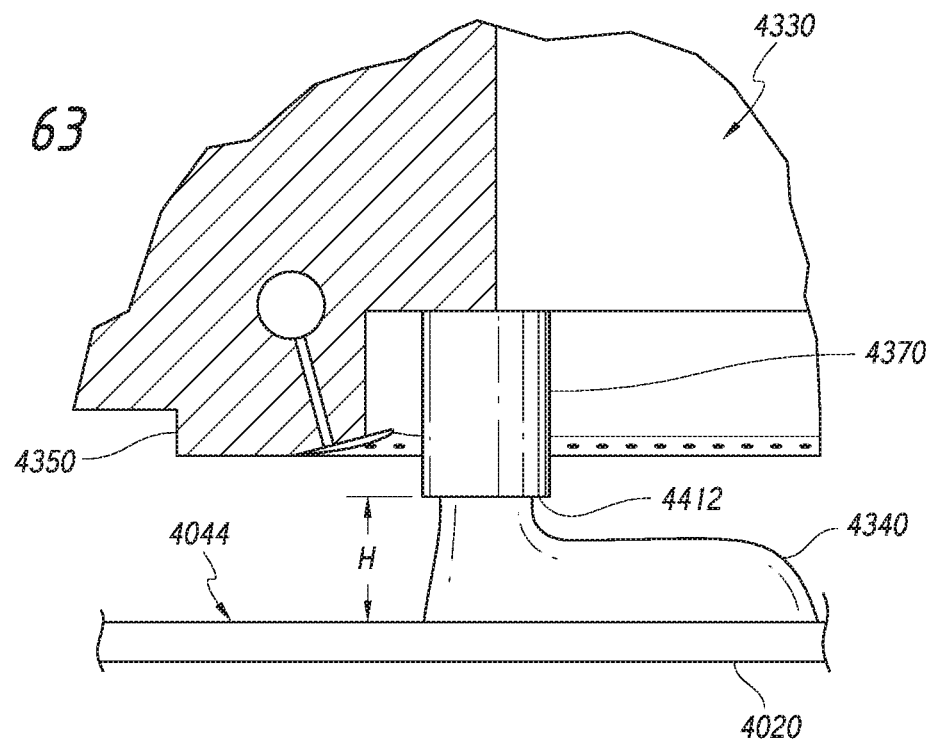
FIG. 63 is a partial cross-sectional side view of the liquid removal device sucking liquid from the slide.

FIGS. 62 and 63 are partial cross-sectional side views of the liquid removal device 4330 positioned above the slide 4020. An angle α (i.e., gas knife angle of attack) between the gas curtain 4360 and the upper surface 4044 of the slide 4020 can be selected based on, without limitation, working pressures, height of the head assembly 4018a, travel speeds of the head assembly, and/or characteristics of the liquid 4340. In some embodiments, the gas curtain 4360 is not perpendicular to the upper surface 4044 of the slide 4020. For example, the angle α can be in a range from about 70 degrees to about 80 degrees. In one embodiment, the angle α is about 4075 degrees (e.g., 75 degrees+/−2 degrees) such that the gas curtain 4360 can effectively push the volume of liquid 4340 along the upper surface 4044 without pushing an appreciable volume of the liquid 4340 off the slide 4020, even when leading portions of the gas curtain 4360 are moved beyond the distal end 4143 of the slide 4020. In one embodiment, the angle α can be about 70 degrees (e.g., 70 degrees+/−2 degrees) to enhance pushing of relatively high viscosity liquids. A constant angle α across the width of the slide 4020 can be selected to push a volume of liquid with generally uniform properties. In other embodiments, a varying angle α can be selected to push a volume of liquid with non-uniform properties. For example, a portion of the gas curtain defining a relatively small angle α can be well suited to push a low viscosity liquid and a portion of the gas curtain defining a relatively large angle α can be well suited to push a high viscosity liquid. Other angles of attack can also be used because the distribution of residual liquid on the slide 4020 can be largely influenced by the gas knife angle α, as well as movements of the head assembly across the slide 4020 and the height of the head assembly relative to a slide 4020.

FIG. 63 shows the suction element 4370 drawing a partial vacuum sufficient to draw the liquid 4340 upwardly through the inlet port 4412 without a solid structure of the head assembly contacting the volume of liquid 4340 and/or the slide 4020. The gas knife pressures can be sufficiently low to minimize or limit overwetting and sufficiently high to keep residual volumes at or below a target level. A height H of the inlet port 4412 can be about 0.8 mm to about 3 mm to achieve relatively low residual volume levels on the slide 4020. In one embodiment, the height H is in a range of about 1 mm to about 2 mm (i.e., 1 mm to 2 mm+/−0.5 mm), but other heights can be selected based on the vacuum level. In some embodiments, the flow rate through the suction element 4370 can be in a range of about 37 liters/minute to about 50 liters/minute at a dynamic pressure between about −1 psi to about −0.2 psi, such as about −0.38 to about −0.3 psi for a height H equal to or less than about 3 mm. However, other heights and pressures can be used based on the liquid properties that impact fluid dynamics, such as viscosity, surface tension, density, or the like. In some embodiments, the suction element 4370 is configured to produce a vacuum level in a range of about 12 mmHg to about 35 mmHg. The operation of the vacuum source 4353 can be adjusted to achieve such vacuum levels or other desired vacuum levels.

FIGS. 64A-66B illustrate stages of removing the liquid 4340 from the slide 4020. After the liquid 4340 has contacted the specimen 4034 for a desired length of time, the gas knife 4350 can deliver one or more streams of gas toward the slide 4020 to produce the gas curtain 4360. The gas knife 4350 can be configured to produce the gas curtain 4360 using no more than one stream of gas or using two or more streams of gas. Before, during, and/or after moving the liquid removal device 4330, the head assembly 4018 can contactlessly remove liquid 4340 from the slide 4020 using the suction element 4370. As the gas knife 4350 moves relative to the slide 4020, for example, the gas curtain 4360 can confine and move the volume of liquid 4340 away from longitudinal edges 4540, 4542 of the slide 4020 while the suction element 4370 draws a partial vacuum to remove the liquid 4340 from the slide 4020 without physically contacting the slide 4020. Different stages of the liquid removal process are discussed below.

Figure 64A:
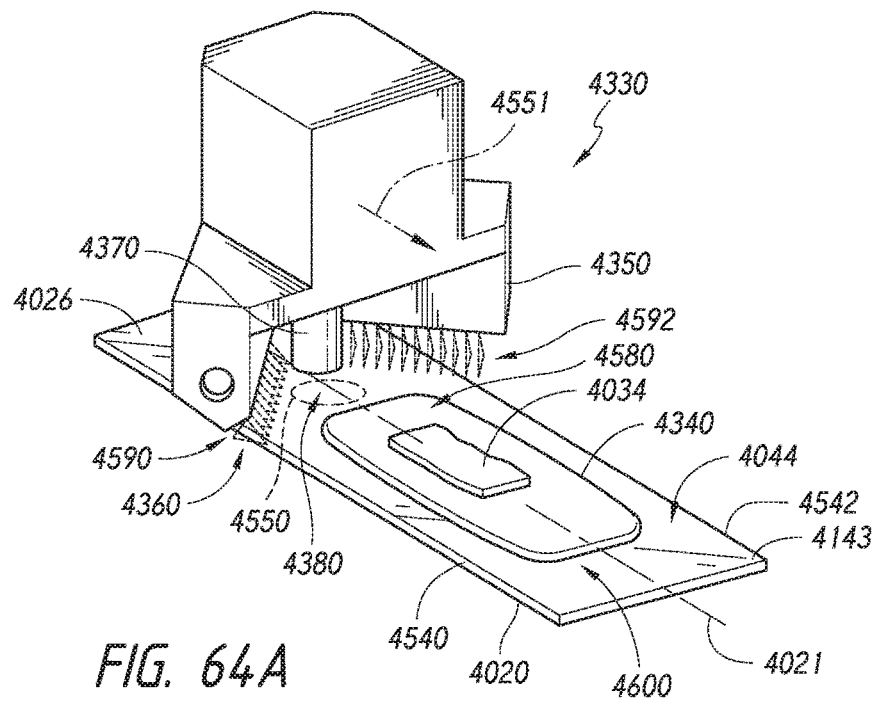
FIG. 64A is an isometric view of a liquid removal device producing a gas curtain positioned along a microscope slide in accordance with an embodiment of the present technology.
Figure 64B:
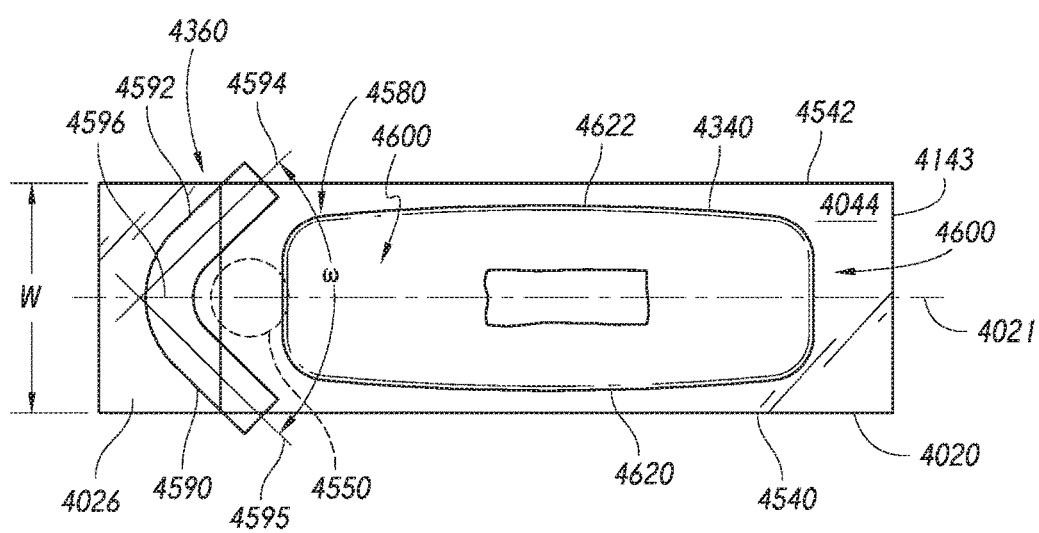
FIG. 64B is a top plan view of the gas curtain and the slide of FIG. 64A.

FIG. 64A shows the liquid removal device 4330 and the substantially V-shaped gas curtain 4360 positioned along the slide 4020. FIG. 64B is a top plan view of the gas curtain 4360 and the slide 4020. Referring to FIGS. 64A and 64B together, the liquid removal device 4330 is located at an initial position and directs the gas curtain 4360 (shown in FIG. 64B) toward the upper surface 4044. The volume of liquid 4340 can be a film (e.g., a thick-film) or puddle with a shape at least partially maintained by surface tension. The gas curtain 4360 in the initial position can be located along the label 4026. In other embodiments, most or all of the gas curtain 4360 in the initial position can be located beyond the label end 4366 of the slide 4020 to enable liquid removal from the most or all of the label 4026. Vacuum collection, however, can be delayed to start beyond the retaining features (e.g., slide retainer, clips, clamps, etc.) that hold the label end 4364 of the slide 4020 so as to prevent liquid 4340 from being actively pulled into retaining features of the slide tray. In yet other embodiments, the gas curtain 4360 in the initial position can be located along the mounting area of the slide 4020, and vacuum collection can begin prior to or after moving the gas curtain 4360 along the slide 4020.

The gas consumption/flow rate of the gas knife 4350 can be in a range of about 8 liters/minute to about 9 liters/minute, for example, about 8.6 liters/minute to provide an input gas knife pressure of about 7 psi+/−0.2 psi. Excessively high gas knife pressures and/or flow rates could lead to loss of removed liquid distribution (overwetting) and excessively low pressures and/or flow rates could lead to residual high residual volumes. The gas knife 4350 and suction element 4370 cooperate to produce a pressure differential to urge the proximal region 4580 of the volume of liquid 4340 away from the longitudinal edges 4540, 4542. In some embodiments, the gas knife 4350 and the suction element 4370 produce a low pressure region 4380 (FIG. 64A) at least partially defining a collection zone 4550 (illustrated in phantom line) in which the liquid 4340 tends to collect. The collection zone 4550 can be positioned directly below the inlet port 4412 of the suction element 4370. For example, the inlet port 4412 can be positioned proximate to the vertex 4596 (FIG. 64B) of the gas curtain 4360 such that most of the collection zone 4550 is positioned generally underneath the inlet port 4412. The vertex 4596 can be angled or curved.

Referring now to FIG. 64B, the gas curtain 4360 has curtain portions 4590, 4592 and a vertex section 4596. The curtain portions 4590, 4592 can be positioned along imaginary planes 4594, 4595 that intersect at an angle ω in a range from about 80 degrees to about 100 degrees. The vertex section 4596 can be moved along a central region 4600 of the upper surface 4044 such that the curtain portions 4590, 4592 confine the proximal region 4580 of the volume of liquid 4340. As the liquid removal device 4330 moves lengthwise along the slide 4020, a pressure differential can urge the liquid 4340 toward a central longitudinal axis 4021 of the slide 4020, as well as the collection zone 4550. In some embodiments, the gas curtain 4360 can be a generally uniform gas curtain that extends across the width W of the slide 4020. For example, the gas curtain 4360 can be generally uninterrupted and continuous gas curtain that extends between the longitudinal edges 4540, 4542.

Figure 65A:
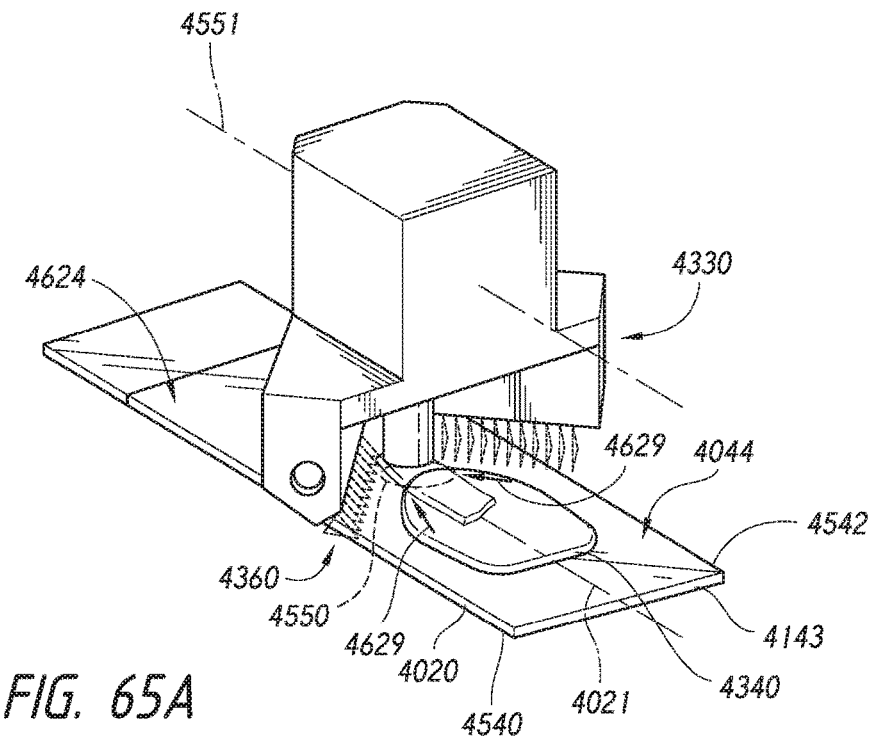
FIG. 65A is an isometric view of the liquid removal device collecting liquid using the gas curtain.
Figure 65B:
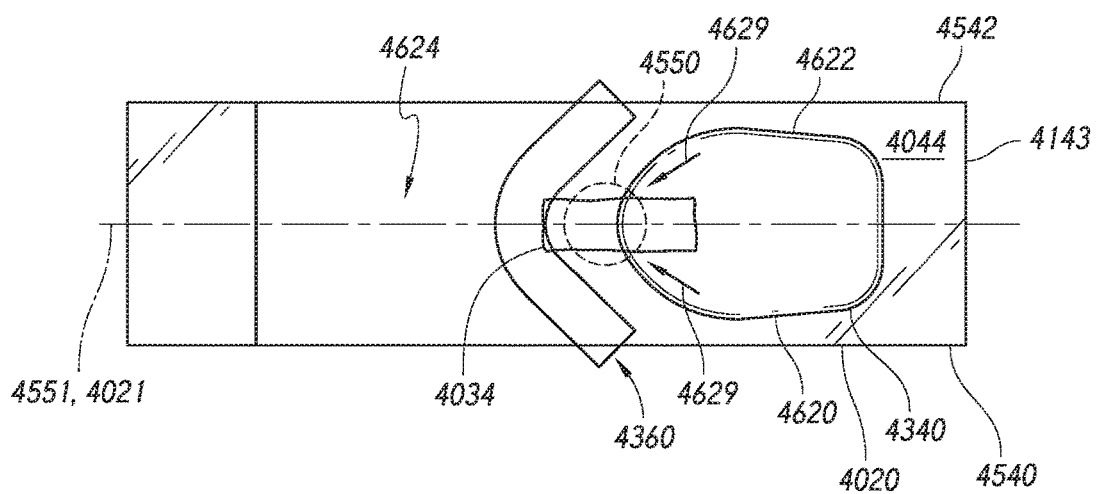
FIG. 65B is a top plan view of the gas curtain and slide of FIG. 65A.

FIGS. 65A and 65B show the liquid removal device 4330 moving along a processing path 4551 generally parallel to the longitudinal axis 4021 of the slide 4020. The suction element 4370 can provide a partial vacuum to produce a low pressure region at the collection zone 4550 where the suction (flow) of the liquid 4340 can occur. A pressure gradient between the low pressure region and the ambient pressure, along with the gas flow interaction between the gas knife 4350 and the suction element 4370, can urge the liquid 4340 toward the collection zone 4550. A region 4624 of the upper surface 4044 positioned behind the gas curtain 4360 can be substantially free of the liquid 4340. There may be, however, a small volume of residual liquid on the region 4624, but most of the total volume of the liquid 4340 on the slide 4020 can be located between the gas curtain 4360 and the end 4143 of the slide 4020. Depending on the characteristics (e.g., surface tension) of the liquid 4340, most or substantially all of the volume of liquid 4340 can be kept in front of the gas curtain 4360 moving along processing path 4551. As the gas curtain 4360 advances distally, the liquid 4340 tends to flow along the curtain portions 4590, 4592, respectively, as indicated by arrows 4629, and the curtain portions 4590, 4592 can urge outer portions 4620, 4622 (FIG. 65B) of the puddle of liquid 4340 away from the longitudinal edges 4540, 4542, respectively, to reduce the likelihood of liquid 4340 falling off the slide 4020. Advantageously, the lengthwise movement and position of the gas curtain 4360 allows the head assembly 4018 to be moved at relatively high speeds while keeping the volume of liquid 4340 on the slide 4020.

The gas knife 4350 and suction element 4370 can be aligned with the slide 4020 such that the liquid 4340 is effectively directed by the gas curtain 4360 toward the suction element 4370 because widthwise position of the liquid removal device 4330 relative to slide edges 4540, 4542 can impact residual volume and residual liquid distribution. As the liquid removal device 4330 moves relative to the slide 4020, the collection zone 4550 can be positioned generally along the central region 4600 of the upper surface 4044. In some embodiments, the gas curtain 4360 and the collection zone 4550 can be centrally aligned above the slide 20 within +/−0.05 inch (1.27 mm) of the longitudinal axis 4021. If the suction element 4370 is not close enough to the upper surface 4044, higher residual volumes can also result. As such, the position of the collection zone 4500, height of the gas knife 4350, height of the suction element 4370 can be selected to achieve desired liquid removal (including amount and distribution of residual volumes)

Figure 66A:
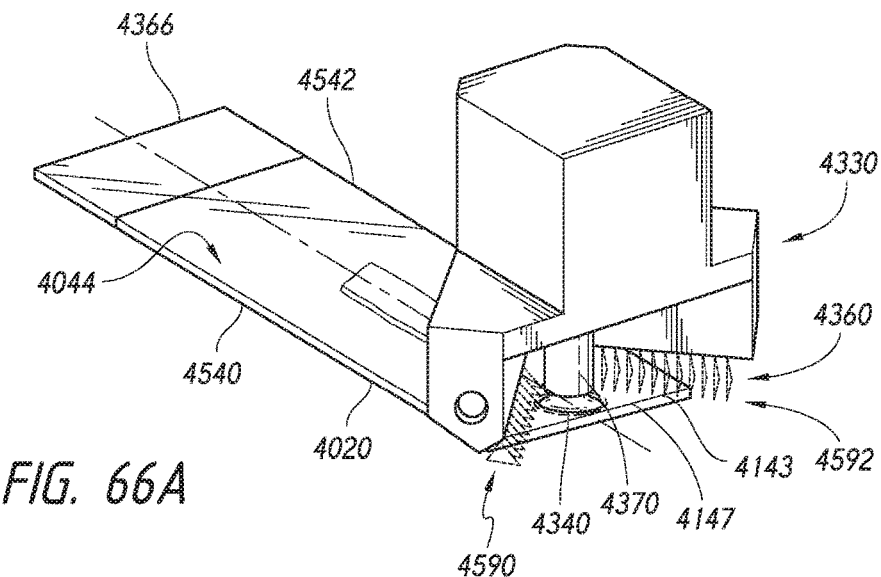
FIG. 66A is an isometric view of the liquid removal device captivating liquid at an end of the slide.
Figure 66B:
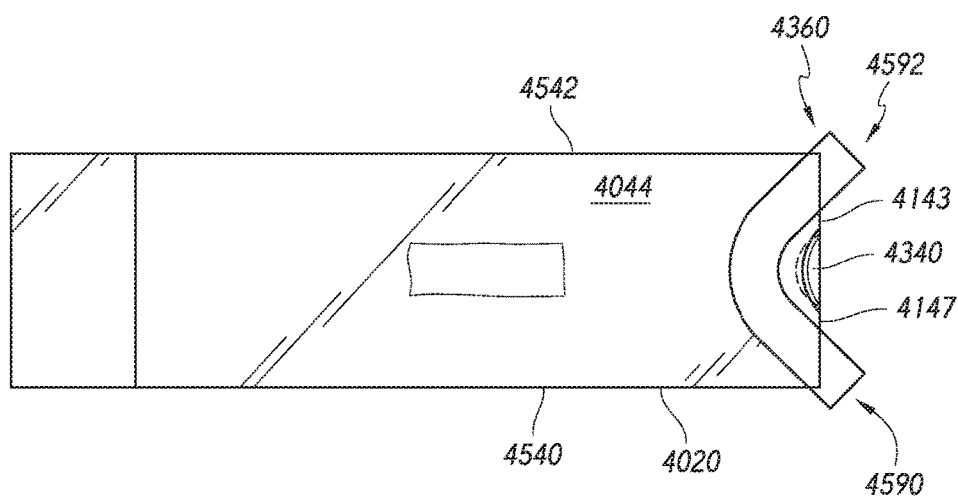
FIG. 66B is a top plan view of the gas curtain and slide of FIG. 66A.

FIG. 66A shows the liquid removal device 4330 positioned at the end 4143 of the slide 4020. FIG. 66B is a top plan view of the gas curtain 4360 of FIG. 66A. The curtain portions 4590, 4592 can extend outwardly past the longitudinal edges 4540, 4542, respectively, and the edge 4147 such that the volume of liquid 4340 is contained by the gas curtain 4360 and the slide edge 4147. The gas knife 4350 and vacuum can be turned off when the suction element 4370 reaches the end 4143 of the slide 4020 to prevent liquid overwetting to the back side of the slide 4020 and, in some embodiments, also leaves a residual droplet (e.g., a small residual droplet at location along the upper surface 4044 underneath the suction element 4370). The size of the droplet can be minimized or limited by the configuration of gas knife 4350 and vacuum characteristics defined by, for example, supply pressures, fluidic design, the geometrical relationship between the gas knife 4350 and the vacuum, and/or the height of the suction element 4370 and gas knife 4350 with respect to the upper surface 4044. If the suction element 4370 is too far off/beyond the upper surface 4044 (or off the edge 4147), liquid capture can be affected and, in some embodiments, may lead to higher residual volumes and potential for overwetting. Thus, the end position of the suction element 4370 can be selected to achieve desired liquid removal while residual volumes and/or overwetting.

To minimize or limit the gap between the inlet port 4412 and the upper surface 4044 of the slide 4020 at the distal end 4143 of the slide 4020, a fixed nominal vertical (e.g., Z-axis) slope is designed into the gas knife assisted vacuum movement axis, bringing the suction element 4370 closer to the upper surface 4044 at the slide end 4143 than at the label end 4366 to achieve relatively small gaps while preventing interferences between the head assembly 4018 and slide and tray features. In some embodiments, the height of the suction element 4370 at the end 4143 can be equal to or less than about 2 mm+1 mm/−0.5 mm.

The liquid removal process of FIGS. 64A-66B can be performed to remove most or substantially all the volume of liquid 4340. In some embodiments, the liquid removal device 4330 can remove at least 90% of the volume of liquid on the upper surface 4044. In other embodiments, the suction element 4370 and gas knife 4350 are configured to cooperate to remove at least 95%, 98%, or 99% by volume of liquid 4340 from the upper surface 4044. Additionally or alternatively, the liquid removal process can be controlled based on target maximum residual volumes. In some embodiments, the liquid removal device 4330 can remove a sufficient volume of the liquid 4340 such that a maximum residual volume on the upper surface 4044 after liquid removal is less than the maximum residual volume. In one process, the volume of liquid 4340 on the upper surface 4044 can be about 0.5 mL to about 0.9 mL of processing liquid, and liquid removal device 4330 can remove a sufficient volume of liquid such that the maximum residual volume of liquid 4340 on upper surface 4044 is equal to or less than about 50 μL. The liquid removal device 4330 can also remove other volumes of liquid to keep the maximum residual volume of liquid on the slide 4020 at or below an acceptable volume, such as 30 μL for deparaffinizating liquids, conditioning liquids (e.g., bridging liquids), washing liquids, and stain-differentiating reagents, 20 μL for staining reagents (e.g., hematoxylin reagents), counterstaining reagents (e.g., eosin reagents), and stain-setting reagents (e.g., bluing), and 10 μL to limit or prevent interference with subsequent processing. For example, the maximum residual volume of conditioning liquid can be kept sufficiently low to prevent interference with subsequent coverslipping, enhance handability, meet archivalability requirements, and/or limit the release of undesirable fumes.

In some embodiments, the gas knife 4350 and suction element 4370 cooperate to draw the liquid 4340 from the slide 4020 while keeping a total volume of the liquid, if any, that falls off the slide 4020 equal to or less than a maximum fall-off volume. The fall-off volume can be equal to about 5%, 3%, or 2% by volume of a total volume of liquid 4340 on the slide 4020 prior the beginning the liquid removal process. As such, the gas knife 4350 and suction element 4370 can be configured to cooperate to draw at least about 95%, 97%, or 98% of the free-standing volume of the liquid 4340 (i.e., liquid 4340 located along the surface 4044 and not incorporated into the specimen 4034) into the suction element 4370.

Figure 67:
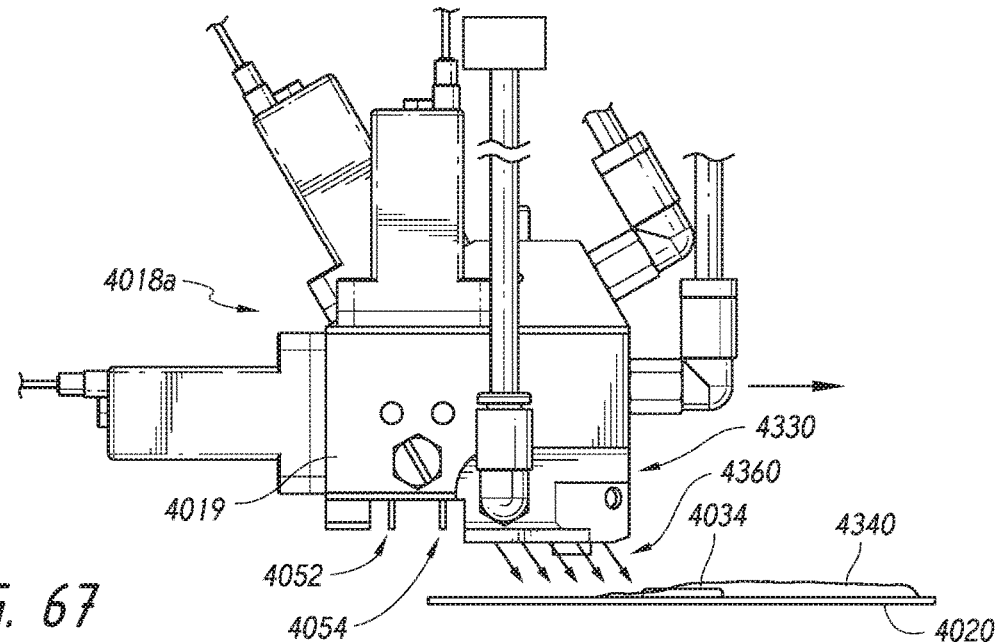
FIGS. 67-70 are side elevation views illustrating stages of removing and dispensing liquids in accordance with an embodiment of the present technology.
Figure 68:
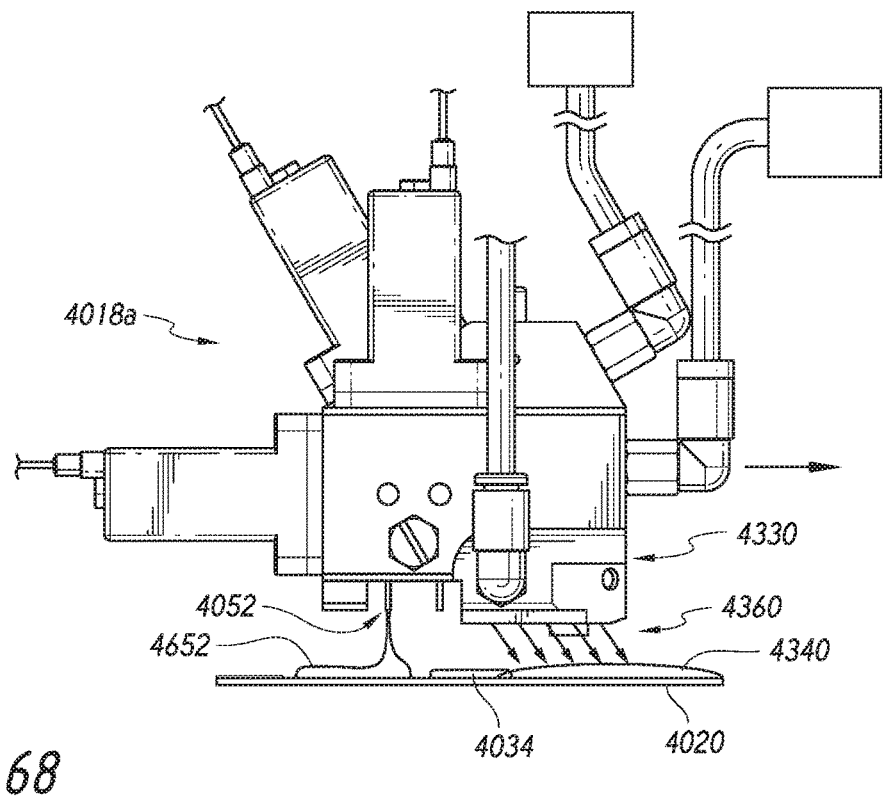
Figure 69:
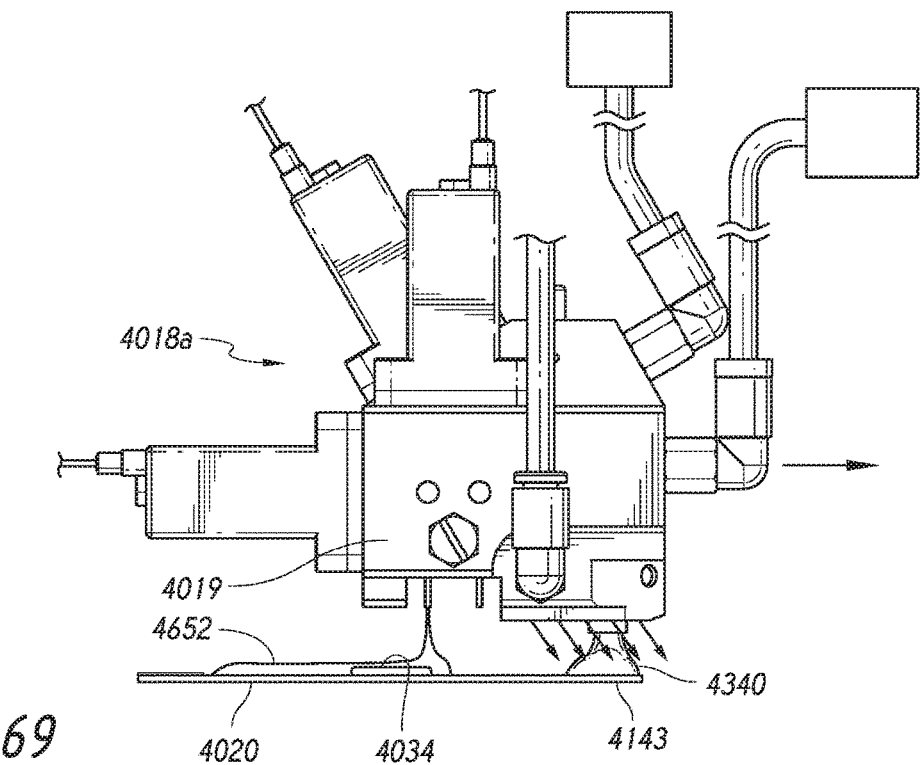
Figure 70:
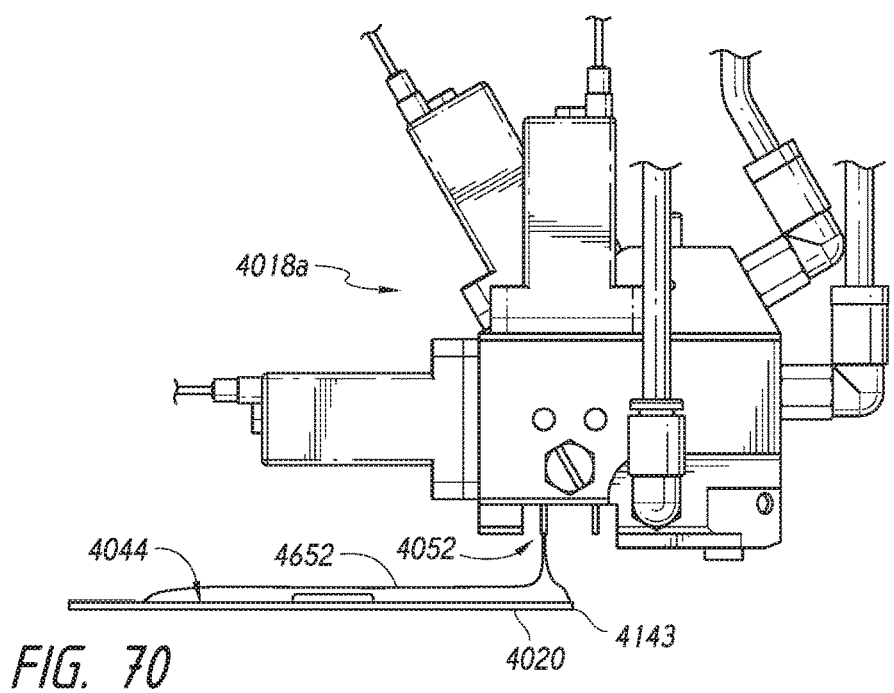

FIGS. 67-70 illustrate stages of removing the liquid 4340 and dispensing another liquid 4652. Generally, the head assembly 4018a can move and/or remove at least portion of the volume of liquid 4340 from the specimen 4034 so as to at least partially uncover the specimen 4034. The head assembly 4018a can dispense liquid 4652 that contacts the uncovered specimen 4034. This process can be repeated to sequentially remove and dispense any number of liquids. FIG. 67 shows the specimen-bearing slide 4020 after the head assembly 4018a has begun uncovering the specimen 4034. Once the nozzles 4052 or nozzles 4054 of the dispenser mechanism 4019 are positioned above the slide 4020, another liquid can be dispensed. The head assembly 4018a can move along the slide 4020 to further uncover the specimen 4034. FIG. 68 shows the specimen-bearing slide 4030 after most of the specimen 4034 has been uncovered. The nozzles 4052 are dispensing liquid 4652 onto the mounting area of the slide 4020 located behind the gas curtain 4360, which serves as a barrier to prevent contact between the volume of the liquid 4340 and the volume of the liquid 4652. As the head assembly 4018a moves and continuously or intermittently dispenses liquid 4652 along the slide 4020, the liquid removal device 4330 can continuously or intermittently remove the liquid 4340 from the slide 4020. FIG. 69 shows the liquid 4652 contacting the specimen 4034 and the suction element 4370 drawing the liquid 4340 from the end 4143 of the slide 4020. As the head assembly 4018a continues to move past the end 4143 of the slide 4020, the dispenser mechanism 4019 can deliver the liquid 4652 to cover the desired length of the mounting area of the slide 4020. FIG. 70 shows the nozzles 4052 positioned generally above the end 4143 of the slide 4020. Most or all of the mounting area of the upper surface 4044 can be covered by the volume of liquid 4340.

The removal and dispense process of FIGS. 67-70 can be used to remove the bulk of staining, counterstaining, and stain-setting reagents without displacing these reagents with continuously flowing washing liquid. This may improve stain quality, counterstain quality, stain controllability, counterstain controllability, and/or other aspects of specimen processing. For example, when the bulk of staining, counterstaining, and stain-setting reagents are displaced with continuously flowing washing liquids, minor changes in the attributes (e.g., stain intensity, counterstain intensity, stain hue, and/or counterstain hue) of specimens may occur. Although often subtle, attribute changes during exchange periods may tend to be imprecise and/or irregular. Therefore, reducing or eliminating attribute changes during exchange periods can be desirable. In at least some cases, removing the bulk of staining, counterstaining, and stain-setting reagents with gas and then removing residual volumes of these reagents with generally stationary volumes of washing liquid is expected to reduce or eliminate attribute changes during exchange periods.

Figure 71:
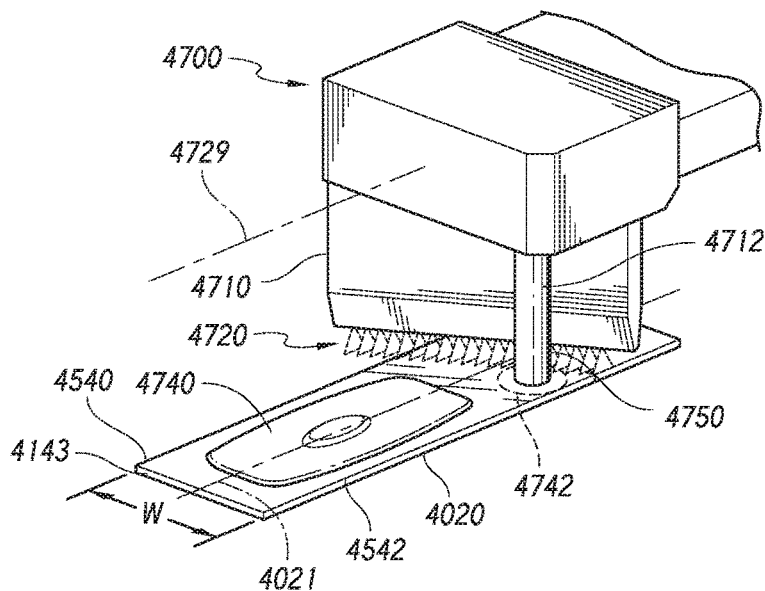
FIG. 71 is an isometric view of a liquid removal device with a linear gas knife in accordance with an embodiment of the present technology.

FIG. 71 is an isometric view of a liquid removal device 4700 with a linear (e.g., uniplanar) gas knife 4710 and a suction element 4712. The gas knife 4710 has a plurality of spaced apart holes configured to generate a gas curtain 4720. The illustrated linear gas curtain 4720 extends across the width W of the slide 4020 such that the gas curtain 4720 extends past the edge 4540 of the slide 4020. The gas knife 4710 can be moved along a processing path 4729 that is generally parallel to a center line or central longitudinal axis 4021 of the slide 4020. The advancing gas curtain 4720 can tend to urge a volume of liquid 4740 toward a low pressure collection zone 4742 (illustrated in phantom line), which is positioned proximate to the edge 4542 of the slide 4020. The suction element 4712 has an inlet nozzle 4750 with an inlet port 4752 positioned to draw in liquid (e.g., collective liquid) at the collection zone 4742.

Figure 72:
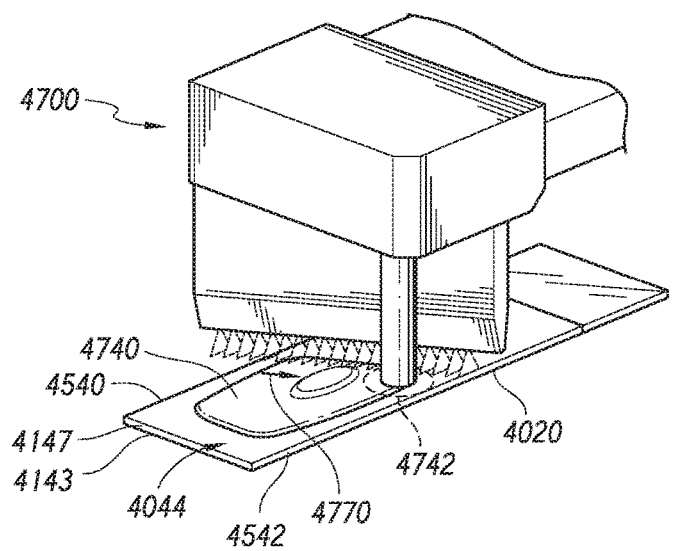
FIG. 72 is an isometric view of the liquid removal device of FIG. 71 collecting liquid along the slide.

FIG. 72 shows the liquid removal device 4700 pushing the liquid 4740 along the slide 4020 while the suction element 4712 sucks in liquid 4740. As the liquid removal device 4700 advances distally toward the end 4143 of the slide 4020, the liquid 4740 tends to flow along the gas curtain 4720 as indicated by arrow 4770. As such, the liquid 4740 can be moved away from the longitudinal edge 4540. If the liquid 4740 reaches the edge 4147, surface tension can help keep the liquid 4740 on the upper surface 4044 of the slide 4020.

Figure 73:
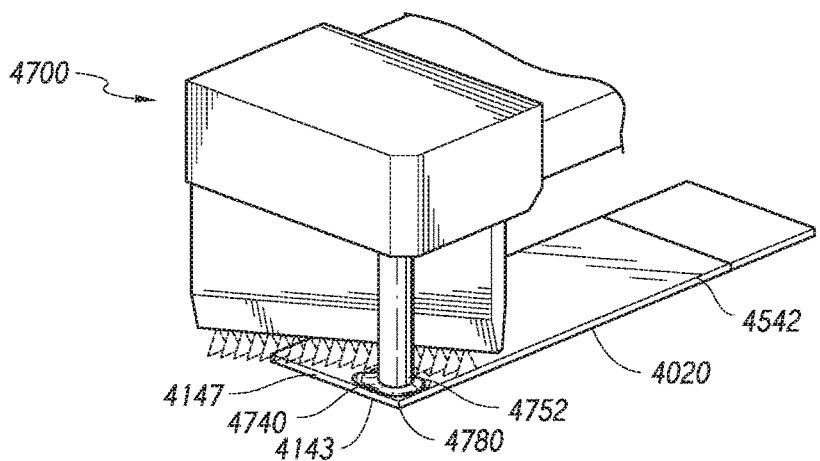
FIG. 73 is an isometric view of the liquid removal device of FIG. 71 removing liquid captivated at a corner of the slide.

FIG. 73 shows the inlet port 4752 positioned at a corner 4780 of the slide 4020. The liquid 4740 is captured between the edges 4147, 4542. In some embodiments, the height of inlet port 4752 can decrease as it approaches the corner 4780 to help pick up the volume of liquid 4740.

Figure 74:
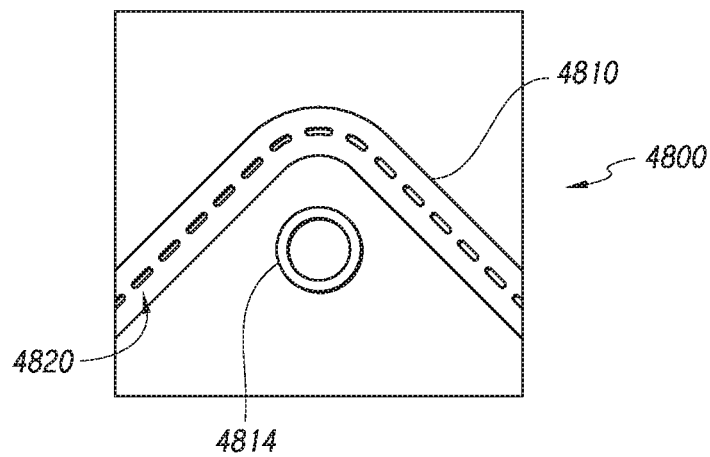
FIG. 74 is a bottom view of a liquid removal device with a gas knife having elongated slots in accordance with an embodiment of the present technology.
Figure 75:
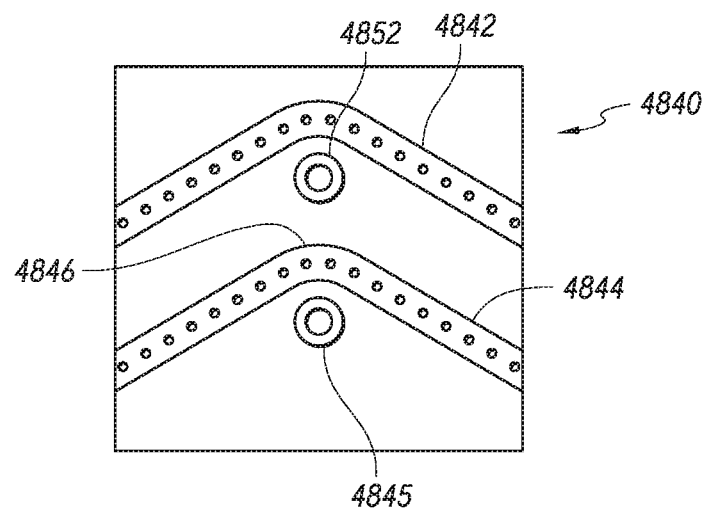
FIG. 75 is a bottom view of a liquid removal device with two gas knives in accordance with an embodiment of the present technology.

Liquid removal devices of the present technology can have a wide range of different types of outlets and gas knives. FIG. 74 is a bottom view of a liquid removal device 4800 including a nonlinear (e.g., multiplanar or nonplanar) gas knife 4810 and a suction element 4814 in accordance with an embodiment of the present technology. The gas knife 4810 can be V-shaped and has a series of elongated slots 4820 through which gas flows to produce a gas curtain. In other embodiments, the gas knife 4810 can be a U-shaped gas knife. The dimensions (e.g., lengths, widths, etc.) of the elongated slots 4820 can be selected to achieve a desired gas curtain. The liquid removal devices can have any number of gas knives of different configurations, including V-shape configurations, U-shape configurations, linear configurations. FIG. 75 is a bottom view of a liquid removal device 4840 with two gas knives 4842, 4844 in accordance with an embodiment of the present technology. A suction element 4852 is located between the gas knives 4842, 4844, and a suction element 4845 is proximate to a vertex 4846 of the gas knife 4844. In operation, the leading gas knife 4844 and suction element 4845 can cooperate to remove most of a volume of liquid on a microscope slide. Residual volumes of liquid can be subsequently removed using the trailing gas knife 4842 and suction element 4852.

The liquid removal devices discloses herein can include a plurality of suction elements capable of simultaneously or sequentially removing liquid from a microscope slide. By way of example, a plurality of suction elements can be positioned between the sides of a gas curtain. The number, position, and spacing of the suction elements can be selected based on the configuration of the gas curtain. For example, two suction elements can be used with a W-shaped gas knife that produces a W-shaped gas curtain. Other numbers of suction elements can be utilized for gas knives having other configurations.

Figure 76:
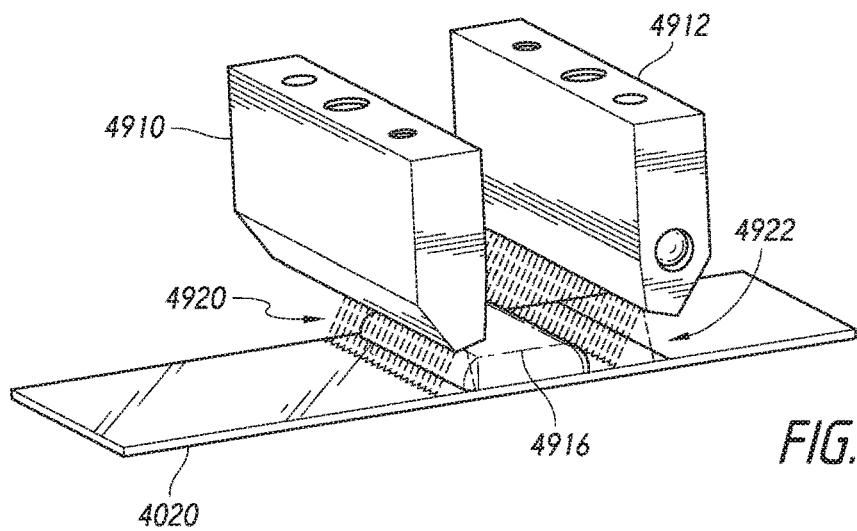
FIG. 76 is an isometric view of two gas knives in accordance with an embodiment of the present technology.
Figure 77:
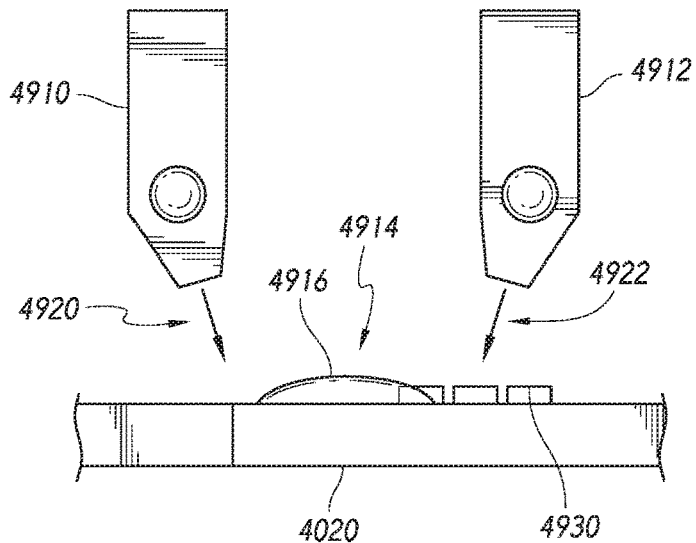
FIGS. 77 and 78 are side elevation views of two gas knives captivating liquid on a microscope slide.
Figure 78:
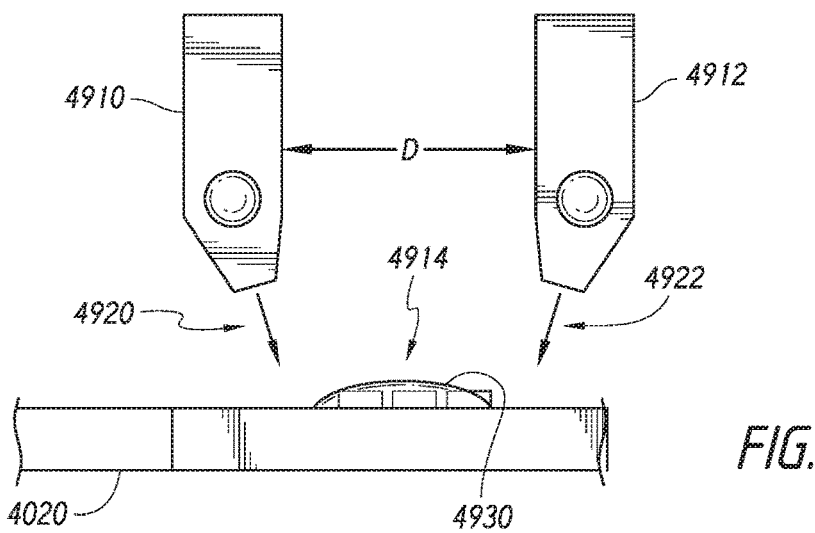

FIG. 76 is an isometric view of two gas knives 4910, 4912 in accordance with an embodiment of the present technology. FIGS. 77 and 78 are side views of the two gas knives 4910, 4912. Referring now to FIG. 76, the gas knives 4910, 4912 are spaced apart to produce gas curtains 4920, 4922, respectively, that define a containment gap 4914 for holding a volume of liquid 4916 (e.g., a film, a puddle, etc.). The gas knives 4910, 4912 can move together to translate the volume of liquid 4916 along the slide 4020. For example, the gas knives 4910, 4912 can move back and forth to translate the volume of liquid 4916 across one or more specimens 4930 (one identified in FIGS. 77 and 78). FIG. 77 shows the volume of liquid 4916 partially covering one specimen 4930, and FIG. 78 shows the volume of liquid 4916 covering three specimens 4930.

The distance D between the gas knives 4910, 4912 can be increased or decreased to increase or decrease the size of the gap 4914.

The specific embodiments of the dispenser apparatuses and its features have been described herein for purposes of illustration, but various features have not been described for clarity and numerous modifications may be made without deviating from the disclosure. The head assemblies, liquid removal devices, and their components configured in accordance with embodiments of the present technology can be used with a variety of vacuum systems, pressurized gas systems, and stainer modules. For example, the liquid removal device 4700 discussed in connection with FIGS. 71-73, liquid removal devices 4800, 4840 discussed in connection with FIGS. 74 and 75, and gas knives 4910, 4912 discussed in connection with FIGS. 76-78 can be incorporated into a wide range of different types of head assemblies and in fluid communication with different types of vacuum systems/pressurized gas systems, etc.

Selected Examples of Thermal Management in Stainers

Implementing enhanced consistency and controllability of processing temperature in an automated histological staining system can be technically challenging for a number of reasons. First, the temperature in a typical histology laboratory typically varies over time due to cycling of heating and air-conditioning equipment and/or other factors. Second, automated histological staining systems are often located near other equipment (e.g., autoclaves, hoods, etc.) that inconsistently cause local heating and/or cooling. Third, temperature sensitivities among the diverse components of an automated histological staining system and among the diverse operations performed within an automated histological staining system can vary significantly. As another consideration, the processing liquids used in conventional automated histological staining systems tend to be highly volatile and, therefore, may evaporate at an unacceptably high rate at high temperatures. Evaporation is generally undesirable because it tends to be associated with inconsistent evaporative cooling of specimens during temperature-dependent processing, premature drying of specimens and associated drying artifacts, noxious odors, and heightened explosion risks, among other issues. Inconsistent evaporative cooling, furthermore, may be proportionally more problematic at high temperatures than at low temperatures since wet bulb depression increases proportionally with dry bulb temperature at constant relative humidity. Issues at relatively low temperatures include, among others, poor (e.g., unacceptably slow) reaction kinetics for at least some staining reactions.

Given the presence of some or all of the associated technical challenges stated above and/or other technical challenges not stated herein, selecting a strategy for enhancing consistency and controllability of processing temperature in an automated histological staining system is not trivial. In a system configured in accordance with a particular embodiment of the present technology, this strategy includes heating an internal environment of a stainer of the system to cause a baseline (e.g., set-point, steady-state, and/or average) temperature of the internal environment to be within a range of greater than ambient temperatures. Processing specimens at elevated temperatures rather than at depressed temperatures can be advantageous, for example, because it can sufficiently distinguish the processing from ambient thermal variability (i.e., ambient thermal "noise") without unduly slowing the kinetics of staining and/or other temperature-dependent specimen-processing reactions. Processing specimens at elevated temperatures can actually improve the kinetics of at least some specimen-processing reactions and, therefore, may increase system throughput. As another potential advantage, maintaining an internal environment of a stainer at a baseline temperature within a range of greater than ambient temperatures may be achievable via heating without accompanying cooling. Avoiding the complexity, bulk, power consumption, and/or other drawbacks of cooling systems can be a significant benefit. In embodiments in which specimens are processed at elevated temperatures, evaporation and other challenges of processing-liquid compatibility can be addressed, for example, by the selection of different (e.g., less volatile) processing liquids. A more detailed discussion of this and other aspects of processing liquids used in conjunction with automated histological staining systems configured in accordance with at least some embodiments of the present technology is provided below in a separate subsection.

A suitable elevated baseline temperature for specimen processing may be selected as an upper limit of expected ambient temperatures plus a suitable buffer. Sustained temperatures in most histology laboratory environments are expected to fall within a range from 15° C. to 32° C. Equipment commonly located near automated histological staining systems in these environments is expected to increase the local temperature around the systems by from 0° C. to 4° C. in most cases. A suitable buffer can be, for example, from 1° C. to 14° C. In at least some cases, the reliability of certain components (e.g., valves) within or near a stainer of an automated histological staining system may begin to diminish unduly and/or other negative consequences may be associated with temperatures over 43° C., 45° C., 50° C., or another suitable threshold. With these and/or other considerations in mind, specimen processing (e.g., staining) in accordance with at least some embodiments of the present technology is carried out at a baseline temperature within a range from 37° C. to 43° C. In a particular embodiment, a baseline temperature of an internal environment within a stainer during specimen processing (e.g., staining) is about 40° C. In other embodiments, other suitable baseline temperatures can be used, such as other suitable baseline temperatures within a range from 35° C. to 50° C.

Stainers within systems configured in accordance with at least some embodiments of the present technology are internally heated by different types of heaters. For example, a stainer configured in accordance with a particular embodiment includes one or more heaters that internally heat the stainer primarily by forced convection and one or more heaters that internally heat the stainer primarily by natural convection and/or thermal radiation. These heaters may operate simultaneously or non-simultaneously. When present, heaters that heat primarily by different respective heating modalities may complement one another. For example, a forced-convection heater may be well suited for elevating the temperature of an internal environment of a stainer to a desired baseline temperature relatively quickly, but also prone to promoting undesirable evaporation of processing liquids used within the internal environment. In contrast, a heater with a significant mass that is heated conductively and transfers heat to an internal environment of a stainer primarily by natural convection and/or thermal radiation may reach a desired baseline temperature relatively slowly, but may be well-suited to maintaining the baseline temperature over time without promoting undesirable evaporation of processing liquids used within the internal environment. Other synergies are also possible.

Figure 79:
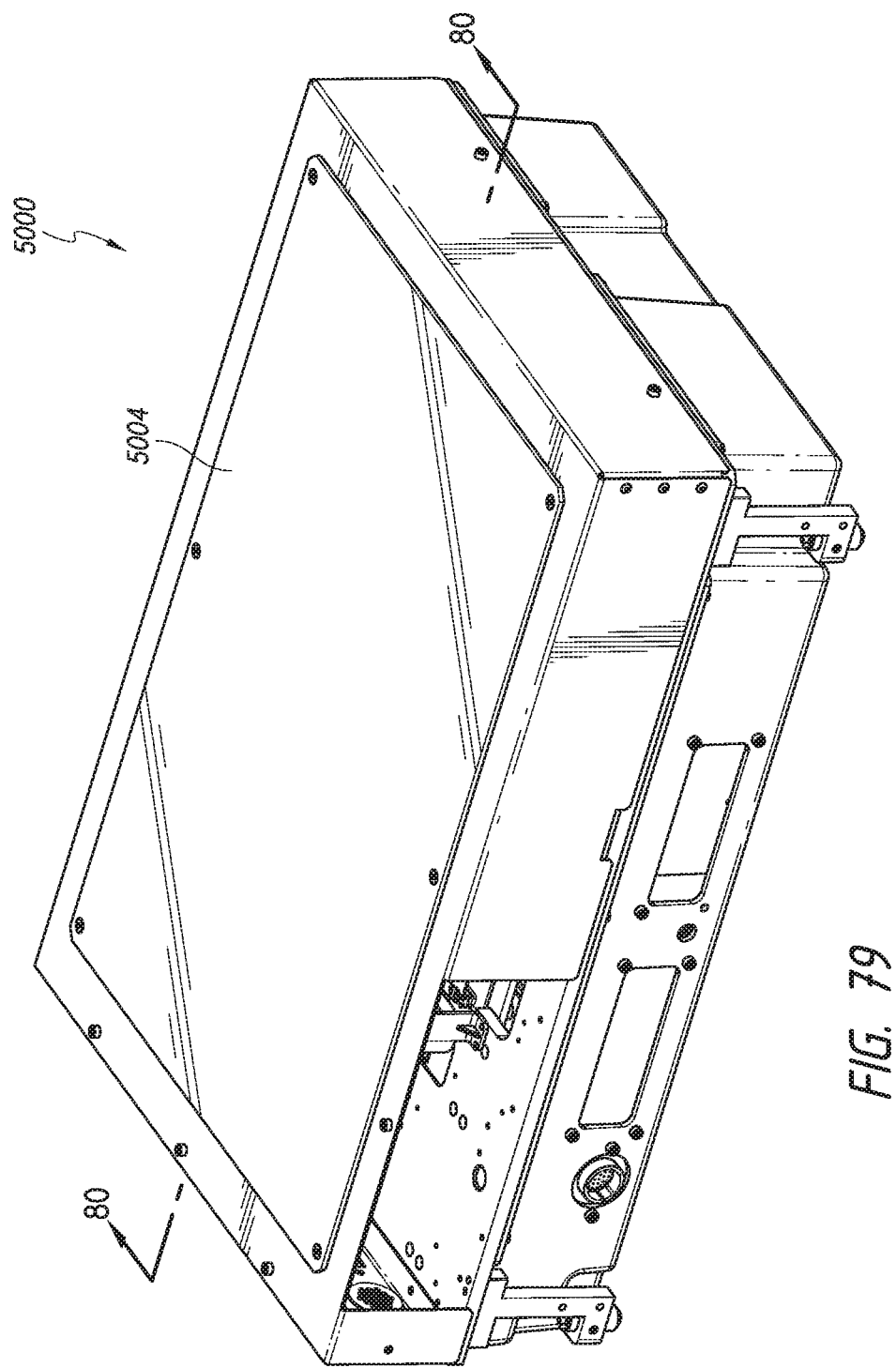
FIG. 79 is an isometric view of a stainer configured in accordance with an embodiment of the present technology.
Figure 80:
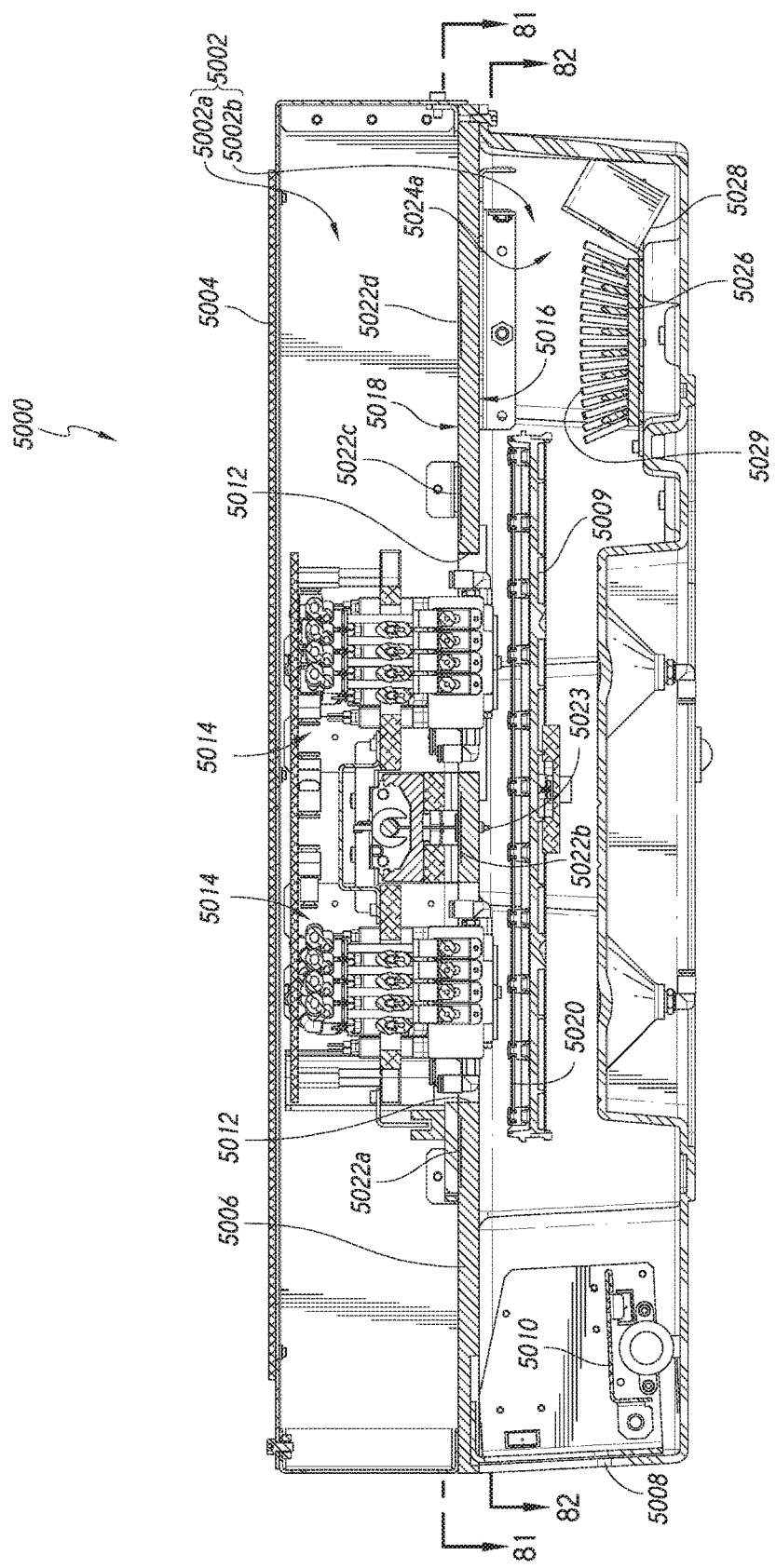
FIG. 80 is a cross-sectional side elevation view taken along the line 80-80 in FIG. 79 showing an internal environment of the stainer.
Figure 81:
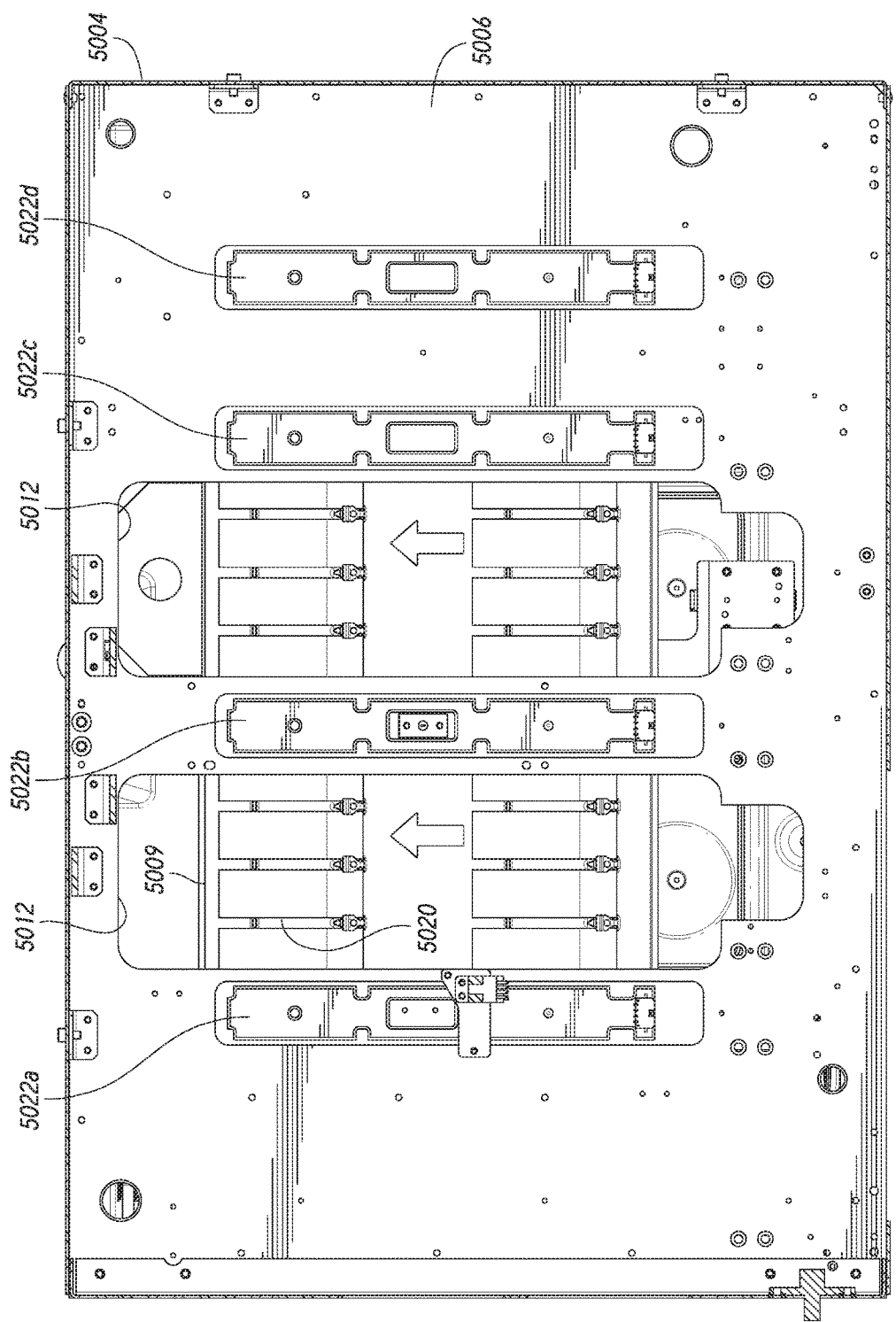
FIGS. 81 and 82 are cross-sectional plan views taken, respectively, along the lines 81-81 and 82-82 in FIG. 80.
Figure 82:
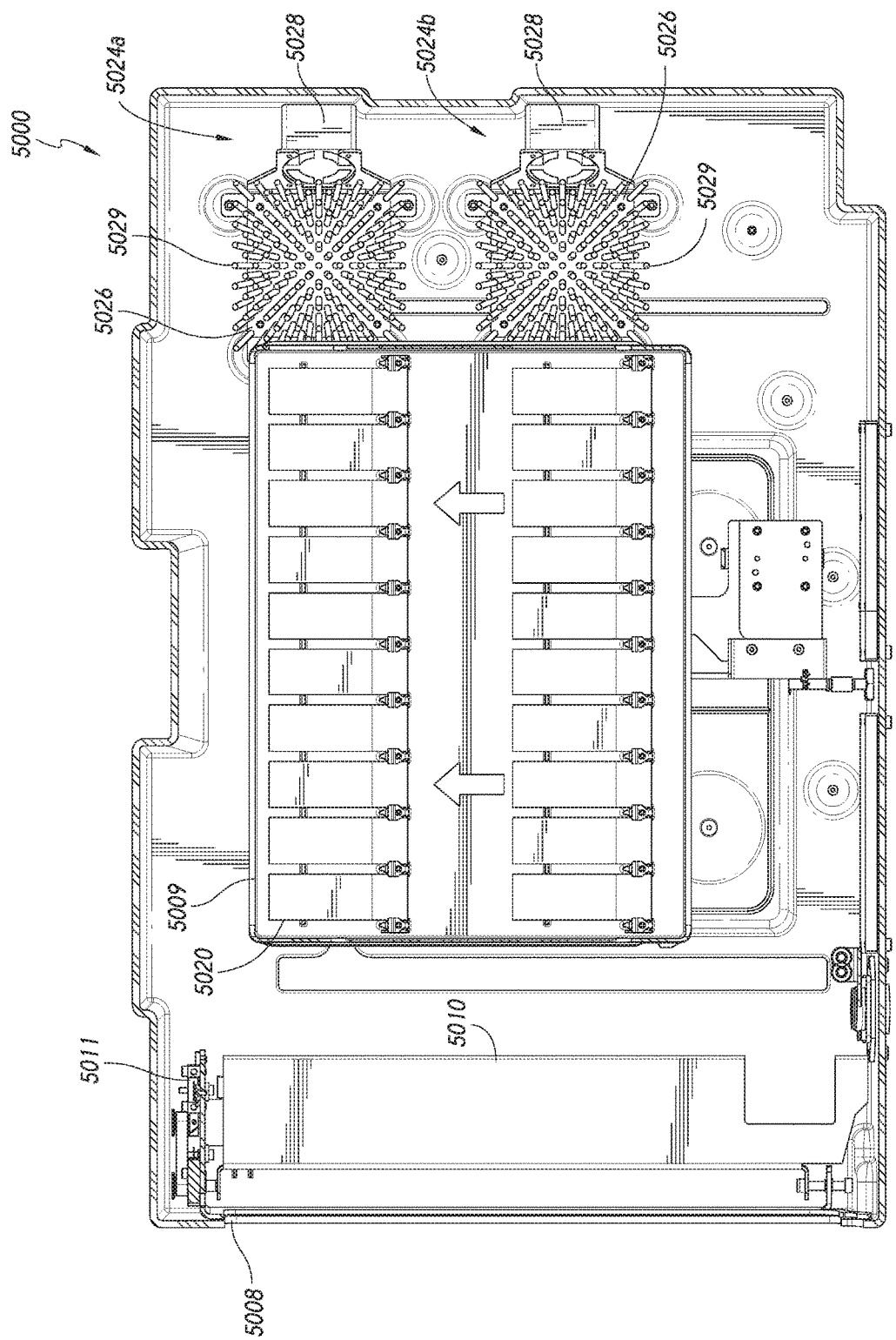

FIG. 79 is an isometric view of a stainer 5000 configured in accordance with an embodiment of the present technology. FIGS. 80-82 are cross-sectional views that illustrate components within an internal environment 5002 of the stainer 5000. In particular, FIG. 80 is a cross-sectional side view taken along the line 80-80 in FIG. 79. FIGS. 81 and 82 are cross-sectional plan views taken, respectively, along the lines 81-81 and 82-82 in FIG. 80. With reference to FIGS. 79-82 together, the stainer 5000 can include a stainer housing 5004 that defines the internal environment 5002. In the illustrated embodiment, the stainer 5000 includes a plate 5006 horizontally disposed at an intermediate elevation within the internal environment 5002. The plate 5006 can act as a thermal mass with sufficient bulk to modulate the amplitude and/or frequency of transient temperature non-uniformities within the internal environment 5002. For example, the plate 5006 can have a uniform or non-uniform thickness greater than 0.5 centimeter, such as greater than 1 centimeter. Furthermore, the plate 5006 can be made of a thermally conductive material, such as aluminum. This may expedite heat transfer between the plate 5006 and gas (e.g., air) within the internal environment 5002, which may, in turn, expedite equilibration of temperature non-uniformities within the internal environment 5002. In other embodiments, the plate 5006 can be replaced or supplemented with a thermal mass having another suitable form, position, and/or composition. In still other embodiments, the stainer 5000 can be without a thermal mass.

The plate 5006 can at least partially compartmentalize the internal environment 5002 into an upper region 5002a and a lower region 5002b. For example, the plate 5006 can occupy at least 50% by area of a planar division between the upper and lower regions 5002a, 5002b. Alternatively, the internal environment 5002 can be uncompartmentalized or compartmentalized by a compartmentalizing structure other than the plate 5006. The stainer 5000 can include a portal 5008 through which a slide carrier 5009 can be received into the lower region 5002b. The portal 5008 can include a door 5010 configured to open by tilting into the internal environment 5002 rather than by tilting away from the internal environment 5002. This can be useful, for example, to prevent the door 5010 from obstructing movement of the slide carrier 5009 laterally to a handoff position just outside the portal 5008 when the door 5010 is open. The portal 5008 can also include a door sensor 5011 configured to detect whether the door 5010 is open or closed. For example, the door sensor 5011 can include two separate sensors that respectively detect the presence of the door 5010 in an open configuration and a closed configuration. The door sensor 5011 can be operably connected to a controller (not shown), which can use information from the door sensor 5011 to manage robotic movement of the slide carrier 5009.

Once inside the internal environment 5002, the slide carrier 5009 can be supported within the lower region 5002b below a pair of openings 5012 in the plate 5006. The stainer 5000 can include processing heads 5014 (e.g., head assemblies) disposed at least primarily within the upper region 5002a. For example, the processing heads 5014 can extend from the upper region 5002a into the lower region 5002b toward the slide carrier 5009 through the openings 5012, such as two processing heads 5014 through one opening 5012 and another two processing heads 5014 through the other opening 5012 or in another suitable arrangement. Alternatively, the processing heads 5014 can be disposed entirely within the upper region 5002a. The plate 5006 can have a first major surface 5016 facing downward toward the slide carrier 5009 and a second major surface 5018 facing upward. Specimens (not shown) carried by slides 5020 (one identified) on the slide carrier 5009 can be relatively near to the first major surface 5016 of the plate 5006. For example, the individual slides 5020 can have a major surface on which a specimen is disposed, and the major surfaces of the slides 5020 can be less than 2 centimeters, less than 3 centimeters, and/or less than 5 centimeters from the first major surface 5016 of the plate 5006. In this vicinity, the temperature modulating effect of the plate 5006 may be stronger than it is at other portions of the internal environment 5002.

The stainer 5000 can include one or more internal heaters. These heaters can be individually configured to internally heat the stainer 5000 primarily by forced convection, natural convection, thermal radiation, or a combination thereof. For example, the stainer 5000 can include one or more conductive heating elements 5022 operably coupled to the plate 5006. In the illustrated embodiment, the stainer 5000 includes four conductive heating elements 5022 (individually identified as conductive heating elements 5022a-5022d) operably coupled to laterally spaced apart portions of the plate 5006 along the second major surface 5018 of the plate 5006. In other embodiments, the stainer 5000 can include another suitable number, type, and/or position of conductive heating elements 5022 or no conductive heating elements 5022. The conductive heating elements 5022 can be independently controlled. For example, the stainer 5000 can include temperature sensors (not shown) operably associated with respective laterally spaced apart portions of the plate 5006. These temperatures sensors can provide input to respective feedback control loops that control operation of respective conductive heating elements 5022. In addition or alternatively, the stainer 5000 can include a temperature sensor 5023 configured to measure an air temperature within the internal environment 5002.

The stainer 5000 can further include one or more forced-convection heaters 5024. In the illustrated embodiment the stainer 5000 includes two forced-convection heaters 5024 (individually identified as forced-convection heaters 5024a and 5024b) disposed within the lower region 5002b. In other embodiments, the stainer 5000 can include another suitable number, type, and/or position of forced-convection heaters 5024 or no forced-convection heaters 5024. The individual forced-convection heaters 5024 can include a heating element (not shown), a heat sink 5026 operably (e.g., conductively) coupled to the heating element, and a fan 5028 configured to propel gas (e.g., air) over a surface of the heat sink 5026. The heat sinks 5026 can made of a thermally conductive material (e.g., aluminum) and can include features with relatively high surface area to promote heat transfer to the propelled gas. For example, the heat sinks 5026 can include, respectively, arrays of upwardly extending cylindrical aluminum whiskers 5029 (one identified). The fans 5028 can be laterally spaced apart from the slide carrier 5009 and configured to blow gas diagonally upward. For example, the fans 5028 can be oriented to have a predominant output direction at an angle from 20 degrees to 70 degrees off horizontal, such as from 30 degrees to 60 degrees off horizontal. Having this orientation, the fans 5028 may tend to blow gas toward a gap between the slide carrier 5009 and the first major surface 5016 of the plate 5006. In at least some cases, steady movement of gas through this gap may enhance temperature uniformity within the gap.

Figure 83:
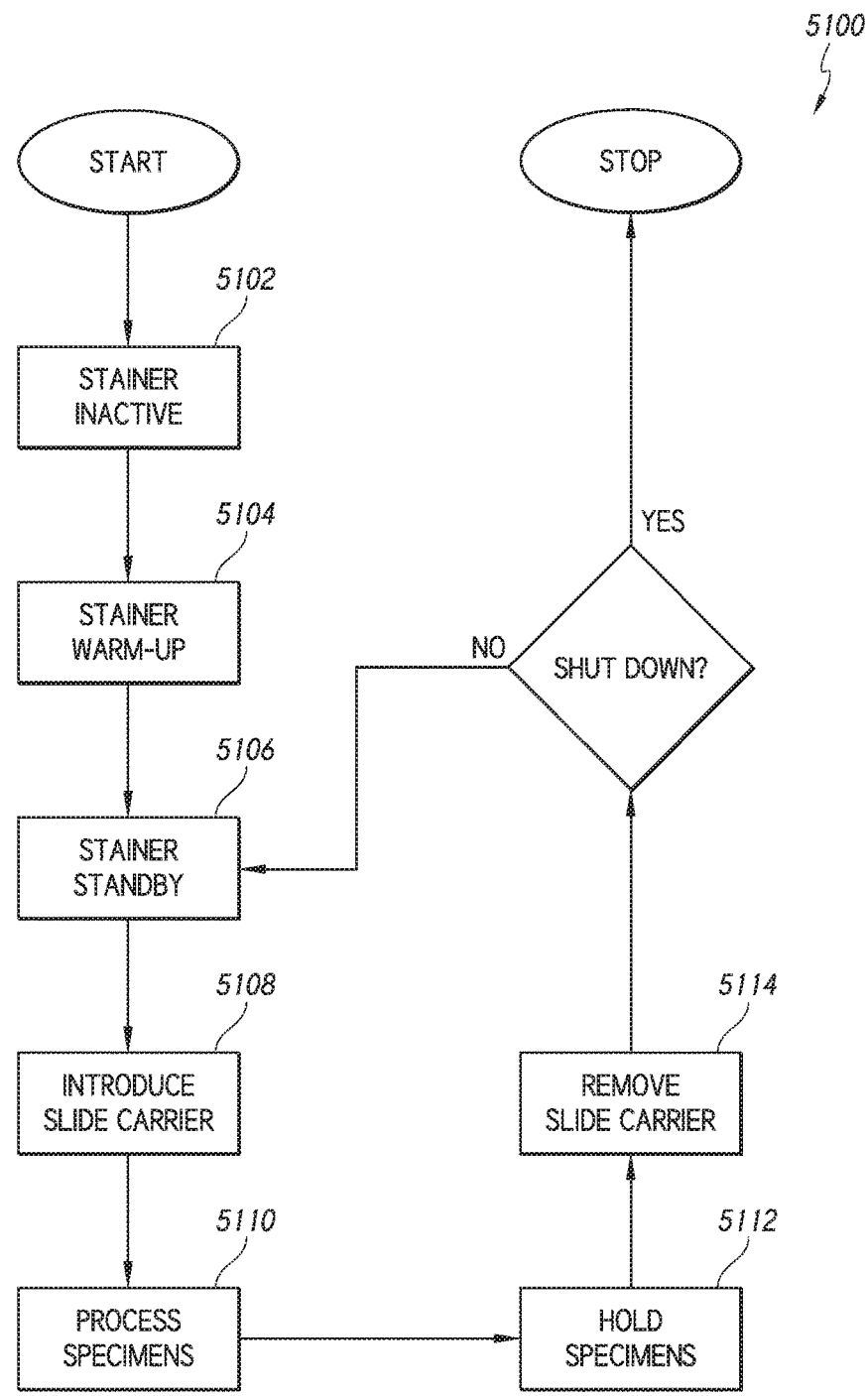
FIG. 83 is a flow chart illustrating a method for operating the stainer shown in FIGS. 79-82 in accordance with an embodiment of the present technology.

FIG. 83 is a flow chart illustrating a method 5100 for operating the stainer 5000 in accordance with an embodiment of the present technology. With reference to FIGS. 79-83 together, the method 5100 can begin with the stainer 5000 in an inactive state (block 5102). In this state, the stainer 5000 may consume little or no power. From the inactive state, the stainer 5000 can be warmed up (block 5104). Warming up the stainer 5000 can include operating the conductive heating elements 5022 and/or the forced-convection heaters 5024 to achieve a suitable baseline temperature within the internal environment 5002. In at least some cases, the stainer 5000 is warmed-up while specimens destined for processing within the internal environment 5002 undergo processing that does not involve use of the stainer 5000, such as processing within a drying oven (not shown). This may allow the stainer 5000 to be warmed-up without delaying processing of the specimens. After the stainer 5000 is warmed up, if processing of specimens using the stainer 5000 is not yet needed, the stainer 5000 can be maintained in a standby state (block 5106). While in the standby state, the internal environment 5002 can be vacant, but still maintained at a baseline temperature within a range of greater than ambient temperatures. In some embodiments, the stainer 5000 is maintained in the standby state at all times or nearly all times when a system including the stainer 5000 is powered on and the stainer 5000 is not in use. This can be useful, for example, to allow the stainer 5000 to have a relatively low wattage allocation while still being ready for processing specimens on demand in an acceptable time period. When a system includes multiple stainers 5000 and in other cases, the wattage allocation available for the stainer 5000 may be relatively small, such as 200 Watts or less.

Processing specimens within the stainer 5000 can begin when the slide carrier 5009 is introduced into the internal environment 5002 (block 5108). Introducing the slide carrier 5009 can include opening the portal 5008, moving (e.g., robotically moving) the slide carrier 5009 toward and into the internal environment 5002, and then closing the portal 5008. Once inside the internal environment 5002, the specimens can be processed (block 5110). A description of specimen processing in accordance with at least some embodiments of the present technology is provided below with reference to FIG. 86. In at least some cases, after the specimens have been processed, the slide carrier 5009 is held for a period of time within the stainer 5000 (block 5112). This may be the case, for example, when a processing station to which the slide carrier 5009 is to be delivered after exiting the stainer 5000 is not yet available. When such a processing station becomes available or at another suitable time, the slide carrier 5009 can be removed from the stainer 5000 (block 5114). Removing the slide carrier 5009 can include opening the portal 5008, moving (e.g., robotically moving) the slide carrier 5009 out of the internal environment 5002, and then closing the portal 5008. Thereafter, the method 5100 can include determining whether the stainer 5000 should be shut down. If not, the stainer 5000 can be put back into the standby state until needed for processing additional specimens.

During all or a suitable portion of the method 5100, the stainer 5000 can be internally heated, such as by operating the conductive heating elements 5022 and/or the forced-convection heaters 5024. This can cause an average temperature within the internal environment 5002 to be greater than an ambient temperature, such as an average environmental temperature around an exterior of the stainer housing 5004 within a main housing (not shown) of a system including the stainer 5000. Operation of the conductive heating elements 5022 and/or the forced-convection heaters 5024 can be controlled to manage the temperature within the internal environment 5002. For example, the conductive heating elements 5022 and/or the forced-convection heaters 5024 can be operated bimodally, progressively, and/or in another suitable manner using one or more feedback loops. Input to the feedback loops can include measurements of air temperature (e.g., from the temperature sensor 5023), measurements of solid-material temperatures (e.g., from one or more temperature sensors connected to the plate 5006), and/or measurements of other suitable dynamic characteristics corresponding to operation of the conductive heating elements 5022 and/or the forced-convection heaters 5024.

In some embodiments, the conductive heating elements 5022 and the forced-convection heaters 5024 operate collectively. In other embodiments, the conductive heating elements 5022 operate collectively and the forced-convection heaters 5024 operate collectively independently from the conductive heating elements 5022. In still other embodiments, one or more of the individual conductive heating elements 5022 operates independently and/or one or more of the individual forced-convection heaters 5024 operates independently. Independent operation of at least some of the individual conductive heating elements 5022 and/or the individual forced-convection heaters 5024 may facilitate modulation of temperature non-uniformities within the internal environment 5002. For example, the individual conductive heating elements 5022 can be operated asynchronously to at least partially compensate for detected temperature non-uniformities between different laterally spaced apart portions of the plate 5006. Alternatively or in addition, the individual conductive heating elements 5022 and the individual forced-convection heaters 5024 can operate independently in some instances and collectively in other instances. For example, if the air temperature within the internal environment 5002 exceeds a set upper threshold, the conductive heating elements 5022 and the forced-convection heaters 5024 can all be shut off to prevent the stainer 5000 from overheating. If the measured temperature continues to rise beyond another threshold, power to the stainer 5000 can be shut off. This can be useful, for example, to reduce or eliminate the risk of thermally damaging specimens within the internal environment 5002.

Figure 84:
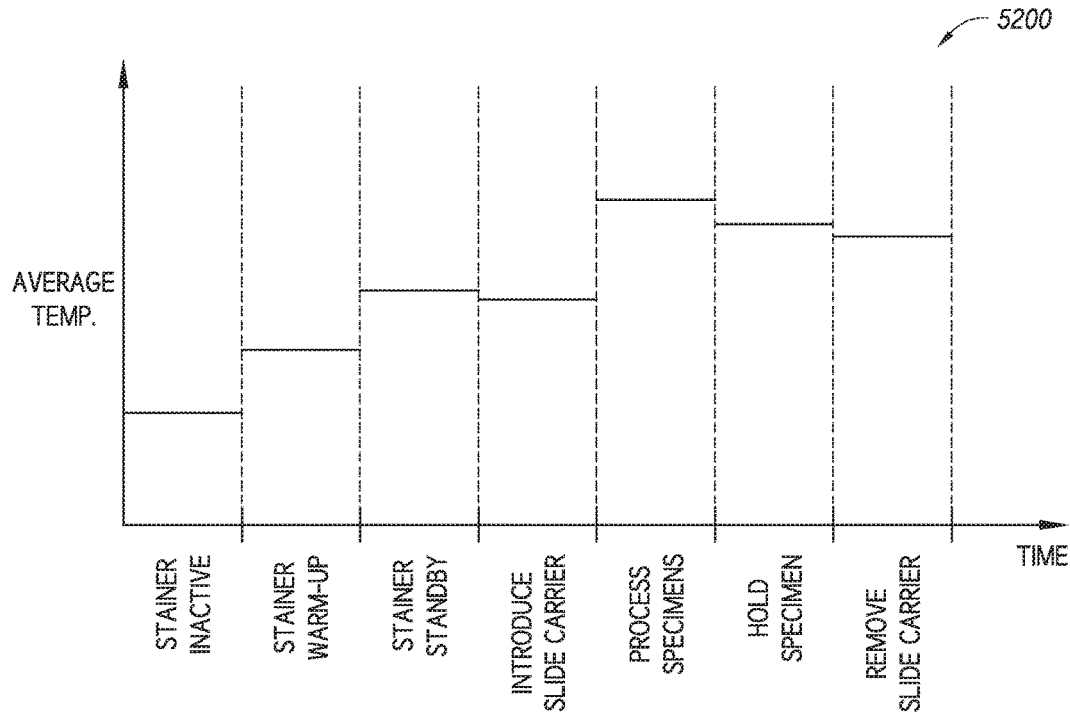
FIGS. 84 and 85 are plots of average temperature and average airflow velocity, respectively, within the internal environment relative to time during the method corresponding to the flow chart shown in FIG. 83.
Figure 85:
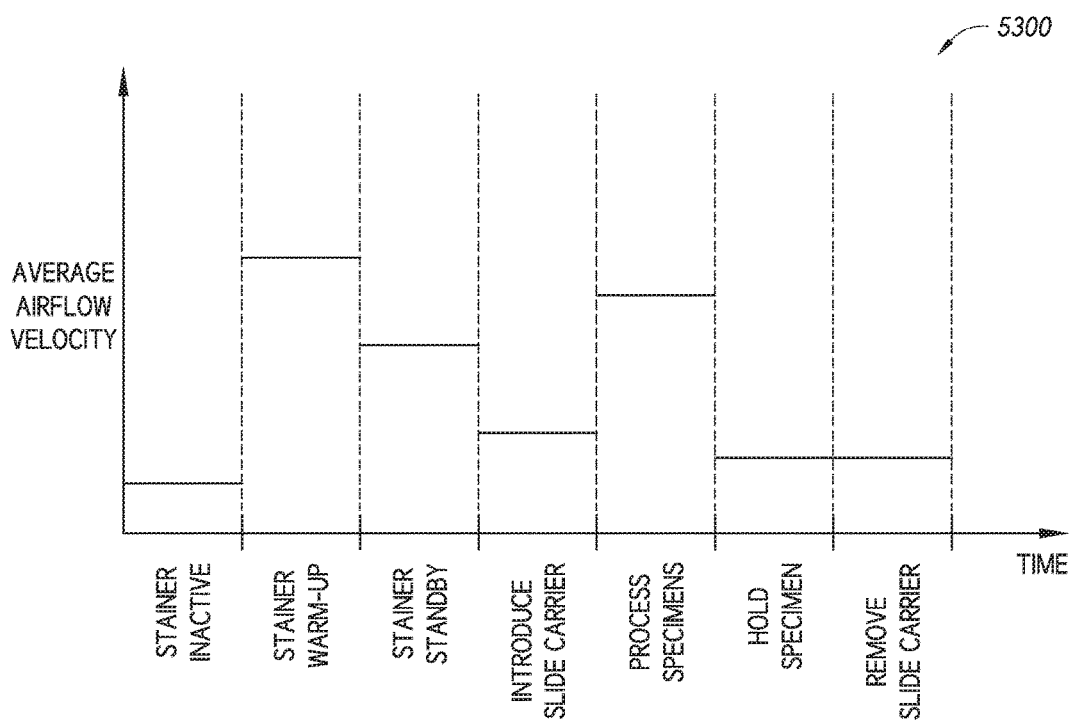

FIG. 84 is a plot 5200 of average temperature within the internal environment 5002 (y-axis) relative to time (x-axis) during the method 5100. Similarly, FIG. 85 is a plot 5300 of average airflow velocity within the internal environment 5002 (y-axis) relative to time (x-axis) during the method 5100. For simplicity of illustration, the average temperature scale, the average airflow velocity scale, and the time scales in FIGS. 84 and 85 are arbitrary. With reference to FIGS. 79-85 together, when the stainer 5000 is inactive, the average temperature can be the same as or near an ambient temperature. During this period, the forced-convection heaters 5024 can be off and the average airflow velocity can be low. In contrast, during the warm-up period, the forced-convection heaters 5024 can be operated aggressively, the average airflow velocity can be high, and the average temperature can increase. When the average temperature reaches a suitable baseline temperature for the standby state, operation of the conductive heating elements 5022 and the forced-convection heaters 5024 can be controlled based on feedback. A duty cycle or other similar operational parameter of the forced-convection heaters 5024 may be lower when the stainer 5000 is in the standby state than when the stainer 5000 is warming-up. Accordingly, as shown in FIG. 85, the average airflow velocity when the stainer 5000 is in the standby state can be less than it is when the stainer 5000 is warming up.

Shortly before the door 5010 is opened and the slide carrier 5009 is introduced into the internal environment 5002, active circulation of gas within the internal environment 5002 can be suspended or slowed to reduce heat loss through the portal 5008. For example, the forced-convection heaters 5024 can be turned off or operated at a relatively low level. This can persist until the slide carrier 5009 is fully introduced into the internal environment 5002 and the door 5010 is again closed. As shown in FIG. 85, the average airflow velocity while the slide carrier 5009 is being introduced can be relatively low, such as less than 0.1 meters per second. Even if the forced-convection heaters 5024 are off while the slide carrier 5009 is being introduced, natural convection, residual forced convection, and/or other phenomena may cause the average airflow velocity to be greater than it is when the stainer 5000 is inactive. As shown in FIG. 84, with less heating from the forced-convection heaters 5024 and with some heat loss through the portal 5008, the average temperature may decrease while the slide carrier 5009 is being introduced. Thereafter, while the slide carrier 5009 is within the internal environment 5002 and the specimens are being processed, the average temperature can be relatively high, such as about 40° C. or another suitable specimen-processing temperature within one of the ranges of specimen-processing temperatures discussed above. The specimens can be at least substantially in thermal equilibrium with the internal environment 5002 while they are processed. For example, an average temperature difference between the specimens can be less than 3° C. (e.g., less than 2° C.) while the specimens are being processed. A more detailed breakdown of the average temperature and the average airflow velocity while the specimens are being processed is provided below with reference to FIGS. 87 and 88.

While the specimens are being held within the internal environment 5002 after processing, active circulation of gas within the internal environment 5002 can be suspended or slowed. For example, the forced-convection heaters 5024 can be turned off or operated at a relatively low level. This can be useful, for example, to reduce unnecessary evaporation of liquid (e.g., conditioning liquid) in which the specimens are immersed. While the slide carrier 5009 is being removed from the internal environment 5002, the forced-convection heaters 5024 can remain off or operating at a relatively low level to reduce heat loss through the portal 5008. As shown in FIG. 85, the average airflow velocity while the specimens are being held and while the slide carrier 5009 is being removed can be relatively low, such as less than 0.1 meters per second. As shown in FIG. 84, with less heating from the forced-convection heaters 5024, the average temperature can decrease while the specimens are being held. Then, with some heat loss through the portal 5008, the average temperature can continue to decrease.

After the slide carrier 5009 is removed and the portal 5008 is closed, the average temperature can progress toward the average temperature when the stainer 5000 is inactive or the average temperature with the stainer 5000 is in the standby state depending on whether the stainer 5000 is needed for processing additional specimens.

Figure 86:
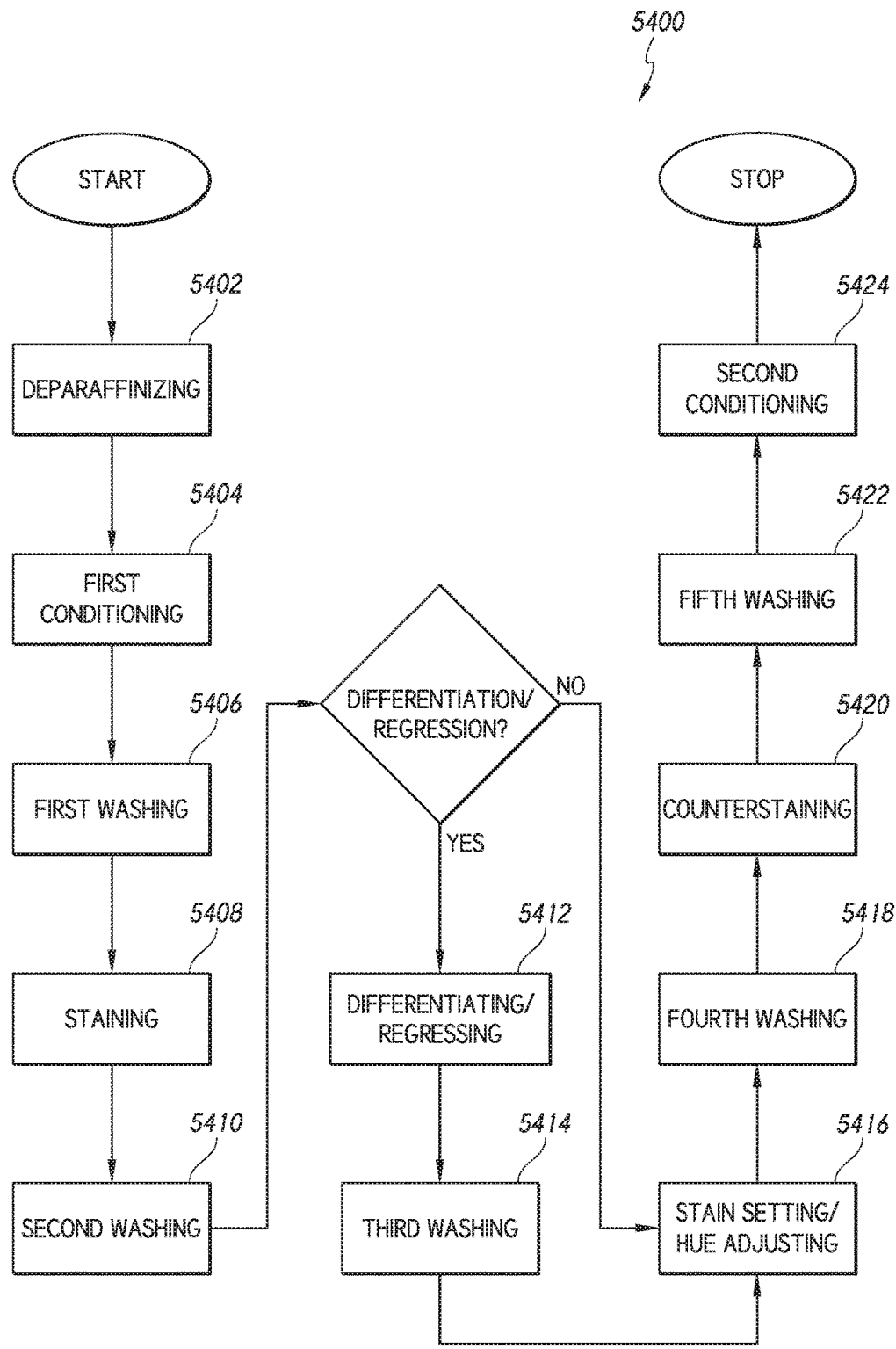
FIG. 86 is a flow chart illustrating a portion of the method corresponding to the flow chart shown in FIG. 83 during which specimens on slides carried by a slide carrier are processed within the internal environment.

FIG. 86 is a flow chart illustrating a specimen-processing method 5400 corresponding to the specimen-processing portion of the method 5100 (FIG. 83). The method 5400 can include first deparaffinizing the specimens (block 5402). Next, the specimens can be conditioned a first time (block 5404), such as by reducing the hydrophobicity of the specimens and/or otherwise chemically preparing the specimens for staining. The specimens can then be subjected to a first washing (block 5406). After the first washing, the specimens can be stained (block 5408) (e.g., non-immunohistochemically stained) and then subjected to a second washing (block 5410). In some cases, the stain is then differentiated and regressed (block 5412) and the specimens are subsequently subjected to a third washing (block 5414). After the third washing, or directly after the second washing if no stain differentiating and regressing is performed, the stain can be set and its hue adjusted (block 5416), such as by bluing or purpling. The specimens can then be subjected to a fourth washing (block 5418). Next, the specimens can be counterstained (block 5420) and then subjected to a fifth washing (block 5422) that can also serve to differentiate and regress the counterstain. Finally, the specimens can be conditioned a second time (block 5424), such as by increasing the hydrophobicity of the specimens and/or otherwise chemically preparing the specimens for coverslipping.

Figure 87:
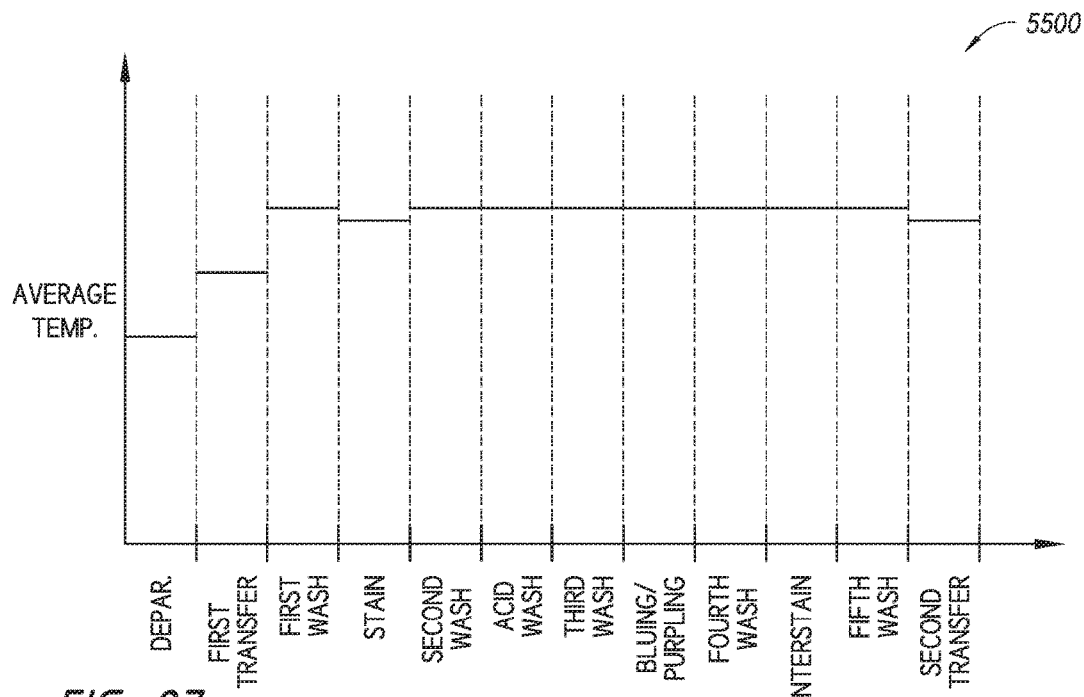
FIGS. 87 and 88 are plots of average temperature and average airflow velocity, respectively, within the internal environment relative to time during the method corresponding to the flow chart shown in FIG. 86.
Figure 88:
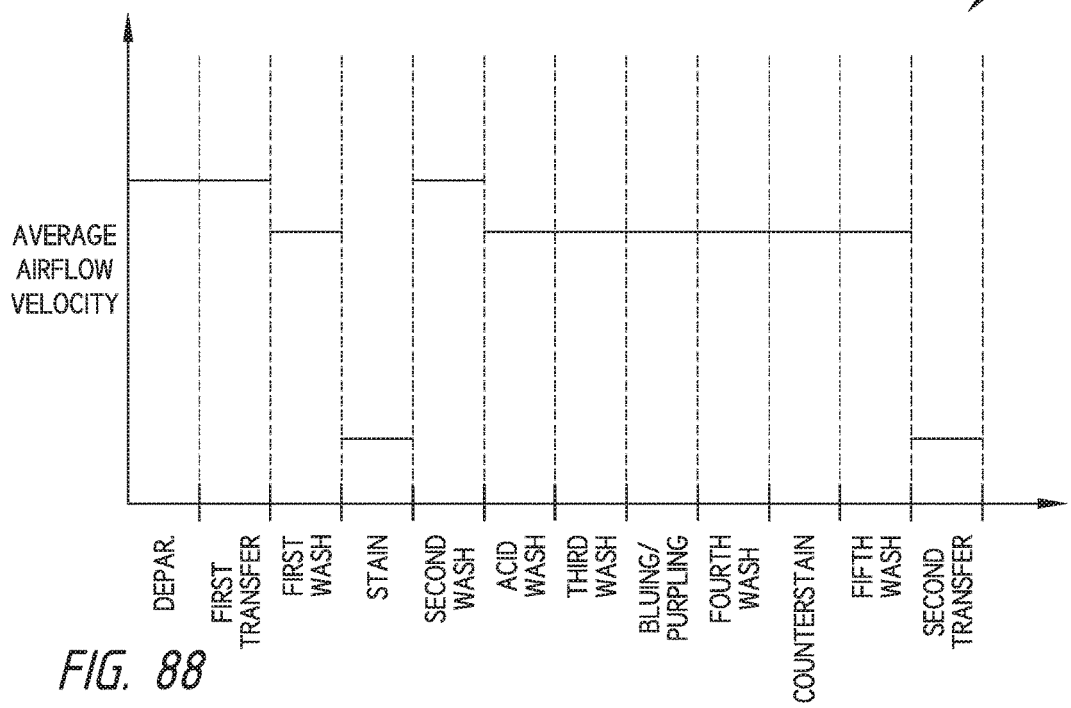

FIG. 87 is a plot 5500 of average temperature within the internal environment 5002 (y-axis) relative to time (x-axis) during the method 5400. Similarly, FIG. 88 is a plot 5600 of average airflow velocity within the internal environment 5002 (y-axis) relative to time (x-axis) during the method 5400. For simplicity of illustration, the average temperature scale, the average airflow velocity scale, and the time scales in FIGS. 87 and 88 are arbitrary. With reference to FIGS. 79-88 together, during the deparaffinizing, the first transfer, and the first wash, the forced-convection heaters 5024 can be operated aggressively, the average airflow velocity can be relatively high, and the average temperature can steadily increase. By the time the first wash is complete, the average temperature and the average airflow velocity can stabilize at respective baseline values. If the deparaffinizing, the first transfer, and the first wash are not included in the method 5400 (e.g., when the method 5400 is based on a "stain only" recipe), the specimens can be held until the baseline temperature is reached.

During staining, active circulation of gas within the internal environment 5002 can be suspended or slowed. For example, the forced-convection heaters 5024 can be turned off or operated at a relatively low level. This can be useful, for example, to reduce unnecessary evaporation of staining liquid in which the specimens are immersed during relatively long incubations. As shown in FIG. 88, the average airflow velocity during staining can be relatively low, such as less than 0.1 meters per second. As shown in FIG. 87, with less heating from the forced-convection heaters 5024, the average temperature can decrease. During the second wash, the average airflow velocity can be relatively high and the average temperature can increase. Thereafter, the average airflow velocity and the average temperature can stabilize at respective baseline values until the second transfer. During the second transfer, operation of the forced-convection heaters 5024 can transition toward the operation described above with reference to FIGS. 84 and 85 while the specimens are being held. For example, during the second transfer, the forced-convection heaters 5024 can be turned off or operated at a relatively low level.

In some embodiments, the average temperature during different portions of the method 5400 is adjustable to affect the attributes of specimens processed using the stainer 5000. For example, the average temperature immediately before and/or during staining can be selected to control the intensity of the resulting stain. Similarly, the average temperature immediately before and/or during counterstaining can be selected to control the intensity of the resulting counterstain. Alternatively or in addition, these average temperatures can be selected in conjunction with one another so as to control the color balance of the stained specimens. For example, the average temperature immediately before and/or during staining can be selected to be the same as or different than the average temperature immediately before and/or during counterstaining. In other embodiments, the average temperature during different portions of the method 5400 can be non-adjustable.

Recipes according to which the specimens are processed may have one or more temperature components. For example, a given recipe may specify an average temperature for staining and an average temperature for counterstaining. When specimens are processed according to the recipe, operation of the conductive heating elements 5022 and the forced-convection heaters 5024 can be controlled to achieve the specified temperatures. The average temperatures can be calculated automatically based on a user's indication of a desired attribute for the specimens. For example, a user may select from a list of specimen attributes (e.g., levels of stain intensity) and the system may calculate appropriate temperatures alone or in conjunction with appropriate times necessary for achieving the selected attributes. The attributes can include, for example, stain intensity, staining hue, counterstain intensity, counterstaining hue, and/or staining color balance. In other embodiments, average temperatures can be entered manually. As with other suitable operations carried out within the system, a controller (not shown) can use processing circuitry (also not shown) to execute computer-readable instructions stored on memory (also not shown) in a non-transitory form to control heating and related operations within the stainer 5000.

Selected Examples of Specimen-Processing Liquids

Specimen processing using an automated histological system may include contacting specimens and a series of liquids. The series of liquids can include, for example, a deparaffinizing liquid, a conditioning liquid, a staining reagent, a stain-differentiating reagent, a stain-setting reagent, a counterstaining reagent, a washing liquid, and a coverslipping liquid. With reference to FIG. 86, during deparaffinizing, a paraffin composition in which the specimens are embedded can be at least partially removed so as to expose the specimens for further processing. In at least some cases, deparaffinizing includes iterations (e.g., 4, 5, 6, 7, 8, or another suitable number of iterations) of dispensing a deparaffinizing liquid onto slides respectively carrying the specimens, allowing the dispensed deparaffinizing liquid to remain in contact with a paraffin composition in which the specimens are embedded for a suitable period of time so as to solubilize a portion of the paraffin composition (e.g., while the deparaffinizing liquid is in the form of a puddle having a shape maintained at least partially by surface tension), and then removing the dispensed deparaffinizing liquid along with a solubilized portion of the paraffin composition. The time during which the dispensed deparaffinizing liquid is in contact with the specimens can be, for example, a time within a range from 15 seconds to 45 seconds. In a particular example, the time is 30 seconds. Conventional deparaffinizing liquids at least typically include xylene, which has relatively high toxicity and volatility and a relatively low flash point. Conventional alternatives to xylene include monoterpenes, such as limonene and pinene. Although monoterpenes tend to be less toxic than xylene, other properties of monoterpenes may be very similar to those of xylene. For example, monoterpenes may have relatively high volatilities and relatively low flash points.

Operating stainers of automated histological systems at elevated baseline temperatures may preclude or at least complicate the use of xylene, monoterpenes, and other conventional deparaffinizing liquids, such as by exacerbating problematic evaporation of these deparaffinizing liquids. The elevated baseline temperatures, however, may also facilitate the use of different deparaffinizing liquids, such as deparaffinizing liquids that would be comparatively poor solvents of paraffin compositions at ambient temperatures. Instead of xylene or monoterpenes, deparaffinizing liquids selected or formulated in accordance with at least some embodiments of the present technology include one or more alkanes, such as one or more petroleum distillate alkanes. The toxicities and volatilities of these deparaffinizing liquids can be lower and the flash points of these deparaffinizing liquids can be higher than those of conventional deparaffinizing liquids, such as xylene and monoterpenes. Due to these and/or other differences, deparaffinizing liquids selected or formulated in accordance with embodiments of the present technology can be relatively well suited for use in stainers that operate at elevated baseline temperatures.

In addition to or instead of being relatively well suited for use in stainers that operate at elevated baseline temperatures, deparaffinizing liquids selected or formulated in accordance with at least some embodiments of the present technology are well-suited for other uses for which xylene, monoterpenes, and other conventional deparaffinizing liquids would be poorly suited. As an example, deparaffinizing liquids selected or formulated in accordance at least some embodiments of the present technology are well-suited for forming hydrophobic barriers on specimen-bearing surfaces of slides. These hydrophobic barriers can at least partially block undesirable migration of less hydrophobic (e.g., hydrophilic) liquids during specimen processing subsequent to deparaffinizing. Forming hydrophobic barriers for reducing wetting of labels on specimen-bearing surfaces of slides is discussed above with reference to FIGS. 36-38. Other uses for hydrophobic barriers are also possible.

Deparaffinizing liquids selected or formulated in accordance with at least some embodiments of the present technology have a C9-C18 alkane concentration greater than 50% by volume, such as a C10-C16 alkane concentration greater than 50% by volume. The alkane concentration can include a single alkane or multiple alkanes. Furthermore, the alkanes can be linear, branched, cyclic, or another suitable form. Deparaffinizing liquids selected or formulated in accordance with at least some embodiments of the present technology have a C14-C16 alkane concentration from 10% to 30% by volume and a C9-C15 alkane concentration from 70% to 90% by volume. For example, a deparaffinizing liquid selected or formulated in accordance with a particular embodiment of the present technology includes 20% by volume C14-C16 alkane petroleum distillate and 80% by volume C9-C15 alkane petroleum distillate. Suitable C14-C16 alkane petroleum distillates include, for example, Linpar® 1416V available from Sasol Limited (Johannesburg, South Africa). Suitable C9-C15 alkane petroleum distillates include, for example, Drakesol® 165AT available from Calumet Specialty Products Partners, L.P. (Indianapolis, Ind.). The flash points of these and other deparaffinizing liquids selected or formulated in accordance with embodiments of the present technology can be greater than 80° C., such as greater than 100° C.

Instead of being completely free of terpenes, deparaffinizing liquids selected or formulated in accordance with some embodiments of the present technology include a monoterpene (e.g., limonene or pinene) or another suitable terpene together with a less volatile component. The terpene, for example, can be well suited for dissolving paraffin and the less volatile component can be well suited for forming a hydrophobic barrier. Examples of suitable less volatile components include lipids, such as vegetable oils (e.g., peanut oil). A deparaffinizing liquid selected or formulated in accordance with a particular embodiment of the present technology includes 80% limonene and 20% vegetable oil. In at least some cases, these deparaffinizing liquids may be biodegradable.

After deparaffinizing, the specimens may have a residual hydrophobicity that would be incompatible with staining. The first conditioning of the specimens after deparaffinizing can include reducing this hydrophobicity. In at least some cases, the first conditioning includes dispensing a conditioning liquid onto the slides, allowing the dispensed conditioning liquid to remain in contact with the specimens for a suitable period of time so as to wholly or incrementally condition the specimens (e.g., while the conditioning liquid is in the form of a puddle having a shape maintained at least partially by surface tension), and then removing the dispensed conditioning liquid. The time during which the dispensed conditioning liquid is in contact with the specimens can be, for example, a time within a range from 5 seconds to 15 seconds. In a particular example, the time is 10 seconds. The conditioning liquid can be a liquid that is soluble in both a hydrophobic deparaffinizing liquid and water.

Conventional methods for conditioning specimens after deparaffinizing and before staining at least typically include contacting specimens with anhydrous ethanol and then with graded ethanol and water mixtures having decreasing concentrations of ethanol and increasing concentrations of water. For example, a conventional method may include contacting specimens with anhydrous ethanol, then a mixture of 95% ethanol and 5% water, and then a mixture of 90% ethanol and 10% water. The initial contact with anhydrous ethanol may serve to displace the deparaffinizing liquid. The subsequent contact with graded ethanol and water mixtures may serve to prepare the specimens for contact with aqueous solutions. Without the initial contact with anhydrous ethanol, residual deparaffinizing liquid would likely persist. Without the subsequent contact with graded ethanol and water mixtures (i.e., if the specimens were contacted with an aqueous solution directly after being contacted with anhydrous ethanol), delicate specimens would likely be damaged.

The use of anhydrous ethanol and graded ethanol and water mixtures for conditioning deparaffinized specimens in conventional methods is problematic for several reasons. Ethanol, like xylene and monoterpenes, has a relatively low flash point and a relatively high volatility. For these and/or other reasons, ethanol may be poorly suited for use at elevated baseline temperatures, which tend to exacerbate problematic evaporation. Problematic evaporation of ethanol may even occur at ambient temperatures. Furthermore, anhydrous ethanol readily absorbs moisture from air. For this reason, protocols associated with storage and use of anhydrous ethanol tend to be burdensome. As yet another drawback, separate plumbing and/or other separate components for anhydrous ethanol and for each different graded ethanol and water mixture can appreciably increase the cost, complexity, and/or bulk of automated histological systems.

Instead of anhydrous ethanol and graded ethanol and water mixtures, conditioning liquids selected or formulated in accordance with at least some embodiments of the present technology include one or more glycol ethers, such as one or more propylene-based glycol ethers (e.g., propylene glycol ethers, di(propylene glycol) ethers, and tri(propylene glycol) ethers, ethylene-based glycol ethers (e.g., ethylene glycol ethers, di(ethylene glycol) ethers, and tri(ethylene glycol) ethers), and functional analogs thereof. The flash points and volatilities of these conditioning liquids can be higher and lower, respectively, than those of conventional conditioning liquids, such as ethanol and graded ethanol and water mixtures. Due to these and/or other differences, conditioning liquids selected or formulated in accordance with embodiments of the present technology can be relatively well suited for use at elevated baseline temperatures. Furthermore, relative to anhydrous alcohol, conditioning liquids selected or formulated in accordance with embodiments of the present technology may have longer shelf lives and may have few, if any, special storage and use requirements.

In at least some cases, conditioning liquids selected or formulated in accordance with embodiments of the present technology are configured for use in a single formulation. For example, in these cases, it may be possible, without determent, to contact a specimen with one or more volumes of a single formulation of a conditioning liquid so as to displace residual quantities of a deparaffinizing liquid (e.g., a C9-C18 alkane) and then contact the specimen with an aqueous wash without intervening contact between the specimen and a diluted formulation of the conditioning liquid. The risk of damage to these specimens may be negligible or at least less than it would be if the specimens were contacted with the same aqueous solution directly after being contacted with anhydrous ethanol. Furthermore, the number of operations involved in conditioning specimens using conditioning liquids selected or formulated in accordance with embodiments of the present technology may be less than it would be using conventional conditioning liquids. For example, conditioning specimens in methods in accordance with at least some embodiments of the present technology includes three or fewer iterations of dispensing a conditioning liquid onto slides respectively carrying the specimens, allowing the dispensed conditioning liquid to remain in contact with the specimens for a suitable period of time so as to wholly or incrementally condition the specimens, and then removing the dispensed conditioning liquid. A specimen-processing method in accordance with a particular embodiment of the present technology includes two such iterations. In contrast, a typical conventional specimen-processing method includes five or more corresponding iterations. The relatively low number of iterations associated with conditioning in specimen-processing methods in accordance with at least some embodiments of the present technology can increase specimen-processing throughput and/or have other benefits.

Conditioning liquids selected or formulated in accordance with at least some embodiments of the present technology have greater volumetric concentrations of polyol than of monohydric alcohol or of water. For example, the conditioning liquids can be non-aqueous and can include greater than 50% by volume glycol ether, such as greater than 50% by volume di(propylene glycol) ether and/or tri(propylene glycol) ether. A non-aqueous conditioning liquid selected or formulated in accordance with a particular embodiment includes at least substantially exclusively a mixture of di(propylene glycol) methyl ether and di(propylene glycol) propyl ether. A non-aqueous conditioning liquid selected or formulated in accordance with another embodiment of the present technology includes at least substantially exclusively di(propylene glycol) propyl ether. Suitable glycol ethers include, for example, DOWANOL products available from Dow Chemical Company (Midland, Mich.). These and other conditioning liquids selected or formulated in accordance with embodiments of the present technology can have flash points greater than 70° C., such as greater than 80° C.

After deparaffinizing and conditioning, the first washing can include iterations (e.g., 2, 3, or another suitable number of iterations) of dispensing a washing liquid onto the slides, allowing the dispensed washing liquid to remain in contact with the specimens for a suitable period of time so as to wholly or incrementally wash the specimens (e.g., while the washing liquid is in the form of a puddle having a shape maintained at least partially by surface tension), and then removing the dispensed washing liquid. The time during which the dispensed washing liquid is in contact with the specimens can be, for example, a time within a range from 5 seconds to 15 seconds. In a specimen-processing method in accordance with a particular embodiment of the present technology, this time is 10 seconds. Conventionally, pure deionized water is used as a washing liquid. In contrast, washing liquids selected or formulated in accordance with embodiments of the present technology can include deionized water along with a solvent. The solvent, for example, can be a polyol, such as propylene glycol. For example, the washing liquid can include from 40% to 60% by volume polyol, such as from 40% to 60% by volume propylene glycol. As further discussed below, the solvent in the washing liquid can be the same as, within the same chemical class as, or otherwise functionally analogous to solvents included in other liquids that contact the specimens after the first washing. Including the solvent in the washing liquid can be useful to condition the specimens for contacting these other liquids. As discussed below, in at least some cases, the washing liquid is used for counterstain differentiating and regressing in addition to washing. In these cases, the solvent concentration in the washing liquid can be selected both to facilitate the performance of the washing liquid for counterstain differentiating and regressing and to promote compatibility with other specimen-processing liquids.

Washing liquids selected or formulated in accordance with at least some embodiments of the present technology include a surfactant to facilitate spreading of the washing liquids over the specimen-bearing surfaces of the slides. The surfactant can be selected to have little or no negative impact on specimen-processing operations subsequent to the first washing. For example, the surfactant can be non-ionic so as to reduce or prevent undesirable buffering. In at least some cases, the surfactant includes an ethoxylated alcohol and/or a glycol ether. Suitable ethoxylated alcohol surfactants include, for example, TOMADOL® 900 available from Air Products and Chemicals, Inc. (Allentown, Pa.) and Merpol SH® available from Stepan Company (Northfield, Ill.). Suitable glycol ether surfactants include, for example, TERGITOL® NP-9 available from Dow Chemical Company (Midland, Mich.).

After the first washing, staining the specimens can include dispensing a staining reagent onto the slides, allowing the dispensed staining reagent to remain in contact with the specimens for a suitable staining incubation time so as to stain the specimens (e.g., while the staining reagent is in the form of a puddle having a shape maintained at least partially by surface tension), and then removing the dispensed staining reagent. The staining incubation time can be, for example, within a range from 1 minute to 20 minutes. In a specimen-processing method in accordance with a particular embodiment of the present technology, the staining incubation time is 2 minutes. The staining reagent can be selected or formulated to adequately stain nuclear components of the specimens without causing unacceptable staining of non-nuclear components of the specimens or other forms of unacceptable non-specific background staining. The staining reagent can be a non-immunohistochemical staining reagent, such as a non-immunohistochemical staining reagent including hematoxylin/hematein, a mordant, and a solvent. The solvent can serve to maintain hematein and hematein-mordant complexes in solution. In conventional staining reagents, the solvent is often ethanol. As discussed above in conjunction with the conditioning liquid, use of ethanol in automated histological systems, such as automated histological systems including stainers configured to operate at elevated baseline temperatures, can be problematic. Furthermore, staining incubations tend to be relatively long, which may exacerbate the potential negative effect of ethanol's tendency to evaporate rapidly.

Instead of ethanol, staining reagents selected or formulated in accordance with at least some embodiments of the present technology include a polyol, such as ethylene glycol, propylene glycol, or a combination thereof. For example, the staining reagents can include greater than 10% by volume polyol, such as from 10% to 40% by volume polyol. As discussed below, staining reagents selected or formulated in accordance with at least some embodiments of the present technology include relatively low concentrations of mordant. This can allow for the use of relatively high concentrations of solvent, such as concentrations greater than 20% by volume. In conventional staining reagents with average or high mordant concentrations, these concentrations of solvent may prevent the mordant from adequately dissolving.

Variables that can affect the intensity and selectivity of hematoxylin stain include the pH of the staining reagent, the concentration of mordant in the staining reagent, the concentration of hematoxylin/hematein in the staining reagent, and the staining incubation temperature. Independently, the pH of the staining reagent, the concentration of hematoxylin/hematein in the staining reagent, and the staining incubation temperature tend to be directly proportional to the rate at which stain intensity increases, while the concentration of mordant in the staining reagent tends to be inversely proportional to the rate at which stain intensity increases. In general, the rate at which stain intensity increases is inversely proportional to staining selectivity. Thus, independently, the pH of the staining reagent, the concentration of hematoxylin/hematein in the staining reagent, and the staining incubation temperature tend to be inversely proportional to staining selectivity, while the concentration of mordant in the staining reagent tends to be directly proportional to staining selectivity. The same correlations may also apply to the effect of the pH of the staining reagent, the concentration of hematoxylin/hematein in the staining reagent, and the concentration of mordant in the staining reagent on shelf-life.

Greater rates at which stain intensity increases, greater staining selectivity, and greater shelf life all tend to be desirable properties. For example, greater rates at which stain intensity increases may enhance specimen-processing throughput, greater shelf life may enhance convenience for users, and greater staining selectivity may enhance stain quality. Although the variables that affect these features can be considered independently, they may actually be highly interrelated. Attributes of staining reagents selected or formulated in accordance with embodiments of the present technology may allow the staining reagents to take advantage of one or more of the interrelationships among these variables to enhance the balance of staining speed, staining selectivity, and shelf-life. Furthermore, staining reagents selected or formulated in accordance with at least some embodiments of the present technology have properties that facilitate adjusting hue and/or intensity of nuclear staining via time and/or temperature. These staining reagents can be well suited for use in at least some stainers having temperature-controlled internal environments in automated histological systems configured in accordance with embodiments of the present technology.

During hematoxylin staining, the stain intensity may increase steadily until equilibrium is reached. At equilibrium, the rate of deposition of hematein-mordant complexes from the staining reagent onto the specimen and the rate of release of hematein-mordant complexes from the specimen into the staining reagent may be approximately equal. The stain intensity at equilibrium tends to be highly dependent on the hematoxylin/hematein concentration in the staining reagent. Staining reagents with relatively low hematoxylin/hematein concentrations may reach equilibrium at relatively low stain intensities. Thus, these staining reagents may not be capable of producing dark stains even after long staining incubation times. This, coupled with the conventional assumption that the low staining incubation times for producing light stains using staining reagents with relatively high hematoxylin/hematein concentrations are too difficult to control, has motivated the conventional use of two or more different formulations of hematoxylin/hematein staining reagents in order to produce a full range of hematoxylin stain intensities. For example, a conventional set of staining reagents for producing a full range of hematoxylin stain intensities at least typically includes one or more staining reagents with relatively high hematoxylin/hematein concentrations for producing dark stains that cannot be produced using staining reagents with relatively low hematoxylin/hematein concentrations and one or more staining reagents with relatively low hematoxylin/hematein concentrations for producing light stains considered too difficult to produce using staining reagents with relatively high hematoxylin/hematein concentrations.

Automated histological systems configured in accordance with embodiments of the present technology and sets of liquids selected or formulated for use with these systems can be capable of reliably achieving a full range of hematoxylin stain intensities using a single hematoxylin staining reagent formulation. For example, the control over staining incubation time achievable with these systems may make it possible to reliably achieve light stains using staining reagents with relatively high hematoxylin/hematein concentrations. Accordingly, staining reagents selected or formulated in accordance with at least some embodiments of the present technology can have relatively high hematoxylin/hematein concentrations, such as hematoxylin/hematein concentrations within a range from 5 to 6.5 grams per liter, within a range from 5.75 to 6.3 grams per liter, or within another suitable range. In at least some cases, the hematoxylin/hematein concentrations of the staining reagents are selected to be as high as possible without unacceptably diminishing shelf life due to the formation of precipitate. The staining reagents can further include sodium iodate or another suitable oxidizing agent to chemically accelerate ripening of hematoxylin into hematein. The concentration of sodium iodate in the staining reagents can be, for example, less than 10% by weight.

Use of staining reagents having relatively high hematoxylin/hematein concentrations can advantageously reduce staining incubation times and thereby increase specimen-processing throughput. It is expected that this advantage may exist even with respect to staining reagents having relatively low pH. Thus, it may be possible to take advantage of the expected benefit of relatively low pH on staining selectivity without unduly sacrificing staining speed. The pH of staining reagents having relatively high hematoxylin/hematein concentrations and other staining reagents selected or formulated in accordance with embodiments of the present technology can be, for example, within a range from 2.4 to 2.6, within a range from 2.45 to 2.54, or within another suitable range. In at least some cases, the pH is selected to be as low as possible without risking unacceptable damage to specimens, such as damage due to acid hydrolysis of lipids within the specimens. These staining reagents can be buffered or unbuffered. When buffered, the staining reagents can include a suitable buffering agent, such as phthalic acid, chloroacetates, sulfates, glycine, and alanine.

Staining reagents selected or formulated in accordance with at least some embodiments of the present technology have enhanced sensitivity to temperature. When used in temperature-controlled stainers of automated histological systems configured in accordance with at least some embodiments of the present technology, staining incubation temperature can be used alone or in conjunction with staining incubation time to control stain intensity. In general, higher temperatures may cause staining speed to increase and staining selectivity to decrease and lower temperatures may cause staining speed to decrease and staining selectivity to increase. Temperature can also affect stain intensity at equilibrium. In at least some cases, temperature-dependent staining reagents selected or formulated in accordance with embodiments of the present technology have relatively low mordant concentrations. The stain intensity at equilibrium using these staining reagents may be significantly more sensitive to temperature than the stain intensity at equilibrium using staining reagents having higher mordant concentrations.

It is expected that staining using a staining reagent having a relatively low mordant concentration can be taken to equilibrium at different staining incubation temperatures to achieve a full range of stain intensities. Alternatively, staining using these staining reagents can be stopped before it reaches equilibrium and temperature and time can be used together to achieve some or all intensities within the full range of stain intensities. In at least some cases, staining incubation temperature and time can be modified readily. Thus, a user may be able to use a single staining reagent and select temperature to favor staining speed at the expense of some staining selectivity or to favor staining selectivity at the expense of some staining speed depending on circumstances. Suitable concentrations of mordant in temperature-dependent staining reagents selected or formulated in accordance with embodiments of the present technology can be less than 150% (e.g., less than 125% or less than 100%) of the concentration of hematoxylin/hematein in the staining reagents. The mordant can be an aluminum salt, such as aluminum sulfate hydrate. Salts of other metals (e.g., iron, copper, vanadium, molybdenum, tungsten, indium, nickel, zinc, barium, cobalt, and manganese) can be used instead of aluminum salt to achieve different stain hues and/or selectivities.

Staining reagents selected or formulated in accordance with embodiments of the present technology can include other suitable components in addition to solvent, hematoxylin/hematein, buffer, and mordant. For example, the staining reagents can include one or more antioxidants. Antioxidants can be useful, for example, to reduce the formation of precipitate and thereby extend the shelf life of staining reagents. When present, suitable antioxidants include, among others, phenolic antioxidants, such as gallic acid and hydroquinone. As another example, the staining reagents can include one or more stabilizers, such as beta-cyclodextrin or other suitable cyclodextrins. A staining reagent selected or formulated in accordance with a particular embodiment of the present technology includes 747 mL of deionized water, 252.7 mL of ethylene glycol, 6.06 grams of hematoxylin, 0.65 grams of sodium iodate, 26.67 grams of aluminum sulfate hydrate, 9.32 grams of hydroquinone, and 11.35 grams of beta-cyclodextrin.

After staining, the second washing can be used to remove residual staining reagent from the specimens and to increase the pH of the liquid content of the specimens sufficiently to halt further staining. The second washing can include use of the same washing liquid and protocol discussed above for the first washing. After the second washing, stain differentiating can be performed to at least partially remove stain from mucin and other non-nuclear portions of the specimens. In at least some cases, stain regressing to lighten nuclear staining of the specimens occurs in conjunction with stain differentiating. Stain differentiating and regressing can include dispensing a stain-differentiating liquid onto the slides, allowing the dispensed stain-differentiating liquid to remain in contact with the specimens for a suitable period of time so as to cause sufficient stain differentiating and regressing (e.g., while the stain-differentiating liquid is in the form of a puddle having a shape maintained at least partially by surface tension), and then removing the dispensed stain-differentiating liquid. The time during which the dispensed stain-differentiating liquid is in contact with the specimens can be, for example, a time within a range from 30 to 120 seconds.

The stain-differentiating liquid can be acidic and can include deionized water, an acid (e.g., acetic acid), and a solvent. As with the washing liquid and the staining reagent, the solvent can be a polyol, such as ethylene glycol, propylene glycol, or a combination thereof. For example, the stain-differentiating liquid can include greater than 10% by volume polyol, such as from 10% to 40% by volume polyol. The use of at least some conventional stain-differentiating liquids, especially in conjunction with relatively long stain-differentiating incubations, may cause morphological damage to structures within specimens. The use of a polyol solvent in stain-differentiating liquids configured in accordance with at least some embodiments of the present technology may help to condition these structures against this type of morphological damage. In addition or alternatively, stain-differentiating liquids configured in accordance with embodiments of the present technology can include relatively low concentrations of acid to further reduce the possibility of causing morphological damage to structures within specimens. For example, the pH of these stain-differentiating liquids can be greater than 2.5, such as greater than 2.7. A stain-differentiating liquid selected or formulated in accordance with a particular embodiment of the present technology includes about 700 mL deionized water, 4 mL glacial acetic acid, and 250 mL of propylene glycol. The pH of the stain-differentiating liquid can be, for example, within a range from 2.9 to 3.1.

In at least some cases, in addition to being used for stain differentiating and regressing, the stain-differentiating liquid can be used to remove and/or reduce formation of hematoxylin-containing precipitates within components of automated histological systems. For example, in these cases, the stain-differentiating liquid can be flushed through lines and other components of the system that ordinarily carry the staining reagent to remove and/or reduce formation of hematoxylin-containing precipitates. In addition to or instead of using the stain-differentiating liquid, systems configured in accordance with embodiments of the present technology can use one or more other cleaning liquids for this purpose and/or other purposes. A cleaning liquid selected or formulated in accordance with a particular embodiment of the present technology includes about 480 mL deionized water, 500 mL propylene glycol, and 16.67 mL 6N hydrochloric acid. A cleaning liquid selected or formulated in accordance with another embodiment of the present technology includes 450 mL deionized water, 500 mL propylene glycol, 59 grams trisodium citrate dihydrate, and 50 mL 1N hydrochloric acid.

After stain differentiating and regressing, the third washing can be used to remove residual stain-differentiating liquid from the specimens. The third washing can include use of the same washing liquid and protocol discussed above in the context of the first and second washings. After the third washing, stain setting and hue adjusting (e.g., bluing or purpling) can include exposing the specimens to an environment that tends to stabilize hematoxylin-mordant-DNA complexes and to change the stain hue. Stain setting and hue adjusting can include dispensing a stain-setting reagent onto the slides, allowing the dispensed stain-setting reagent to remain in contact with the specimens for a suitable period of time so as to cause sufficient stain setting and hue adjusting (e.g., while the stain-setting reagent is in the form of a puddle having a shape maintained at least partially by surface tension), and then removing the dispensed stain-setting reagent. The time during which the dispensed stain-setting reagent is in contact with the specimens can be, for example, about 30 seconds. The stain-setting reagent can include an alkaline solution (e.g., a buffered alkaline solution) and a solvent. As with the washing liquid, the staining reagent, and the stain-differentiating liquid, the solvent can be a polyol, such as ethylene glycol, propylene glycol, or a combination thereof. For example, the stain-setting reagent can include greater than 10% by volume polyol, such as from 10% to 60% by volume polyol. A stain-setting reagent selected or formulated in accordance with a particular embodiment of the present technology includes about 700 mL deionized water, 12.1 grams of tris(hydroxymethyl) aminomethane, 28.4 mL of hydrochloric acid, and 250 mL of propylene glycol.

The pH of the stain-setting reagent can be selected to change the hue of the stain. For example, stain-setting reagents having higher pH can cause more rapid progression to a blue color than stain-setting reagents having lower pH. Thus, given a set period of time during which specimens are exposed to a stain-setting reagent, if the stain-setting reagent has a relatively high pH (e.g., greater than 9), the resulting stain may be blue, whereas if the stain-setting reagent has a relatively low pH (e.g., less than 8), the resulting stain may be purple. Furthermore, when the period of time during which specimens are exposed to a stain-setting reagent is relatively long and the stain-setting reagent has a relatively low pH (e.g., less than 8), the temperature during stain setting and hue adjusting can be used to change stain hue, such as the relative level of bluing. As discussed above in the context of changing temperature to adjust stain intensity, temperature can be more convenient to adjust than the properties (e.g., pH) of a liquid used during specimen-processing. Therefore, the ability to control hue via temperature can be a useful feature. Temperature adjustment can also be used in conjunction with pH adjustment to achieve a desired hue, such as a desired level of bluing.

After stain setting and hue adjusting, the fourth washing can be used to remove residual stain-setting reagent from the specimens. The fourth washing can include use of the same washing liquid discussed above in the context of the first, second, and third washings. In at least some cases, the fourth washing includes a greater number of iterations than the first, second, and third washings, such as three instead of two. After the fourth washing, counterstaining the specimens can include dispensing a counterstaining reagent onto the slides, allowing the dispensed counterstaining reagent to remain in contact with the specimens for a suitable counterstaining incubation time so as to counterstaining the specimens (e.g., while the counterstaining reagent is in the form of a puddle having a shape maintained at least partially by surface tension), and then removing the dispensed counterstaining reagent. The counterstaining incubation time can be, for example, a time within a range from 30 seconds to 5 minutes. In a specimen-processing method in accordance with a particular embodiment of the present technology, the counterstaining incubation time is 2 minutes.

The counterstaining reagent can be selected or formulated to adequately counterstain the specimens, such as to allow for proper differentiation between cytoplasmic and connective tissue. Furthermore, the counterstaining reagent can be further selected or formulated to achieve a desired stain hue, such as to have a pH that causes a desired stain hue. Counterstaining reagents selected or formulated in accordance with embodiments of the present technology can include deionized water, a counterstaining dye (e.g., eosin), and a solvent to maintain the counterstaining dye in solution. As with the washing liquid, the staining reagent, the stain-differentiating liquid, and the stain-setting reagent, the solvent can be a polyol, such as ethylene glycol, propylene glycol, or a combination thereof. For example, the counterstaining reagent can include greater than 30% by volume polyol, such as from 30% to 70% by volume polyol and, in some cases, from 40% to 60% polyol. A counterstaining reagent selected or formulated in accordance with a particular embodiment of the present technology includes about 500 mL deionized water, 750 milligrams of eosin Y, 1 mL of glacial acetic acid, and 500 mL of propylene glycol. The counterstaining reagent can have a pH, for example, within a range from 3.65 to 4.25. This pH may be lower than the pH of conventional eosin counterstaining reagents. It may be possible, for example, to prevent eosin Y from converting into a free acid at lower pH values (e.g., pH values less than 4) in propylene glycol than in ethanol. Counterstaining reagents selected or formulated in accordance with other embodiments of the present technology can include higher concentrations of eosin, such as a concentration of 5.4 grams of eosin Y per liter. These counterstaining reagents, for example, can rely heavily on regression to achieve a desired counterstain intensity.

After counterstaining, the fifth washing can be used to remove residual counterstaining reagent from the specimens. The fifth washing can also be used to differentiate and regress the counterstain. When the counterstain is an eosin counterstain, the counterstain differentiating can cause erythrocytes, collagen, and cytoplasm of muscle or epithelial cells within the specimens to be stained three different shades of pink, with cytoplasm having the lightest shade, erythrocytes having the darkest shade, and collagen having an intermediate shade. Conventional counterstain differentiating and regressing is at least typically carried out in conjunction with dehydrating specimens. For example, conventional counterstain differentiating and regressing at least typically includes contacting specimens with graded ethanol and water mixtures having increasing concentrations of ethanol and decreasing concentrations of water and then contacting the specimens with anhydrous alcohol.

The fifth washing can include use of the same washing liquid discussed above in the context of the first, second, third, and fourth washings. In some cases, the duration of one or more iterations of the fifth washing is adjustable to control the level of counterstain differentiating and regressing. For example, the fifth washing can include a first iteration during which the specimens are exposed to the washing liquid for about 20 seconds, followed by a second iteration during which the specimens are exposed to the washing liquid for a period of time within a range from 30 to 80 seconds. In a specimen-processing method in accordance with a particular embodiment of the present technology, the period of time during which the specimens are exposed to the washing liquid during the second iteration is 50 seconds. The first iteration can function primarily to remove residual counterstaining reagent from the specimens. The second iteration can function primarily to allow for variable differentiating and regressing of the counterstain. Eosin staining tends to be relatively sensitive to unevenness associated with evaporation during counterstain differentiating and regressing. Thus, in at least some cases, the total time during which the specimens contact the washing liquid during the fifth washing is less than 100 seconds. The performance of the washing liquid for counterstain differentiating and regressing can influence its formulation. For example, water concentrations significantly greater than 50% in the washing liquid may tend to cause non-standard counterstain differentiating, such as cytoplasm of the specimens being darker than erythrocytes of the specimens. Water concentrations significantly less than 50% in the washing liquid may tend to produce inadequate levels of counterstain differentiating and regressing. Thus, as described above, the washing liquid can have a water concentration of about 50%, such as 50%+/−3%.

After the fifth washing, the specimens may have a residual hydrophilicity that would be incompatible with coverslipping. The second conditioning of the specimens after the fifth washing can include reducing this hydrophilicity. In at least some cases, the second conditioning includes dispensing a conditioning liquid onto the slides, allowing the dispensed conditioning liquid to remain in contact with the specimens for a suitable period of time so as to wholly or incrementally condition the specimens (e.g., while the conditioning liquid is in the form of a puddle having a shape maintained at least partially by surface tension), and then removing the dispensed conditioning liquid. The time during which the dispensed conditioning liquid is in contact with the specimens can be, for example, a time within a range from 5 seconds to 15 seconds. In a particular example, the time is 10 seconds. The conditioning liquid can be the same conditioning liquid used during the first conditioning. In at least some cases, in addition to being well suited for changing the hydrophobicity/hydrophilicity of specimens, the conditioning liquid is well suited for protecting specimens during the time period between the fifth washing and coverslipping. For example, di(propylene glycol) ethers and tri(propylene glycol) ethers (e.g., tri(propylene glycol)butyl ether) and other conditioning liquids selected or formulated in accordance with embodiments of the present technology may be superior to xylene for preventing potentially destructive drying of tissue during this time period. Thus, use of these conditioning liquids may reduce or eliminate restrictions on the length of this time period. This can be useful, for example, to reduce time constraints on lockstep process management and/or to provide a time window during which additional operations can be performed on the specimens.

As discussed above, conventional conditioning of specimens for coverslipping is at least typically carried out in conjunction with counterstain differentiating using graded ethanol and water mixtures followed by anhydrous ethanol. Thereafter, the specimens are at least typically contacted with xylene to stop the counterstain differentiating and to further condition the specimens for interaction with a coverslipping adhesive. As discussed above in the context of the first conditioning, however, use of ethanol and xylene in automated histological systems can be problematic, particularly when the systems operate at elevated baseline temperatures. Di(propylene glycol) ether and other conditioning liquids selected or formulated in accordance with embodiments of the present technology may reduce or eliminate the need for ethanol. In at least some cases, the conditioning liquids partially condition the specimens for coverslipping and a coverslipping liquid is used in place of xylene after the conditioning liquid during the second conditioning to further condition the specimens for interaction with a coverslipping adhesive. The coverslipping liquid can be selected or formulated to be immiscible with water (e.g., to reduce or eliminate leaching of dye from archived specimens) and to be volatile enough to adequately cure during a drying process of reasonable duration (e.g., 5 minutes).

The coverslipping liquid can include a terpene, such as a monoterpene (e.g., limonene). A coverslipping liquid selected or formulated in accordance with a particular embodiment of the present technology includes about 100% d-limonene with a suitable preservative, such as 500 parts per million butylated hydroxytoluene. Use of monoterpenes in the coverslipping liquid tends to be significantly less problematic than use of monoterpenes in the conditioning liquid. For example, the amount of monoterpene coverslipping liquid sufficient to prepare specimens for coverslipping following use of di(propylene glycol) ether conditioning liquid can be far less than the amount of the di(propylene glycol) ether conditioning liquid used during the first conditioning and the initial phase of the second conditioning. In at least some cases, the utilized amount of monoterpene coverslipping liquid is low enough that it fully evaporates after its use without causing noticeable noxious fumes. In these cases, since there may be no liquid monoterpene waste, there may also be no need for special protocols, if any, for remediating and/or handling of system waste liquids due to the presence of monoterpenes in these liquids.

In automated histological systems configured in accordance with embodiments of the present technology, the coverslipping liquid can be applied to specimens within a stainer, within a coverslipper after the specimens exit the stainer, or at another suitable location. Use of the coverslipping liquid can include first dispensing the coverslipping liquid onto the slides and then removing the dispensed coverslipping liquid. For example, the coverslipping liquid can be dispensed near the edges of the slides and swept across the slides using an air knife. This can serve to remove any residual conditioning liquid remaining on the slides. Thereafter, the coverslipping liquid can be dispensed once, twice, three times, or another suitable number of times near the centers of the slides and left in place while coverslips are applied to the slides.

As discussed above, staining reagents and counterstaining reagents selected or formulated in accordance with embodiments of the present technology can include non-ethanol solvents to respectively maintain the stain and counterstain in solution. It can be advantageous for these solvents to be common, such as the same, within the same chemical class, or otherwise functionally analogous. Furthermore, it can be advantageous for one or more other liquids used in conjunction with a given staining reagent and counterstaining reagent to include a solvent the same as, within the same chemical class as, or otherwise functionally analogous to the common solvent of the staining reagent and the counterstaining reagent. This use of a common solvent is expected to enhance specimen-processing consistency and quality. This benefit, for example, may be associated with enhanced efficiency and/or consistency with which a given liquid displaces residual amounts of a previously dispensed liquid when the liquids have a common solvent. Other supplemental or alternative benefits and mechanisms are also possible.

In sets of liquids selected or formulated in accordance with at least some embodiments of the present technology, a staining reagent, a counterstaining reagent, and a washing liquid individually include greater than 10% by volume polyol. In at least some of these and other sets of liquids selected or formulated in accordance with embodiments of the present technology, all, all but one, or all but two of a staining reagent, a stain-differentiating liquid, a stain-setting reagent, a counterstaining reagent, and a washing liquid include greater than 10% by volume polyol, such as greater than 10% by volume of the same polyol, such as greater than 10% by volume propylene glycol. In specimen-processing methods in accordance with at least some embodiments of the present technology, a total of all liquid dispensed onto slides after the slides are moved into a stainer (e.g., into a temperature-controlled internal environment of a stainer) and before the slides exit the stainer has a greater volumetric concentration of polyol than of monohydric alcohol. In at least some cases, the total liquid dispensed is at least substantially free of monohydric alcohol or at least has a volumetric concentration of monohydric alcohol less than 3%. Furthermore, the total liquid dispensed can be at least substantially free of xylene.

Due, at least in part, to use of relatively few (e.g., one) conditioning liquid formulations, use of the same liquid for both washing and counterstain differentiating, the ability to achieve a full range of staining intensities with relatively few (e.g., one) staining reagent formulation, and/or other factors, specimen-processing methods in accordance with embodiments of the present technology can include use of fewer different types of liquids than would be used during conventional specimen-processing methods. Similarly, complete sets of liquids selected or formulated in accordance with embodiments of the present technology can include fewer constituent liquids than conventional sets with corresponding functionality. Liquids belonging to sets of liquids selected or formulated in accordance with embodiments of the present technology can be respectively held in and drawn from different corresponding supply containers of automated histological systems configured in accordance with embodiments of the present technology. These systems can be fluidically self-contained and operable with fewer supply containers, plumbing lines, and/or other liquid-handling components than are included in conventional systems of corresponding functionality. Among other potential benefits, this can reduce the cost, complexity, and/or bulk of automated histological systems configured in accordance with at least some embodiments of the present technology.

The selection of processing liquids, the order in which the selected processing liquids are dispensed, the number of dispensing and removing iterations for each processing liquid, and the duration of liquid-to-specimen contact (e.g., incubation time) for each iteration can be based on a predetermined recipe. In at least some cases, specimens immersed in a given liquid volume are at least partially uncovered before being contacted with another liquid volume of the same processing liquid (e.g., in a subsequent iteration of the same processing operation) or of a different processing liquid (e.g., to begin a new processing operation). As discussed above, this may enhance the performance (e.g., precision) of at least some specimen-processing operations. In some cases, these enhancements are more pronounced in the context of progressive staining than in the context of regressive staining. As such, there may be less need for stain differentiating and regressing in at least some specimen-processing methods in accordance with embodiments of the present technology than there is in conventional specimen-processing methods.

Specimen-processing methods in accordance with embodiments of the present technology can include, within a stainer, automatically dispensing liquids of no more than 6 different formulations onto slides according to a predetermined recipe for at least deparaffinizing, staining, stain setting, counterstaining, and counterstain differentiating specimens carried by the slides. A complete set of liquids for executing a methods can include a deparaffinizing liquid, a conditioning liquid, a staining reagent, a stain-setting reagent, a counterstaining reagent, and a washing liquid. Similarly, specimen-processing methods in accordance with embodiments of the present technology can include, within a stainer, automatically dispensing liquids of no more than 7 different formulations onto slides according to a predetermined recipe for at least deparaffinizing, staining, stain differentiating, counterstaining, and counterstain differentiating specimens carried by the slides. A complete set of liquids for executing these methods can include a deparaffinizing liquid, a conditioning liquid, a staining reagent, a stain-differentiating liquid, a stain-setting reagent, a counterstaining reagent, and a washing liquid. Other liquids that can be included in these and other sets of liquids selected or formulated in accordance with embodiments of the present technology include, for example, a coverslipping liquid and a cleaning liquid. In at least some cases, all constituents of complete sets of liquids selected or formulated in accordance with embodiments of the present technology are configured for use without dilution.

Selected Examples of Support Systems

Figure 89:
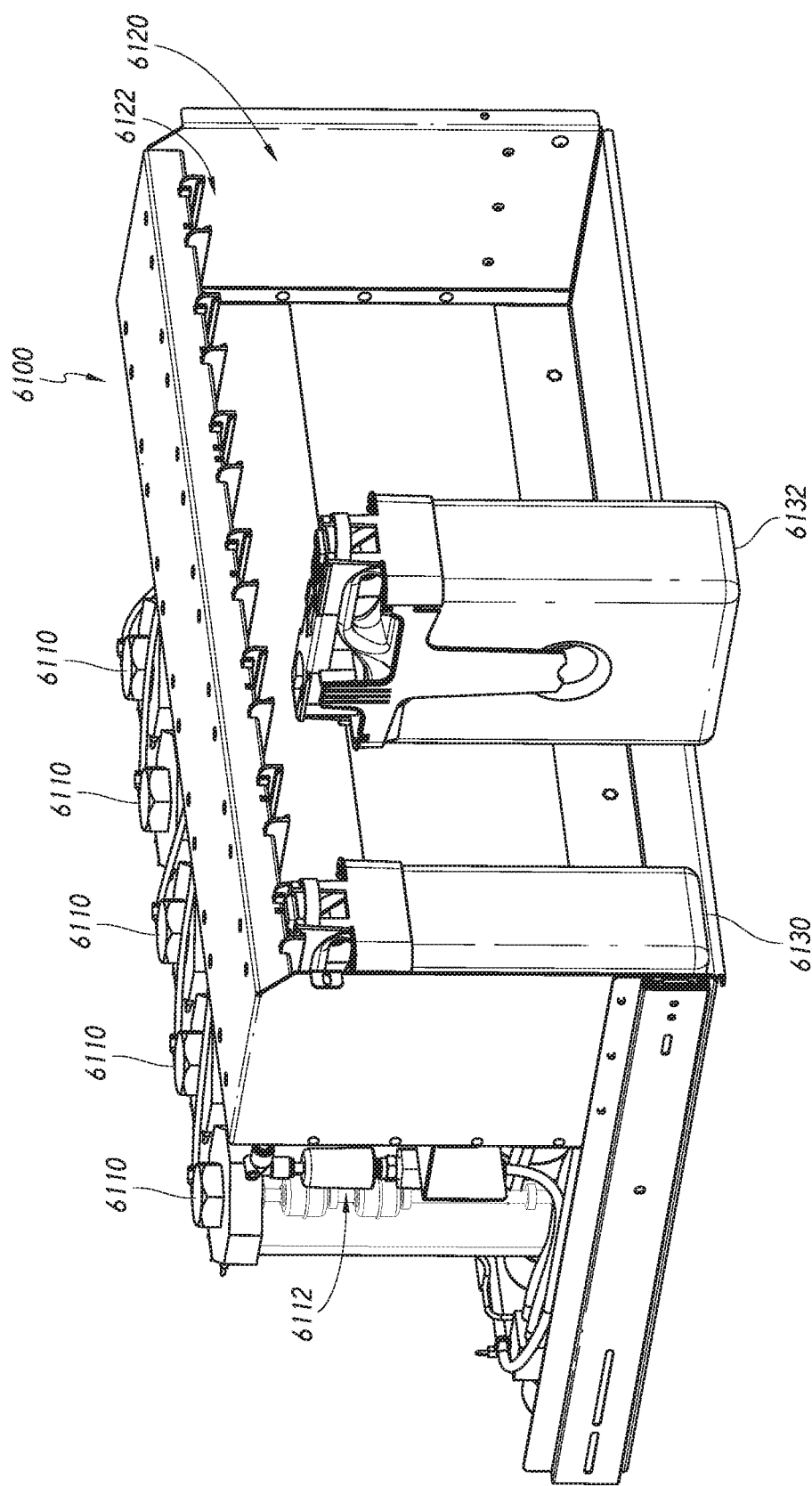
FIG. 89 is a perspective view of a liquid supply in accordance with one embodiment of the present technology.

FIG. 89 is a perspective view of the liquid supply 6100 in accordance with an embodiment of the technology. The liquid supply 6100 can include one or more pumps 6110, filters 6112 (one identified), and a container bay 6120. The container bay 6120 can include a series of container slots 6122 (one identified) for holding containers. Containers holding processing liquids can be placed in the slots 6122 and connected to the various pumps 6110, which pump the processing liquids to the stainers 6. FIG. 89 shows a container 6130 positioned in a slot 6122 and another container 6132 ready to be inserted into another slot 6122. When a container is empty, the liquid supply 6100 can automatically switch over to another container and, in some embodiments, can alert a user so that the empty container can be replaced with a new container without interrupting system workflow. Processing liquids used in high quantities, such as deparaffinizing liquid and washing liquid, can be supplied from a bulk liquid container or multiple containers. A wide range of different fittings can be used to fluidically couple the containers to fluidic components of the liquid supply 6100.

The container 6132 can include one or more features for ensuring that correct liquids are pumped into the appropriate components. The bay 6120 can include one or more readers positioned to obtain processing-liquid information from each container, and such processing-liquid information can be part of a bar code, a magnetic element (e.g., a magnetic strip), or RFID tag. Where an RFID tag is included on the container 6132, the bay 6120 can read the RFID tag to confirm that the proper liquid has been installed in the appropriate bay. Referring to FIGS. 2 and 89, the controller 18 (FIG. 2) can receive the information from the bay 6120 to (1) determine staining protocols based on available processing liquids, (2) track processing-liquid usage to determine scheduled container replacement, and/or (3) otherwise command components of the system 2 based, at least in part, on the number and types of available processing liquids.

FIG. 90 is an isometric exploded view of the container 6132 in accordance with an embodiment of the present technology. The container 6132 can include a hat assembly 6200 and a receptacle 6202. The hat assembly 6200 can include arms 6210 for securely holding onto the receptacle 6202 when arcuate members 6220 (one identified) of the arms 6210 are positioned in a receiving feature 6230 (e.g., a through-holes, recesses, etc.) of the receptacle 6202. The arms 6210 can be biased inward to keep the arcuate members 6220 locked into the receiving feature 6230. A user can pull the arms 6210 apart until the arcuate members 6220 are moved out of the receiving feature 6230 and can then move the hat assembly 6200 away from the receptacle 6202.

FIG. 91 is a partial cross-sectional view of the container 6132. The hat assembly 6200 and receptacle 6202 can have mateable handles 6300, 6302, respectively. When assembled, a user can conveniently grip the handles 6300, 6302 to manually transport the container 6132. Other types of handle arrangements can also be used, if needed or desired. The hat assembly 6200 can include a conduit 6250 (e.g., a tubular member) extending downwardly through a chamber 6252 of the receptacle 6202. An end 6254 of the conduit 6250 can be positioned at least proximate to a bottom 6256 of the chamber 6252, or at any other desired location with the chamber 6252. In some embodiments, the end 6254 can be positioned within at threshold distance (e.g., 0.5 inch (1.3 cm)) of the bottom 6256. The conduit 6250 can have an angled section 6261 such that the end 6254 is located adjacent to a side wall 6260 and positioned at the deepest region of the chamber 6252 used to limit dead volume. The liquid can be drawn through the conduit 6250 even when a minimal volume of liquid is held by the receptacle 6202. As shown in FIG. 91, a relatively deep region of the chamber 6252 can be positioned proximate to a side wall 6260 of the receptacle 6202 to further minimize dead volumes, if any.

The systems disclosed herein can also use other types of containers, including bag-in-the-box containers that include, without limitation, collapsible bags, tubes sealed into the bags, cover, and boxes. Non-exemplary embodiments of bag-in-the-box containers are disclosed in U.S. Pat. No. 7,303,725.

Figure 92:
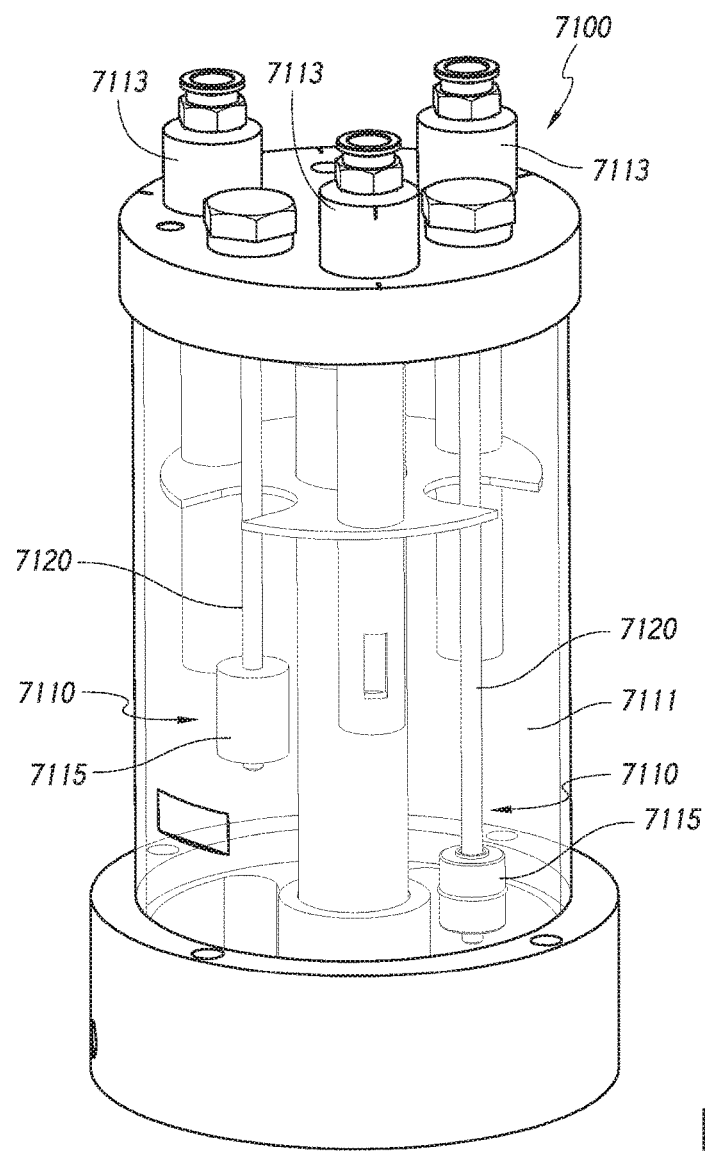
FIG. 92 is an isometric view of a waste container in accordance with one embodiment of the present technology.

FIG. 92 is an isometric view of a waste container in accordance with one embodiment. The waste container 7100 can include one or more sensor assemblies 7110 capable sensing the amount of liquid waste in a chamber 7111. Waste can be delivered through feed tubes 7113 into the chamber 7111. The sensor assemblies 7110 can include sensors 7115 and guide rods 7120 along which sensors 7115 move in the vertical direction. The waste container 7100 can be part of waste containers (e.g., waste containers 32, 34 of FIG. 2) or at any other location within the system 2.

FIG. 93 is a cross-sectional view of the sensor 7115 in accordance with one embodiment of the present technology. The sensor 7115 can float to sense the volume of waste held in the chamber 7111 and can include a float sensor 7142 and a protective shield 7144. The protective shield 7144 can keep particles (e.g., precipitate from staining reagent) from entering an sensor chamber 7145. The sensor 7142 and the protective shield 7144 can slide together along the rod 7120 while the protective shield 7144 prevents or limits substances (e.g., particles that can affect operation of the sensor 7142) from entering the chamber 7145. Other configurations of sensors can be utilized.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. For example, while processing liquids selected or formulated in accordance with some embodiments of the present technology are free of monohydric alcohol (e.g., ethanol) and/or xylene, processing liquids selected or formulated in accordance with other embodiments of the present technology may include monohydric alcohol (e.g., ethanol) and/or xylene. This disclosure and associated technology can encompass a variety of embodiments not expressly shown or described herein.

Certain aspects of the present technology may take the form of computer-executable instructions, including routines executed by a controller or other data processor. In at least some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

The methods disclosed herein include and encompass, in addition to methods of practicing the present technology (e.g., methods of making and using the disclosed devices and systems), methods of instructing others to practice the present technology. For example, a method in accordance with a particular embodiment includes positioning a slide carrier at a first position while the slide carrier holds a plurality microscope slides, robotically moving the slide carrier from the first position to a second position to move the slide carrier into a circulation loop defined by a heater apparatus, and convectively heating the slides while the slide carrier is at the second position. A method in accordance with another embodiment includes instructing such a method.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A method for processing specimens carried by slides within an automated histological staining system, the method comprising:
    moving a slide carrier toward and into a temperature-controlled internal environment of a stainer within the system, the slide carrier carrying a first slide and a second slide, the first and second slides carrying a first specimen and a second specimen, respectively;
    staining the first and second specimens with at least one of a staining reagent and a counterstaining reagent while the first and second slides are within the internal environment and while an average temperature of the internal environment is greater than ambient temperature, wherein staining the first and second specimens includes staining the first and second specimens with a hematoxylin reagent;
    actively circulating gas within the internal environment before staining the first and second specimens with the hematoxylin reagent and after moving the slide carrier toward and into the internal environment;

suspending active circulation of gas within the internal environment while staining the first and second specimens with the hematoxylin reagent; and, moving the slide carrier out of the internal environment after staining the first and second specimens.

2. The method of claim 1, wherein:
moving the slide carrier toward and into the internal environment includes robotically moving the slide carrier toward and into the internal environment; and
moving the slide carrier out of the internal environment includes robotically moving the slide carrier out of the internal environment.

3. The method of claim 1, wherein:
the stainer includes a stainer housing within a main housing of the system; and
the method further comprises internally heating the stainer such that the average temperature of the internal environment is greater than an average environmental temperature within the main housing around an exterior of the stainer housing while staining the first and second specimens.

4. The method of claim 1, wherein staining the first and second specimens includes staining the first and second specimens while the first and second specimens are at least substantially in thermal equilibrium with the internal environment.

5. The method of claim 1, wherein staining the first and second specimens includes staining the first and second specimens while the average temperature of the internal environment is from 35° C. to 50° C.

6. The method of claim 1, wherein staining the first and second specimens includes staining the first and second specimens while the average temperature of the internal environment is from 37° C. to 43° C.

7. The method of claim 1, wherein staining the first and second specimens includes staining the first and second specimens while an average temperature of the first specimen is from 35° C. to 50° C., while an average temperature of the second specimen is from 35° C. to 50° C., and while an average difference between the average temperature of the first specimen and the average temperature of the second specimen is less than 3° C.

8. The method of claim 1, further comprising maintaining the average temperature of the internal environment above an ambient temperature during a standby period occurring while the internal environment is vacant immediately before moving the slide carrier into the internal environment.

9. The method of claim 1, wherein staining the first and second specimens includes staining the first and second specimens with at least one of a hematoxylin reagent and an eosin reagent.

10. The method of claim 1, further comprising automatically dispensing the at least one of the staining reagent and the counterstaining reagent so as to form a freestanding first puddle and a freestanding second puddle on the first and second slides, respectively, while the first and second slides are within the internal environment, wherein staining the first and second specimens includes staining the first and second specimens while the first and second specimens are in contact with the first and second puddles, respectively.

11. The method of claim 1, wherein staining the first and second specimens includes:
staining the first and second specimens with a hematoxylin reagent; and
staining the first and second specimens with an eosin reagent.

12. The method of claim 1, further comprising:
holding the slide carrier within the internal environment for a holding period during which no fluid is dispensed onto the first and second slides, the holding period occurring immediately before moving the slide carrier out of the internal environment;
actively circulating gas within the internal environment before staining the first and second specimens and after moving the slide carrier toward and into the internal environment; and
suspending active circulation of gas within the internal environment during the holding period.

13. The method of claim 1,
further comprising circulating gas within the internal environment at a first average rate before staining the first and second specimens with the hematoxylin reagent and after moving the slide carrier toward and into the internal environment; and
circulating gas within the internal environment at a second average rate while staining the first and second specimens with the hematoxylin reagent, the second average rate being less than the first average rate.

14. The method of claim 13, wherein:
the first average rate is greater than 0.1 meters per second; and
the second average rate is less than 0.1 meters per second.

15. The method of claim 1, further comprising:
holding the slide carrier within the internal environment for a holding period during which no fluid is dispensed onto the first and second slides, the holding period occurring immediately before moving the slide carrier out of the internal environment;
circulating gas within the internal environment at a first average rate before staining the first and second specimens and after moving the slide carrier toward and into the internal environment; and
circulating gas within the internal environment at a second average rate during the holding period, the second average rate being less than the first average rate.

16. The method of claim 15, wherein:
the first average rate is greater than 0.1 meters per second; and
the second average rate is less than 0.1 meters per second.

17. The method of claim 1, wherein staining the first and second specimens includes:
staining the first and second specimens with the staining reagent; and
staining the first and second specimens with the counterstaining reagent.

18. The method of claim 17, further comprising:
controlling the average temperature of the internal environment while staining the first and second specimens with the staining reagent; and
controlling the average temperature of the internal environment while staining the first and second specimens with the counterstaining reagent to be different than the average temperature of the internal environment while staining the first and second specimens with the staining reagent.

19. The method of claim 1, further comprising conductively heating a thermal mass positioned above the first and second slides while the first and second slides are within the internal environment.

20. The method of claim 19, further comprising detecting a temperature non-uniformity within the internal environment, wherein conductively heating the thermal mass includes selectively heating laterally spaced apart portions of the thermal mass to at least partially compensate for the detected temperature non-uniformity.

21. The method of claim 19, wherein conductively heating the thermal mass includes asynchronously operating two or more conductive heating elements operably coupled, respectively, to laterally spaced apart portions of the thermal mass.

22. The method of claim 1, further comprising heating the internal environment by forced convection while the first and second slides are within the internal environment.

23. The method of claim 22, wherein heating the internal environment by forced convection includes actively circulating gas within the internal environment through a fan positioned below the first and second slides.

24. The method of claim 23, wherein:
heating the internal environment by forced convection includes conductively heating a heat sink positioned below the first and second slides; and
actively circulating the gas includes blowing the gas diagonally upward across a surface of the heat sink toward a gap between the slide carrier and a thermal mass positioned above the slide carrier.

25. The method claim 1, further comprising operating one or more heaters of the stainer to maintain the average temperature of the internal environment above an ambient temperature.

26. The method of claim 25, wherein the range is from 35° C. to 50° C.

27. The method of claim 25, wherein the range is from 37° C. to 43° C.

28. The method of claim 25, wherein operating the one or more heaters includes operating a forced-convection heater positioned below the slide carrier.

29. The method of claim 1, wherein the stainer includes a stainer housing having a portal, moving the slide carrier into the internal environment includes moving the slide carrier into the internal environment via the portal, and moving the slide carrier out of the internal environment after staining the first and second specimens includes moving the slide carrier out of the internal environment via the portal, and wherein the method further comprises;
automatically opening the portal before moving the slide carrier into the internal environment;
automatically closing the portal after moving the slide carrier into the internal environment and before staining the first and second specimens;
automatically opening the portal before moving the slide carrier out of the internal environment; and,
automatically closing the portal after moving the slide carrier out of the internal environment.

30. The method of claim 29, further comprising:
actively circulating gas within the internal environment while the portal is closed and the slide carrier is within the internal environment; and
suspending active circulation of gas within the internal environment while the portal is open and the slide carrier is entering the internal environment.

31. The method of claim 29, wherein automatically opening the portal includes automatically opening a door of the portal by tilting the door into the internal environment.

32. The method of claim 29, further comprising:
circulating gas within the internal environment at a first average rate while the portal is closed and the slide carrier is within the internal environment; and
circulating gas within the internal environment at a second average rate while the portal is open and the slide carrier is entering the internal environment, the second average rate being less than the first average rate.

33. The method of claim 32, wherein:
the first average rate is greater than 0.1 meters per second; and
the second average rate is less than 0.1 meters per second.

34. The method of claim 1, further comprising using a user interface of the system to select a recipe, wherein staining the first and second specimens includes staining the first and second specimens while the average temperature of the internal environment is controlled based on the selected recipe so as to cause a desired staining attribute for the first and second specimens.

35. The method of claim 34 wherein the staining attribute is a staining intensity.

36. The method of claim 34, wherein the staining attribute is a staining hue.

37. The method of claim 34, wherein the staining attribute is a counterstaining intensity.

38. The method of claim 34, wherein the staining attribute is a counterstaining hue.

39. The method of claim 34, wherein the staining attribute is a staining color balance.

40. A method for processing specimens carried by slides within an automated histological staining system, the method comprising:
moving a slide carrier toward and into a temperature-controlled internal environment of a stainer within the system, the slide carrier carrying a first slide and a second slide, the first and second slides carrying a first specimen and a second specimen, respectively;
staining the first and second specimens with at least one of a staining reagent and a counterstaining reagent while the first and second slides are within the internal environment and while an average temperature of the internal environment is greater than ambient temperature;
conductively heating a thermal mass positioned above the first and second slides while the first and second slides are within the internal environment, wherein conductively heating the thermal mass includes asynchronously operating two or more conductive heating elements operably coupled, respectively, to laterally spaced apart portions of the thermal mass; and,
moving the slide carrier out of the internal environment after staining the first and second specimens.

41. A method for processing specimens carried by slides within an automated histological staining system, the method comprising:
moving a slide carrier toward and into a temperature-controlled internal environment of a stainer within the system, the slide carrier carrying a first slide and a second slide, the first and second slides carrying a first specimen and a second specimen, respectively;
staining the first and second specimens with at least one of a staining reagent and a counterstaining reagent while the first and second slides are within the internal environment and while an average temperature of the internal environment is greater than ambient temperature;
heating the internal environment by forced convection while the first and second slides are within the internal environment, wherein heating the internal environment by forced convection includes actively circulating gas within the internal environment through a fan positioned below the first and second slides and further includes conductively heating a heat sink positioned below the first and second slides, and wherein actively circulating the gas includes blowing the gas diagonally upward across a surface of the heat sink toward a gap between the slide carrier and a thermal mass positioned above the slide carrier; and, moving the slide carrier out of the internal environment after staining the first and second specimens.

* * * * *